United States Patent
Cerezo-Galvez et al.

(10) Patent No.: US 10,294,243 B2
(45) Date of Patent: May 21, 2019

(54) BICYCLIC COMPOUNDS AS PESTICIDES

(71) Applicant: BAYER CROPSCIENCE AKTIENGESELLSCHAFT, Duesseldorf (DE)

(72) Inventors: Silvia Cerezo-Galvez, Langenfeld (DE); Thomas Bretschneider, Lohmar (DE); Reiner Fischer, Monheim (DE); Martin Fuesslein, Duesseldorf (DE); Joerg Greul, Leverkusen (DE); Peter Jeschke, Bergisch Gladbach (DE); Joachim Kluth, Langenfeld (DE); Arnd Voerste, Cologne (DE); Kerstin Ilg, Cologne (DE); Olga Malsam, Roesrath (DE); Peter Loesel, Leverkusen (DE); Ulrich Goergens, Ratingen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 77 days.

(21) Appl. No.: 15/315,915

(22) PCT Filed: Jun. 2, 2015

(86) PCT No.: PCT/EP2015/062211
§ 371 (c)(1),
(2) Date: Dec. 2, 2016

(87) PCT Pub. No.: WO2015/185531
PCT Pub. Date: Dec. 10, 2015

(65) Prior Publication Data
US 2017/0101422 A1    Apr. 13, 2017

(30) Foreign Application Priority Data

Jun. 5, 2014  (EP) ..................... 1417338

(51) Int. Cl.
*C07D 513/04* (2006.01)
*C07D 417/04* (2006.01)
*C07D 417/14* (2006.01)
*A01N 43/90* (2006.01)
*A61P 33/00* (2006.01)

(52) U.S. Cl.
CPC ........... *C07D 513/04* (2013.01); *A01N 43/90* (2013.01); *A61P 33/00* (2018.01); *C07D 417/04* (2013.01); *C07D 417/14* (2013.01)

(58) Field of Classification Search
CPC ................................................. C07D 513/04
See application file for complete search history.

(56) References Cited

U.S. PATENT DOCUMENTS

| 3,755,581 A | 8/1973 | Janiak et al. |
| 4,260,765 A | 4/1981 | Harrison et al. |
| 9,428,487 B2 | 8/2016 | Bretschneider et al. |

FOREIGN PATENT DOCUMENTS

| WO | 9857969 A1 | 12/1998 |
| WO | 03/033476 A1 | 4/2003 |
| WO | 2004/014916 A1 | 2/2004 |
| WO | 2008/152390 A1 | 12/2008 |
| WO | 2009149858 A1 | 12/2009 |
| WO | 2010100189 A1 | 9/2010 |
| WO | 2012102387 A1 | 8/2012 |

OTHER PUBLICATIONS

Hager et al. "Oxazolopyrimidine and Thiazolopyrimidine Derivatives Related to the Xanthines", Journal of the American Pharmaceutical Association (1955) vol. 44 193-196.
Cook et al. "Studies in the Azole Series" Journal of the Chemical Society (1949) 1064-1068.
McCoull et al. "Identification of pyrazolo-pyrimidinones as GHS-R1a antagonists and inverse agonists for the treatment of obesity†", Med. Chem. Commun., (2013) 4, 456-462.
Herrtzog et al. "The discovery and optimization of pyrimidinone-containing MCH R1 antagonists", Bioorg. Med. Chem. Lett. 16 (2006) 4723-4727.
International Search Report of PCT/EP2015/062211 dated Jun. 29, 2015.

*Primary Examiner* — Shawquia Jackson
(74) *Attorney, Agent, or Firm* — McBee Moore Woodward & Vanik IP, LLC

(57) ABSTRACT

The present application relates to novel bicyclic compounds, to their use for controlling animal pests and to processes and intermediates for their preparation.

16 Claims, No Drawings

BICYCLIC COMPOUNDS AS PESTICIDES

CROSS REFERENCE TO RELATED APPLICATIONS

This application is a § 371 National State Application of PCT/EP2015/062211, filed Jun. 2, 2015, which claims priority to European Application No. 14171338.8 filed Jun. 5, 2014.

BACKGROUND OF THE INVENTION

Field of the Invention

The present application relates to novel bicyclic compounds, to their use for controlling animal pests and to processes and intermediates for their preparation.

Description of Related Art

WO 2012/102387 A1 describes heterocyclic compounds which can be used particularly as insecticides and acaricides.

WO 2003/033476 A1, WO 2004/014916 A1, WO 2008/152390, MedChemComm (2013), 4(2), 456-462, Bioorganic & Medicinal Chemistry Letters (2006), 16(18), 4723-4727, Journal of the American Pharmaceutical Association (1912-1977) (1955), 44, 193-6 and Journal of the Chemical Society (1949), 1064-8 report on the synthesis and pharmacological properties of certain [1,3]thiazolo[4,5-d]pyrimidin-7(6H)-ones or [1,3]oxazolo[4,5-d]pyrimidin-7(6H)-ones.

Modern crop protection compositions have to meet many demands, for example in relation to extent, persistence and spectrum of their action and possible use. Questions of toxicity and of combinability with other active compounds or formulation auxiliaries play a role, as does the question of the expense that the synthesis of an active compound requires. In addition, resistances can occur. For all these reasons alone, the search for novel crop protection compositions cannot be considered complete, and there is a constant need for novel compounds having improved properties compared to the known compounds, at least in relation to individual aspects.

SUMMARY

It was an object of the present invention to provide compounds which widen the spectrum of the pesticides in various aspects.

This object, and further objects which are not stated explicitly but can be discerned or derived from the connections discussed herein, are achieved by novel compounds of the formula (I)

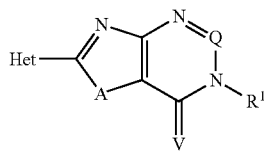

in which
Het represents a radical from the group of

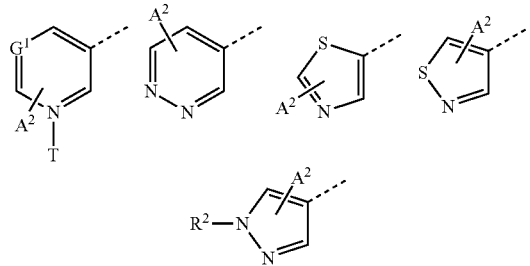

where the dotted line represents the bond to the carbon atom in the N═C-A group attached to Het and
  $G^1$ represents N or C-$A^1$,
  $A^1$ represents hydrogen, halogen, cyano, nitro, alkyl, haloalkyl, alkoxy, haloalkoxy or in each case optionally substituted cycloalkyl or cycloalkenyl,
  $A^2$ represents hydrogen, halogen, cyano, nitro, alkyl, haloalkyl, alkoxy, haloalkoxy or in each case optionally substituted cycloalkyl or cycloalkenyl,
  T represents oxygen or an electron pair,
  $R^2$ represents hydrogen, alkyl, haloalkyl or optionally substituted cycloalkyl,
  $R^1$ represents a radical from the group consisting of hydrogen, alkyl, haloalkyl, cyanoalkyl, alkenyl, haloalkenyl, alkynyl, haloalkynyl, alkoxy, haloalkoxy, optionally halogen-substituted alkoxyalkyl, optionally halogen-substituted bis(alkoxy)alkyl, optionally halogen-substituted alkylsulphanylalkyl, optionally halogen-substituted alkylcarbonylalkyl, optionally halogen-substituted alkylsulphinylalkyl, optionally halogen-substituted alkylsulphonylalkyl, dialkylaminosulphanylalkyl, dialkylaminosulphinylalkyl, dialkylaminosulphonylalkyl, optionally halogen-substituted alkoxy carbonyl, optionally halogen-substituted alkoxycarbonylalkyl, optionally halogen-substituted alkynyloxy, optionally halogen-substituted alkynyloxycarbonyl, dialkylaminocarbonyl, N-alkyl-N-cycloalkylaminocarbonyl, dialkylaminocarbonylalkyl, N-alkyl-N-cycloalkylaminocarbonylalkyl, heterocyclylcarbonylalkyl, alkylsulphanyl, haloalkylsulphanyl, alkylsulphinyl, haloalkylsulphinyl, alkylsulphonyl, haloalkylsulphonyl, optionally halogen-, cyano-, nitro-, alkyl-, cycloalkyl-, haloalkyl-, alkoxy-, haloalkoxy-, alkoxycarbonyl-, haloalkoxycarbonyl- or hetaryl- (which for its part may optionally be alkyl- or halogen-substituted) substituted cycloalkyl, optionally halogen-, cyano-, nitro-, alkyl-, haloalkyl-, cycloalkyl-, alkoxy-, haloalkoxy-, alkoxycarbonyl-, haloalkoxycarbonyl- or hetaryl- (which for its part may optionally be alkyl- or halogen-substituted) substituted cycloalkylcarbonyl, optionally halogen-, cyano-, nitro-, alkyl-, haloalkyl-, cycloalkyl-, alkoxy-, haloalkoxy-, alkoxycarbonyl-, haloalkoxycarbonyl- or hetaryl- (which for its part may optionally be alkyl- or halogen-substituted) substituted cycloalkylalkyl, optionally substituted heterocyclyl, optionally halogen-, cyano- (also in the alkyl part), nitro-, hydroxy-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted heterocyclylalkyl, optionally halogen-, cyano-, nitro-, hydroxy-, amino-, alkyl-, haloalkyl-, cycloalkyl- (which is optionally substituted) alkoxy- or haloalkoxy-substituted aryl, optionally halogen-, cyano- (also in the alkyl part), nitro-, hydroxy-, amino-, alkyl-, cycloalkyl- (which is optionally substituted), haloalkyl-, alkoxy- or haloalkoxy-substituted arylalkyl, optionally halogen-, cyano-, nitro-, hydroxy-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylaminocarbonyl-, dialkylaminocarbonyl-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetaryl, optionally halogen-, cyano- (also in the alkyl part), nitro-, hydroxy-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetarylalkyl, $R^1$ also represents a radical from the group consisting of

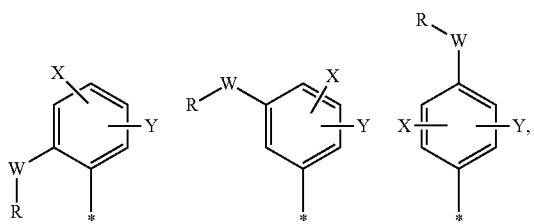

in which the bond to the nitrogen atom in the C(=V)—N-Q group in formula (I) is marked by the asterisk (*), R represents $NR^7R^8$, or represents an in each case optionally substituted radical from the group consisting of alkyl, alkenyl, alkynyl, alkoxyalkyl, alkyl-S(O)$_m$-alkyl, $R^7$—CO-alkyl, $NR^7R^8$—CO-alkyl, cycloalkyl, cycloalkenyl, cycloalkylalkyl, cycloalkenylalkyl, heterocyclyl, heterocyclylalkyl, phenyl, phenylalkyl, hetaryl and hetarylalkyl, W represents a radical from the group consisting of O, S, SO and $SO_2$, X represents a radical from the group consisting of hydrogen, halogen, cyano, nitro, alkyl, haloalkyl, alkoxy, haloalkoxy and cycloalkyl, Y represents a radical from the group consisting of hydrogen, halogen, alkyl, cycloalkyl, haloalkyl, alkoxy, haloalkoxy, cyano and $NR^5R^6$, A represents oxygen or sulphur, Q represents nitrogen or C—$R^3$ in which $R^3$ represents a radical from the group consisting of hydrogen, alkyl, cycloalkyl, haloalkyl, OH, alkoxy, haloalkoxy, SH, alkylsulphanyl, alkylsulphinyl, alkylsulphonyl, $NH_2$, alkylamino and dialkylamino, V represents a radical from the group consisting of oxygen, sulphur and $NR^4$, $R^4$ represents a radical from the group consisting of hydrogen, cyano, alkyl, haloalkyl and cycloalkyl, $R^5$ represents a radical from the group consisting of hydrogen, alkyl, cycloalkyl and haloalkyl, $R^6$ represents a radical from the group consisting of hydrogen, alkyl, cycloalkyl and haloalkyl, or $R^5$ and $R^6$ together with the nitrogen to which they are bonded represent an optionally substituted saturated or unsaturated 3- to 6-membered ring which optionally contains one or more further heteroatoms, $R^7$ represents hydrogen, hydroxy or an in each case optionally substituted radical from the group consisting of alkyl, alkoxy, alkoxyalkyl, alkylcarbonyl, alkyl-S(O)$_m$-alkyl, alkoxycarbonyl, cycloalkyl, cycloalkenyl, cycloalkylalkyl, cycloalkenylalkyl, heterocyclyl, heterocyclylalkyl, phenyl, phenylalkyl, hetaryl and hetarylalkyl, $R^8$ represents hydrogen, a metal ion, an optionally substituted ammonium ion or an in each case optionally substituted radical from the group consisting of alkyl, alkoxy, alkoxyalkyl, alkyl-S(O)$_m$-alkyl and m represents a number from the group consisting of 0, 1 and 2.

Preferred substituents or ranges for the radicals shown in the compounds of the formula (I) are elucidated below. The combination thereof forms the range of preference (1).

Het represents a radical from the group consisting of

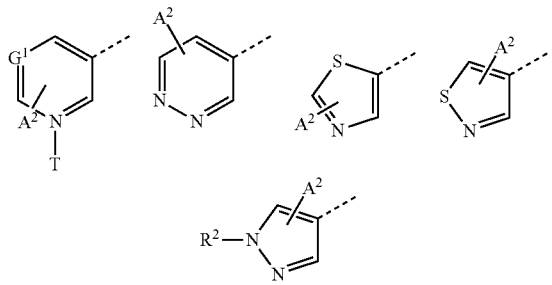

where the dotted line represents the bond to the carbon atom in the N=C-A group attached to Het.

$G^1$ represents N or C-$A^1$.

$A^1$ represents a radical from the group consisting of hydrogen, halogen, $C_1$-$C_6$-alkyl and $C_1$-$C_4$-haloalkyl.

$A^2$ represents a radical from the group consisting of hydrogen, halogen, $C_1$-$C_6$-alkyl and $C_1$-$C_4$-haloalkyl.

T represents oxygen or an electron pair.

$R^2$ represents a radical from the group consisting of hydrogen, $C_1$-$C_6$-alkyl, $C_1$-$C_6$-haloalkyl and $C_3$-$C_6$-cycloalkyl which is optionally mono- to trisubstituted by halogen, cyano, nitro, $C_1$-$C_3$-alkyl, $C_1$-$C_3$-alkoxy and monosubstituted by $C_3$-$C_6$-cycloalkyl.

$R^1$ represents a radical from the group consisting of hydrogen, $C_1$-$C_6$-alkyl, $C_2$-$C_6$-haloalkyl, cyano-$C_1$-$C_6$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_6$-alkoxy, $C_1$-$C_6$-haloalkoxy, optionally halogen-substituted $C_1$-$C_6$-alkoxy-$C_1$-$C_6$-alkyl, optionally halogen-substituted bis ($C_1$-$C_6$-alkoxy)-$C_1$-$C_6$-alkyl, optionally halogen-substituted $C_1$-$C_6$-alkylsulphanyl-$C_1$-$C_6$-alkyl, optionally halogen-substituted $C_1$-$C_4$-alkylcarbonyl-$C_1$-$C_4$-alkyl, optionally halogen-substituted $C_1$-$C_6$-alkylsulphinyl-$C_1$-$C_6$-alkyl, optionally halogen-substituted $C_1$-$C_6$-alkylsulphonyl-$C_1$-$C_6$-alkyl, di-($C_1$-$C_6$-alkyl)-aminosulphanyl-$C_1$-$C_6$-alkyl, di-($C_1$-$C_6$)-alkylaminosulphinyl-$C_1$-$C_6$-alkyl, di-($C_1$-$C_6$-alkyl)- aminosulphonyl-$C_1$-$C_6$-alkyl, optionally halogen-substituted $C_1$-$C_6$-alkoxycarbonyl, optionally halogen-substituted $C_1$-$C_6$-alkoxycarbonyl-$C_1$-$C_6$-alkyl, optionally halogen-substituted $C_2$-$C_4$-alkynyloxy, optionally halogen-substituted $C_2$-$C_4$-alkynyloxycarbonyl, di-($C_1$-$C_6$-alkyl)-aminocarbonyl, N—$C_1$-$C_6$-alkyl-N—$C_3$-$C_6$-cycloalkylaminocarbonyl, di-($C_1$-$C_6$-alkyl)-aminocarbonyl-$C_1$-$C_6$-alkyl, N—$C_1$-$C_6$-alkyl-N—$C_3$-$C_6$-cycloalkylaminocarbonyl-$C_1$-$C_6$-alkyl, heterocyclylcarbonyl-$C_1$-$C_6$-alkyl, $C_1$-$C_6$-alkylsulphanyl, $C_1$-$C_6$-haloalkylsulphanyl, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl- (which for its part is optionally $C_1$-$C_6$-alkyl- or halogen-substituted) substituted $C_3$-$C_6$-cycloalkyl, optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl- (which for its part is optionally $C_1$-$C_6$-alkyl- or halogen-substituted) substituted $C_3$-$C_6$-cycloalkylcarbonyl, optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl- (which for its part is optionally $C_1$-$C_6$-alkyl- or halogen-substituted) substituted $C_3$-$C_6$-cycloalkyl-$C_1$-$C_6$-alkyl, optionally halogen-, cyano- (also in the $C_1$-$C_6$-alkyl part of heterocyclyl-$C_1$-$C_6$-alkyl), nitro-, hydroxy-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di-($C_1$-$C_6$-alkyl)-amino-, $C_1$-$C_6$-alkylcarbonylamino-, $C_1$-$C_6$-alkoxy carbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted heterocyclyl-$C_1$-$C_6$-alkyl, optionally halogen-, cyano-, nitro-, hydroxy-, amino-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy- or $C_1$-$C_6$-haloalkoxy-substituted aryl, optionally halogen-, cyano- (also in the $C_1$-$C_6$-alkyl part of aryl-$C_1$-$C_6$-alkyl), nitro-, hydroxy-, amino-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy- or $C_1$-$C_6$-haloalkoxy-substituted aryl-$C_1$-$C_6$-alkyl, optionally halogen-, cyano-, nitro-, hydroxy-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di-($C_1$-$C_6$-alkyl)-amino-, $C_1$-$C_6$-alkylcarbonylamino-, $C_1$-$C_6$-alkylaminocarbonyl-, di-($C_1$-$C_6$-alkyl)-aminocarbonyl-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted hetaryl, optionally halogen-, cyano- (also in the $C_1$-$C_6$-alkyl part of hetaryl-$C_1$-$C_6$-alkyl), nitro-, hydroxy-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di-($C_1$-$C_6$-alkyl)-amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted hetaryl-$C_1$-$C_6$-alkyl.

$R^1$ also represents a radical from the group consisting of

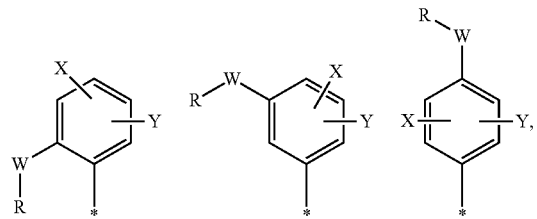

in which the bond to the nitrogen atom in the C(=V)—N-Q group in formula (I) is marked by the asterisk (*).

R represents $NR^7R^8$ or represents in each case optionally halogen-, oxygen- (leads to C=O) or cyano-substituted $C_1$-$C_6$-alkyl, $C_3$-$C_6$-alkenyl, $C_3$-$C_6$-alkynyl, $C_1$-$C_6$-alkoxy-$C_1$-$C_4$-alkyl, $C_1$-$C_6$-alkyl-S(O)$_m$—$C_1$-$C_4$-alkyl, represents $R^7$—CO—$C_1$-$C_4$-alkyl, represents $NR^7R^8$—CO—$C_1$-$C_4$-alkyl, represents $C_3$-$C_6$-cycloalkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents $C_3$-$C_6$-cycloalkenyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents $C_3$-$C_6$-cycloalkyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents $C_3$-$C_6$-cycloalkenyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents heterocyclyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents heterocyclyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl or represents phenyl, phenyl-$C_1$-$C_4$-alkyl, hetaryl or hetaryl-$C_1$-$C_4$-alkyl, each of which is optionally mono- to trisubstituted by halogen, cyano, $C_1$-$C_4$-alkyl, $C_3$-$C_6$-cycloalkyl, $C_1$-$C_4$-haloalkyl, $C_1$-$C_4$-alkoxy or $C_1$-$C_4$-haloalkoxy.

W represents a radical from the group consisting of O, S, SO and $SO_2$.

X represents a radical from the group consisting of hydrogen, halogen, cyano, nitro, $C_1$-$C_6$-alkyl, $C_1$-$C_6$-haloalkyl, $C_3$-$C_6$-cycloalkyl, $C_1$-$C_6$-alkoxy and $C_1$-$C_6$-haloalkoxy.

Y represents a radical from the group consisting of hydrogen, halogen, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, cyano and $NR^5R^6$.

A represents sulphur.

Q represents nitrogen or C—$R^3$.

$R^3$ represents a radical from the group consisting of hydrogen, $C_1$-$C_6$-alkyl, $C_1$-$C_6$-haloalkyl, $C_3$-$C_6$-cycloalkyl, OH, $C_1$-$C_6$-alkoxy, $C_1$-$C_6$-haloalkoxy, SH, $C_1$-$C_6$-alkylsulphanyl, $C_1$-$C_6$-alkylsulphinyl, $C_1$-$C_6$-alkylsulphonyl, $NH_2$, $C_1$-$C_6$-alkylamino and di-($C_1$-$C_6$-alkyl)-amino.

V represents a radical from the group consisting of oxygen, sulphur and $NR^4$.

$R^4$ represents a radical from the group consisting of hydrogen, cyano, $C_1$-$C_6$-alkyl, $C_2$-$C_6$-haloalkyl and $C_3$-$C_6$-cycloalkyl.

$R^5$ represents a radical from the group consisting of hydrogen, $C_1$-$C_6$-alkyl, $C_3$-$C_6$-cycloalkyl and $C_2$-$C_6$-haloalkyl.

$R^6$ represents a radical from the group consisting of hydrogen, $C_1$-$C_6$-alkyl, $C_3$-$C_6$-cycloalkyl and $C_2$-$C_6$-haloalkyl.

$R^5$ and $R^6$ together with the nitrogen atom to which they are attached may also represent a saturated to triunsaturated 3- to 6-membered ring which is optionally substituted by halogen, cyano, $C_1$-$C_4$-alkyl, $C_1$-$C_4$-haloalkyl, $C_1$-$C_4$-alkoxy, $C_1$-$C_4$-haloalkoxy, in particular aziridinyl, azirenyl, diaziridinyl, diazirenyl, azetidinyl, dihydroazetyl, diazetidinyl, dihydrodiazetyl, oxazetidinyl, oxazetyl, thiazetidinyl, thiazetyl, pyrrolidinyl, dihydropyrrolyl, pyrazolidinyl, dihydropyrazolyl, imidazolidinyl, dihydroimidazolyl, oxazolidinyl, dihydrooxazolyl, thiazolidinyl, dihydrothyazolyl, piperidinyl, piperazinyl, hexahydropyridazinyl, hexahydropyrimidinyl, morpholinyl, dioxazinanyl, thiomorpholine, dithiazinane, pyrrolyl, pyrazolyl, imidazolyl, triazolyl and tetrazolyl.

$R^7$ represents a radical from the group consisting of hydrogen, hydroxy, and $C_1$-$C_6$-alkyl, $C_1$-$C_6$-alkoxy, $C_1$-$C_6$-alkoxy-$C_1$-$C_4$-alkyl, $C_1$-$C_6$-alkyl-S(O)$_m$—$C_1$-$C_4$-alkyl, $C_1$-$C_6$-alkylcarbonyl, $C_1$-$C_6$-alkoxycarbonyl, $C_3$-$C_6$-cycloalkyl, $C_3$-$C_6$-cycloalkenyl, $C_3$-$C_6$-cycloalkyl-$C_1$-$C_3$-alkyl, $C_3$-$C_6$-cycloalkenyl-$C_1$-$C_3$-alkyl, heterocyclyl, heterocyclyl-$C_1$-$C_3$-alkyl, each of which is optionally mono- or polysubstituted by halogen or mono- or disubstituted by cyano, and represents phenyl, phenyl-$C_1$-$C_3$-alkyl, hetaryl and hetaryl-$C_1$-$C_3$-alkyl, each of which is optionally mono- to tetrasubstituted by $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, halogen or cyano.

$R^8$ represents hydrogen, an alkali or alkaline earth metal ion, or represents an ammonium ion which is optionally mono- to tetrasubstituted by $C_1$-$C_4$-alkyl, or represents a radical from the group consisting of $C_1$-$C_4$-alkyl, $C_1$-$C_4$-alkoxy, $C_1$-$C_4$-alkoxy-$C_1$-$C_4$-alkyl and $C_1$-$C_4$-alkyl-S(O)$_m$—$C_1$-$C_4$-alkyl, each of which is optionally mono- or polysubstituted by halogen or mono- or disubstituted by cyano.

m represents a number from the group consisting of 0, 1 and 2.

DETAILED DESCRIPTION OF A PREFERRED EMBODIMENT

Particularly preferred substituents or ranges for the radicals shown in the compounds of formula (I) are elucidated below. The combination thereof forms the range of preference (2).

Het represents a radical from the group consisting of

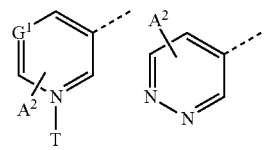

where the dotted line represents the bond to the carbon atom in the N═C-A group attached to Het.

$G^1$ represents N or C-$A^1$.

$A^1$ represents a radical from the group consisting of hydrogen, halogen, $C_1$-$C_4$-alkyl and $C_1$-$C_4$-haloalkyl.

$A^2$ represents a radical from the group consisting of hydrogen, halogen, $C_1$-$C_4$-alkyl and $C_1$-$C_4$-haloalkyl.

T represents oxygen or an electron pair.

$R^1$ represents a radical from the group consisting of hydrogen, $C_1$-$C_4$-alkyl, $C_2$-$C_4$-haloalkyl, cyano-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, optionally halogen-substituted $C_1$-$C_2$-alkoxy-$C_1$-$C_4$-alkyl, optionally halogen-substituted bis ($C_1$-$C_2$-alkoxy)-$C_1$-$C_4$-alkyl, optionally halogen-substituted $C_1$-$C_4$-alkylsulphanyl-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, di-($C_1$-$C_4$-alkyl)-aminosulphanyl-$C_1$-$C_4$-alkyl, di-($C_1$-$C_4$-alkyl)-aminosulphinyl-$C_1$-$C_4$-alkyl, di-($C_1$-$C_4$-alkyl)-aminosulphonyl-$C_1$-$C_4$-alkyl, optionally halogen-substituted $C_1$-$C_4$-alkoxycarbonyl, optionally halogen-substituted $C_1$-$C_4$-alkoxycarbonyl-$C_1$-$C_4$-alkyl, optionally halogen-substituted $C_2$-$C_4$-alkynyloxy, optionally halogen-substituted $C_2$-$C_4$-alkynyloxycarbonyl, di-($C_1$-$C_4$-alkyl)-aminocarbonyl, cycloalkylaminocarbonyl, di-($C_1$-$C_4$-alkyl)-aminocarbonyl-$C_1$-$C_4$-alkyl, N—$C_1$-$C_4$-alkyl-N—$C_3$-$C_6$-cycloalkylaminocarbonyl-$C_1$-$C_4$-alkyl, heterocyclylcarbonyl-$C_1$-$C_4$-alkyl, $C_1$-$C_4$-alkylsulphanyl, $C_1$-$C_4$-haloalkylsulphanyl, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, optionally halogen-, cyano-, nitro-, $C_1$-$C_4$-alkyl-, $C_1$-$C_4$-haloalkyl-, $C_3$-$C_6$-cycloalkyl-$C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl- (which for its part is optionally substituted by $C_1$-$C_4$-alkyl or halogen) substituted $C_3$-$C_6$-cycloalkyl, optionally halogen-, cyano-, nitro-, $C_1$-$C_4$-alkyl-, $C_1$-$C_4$-haloalkyl-, $C_3$-$C_6$-cycloalkyl-$C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl- (which for its part is optionally substituted by $C_1$-$C_4$-alkyl or halogen) substituted $C_3$-$C_6$-cycloalkylcarbonyl, optionally halogen-, cyano-, nitro-, $C_1$-$C_4$-alkyl-, $C_1$-$C_4$-haloalkyl-, $C_3$-$C_6$-cycloalkyl-$C_1$-$C_4$-alkoxy-, $C_1$-$C_4$-haloalkoxy-, $C_1$-$C_4$-alkoxycarbonyl-, $C_1$-$C_4$-haloalkoxycarbonyl-, pyridyl-, pyrimidyl-, pyrazanyl-, pyridazinyl-, thiazolyl-, isothiazolyl-, thiadiazolyl-, oxazolyl-, isoxazolyl-, oxadiazolyl-, pyrazolyl-, triazinyl- or triazolyl- (where the hetaryls mentioned for their part are optionally substituted by $C_1$-$C_4$-alkyl or halogen) substituted $C_3$-$C_6$-cycloalkyl-$C_1$-$C_4$-alkyl, optionally halogen-, cyano- (also in the $C_1$-$C_4$-alkyl part of heterocyclyl-$C_1$-$C_4$-alkyl), nitro-, hydroxy-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino, —$C_1$-$C_4$-alkylamino-, di-($C_1$-$C_4$-alkyl)-amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted heterocyclyl-$C_1$-$C_4$-alkyl, optionally halogen-, cyano-, nitro-, hydroxy-, amino-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy- or $C_1$-$C_4$-haloalkoxy-substituted aryl, optionally halogen-, cyano- (also in the $C_1$-$C_4$-alkyl part of aryl-$C_1$-$C_4$-alkyl), nitro-, hydroxy-, amino-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy- or $C_1$-$C_4$-haloalkoxy-substituted aryl-$C_1$-$C_4$-alkyl, optionally halogen-, cyano-, nitro-, hydroxy-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di-($C_1$-$C_4$-alkyl)-amino-, $C_1$-$C_4$-alkylcarbonylamino-, $C_1$-$C_4$-alkylaminocarbonyl-, di-($C_1$-$C_4$-alkyl)-aminocarbonyl-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted hetaryl, optionally halogen-, cyano- (also in the $C_1$-$C_4$-alkyl part of hetaryl-$C_1$-$C_4$-alkyl), nitro-, hydroxy-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted hetaryl-$C_1$-$C_4$-alkyl.

$R^1$ also represents a radical from the group consisting of

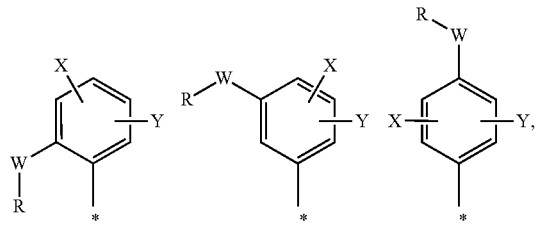

in which the bond to the nitrogen atom in the C(=V)—N-Q group in formula (I) is marked by the asterisk (*).

R represents $NR^7R^8$ or represents $C_1$-$C_6$-alkyl, $C_3$-$C_6$-alkenyl, $C_3$-$C_6$-alkynyl, $C_1$-$C_4$-alkoxy-$C_1$-$C_3$-alkyl, $C_1$-$C_4$-alkyl-$S(O)_m$—$C_1$-$C_3$-alkyl, each of which is optionally mono- to heptasubstituted by halogen, mono- or disubstituted by oxygen (leads to C=O) or mono- or disubstituted by cyano, represents $R^7$—CO—$C_1$-$C_2$-alkyl, represents $NR^7R^8$—CO—$C_1$-$C_2$-alkyl, represents $C_3$-$C_8$-cycloalkyl which is optionally mono- or disubstituted by oxygen (leads to C=O), $C_1$-$C_4$-alkyl, $C_3$-$C_6$-cycloalkyl, $C_1$-$C_4$-alkoxy or $C_1$-$C_4$-haloalkyl, represents $C_3$-$C_8$-cycloalkenyl which is optionally mono- or disubstituted by oxygen (leads to C=O), $C_1$-$C_4$-alkyl, $C_3$-$C_6$-cycloalkyl, $C_1$-$C_4$-alkoxy or $C_1$-$C_4$-haloalkyl, represents $C_3$-$C_6$-cycloalkyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy or $C_1$-$C_4$-haloalkyl, represents $C_3$-$C_6$-cycloalkenyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy or $C_1$-$C_4$-haloalkyl, represents heterocyclyl which is optionally mono- or disubstituted by oxygen (leads to C=O), $C_1$-$C_4$-alkyl, $C_3$-$C_6$-cycloalkyl, $C_1$-$C_4$-alkoxy or $C_1$-$C_4$-haloalkyl, represents heterocyclyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy or $C_1$-$C_4$-haloalkyl or represents phenyl, phenyl-$C_1$-$C_4$-alkyl, hetaryl or hetaryl-$C_1$-$C_4$-alkyl, each of which is optionally mono- to trisubstituted by halogen, cyano, $C_1$-$C_4$-alkyl, $C_1$-$C_4$-haloalkyl, $C_3$-$C_6$-cycloalkyl, $C_1$-$C_4$-alkoxy or $C_1$-$C_4$-haloalkoxy.

W represents a radical from the group consisting of S, SO and $SO_2$.

X represents a radical from the group consisting of hydrogen, fluorine, chlorine, bromine, iodine, cyano, nitro, $C_1$-$C_4$-alkyl, $C_1$-$C_4$-haloalkyl, $C_3$-$C_6$-cycloalkyl, $C_1$-$C_4$-alkoxy and $C_1$-$C_4$-haloalkoxy.

Y represents a radical from the group consisting of hydrogen, fluorine, chlorine, bromine, iodine, cyano, $C_1$-$C_4$-alkyl, $C_1$-$C_4$-haloalkyl, $C_3$-$C_6$-cycloalkyl, $C_1$-$C_4$-alkoxy and $C_1$-$C_4$-haloalkoxy.

A represents sulphur.

Q represents nitrogen or C—$R^3$.

$R^3$ represents a radical from the group consisting of hydrogen, $C_1$-$C_4$-alkyl, $C_1$-$C_4$-haloalkyl, $C_3$-$C_6$-cycloalkyl, OH, $C_1$-$C_4$-alkoxy, $C_1$-$C_4$-haloalkoxy, SH, $C_1$-$C_4$-alkylsulphanyl, $C_1$-$C_4$-alkylsulphinyl, $C_1$-$C_4$-alkylsulphonyl, $NH_2$, $C_1$-$C_4$-alkylamino and di-($C_1$-$C_4$-alkyl)-amino.

V represents oxygen.

$R^7$ represents a radical from the group consisting of hydrogen, hydroxy, or $C_1$-$C_4$-alkyl, $C_1$-$C_4$-alkoxy, $C_1$-$C_4$-alkoxy-$C_1$-$C_4$-alkyl, $C_1$-$C_4$-alkyl-S(O)$_m$—$C_1$-$C_3$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_3$-alkyl, heterocyclyl and heterocyclyl-$C_1$-$C_3$-alkyl, each of which is optionally mono- or polysubstituted by halogen or mono- or disubstituted by cyano, or represents phenyl, benzyl, pyridyl, pyrimidyl, thiazolyl, oxazolyl, pyrazolyl, thienyl, furanyl, pyridinylmethyl or thiazolylmethyl, each of which is optionally mono- to trisubstituted by $C_1$-$C_4$-alkyl, $C_1$-$C_3$-haloalkyl, $C_1$-$C_3$-alkoxy, $C_1$-$C_3$-haloalkoxy, cyclopropyl, fluorine, chlorine, bromine or cyano.

$R^8$ represents hydrogen, represents an alkali or alkaline earth metal ion, or represents an ammonium ion which is optionally mono- to tetrasubstituted by $C_1$-$C_4$-alkyl, or represents a radical from the group consisting of $C_1$-$C_4$-alkyl, $C_1$-$C_4$-alkoxy, $C_1$-$C_4$-alkoxy-$C_1$-$C_2$-alkyl and $C_1$-$C_4$-alkyl-S(O)$_m$—$C_1$-$C_2$-alkyl, each of which is optionally mono- or polysubstituted by halogen or mono- or disubstituted by cyano.

m represents a number from the group consisting of 0, 1 and 2.

Very particularly preferred substituents or ranges of the radicals shown in the compounds of the formula (I) are elucidated below. The combination thereof forms the range of preference (3).

Het represents a radical from the group consisting of

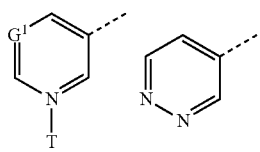

where the dotted line represents the bond to the carbon atom in the N=C-A group attached to Het.

$G^1$ represents N or C-$A^1$.

$A^1$ represents a radical from the group consisting of hydrogen, fluorine and chlorine.

T represents oxygen or an electron pair.

$R^1$ represents a radical from the group consisting of methyl, ethyl, isopropyl, n-propyl, n-butyl, isobutyl, sec-butyl, tert-butyl, 2,2,2-trifluoroethyl, 2,2-difluoroethyl, 2,2-difluoro-n-propyl, methylsulphanylmethyl, methylsulphanylethyl, methylsulphanyl-n-propyl, trifluoromethylsulphonylmethyl, ethylsulphonylmethyl, 2,2,2-trifluoroethylsulphonylmethyl, 2,2-difluoroethylsulphonylmethyl, isopropylsulphanylmethyl, methylsulphinylmethyl, trifluoromethylsulphinylmethyl, ethylsulphinylmethyl, 2,2,2-trifluoroethylsulphinylmethyl, 2,2-difluoroethylsulphinylmethyl, isopropylsulphinylmethyl, methylsulphonylmethyl, trifluoromethylsulphonylmethyl, ethylsulphonylmethyl, 2,2,2-trifluoroethylsulphonylmethyl, 2,2-difluoroethylsulphonylmethyl, isopropylsulphonylmethyl, methoxycarbonyl, ethoxy carbonyl, methoxycarbonylmethyl, ethoxycarbonylmethyl, methoxycarbonylethyl, ethoxycarbonylethyl, dimethylaminocarbonyl, diethylaminocarbonyl, N-ethyl-N-methylaminocarbonyl, N-isopropyl-N-methylaminocarbonyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, methylsulphanyl, trifluoromethylsulphanyl, ethylsulphanyl, 2,2,2-trifluoroethylsulphanyl, 2,2-difluoroethylsulphanyl, isopropylsulphanyl, methylsulphinyl, trifluoromethylsulphinyl, ethylsulphinyl, 2,2,2-trifluoroethylsulphinyl, 2,2-difluoroethylsulphinyl, isopropylsulphinyl, methylsulphonyl, trifluoromethylsulphonyl, ethylsulphonyl, 2,2,2-trifluoroethylsulphonyl, 2,2-difluoroethylsulphonyl, isopropylsulphonyl, cyclopropyl, 1-cyanocyclopropyl, 1-chlorocyclopropyl, 1-fluorocyclopropyl, 2-cyanocyclopropyl, 2-chlorocyclopropyl, 2-fluorocyclopropyl, 2,2,3,3-tetrafluorocyclopropyl, 2-cyclopropylcyclopropyl, cyclobutyl, cyclopentyl, cyclohexyl, 4-trifluoromethylcyclohexyl, cyclopropylmethyl, cyclopropylethyl, cyclobutylmethyl, N-cyclopropyl-N-methylaminocarbonyl, morpholin-4-ylcarbonylmethyl, piperazin-1-ylcarbonylmethyl, 4-methylpiperazin-1-ylcarbonylmethyl, of heterocyclylmethyl and heterocyclylethyl, each of which is optionally mono-, di- or trisubstituted by identical or different substitutents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy and difluoromethoxy, of in each case cyclopropyl-substituted heterocyclylmethyl and heterocyclylethyl, where the cyclopropyl radical is optionally mono- or disubstituted by methyl, fluorine, chlorine, cyano or monosubstituted by cyclopropyl, of hetaryl which is optionally mono- or disubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy, dimethylaminocarbonyl, of hetaryl substituted by cyclopropyl, where the cyclopropyl radical is optionally mono- or disubstituted by methyl, fluorine, chlorine, cyano or monosubstituted by cyclopropyl, of aryl which is optionally mono-, di- or trisubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy and trifluoroethoxy, of aryl substituted by cyclopropyl, where the cyclopropyl radical is optionally mono- or disubstituted by methyl, fluorine, chlorine, cyano or monosubstituted by cyclopropyl, of arylmethyl and arylethyl, each of which is optionally mono-, di- or trisubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy, of arylmethyl and arylethyl in each case substituted by cyclopropyl, where the cyclopropyl radical is optionally mono- or disubstituted by methyl, fluorine, chlorine, cyano or monosubstituted by cyclopropyl, of hetarylmethyl and hetarylethyl, each of which is optionally mono- or disubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy, of hetarylmethyl and hetarylethyl in each case substituted by cyclopropyl, where the cyclopropyl radical is optionally mono- or disubstituted by methyl, fluorine, chlorine, cyano or monosubstituted by cyclopropyl.

$R^1$ also represents a radical from the group consisting of

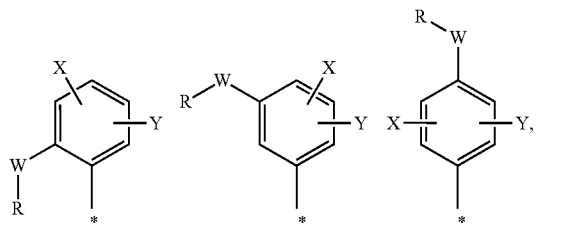

in which the bond to the nitrogen atom in the C(=V)—N-Q group in formula (I) is marked by the asterisk (*).

R represents $NR^7R^8$ or represents a radical from the group consisting of $C_1$-$C_4$-alkyl, $C_3$-$C_4$-alkenyl, $C_3$-$C_4$-alkynyl, $C_1$-$C_2$-alkoxy-$C_1$-$C_2$-alkyl and $C_1$-$C_2$-alkyl-$S(O)_m$—$C_1$-$C_2$-alkyl, each of which is optionally mono-, di-, tri-, tetra- or pentasubstituted by fluorine, chlorine or mono- or disubstituted by cyano, represents $R^7$—CO—$C_1$-$C_2$-alkyl, represents $NR^7R^8$—CO—$C_1$-$C_2$-alkyl, represents $C_3$-$C_6$-cycloalkyl which is optionally mono- or disubstituted by $C_1$-$C_2$-alkyl, $C_1$-$C_2$-alkoxy or $C_1$-$C_2$-haloalkyl or by an oxygen atom (leads to C=O), represents $C_3$-$C_6$-cycloalkenyl which is optionally mono- or disubstituted by $C_1$-$C_2$-alkyl, $C_1$-$C_2$-alkoxy or $C_1$-$C_2$-haloalkyl or by an oxygen atom (leads to C=O), represents $C_3$-$C_6$-cycloalkyl-$C_1$-$C_2$-alkyl which is optionally mono- or disubstituted by $C_1$-$C_2$-alkyl, $C_1$-$C_2$-alkoxy or $C_1$-$C_2$-haloalkyl, represents $C_3$-$C_6$-cycloalkenyl-$C_1$-$C_2$-alkyl which is optionally mono- or disubstituted by $C_1$-$C_2$-alkyl, $C_1$-$C_2$-alkoxy or $C_1$-$C_2$-haloalkyl, represents heterocyclyl which is optionally mono- or disubstituted by $C_1$-$C_2$-alkyl, $C_1$-$C_2$-alkoxy or $C_1$-$C_2$-haloalkyl, represents heterocyclyl-$C_1$-$C_2$-alkyl which is optionally mono- or disubstituted by $C_1$-$C_2$-alkyl, $C_1$-$C_2$-alkoxy or $C_1$-$C_2$-haloalkyl or represents phenyl, benzyl, pyridyl, pyrimidyl, thiazolyl, oxazolyl, pyrazolyl, thienyl, furanyl, pyridinylmethyl or thiazolylmethyl, each of which is optionally mono- or disubstituted by fluorine, chlorine, bromine, cyano, methyl, ethyl, difluoromethyl, trifluoromethyl, methoxy, ethoxy, difluoromethoxy or trifluoromethoxy.

W represents a radical from the group consisting of S, SO and $SO_2$.

X represents a radical from the group consisting of hydrogen, fluorine, chlorine, bromine, cyano, methyl, ethyl, trifluoromethyl, methoxy, ethoxy, difluoromethoxy and trifluoromethoxy.

Y represents a radical from the group consisting of hydrogen, fluorine, chlorine, bromine, cyano, methyl, ethyl, trifluoromethyl, methoxy, ethoxy, difluoromethoxy and trifluoromethoxy.

A represents sulphur.

Q represents nitrogen or C—$R^3$.

$R^3$ represents hydrogen.

V represents oxygen.

$R^7$ represents a radical from the group consisting of hydrogen, hydroxy, or represents $C_1$-$C_4$-alkyl, $C_1$-$C_4$-alkoxy, $C_1$-$C_4$-alkoxy-$C_1$-$C_4$-alkyl, $C_1$-$C_4$-alkyl-$S(O)_m$—$C_1$-$C_2$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_3$-alkyl, heterocyclyl or heterocyclyl-$C_1$-$C_3$-alkyl, each of which is optionally mono-, di-, tri-, tetra- or pentasubstituted by fluorine, chlorine or mono- or disubstituted by cyano, or represents phenyl, benzyl, pyridyl, pyrimidyl, thiazolyl, oxazolyl, pyrazolyl, thienyl, furanyl, pyridinylmethyl or thiazolylmethyl, each of which is optionally mono- to trisubstituted by $C_1$-$C_4$-alkyl, $C_1$-$C_3$-haloalkyl, $C_1$-$C_3$-alkoxy, $C_1$-$C_3$-haloalkoxy, cyclopropyl, fluorine, chlorine, bromine or cyano.

$R^8$ represents hydrogen, an alkali or alkaline-earth metal ion, an ammonium ion which is optionally mono- to tetrasubstituted by $C_1$-$C_4$-alkyl, or represents a radical from the group consisting of $C_1$-$C_4$-alkyl, $C_1$-$C_4$-alkoxy, $C_1$-$C_4$-alkoxy-$C_1$-$C_2$-alkyl and $C_1$-$C_4$-alkyl-$S(O)_m$—$C_1$-$C_2$-alkyl, each of which is optionally mono-, di-, tri-, tetra- or pentasubstituted by fluorine, chlorine or is mono- or disubstituted by cyano.

m represents a number from the group consisting of 0, 1 and 2.

Especially preferred substituents or ranges for the radicals shown in the compounds of formula (I) are elucidated below. The combination thereof forms the range of preference (4).

Het represents a radical from the group consisting of

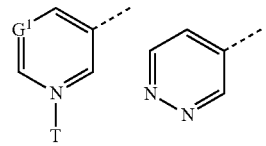

where the dotted line represents the bond to the carbon atom in the N=C-A group attached to Het.

$G^1$ represents N or C-$A^1$.

$A^1$ represents a radical from the group consisting of hydrogen, fluorine and chlorine.

T represents oxygen or an electron pair.

$R^1$ represents a radical from the group consisting of methyl, ethyl, isopropyl, n-propyl, n-butyl, isobutyl, sec-butyl, tert-butyl, 2,2,2-trifluoroethyl, 2,2-difluoroethyl, 2,2-difluoro-n-propyl, methylsulphanylmethyl, methylsulphanylethyl, methylsulphanyl-n-propyl, trifluoromethylsulphonylmethyl, ethylsulphonylmethyl, 2,2,2-trifluoroethylsulphonylmethyl, 2,2-difluoroethylsulphonylmethyl, isopropylsulphanylmethyl, methylsulphinylmethyl, trifluoromethylsulphinylmethyl, ethylsulphinylmethyl, 2,2,2-trifluoroethylsulphinylmethyl, 2,2-difluoroethylsulphinylmethyl, isopropylsulphinylmethyl, methylsulphonylmethyl, trifluoromethylsulphonylmethyl, ethylsulphonylmethyl, 2,2,2-trifluoroethylsulphonylmethyl, 2,2-difluoroethylsulphonylmethyl, isopropylsulphonylmethyl, methoxycarbonyl, ethoxycarbonyl, methoxycarbonylmethyl, ethoxycarbonylmethyl, methoxycarbonylethyl, ethoxycarbonylethyl, dimethylaminocarbonyl, diethylaminocarbonyl, N-ethyl-N-methylaminocarbonyl, N-isopropyl-N-methylaminocarbonyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, methylsulphanyl, trifluoromethylsulphanyl, ethylsulphanyl, 2,2,2-trifluoroethylsulphanyl, 2,2-difluoroethylsulphanyl, isopropylsulphanyl, methylsulphinyl, trifluoromethylsulphinyl, ethylsulphinyl, 2,2,2-trifluoroethylsulphinyl, 2,2-difluoroethylsulphinyl, isopropylsulphinyl, methylsulphonyl, trifluoromethylsulphonyl, ethylsulphonyl, 2,2,2-trifluoroethylsulphonyl, 2,2-difluoroethylsulphonyl, isopropylsulphonyl, cyclopropyl, 1-cyanocyclopropyl, 1-chlorocyclopropyl, 1-fluorocyclopropyl, 2-cyanocyclopropyl, 2-chlorocyclopropyl, 2-fluorocyclopropyl, 2,2,3,3-tetrafluorocyclopropyl, 2-cyclopropylcyclopropyl, cyclobutyl, cyclopentyl, cyclohexyl, 4-trifluoromethylcyclohexyl, cyclopropylmethyl, cyclopropylethyl, cyclobutylmethyl, N-cyclopropyl-N-methylaminocarbonyl, morpholin-4-ylcarbonylmethyl, piperazin-1-ylcarbonylmethyl, 4-methylpiperazin-1-ylcarbonylmethyl, of heterocyclylmethyl and heterocyclylethyl, each of which is optionally mono-, di- or trisubstituted by identical or different substitutents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy and difluoromethoxy, of in each case cyclopropyl-substituted heterocyclylmethyl and heterocyclylethyl, where the cyclopropyl radical is optionally mono- or disubstituted by methyl, fluorine, chlorine, cyano or monosubstituted by cyclopropyl, of hetaryl which is optionally mono- or disubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy, dimethylaminocarbonyl, of hetaryl substituted by cyclopropyl, where the cyclopropyl radical is optionally mono- or disubstituted by methyl, fluorine, chlorine, cyano or monosubstituted by cyclopropyl, of aryl which is optionally mono-, di- or trisubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy and trifluoroethoxy, of aryl substituted by cyclopropyl, where the cyclopropyl radical is optionally mono- or disubstituted by methyl, fluorine, chlorine, cyano or monosubstituted by cyclopropyl, of arylmethyl and arylethyl, each of which is optionally mono-, di- or trisubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy, of arylmethyl and arylethyl in each case substituted by cyclopropyl, where the cyclopropyl radical is optionally mono- or disubstituted by methyl, fluorine, chlorine, cyano or monosubstituted by cyclopropyl, of hetarylmethyl and hetarylethyl, each of which is optionally mono- or disubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy, of hetarylmethyl and hetarylethyl in each case substituted by cyclopropyl, where the cyclopropyl radical is optionally mono- or disubstituted by methyl, fluorine, chlorine, cyano or monosubstituted by cyclopropyl.

$R^1$ also represents the radical of the formula

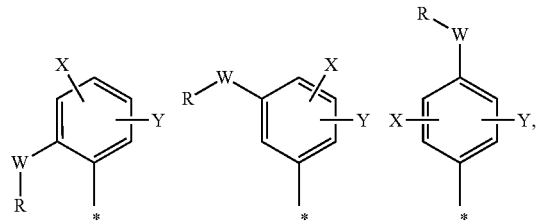

in which the bond to the nitrogen atom in the C(=V)—N-Q group in formula (I) is marked by the asterisk (*).

R represents methyl, ethyl, propyl, isopropyl, n-butyl, isobutyl, sec-butyl, tert-butyl, allyl, 2-butenyl, propargyl, 2-butynyl, each of which is optionally mono-, di- or trisubstituted by fluorine or monosubstituted by cyano, or represents $C_3$-$C_6$-cycloalkyl which is optionally monosubstituted by methyl, ethyl, methoxy, ethoxy or trifluoromethyl, or represents $C_3$-$C_6$-cycloalkylmethyl which is optionally monosubstituted by methyl, ethyl, methoxy or trifluoromethyl, or represents phenyl, benzyl, pyridyl, pyrimidyl, thiazolyl and pyridinylmethyl, each of which is optionally mono- or disubstituted by fluorine, chlorine, bromine, cyano, methyl, ethyl, isopropyl, tert-butyl, trifluoromethyl, difluoromethyl, methoxy, ethoxy, difluoromethoxy or trifluoromethoxy.

W represents a radical from the group consisting of S, SO and $SO_2$.

X represents a radical from the group consisting of hydrogen, fluorine, chlorine, bromine, cyano, methyl, ethyl, trifluoromethyl, methoxy, ethoxy, difluoromethoxy and trifluoromethoxy.

Y represents a radical from the group consisting of hydrogen, fluorine, chlorine, bromine, cyano, methyl, ethyl, trifluoromethyl, methoxy, ethoxy, difluoromethoxy and trifluoromethoxy.

A represents sulphur.

Q represents nitrogen or C—$R^3$.

$R^3$ represents hydrogen or methyl.

V represents oxygen.

A further preferred embodiment of the invention relates to compounds of the formula (I) in which the substituents have the meanings below. The combination thereof forms the range of preference (5).

Het represents

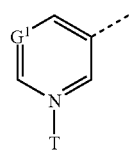

where the dotted line represents the bond to the carbon atom in the N=C-A group attached to Het.
$G^1$ represents C-$A^1$.
$A^1$ represents hydrogen.
T represents oxygen or an electron pair.
$R^1$ represents
methyl, ethyl, isopropyl, n-propyl, n-butyl, isobutyl, sec-butyl, tert-butyl, 2,2,2-trifluoroethyl, 2,2-difluoroethyl, 2,2-difluoro-n-propyl, dimethylaminocarbonyl, diethylaminocarbonyl, N-ethyl-N-methylaminocarbonyl, N-isopropyl-N-methylaminocarbonyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, cyclopropyl, cyclobutyl, cyclopentyl, cyclohexyl, represents hetarylmethyl or hetarylethyl, each of which is optionally mono- or disubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy.
$R^1$ also represents

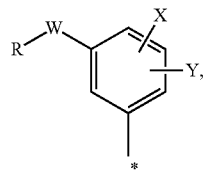

in which the bond to the nitrogen atom in the C(=V)—N-Q group in formula (I) is marked by the asterisk (*).
R represents $C_1$-$C_4$-alkyl which is optionally mono- to trisubstituted by fluorine or chlorine.
W represents a radical from the group consisting of S and SO.
X represents a radical from the group consisting of hydrogen, fluorine, chlorine, bromine, methyl, ethyl, difluoromethyl and trifluoromethyl.
Y represents a radical from the group consisting of hydrogen, fluorine, chlorine, bromine, iodine (in particular fluorine), methyl and ethyl.
A represents sulphur.
Q represents nitrogen or C—$R^3$.
$R^3$ represents hydrogen.
V represents oxygen.
A further preferred embodiment of the invention relates to compounds of the formula (I) in which the substituents have the meanings below. The combination thereof forms the range of preference (6).
Het represents

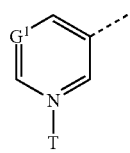

where the dotted line represents the bond to the carbon atom in the N=C-A group attached to Het.
$G^1$ represents C-$A^1$ or N.
$A^1$ represents hydrogen or fluorine.
T represents oxygen or an electron pair.
$R^1$ represents
methyl, ethyl, isopropyl, n-propyl, n-butyl, isobutyl, sec-butyl, tert-butyl, 2,2,2-trifluoroethyl, 2,2-difluoroethyl, 2,2-difluoro-n-propyl, dimethylaminocarbonyl, diethylaminocarbonyl, N-ethyl-N-methylaminocarbonyl, N-isopropyl-N-methylaminocarbonyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, cyclopropyl, cyclobutyl, cyclopentyl, cyclohexyl, cyclopropylmethyl, optionally dimethylaminocarbonyl-substituted benzothienyl, optionally halogen-, methyl- or trifluoroethoxy-substituted phenyl, optionally methyl-, methoxy-, difluoromethoxy- or halogen-substituted phenylmethyl, represents hetarylmethyl or hetarylethyl, each of which is optionally mono- or disubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy.
$R^1$ also represents

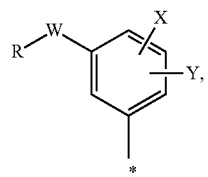

in which the bond to the nitrogen atom in the C(=V)—N-Q group in formula (I) is marked by the asterisk (*).
R represents $C_1$-$C_4$-alkyl which is optionally mono- to trisubstituted by fluorine or chlorine.
W represents a radical from the group consisting of S, SO and $SO_2$.
X represents a radical from the group consisting of hydrogen, fluorine, chlorine, bromine, methyl, ethyl, difluoromethyl and trifluoromethyl.
Y represents a radical from the group consisting of hydrogen, fluorine, chlorine, bromine, iodine (in particular fluorine), methyl and ethyl.
A represents sulphur.
Q represents nitrogen or C—$R^3$.
$R^3$ represents hydrogen or methyl.
V represents oxygen.
In the preferred definitions, whose combination forms the range of preference (1), unless stated otherwise,
alkali metal ion is selected from the group consisting of lithium, sodium, potassium, rubidium, caesium, preferably from the group consisting of lithium, sodium and potassium, alkaline earth metal ion is selected from the group consisting of beryllium, magnesium, calcium, strontium, barium, preferably from the group consisting of magnesium and calcium, halogen is selected from the group consisting of fluorine, chlorine, bromine and iodine, preferably in turn from the group consisting of fluorine, chlorine and bromine, aryl (including as part of a larger unit, for example arylalkyl) is selected from the group consisting of phenyl, naphthyl, anthryl, phenanthrenyl, and represents preferably in turn phenyl, hetaryl (synonymous with heteroaryl, including as part of a larger unit, for example hetarylalkyl) is selected from the group consisting of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2, 4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzoisofuryl, benzothienyl, benzoisothienyl, indolyl, isoindolyl, indazolyl, benzothiazolyl, benzoisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, heterocyclyl represents a saturated 4-, 5- or 6-membered ring containing 1 or 2 nitrogen atoms and/or one oxygen atom and/or one sulphur atom, for example azetidinyl, azolidinyl, azinanyl, oxetanyl, oxolanyl, oxanyl, dioxanyl, thiethanyl, thiolanyl, thianyl, tetrahydrofuryl, piperazinyl, morpholinyl.

In the particularly preferred definitions whose combination forms the range of preference (2), unless stated otherwise, alkali metal ion is selected from the group consisting of lithium, sodium, potassium, rubidium, caesium, preferably from the group consisting of lithium, sodium and potassium, alkaline earth metal ion is selected from the group consisting of beryllium, magnesium, calcium, strontium, barium, preferably from the group consisting of magnesium and calcium, halogen is selected from the group consisting of fluorine, chlorine, bromine and iodine, preferably in turn from the group consisting of fluorine, chlorine and bromine, aryl (including as part of a larger unit, for example arylalkyl) is selected from the group of phenyl, naphthyl, anthryl and phenanthrenyl, and is preferably in turn phenyl, hetaryl (synonymous with heteroaryl, also as part of a larger unit such as, for example, hetarylalkyl) is selected from the group consisting of pyrazolyl, imidazolyl, 1,2,3-triazolyl, 1,2,4-triazolyl, oxazolyl, isoxazolyl, thiazolyl, isothiazolyl, pyridyl, pyrimidinyl, pyridazinyl, pyrazinyl, 1,2,3-triazinyl, 1,2,4-triazinyl, 1,3,5-triazinyl, benzothienyl, heterocyclyl is selected from the group consisting of azetidinyl, azolidinyl, azinanyl, oxetanyl, oxolanyl, oxanyl, dioxanyl, thiethanyl, thiolanyl, thianyl, tetrahydrofuryl, piperazinyl, morpholinyl.

In the very particularly preferred definitions and the especially preferred definitions whose combination forms the range of preference (3) and the range of preference (4), respectively, unless stated otherwise, alkali metal ion represents an ion from the group consisting of lithium, sodium, potassium, rubidium, caesium, preferably from the group consisting of lithium, sodium, potassium, alkaline earth metal ion represents an ion from the group consisting of beryllium, magnesium, calcium, strontium and barium, preferably from the group consisting of magnesium and calcium, halogen represents fluorine, chlorine, bromine and iodine, preferably in turn fluorine, chlorine and bromine, heterocyclyl represents a radical from the group consisting of oxetanyl, thiethanyl, tetrahydrofuryl and morpholinyl, aryl represents phenyl and hetaryl (synonymous with heteroaryl, including as part of a larger unit such as, for example, hetarylalkyl) represents a radical from the group consisting of pyridyl, pyrimidyl, pyrazinyl, pyridazinyl, thiazolyl, pyrazolyl and benzothienyl.

In the definitions which form the range of preference (5) and the range of preference (6), halogen represents fluorine, chlorine, bromine and iodine, preferably in turn fluorine, chlorine and bromine, and hetaryl represents pyridyl, pyrimidinyl, thiazolyl, pyrazolyl and benzothienyl.

Halogen-substituted radicals, for example haloalkyl, are mono- or polyhalogenated, up to the maximum number of possible substituents. In the case of polyhalogenation, the halogen atoms can be identical or different. In this case, halogen represents fluorine, chlorine, bromine or iodine, especially fluorine, chlorine or bromine Saturated or unsaturated hydrocarbon radicals, such as alkyl or alkenyl, may each be straight-chain or branched if possible, including in combination with heteroatoms, as, for example, in alkoxy.

Unless stated otherwise, optionally substituted radicals may be mono- or polysubstituted, where the substituents in the case of poly substitution may be the same or different.

If T in the radical Het of the formula

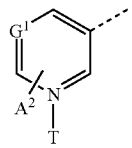

represents an electron pair, the radical is present as a pyridine derivative of the formula

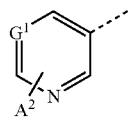

If T in the radical Het of the formula

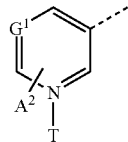

represents oxygen, the radical is present as a pyridine N-oxide derivative of the formula

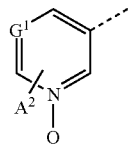

Here, the formal charges (+ at nitrogen and − at oxygen) were omitted from the illustration (however, cf. Example 24 in Table 1).

The radical definitions or elucidations given above in general terms or within areas of preference apply to the end products and correspondingly to the starting materials and intermediates. These radical definitions can be combined with one another as desired, i.e. including combinations between the respective ranges of preference.

According to the invention, preference is given to compounds of the formula (I) which contain a combination of the definitions listed above as being preferred (range of preference (1)).

According to the invention, particular preference is given to compounds of the formula (I) which contain a combination of the definitions listed above as being particularly preferred (range of preference (2)).

According to the invention, very particular preference is given to compounds of the formula (I) which contain a combination of the definitions listed above as being very particularly preferred (range of preference (3)).

According to the invention, special preference is given to compounds of the formula (I) which contain a combination of the definitions listed above as being especially preferred (range of preference (4)).

A further group of compounds of the formula (I) which are emphasized are those which form the range of preference (5).

A further group of compounds of the formula (I) which are emphasized are those which form the range of preference (6).

A further preferred embodiment of the invention relates to compounds of the formula (I) in which Het represents the radical of the formula

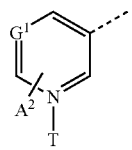

A further preferred embodiment of the invention relates to compounds of the formula (I) in which Het represents pyridin-3-yl.

A further preferred embodiment of the invention relates to compounds of the formula (I) in which Het represents 5-fluoropyridin-3-yl.

A further preferred embodiment of the invention relates to compounds of the formula (I) in which Het represents pyrimidin-5-yl.

A further preferred embodiment of the invention relates to compounds of the formula (I) in which Het represents pyridazin-4-yl.

A further preferred embodiment of the invention relates to compounds of the formula (I) in which R' represents the radical

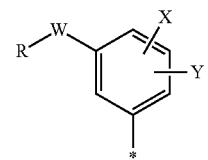

A further preferred embodiment of the invention relates to compounds of the formula (I) in which Q represents C—H.

The compounds of the formula (I) may possibly also, depending on the nature of the substituents, be in the form of stereoisomers, i.e. in the form of geometric and/or optical isomers or isomer mixtures of varying composition. This invention provides both the pure stereoisomers and any desired mixtures of these isomers, even though it is generally only compounds of the formula (I) that are discussed here.

However, preference is given in accordance with the invention to using the optically active, stereoisomeric forms of the compounds of the formula (I) and salts thereof.

The invention therefore relates both to the pure enantiomers and diastereomers and to mixtures thereof for controlling animal pests, including arthropods and particularly insects.

It has additionally been found that the novel compounds of the formula (I) can be prepared by the processes described below.

The compounds of the formula (I) can be prepared, for example, by process A in two steps, as shown in the scheme below. The aminothiazoles of the formula (III) required for this purpose can be prepared, for example, by process B from the heteroarylthioamides.

The compounds of the formula (II) also form part of the subject-matter of the invention and can be prepared as described in the processes below.

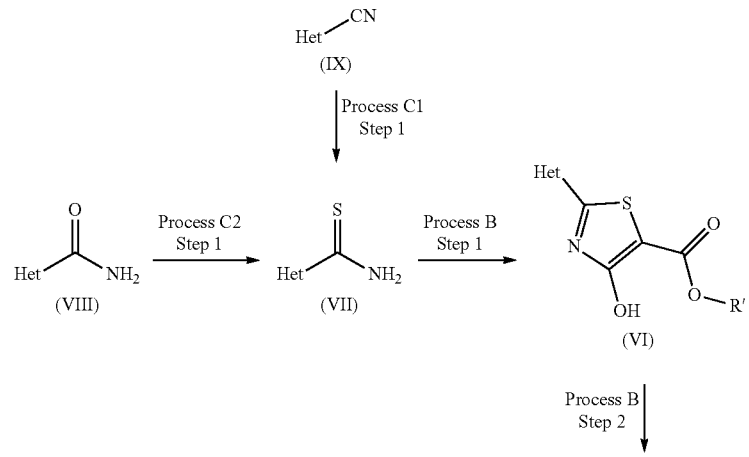

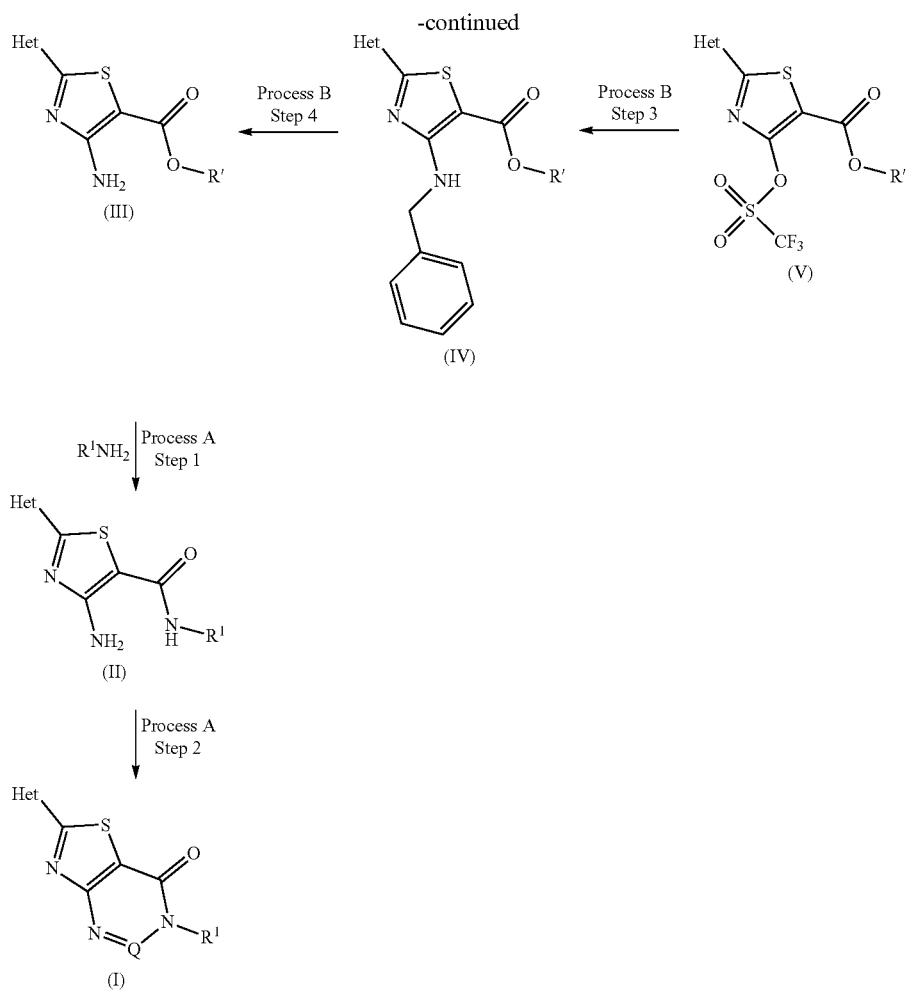

where Het, Q and $R^1$ have the meanings given above and $R^1$ represents hydrogen or alkyl (in particular methyl and ethyl).

Process A

The compounds of the formula (I) can be synthesized in two steps using methods known from the literature.

In the first synthesis step, compounds of the formula (III) can be converted by various methods into carboxamides of the formula (II). When R'=alkyl, this conversion can take place without activation (cf. B. M. Trost and I. Fleming in Comprehensive Organic Synthesis, Ed. Pergamon, 1991, Vol. 6). As an alternative, the literature discloses activation methods by formation of an aluminium amide (see T. Ooi and K. Marouka in Science of Synthesis, Ed. Georg Thieme, 2003, Vol. 7, 225-246). These aluminium amides can be prepared, for example from the amines or salts thereof by reaction with trimethylaluminium or their air-stable adduct with 1,4-diazobicyclo[2.2.3]octane (DABCO) (cf. S. Woodward in Tet. Lett. 2006, 47, 5767-5769).

As an alternative, the aminothiazoles of the formula (III) where R'=alkyl can be converted in two stages to the amides of the formulae (II): first hydrolysis to give the carboxylates, for example by reaction with an inorganic base (preferably sodium hydroxide and potassium hydroxide solutions), optionally with an inert organic solvent, optionally it is possible by acidification with a diluted acid (for example aqueous hydrochloric acid) to prepare and isolate the carboxylic acids of the formula (III) where R'=hydrogen; subsequent amidation reaction with the desired amines leads to the compounds of the formula (II). A number of reaction conditions have been described for the amidation step, for example G. Benz in Comprehensive Organic Synthesis, $1^{st}$ Ed., Pergamon Press, Oxford, 1991, Vol. 6, pp. 381-417; P. D. Bailey et al. in Comprehensive Organic Functional Group Transformation, 1st Ed., Elsevier Science Ltd., Oxford, 1995, Vol. 5, pp. 257-308 and R. C. Larock in Comprehensive Organic Transformations, 2nd Ed., Wiley-VCH, New York, Weinheim, 1999, pp. 1929-1994. Some of these reactions proceed via intermediate carbonyl chlorides, which can be used in isolated form or having been generated in situ.

The amidation reactions are optionally effected in the presence of a condensing agent, optionally in the presence of an acid acceptor and optionally in the presence of a solvent.

Useful condensing agents are all the condensing agents typically usable for such amidation reactions. Examples include acid halide formers such as phosgene, phosphorus trichloride, oxalyl chloride or thionyl chloride; carbodiimides such as N,N'-dicyclohexylcarbodiimide (DCC) and 1-(3-dimethylaminopropyl)-3-ethylcarbodiimide (EDCI), or other customary condensing agents such as phosphorus pentoxide, polyphosphoric acid, N,N'-carbonyldiimidazole, 2-chloropyridine 1-methiodide (Mukaiyama's reagent), 2-ethoxy-N-ethoxycarbonyl-1,2-dihydroquinoline (EEDQ), triphenylphosphine/carbon tetrachloride, bromotripyrrolidinophosphonium hexafluorophosphate (BROP), O-(1H-benzotriazol-1-yloxy)tris(dimethylamino)phosphonium hexafluorophosphate (BOP), N,N,N',N'-bis(tetramethylene)chlorouronium tetrafluoroborate, O-(1H-benzotriazol-1-yl)-N,N,N',N'-tetramethyluronium hexafluorophosphate (HBTU), O-(1H-benzotriazol-1-yl)-N, N,N',N'-bis(tetramethylene)uronium hexafluorophosphate, O-(1H-benzotriazol-1-yl)-N,N,N',N'-tetramethyluronium tetrafluoroborate (TBTU), O-(1H-benzotriazol-1-yl)-N,N,N',N'-bis(tetramethylene)uronium tetrafluoroborate, O-(7-azabenzotriazol-1-yl)-N,N,N',N'-tetramethyluronium hexafluorophosphate (HATU), 1-hydroxybenzotriazole (HOBt) and 4-(4,6-dimethoxy-1,3,5-triazin-2-yl)-4-methylmorpholinium salt (DMT.MM), usually available as the chloride. These reagents can be used separately or, if appropriate, in combination.

Useful acid acceptors are all customary inorganic or organic bases, for example triethylamine, diisopropylethylamine, N-methylmorpholine or N,N-dimethylaminopyridine. Process A according to the invention is optionally carried out in the presence of a suitable reaction auxiliary, for example N,N-dimethylformamide or N,N-dimethylaminopyridine. Useful solvents or diluents include all inert organic solvents, for example aliphatic or aromatic hydrocarbons (such as petroleum ether, toluene), halogenated hydrocarbons (such as chlorotoluene, dichloromethane, chloroform, 1,2-dichloroethane), ethers (such as diethyl ether, dioxane, tetrahydrofuran, 1,2-dimethoxyethane), esters (such as ethyl or methyl acetate), nitrohydrocarbons (such as nitromethane, nitroethane, nitrobenzene), nitriles (such as acetonitrile, benzonitrile), amides (such as N,N-dimethylformamide, N,N-dimethylacetamide, N-methylformanilide, N-methylpyrrolidone, hexamethylphosphortriamide), and also dimethyl sulphoxide or water or mixtures of the solvents mentioned.

It is also possible to use mixed anhydrides for the preparation of compounds of the formula (III) (cf. J. Am. Chem. Soc. 1967, 5012). In this process, it is possible to use various chloroformic esters, for example isobutyl chloroformate and isopropyl chloroformate. It is likewise possible to use diethylacetyl chloride, trimethylacetyl chloride and the like for this purpose.

In a second synthesis step, the carboxamides of the formula (II) can be cyclized to the compounds of the formula (I).

In the case that Q=C—$R^3$ in which $R^3$ is H or alkyl, the cyclization of carboxamides of the formula (II) can be performed with an orthoester, such as triethyl orthoformate or triethyl orthoacetate, optionally in the presence of a solvent or diluent (for example in the presence of alcohols such as ethanol, but also in the presence of N,N-dimethylformamide or N,N-dimethylacetamide), optionally in the presence of an organic acid (for example para-toluenesulphonic acid or acetic acid) or inorganic acid (for example hydrochloric acid or sulphuric acid) in catalytic or stoichiometric amounts or in excess. The acids mentioned can also be used in place of the solvent or diluent. In the case that $R^3$=H there are examples of such reactions with triethyl orthoformate in Archiv der Pharmazie 2000, 333(8), 261-266 (for the preparation of quinazolinones), J. Het. Chem. 1990, 27(7), 1953-1956 (idem.), WO2010/54398 (for the preparation of pyrazinopyrimidinones). In the case that $R^3$=methyl, see, for example, WO2010/100189 (for preparation of quinazolinones).

In the case that Q=C—$R^3$, in which $R^3$ represents alkyl or haloalkyl, the thiazolopyrimidinones of the formula (I) can also be prepared by reaction of the carboxamides of the formula (II) with appropriate carbonyl halides or carboxylic anhydrides by methods known from the literature, such as described, for example, in WO2009/143049 in the case that $R^3$=methyl and in WO 2008/039489 in the case that $R^3$=trifluoromethyl.

In the case that Q+N, the thiazolopyrimidinones of the formula (I) can be prepared by azodiazotization of the carboxamides of the formula (II) according to methods known from the literature. For example, compounds of the formula (II) are treated at 0 to 5° C. with a nitrite source, such as sodium nitrite or isobutyl nitrite, typically in water, alcohol or a polar inert solvent, and in the presence of an organic or inorganic acid. Examples of reaction conditions can be found in WO 2004/242572 or in J. Amer. Chem. Soc. Perkin Trans. 1, 1980, 633-638).

The compounds of the formula (II)/(III) are novel and also form part of the subject matter of the invention.

General Processes for the Oxidation of Thioethers to Sulphoxides and Sulphones

Compounds of the formula (I) in which W represents SO (sulphoxides) or W represents $SO_2$ (sulphones) can be prepared by oxidation by processes known from the literature from compounds of the formula (I) in which W represents S (thioethers), for example by an oxidizing agent in a suitable solvent or diluent. Suitable oxidizing agents are, for example, diluted nitric acid, hydrogen peroxide, Oxone® and peroxycarboxylic acids, for example meta-chloroperbenzoic acid. Suitable solvents or diluents are inert organic solvents, typically acetonitrile and halogenated solvents such as dichloromethane, chloroform or dichloroethane, and water and alcohols such as methanol for the reaction with Oxone®.

It is also possible to introduce suitable anilines $R^1$—$NH_2$, halides $R^1$-hal or boronic acids $R^1$—$B(OH)_2$, in which W represents SO or $SO_2$, by process A-1 or A-2. These can be oxidized from the corresponding precursors in which W represents S by processes known from the literature, such as, for example, those described in WO 2013/092350.

A large number of different methods are suitable for generating enantiomerically enriched sulphoxides, as described by A. R. Maguire in ARKIVOC, 2011 (i), 1-110: metal-catalysed asymmetric oxidations of thioethers, for example with titanium or vanadium as the most frequently employed catalyst sources, in the form of $Ti(O^iPr_4)$ or $VO(acac)_2$, together with a chiral ligand and an oxidizing agent such as tert-butyl hydroperoxide (TBHP), 2-phenylpropan-2-yl hydroperoxide (CHP) or hydrogen peroxide; non-metal-catalysed asymmetric oxidations employing chiral oxidizing agents or chiral catalysts; electrochemical or biological asymmetric oxidations and also kinetic resolution of sulphoxides and nucleophilic shift (according to Andersen's method).

The enantiomers can also be obtained from the racemate, for example by preparative separation by means of a chiral HPLC.

The aminothiazoles of the formula (III) required in process A can be prepared, for example, by process B. In the case of not commercially available heteroarylthioamides as starting materials for process B, these can be prepared in a known manner by process C1 or C2:

Process C1

Heteroarylthioamides of the formula (VII) can be prepared in one step by methods known in principle from the corresponding commercially available heteroarylcarboxamides of the formula (VIII) and suitable sulphur donors. Thus, WO 2013/104415 by Petterson et al. describes a method for transforming carbonyl groups into thiocarbonyl groups by reacting the corresponding starting materials at a temperature between 50° C. and 100° C. with a suitable sulphur compound, for example diphosphorus pentasulphide-dipyridine complex, optionally in an inert organic solvent (e.g. acetonitrile).

Process C2

As an alternative to process B1, heteroarylthioamides of the formula (VII) can be prepared in one step by methods known in principle from the corresponding commercially available heteroarylnitriles of the formula (IX) and suitable sulphur donors. For example according to Mahammed et al. (Journal of Sulfur Chemistry, 28(3), 233-237; 2007) by reaction with thioacetic acid in the presence of calcium hydride at a temperature between 50° C. and 100° C. in a solvent-free environment. An alternative microwave-supported synthesis, for example, has also been described (Synlett, (14), 2615-2617; 2004) where the corresponding nitriles are reacted at a temperature between 50° C. and 100° C. with ammonium sulphide in an inert organic solvent (e.g. alcohols).

Process B

Examples of the conversion of thioamides into thiazole derivatives of type (VI) are described in WO 2013/092711 A1 (cf. also Bioorganic & Medicinal Chemistry Letters (2010), 20(9), 2828-2831). The thioamides (VII), which are commercially available or can be prepared according to process C1 or C2, are initially reacted in a suitable inert solvent (e.g. dioxane or toluene) under reflux temperature, optionally in the presence of a base (e.g. pyridine) with dimethyl 2-chloromalonate or dimethyl 2-bromomalonate to give the desired compound (VI).

The preparation of the compound (V) is then carried out (for example according to Bioorganic & Medicinal Chemistry Letters (2010), 20(9), 2828-2831) by reacting (VI) with trifluoromethanesulphonic anhyride in the presence of a suitable base (e.g. triethylamine, sodium carbonate, pyridine or lutidine) in an inert solvent (e.g. dichloromethane) at a temperature between −20° C. and room temperature.

It is known that compounds of type (V) can be transformed (for example according to WO 2003/101985 A1) into compounds of type (IV) by heating with benzylamines in inert solvents (e.g. dioxane) at temperatures between 50 and 100° C.

Removal of the benzylamine function for preparing the target compounds of type (III) can be carried out by methods known in principle (for example WO 2003/066629 A2) by heating in suitable acids (e.g. trifluoroacetic acid or sulphuric acid) at temperatures between 20 and 80° C. Any acid amides formed in this reaction are hydrolyzed by heating with potassium carbonate in a water/methanol mixture to afford the target compound (III).

The thiazole derivatives of the formulae (VI) to (III) prepared in this way can be separated, for example by chromatographic separation on silica gel or RP(C-18), or by trituration or recrystallization using suitable solvents.

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. The invention thus encompasses pure stereoisomers and any desired mixtures of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" in each case also always comprises the term "crop protection agent".

The compounds of the formula (I), given good plant tolerance, favourable toxicity to warm-blooded species and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are effective against normally sensitive and resistant species and against all or some stages of development. The abovementioned pests include:

pests from the phylum of the Arthropoda, especially from the class of the Arachnida, for example *Acarus* spp., for example *Acarus siro*, *Aceria kuko*, *Aceria sheldoni*, *Aculops* spp., *Aculus* spp., for example *Aculus fockeui*, *Aculus schlechtendali*, *Amblyomma* spp., *Amphitetranychus viennensis*, *Argas* spp., *Boophilus* spp., *Brevipalpus* spp., for example *Brevipalpus phoenicis*, *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., for example *Eotetranychus hicoriae*, *Epitrimerus pyri*, *Eutetranychus* spp., for example *Eutetranychus banksi*, *Eriophyes* spp., for example *Eriophyes pyri*, *Glycyphagus domesticus*, *Halotydeus destructor*, *Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis*, *Nuphersa* spp., *Oligonychus* spp., for example *Oligonychus coniferarum*, *Oligonychus ilicis*, *Oligonychus indicus*, *Oligonychus mangiferus*, *Oligonychus pratensis*, *Oligonychus punicae*, *Oligonychus yothersi*, *Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora*, *Platytetranychus multidigituli*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., for example *Tarsonemus confusus*, *Tarsonemus pallidus*, *Tetranychus* spp., for example *Tetranychus canadensis*, *Tetranychus cinnabarinus*, *Tetranychus turkestani*, *Tetranychus urticae*, *Trombicula alfreddugesi*, *Vaejovis* spp., *Vasates lycopersici*;

from the class of the Chilopoda, for example *Geophilus* spp., *Scutigera* spp.;

from the order or the class of the Collembola, for example *Onychiurus armatus*; *Sminthurus viridis*;

from the class of the Diplopoda, for example *Blaniulus guttulatus*;

from the class of the Insecta, for example from the order of the Blattodea, for example *Blatta orientalis*, *Blattella* asahinai, Blattella germanica, Leucophaea maderae, Panchlora spp., Parcoblatta spp., Periplaneta spp., for example Periplaneta americana, Periplaneta australasiae, Supella longipalpa;

from the order of the Coleoptera, for example *Acalymma vittatum, Acanthoscelides obtectus, Adoretus* spp., *Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides*;

from the order of the Diptera, for example, *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* spp., for example *Pegomya betae, Pegomya hyoscyami, Pegomya rubivora, Phlebotomus* spp., *Phorbia* spp., *Phormia* spp., *Piophila casei, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex*;

from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp.,

*Dialeurodes citri, Diaphorina citri, Diaspis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni* (=*Parthenolecanium corni*), *Lepidosaphes* spp., for example *Lepidosaphes ulmi, Lipaphis erysimi, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Nephotettix* spp., for example *Nephotettix cincticeps, Nephotettix nigropictus, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Monalonion atratum, Nezara* spp., for example *Nezara viridula, Oebalus* spp., *Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Diprion* spp., for example *Diprion similis, Hoplocampa* spp., for example *Hoplocampa cookei, Hoplocampa testudinea, Lasius* spp., *Linepithema humile, Monomorium pharaonis, Sirex* spp., *Solenopsis invicta, Tapinoma* spp., *Urocerus* spp., *Vespa* spp., for example *Vespa crabro, Xeris* spp.;

from the order of the Isopoda, for example *Armadillidium vulgare, Oniscus asellus, Porcellio scaber*;

from the order of the Isoptera, for example *Coptotermes* spp., for example *Coptotermes formosanus, Cornitermes cumulans, Cryptotermes* spp., *Incisitermes* spp., *Microtermes obesi, Odontotermes* spp., *Reticulitermes* spp., for example *Reticulitermes flavipes, Reticulitermes hesperus*;

from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Etiella* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Laphygma* spp., *Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., for example *Ostrinia nubilalis, Oulema melanopus, Oulema oryzae, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plu-* tella xylostella (=Plutella maculipennis), Prays spp., Prodenia spp., Protoparce spp., Pseudaletia spp., for example Pseudaletia unipuncta, Pseudoplusia includens, Pyrausta nubilalis, Rachiplusia nu, Schoenobius spp., for example Schoenobius bipunctifer, Scirpophaga spp., for example Scirpophaga innotata, Scotia segetum, Sesamia spp., for example Sesamia inferens, Sparganothis spp., Spodoptera spp., for example Spodoptera eradiana, Spodoptera exigua, Spodoptera frugiperda, Spodoptera praefica, Stathmopoda spp., Stomopteryx subsecivella, Synanthedon spp., Tecia solanivora, Thermesia gemmatalis, Tinea cloacella, Tinea pellionella, Tineola bisselliella, Tortrix spp., Trichophaga tapetzella, Trichoplusia spp., for example Trichoplusia ni, Tryporyza incertulas, Tuta absoluta, Virachola spp.;

from the order of the Orthoptera or Saltatoria, for example Acheta domesticus, Dichroplus spp., Gryllotalpa spp., for example Gryllotalpa gryllotalpa, Hieroglyphus spp., Locusta spp., for example Locusta migratoria, Melanoplus spp., for example Melanoplus devastator, Paratlanticus ussuriensis, Schistocerca gregaria;

from the order of the Phthiraptera, for example Damalinia spp., Haematopinus spp., Linognathus spp., Pediculus spp., Phylloxera vastatrix, Phthirus pubis, Trichodectes spp.;

from the order of the Psocoptera, for example Lepinotus spp., Liposcelis spp.;

from the order of the Siphonaptera, for example Ceratophyllus spp., Ctenocephalides spp., for example Ctenocephalides canis, Ctenocephalides felis, Pulex irritans, Tunga penetrans, Xenopsylla cheopis;

from the order of the Thysanoptera, for example Anaphothrips obscurus, Baliothrips biformis, Drepanothrips reuteri, Enneothrips flavens, Frankliniella spp., for example Frankliniella fusca, Frankliniella occidentalis, Frankliniella schultzei, Frankliniella tritici, Frankliniella vaccinii, Frankliniella williamsi, Heliothrips spp., Hercinothrips femoralis, Rhipiphorothrips cruentatus, Scirtothrips spp., Taeniothrips cardamomi, Thrips spp., for example Thrips palmi, Thrips tabaci;

from the order of the Zygentoma (=Thysanura), for example Ctenolepisma spp., Lepisma saccharina, Lepismodes inquilinus, Thermobia domestica;

from the class of the Symphyla, for example Scutigerella spp., for example Scutigerella immaculata;

pests from the phylum of the Mollusca, in particular from the class of the Bivalvia, for example Dreissena spp.;

and also from the class of the Gastropoda, for example Anion spp., for example Anion ater rufus, Biomphalaria spp., Bulinus spp., Deroceras spp., for example Deroceras laeve, Galba spp., Lymnaea spp., Oncomelania spp., Pomacea spp., Succinea spp.;

animal and human parasites from the phyla of the Platyhelminthes and Nematoda, for example Aelurostrongylus spp., Amidostomum spp., Ancylostoma spp., Angiostrongylus spp., Anisakis spp., Anoplocephala spp., Ascaris spp., Ascaridia spp., Baylisascaris spp., Brugia spp., Bunostomum spp., Capillaria spp., Chabertia spp., Clonorchis spp., Cooperia spp., Crenosoma spp., Cyathostoma spp., Dicrocoelium spp., Dictyocaulus spp., Diphyllobothrium spp., Dipylidium spp., Dirofilaria spp., Dracunculus spp., Echinococcus spp., Echinostoma spp., Enterobius spp., Eucoleus spp., Fasciola spp., Fascioloides spp., Fasciolopsis spp., Filaroides spp., Gongylonema spp., Gyrodactylus spp., Habronema spp., Haemonchus spp., Heligmosomoides spp., Heterakis spp., Hymenolepis spp., Hyostrongylus spp., Litomosoides spp., Loa spp., Metastrongylus spp., Metorchis spp., Mesocestoides spp., Moniezia spp., Muellerius spp., Necator spp., Nematodirus spp., Nippostrongylus spp., Oesophagostomum spp., Ollulanus spp., Onchocerca spp., Opisthorchis spp., Oslerus spp., Ostertagia spp., Oxyuris spp., Paracapillaria spp., Parafilaria spp., Paragonimus spp., Paramphistomum spp., Paranoplocephala spp., Parascaris spp., Passalurus spp., Protostrongylus spp., Schistosoma spp., Setaria spp., Spirocerca spp., Stephanofilaria spp., Stephanurus spp., Strongyloides spp., Strongylus spp., Syngamus spp., Taenia spp., Teladorsagia spp., Thelazia spp., Toxascaris spp., Toxocara spp., Trichinella spp., Trichobilharzia spp., Trichostrongylus spp., Trichuris spp., Uncinaria spp., Wuchereria spp.;

plant pests from the phylum of the Nematoda, i.e. phytoparasitic nematodes, especially Aglenchus spp., for example Aglenchus agricola, Anguina spp., for example Anguina tritici, Aphelenchoides spp., for example Aphelenchoides arachidis, Aphelenchoides fragariae, Belonolaimus spp., for example Belonolaimus gracilis, Belonolaimus longicaudatus, Belonolaimus nortoni, Bursaphelenchus spp., for example Bursaphelenchus cocophilus, Bursaphelenchus eremus, Bursaphelenchus xylophilus, Cacopaurus spp., for example Cacopaurus pestis, Criconemella spp., for example Criconemella curvata, Criconemella onoensis, Criconemella ornata, Criconemella rusium, Criconemella xenoplax (=Mesocriconema xenoplax), Criconemoides spp., for example Criconemoides ferniae, Criconemoides onoense, Criconemoides ornatum, Ditylenchus spp., for example Ditylenchus dipsaci, Dolichodorus spp., Globodera spp., for example Globodera pallida, Globodera rostochiensis, Helicotylenchus spp., for example Helicotylenchus dihystera, Hemicriconemoides spp., Hemicycliophora spp., Heterodera spp., for example Heterodera avenae, Heterodera glycines, Heterodera schachtii, Hoplolaimus spp., Longidorus spp., for example Longidorus africanus, Meloidogyne spp., for example Meloidogyne chitwoodi, Meloidogyne fallax, Meloidogyne hapla, Meloidogyne incognita, Meloinema spp., Nacobbus spp., Neotylenchus spp., Paraphelenchus spp., Paratrichodorus spp., for example Paratrichodorus minor, Pratylenchus spp., for example Pratylenchus penetrans, Pseudohalenchus spp., Psilenchus spp., Punctodera spp., Quinisulcius spp., Radopholus spp., for example Radopholus citrophilus, Radopholus similis, Rotylenchulus spp., Rotylenchus spp., Scutellonema spp., Subanguina spp., Trichodorus spp., for example Trichodorus obtusus, Trichodorus primitivus, Tylenchorhynchus spp., for example Tylenchorhynchus annulatus, Tylenchulus spp., for example Tylenchulus semipenetrans, Xiphinema spp., for example Xiphinema index.

In addition, it is possible to control, from the sub-kingdom of the Protozoa, the order of the Coccidia, for example Eimeria spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (mycoplasma-like organisms) and RLO (rickettsia-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve the action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers 173, prepared by the FAO/WHO Joint Meeting on Pesticide Specifications, 2004, ISBN: 9251048576. The formulations, in addition to one or more compounds of the formula (I), optionally comprise further agrochemical active ingredients.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic minerals such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Especially suitable are those extenders or carriers which are gaseous at standard temperature and under standard pressure, for example aerosol propellants such as halogenated hydrocarbons, and also butane, propane, nitrogen and carbon dioxide.

Examples of emulsifiers and/or foam formers, dispersants or wetting agents with ionic or nonionic properties, or mixtures of these surfactants, include salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve the chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and hence increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I) or, with particular preference, between 0.01% and 95% by weight of the compound of the formula (I), more preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. The application is accomplished in a customary manner appropriate for the use forms.

Mixtures

The compounds of the formula (I) may also be employed as a mixture with one or more suitable fungicides, bactericides, acaricides, molluscicides, nematicides, insecticides, microbiologicals, beneficial species, herbicides, fertilizers, bird repellents, phytotonics, sterilants, safeners, semiochemicals and/or plant growth regulators, in order thus, for example, to broaden the spectrum of action, to prolong the duration of action, to increase the rate of action, to prevent repulsion or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

Furthermore, the compounds of the formula (I) can be present in a mixture with other active compounds or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment of the invention, the compounds of the formula (I) are in the form of formulations or the use forms prepared from these formulations in a mixture with further compounds, preferably those as described below.

If one of the compounds mentioned below can occur in various tautomeric forms, these forms are also included even if not explicitly mentioned in each case.

Insecticides/Acaricides/Nematicides

The active compounds identified here by their common names are known and are described, for example, in the pesticide handbook ("The Pesticide Manual" 16th Ed., British Crop Protection Council 2012) or can be found on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxy fos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrins (pyrethrum), resmethrin, silafluofen, tefluthrin, tetramethrin, tetramethrin [(1R) isomers], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor.

(5) Allosteric activators of the nicotinergic acetylcholine receptor (nAChR), for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone imitators, for example, juvenile hormone analogues, e.g. hydroprene, kinoprene and methoprene or fenoxycarb or pyriproxyfen.

(8) Active compounds with unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab 1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (in particular for Diptera, i.e. dipterans) such as, for example, cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon or acequinocyl or fluacrypyrim.

(21) Complex-I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide, further active compounds, for example afidopyropen, azadirachtin, benclothiaz, benzoximate, bifenazate, bromopropylate, chinomethionat, cryolite, dicofol, diflovidazin, fluensulfone, flometoquin, flufenerim, flufenoxystrobin, flufiprole, fluopyram, flupyradifurone, fufenozide, heptafluthrin, imidaclothiz, iprodione, meperfluthrin, paichongding, pyflubumide, pyrifluquinazon, pyriminostrobin, tetramethylfluthrin and iodomethane; and also preparations based on *Bacillus firmus* (I-1582, BioNeem, Votivo), and also the following compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) and 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro-5-methoxyphenyl)sulphonyl]-6-(trifluoromethyl)imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl)methyl]-9-nitro-2,3,5,6,7,8-hexahydro-1H-5,8-epoxyimidazo[1,2-a]azepine (known from WO2010/069266), (2E)-1-[(6-chloropyridin-3-yl)methyl]-N'-nitro-2-pentylidenehydrazinecarboximidamide (known from WO2010/060231), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Fungicides

The active compounds specified herein by their common name are known and described, for example, in "Pesticide Manual" or on the Internet (for example: http://www.alanwood.net/pesticides).

(1) Ergosterol biosynthesis inhibitors, for example (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole-1-carbothioate, (1.65) pyrisoxazole.

(2) Respiration inhibitors (respiratory chain inhibitors), for example (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam mixture of the syn-epimeric racemate 1RS,4SR,9RS and the anti-empimeric racemate 1RS,4SR,9SR, (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid.

(3) Respiration inhibitors (respiratory chain inhibitors) that act on complex III of the respiratory chain, for example (3.1) ametoctradin, (3.2) amisulbrom, (3.3) azoxystrobin, (3.4) cyazofamid, (3.5) coumethoxystrobin, (3.6) coumoxystrobin, (3.7) dimoxystrobin, (3.8) enestroburin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylethanamide, (3.24) (2E)-2-(methoxyimino)-N-methyl-2-(2-{[({(1E)-1-[3-(trifluoromethyl)phenyl]ethylidene}amino)oxy]methyl}phenyl)ethanamide, (3.25) (2E)-2-(methoxyimino)-N-methyl-2-{2-[(E)-({1-[3-(trifluoromethyl)phenyl]ethoxy}imino)methyl]phenyl}ethanamide, (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide, (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulphanyl)methyl]phenyl}-3-methoxyprop-2-enoate, (3.31) N-(3-ethyl-3,5,5-trimethylcyclohexyl)-3-(formylamino)-2-hydroxybenzamide, (3.32) 2-{2-[(2,5-dimethylphenoxy)methyl]phenyl}-2-methoxy-N-methylacetamide (4) inhibitors of mitosis and cell division, for example (4.1) benomyl, (4.2) carbendazim, (4.3) chlorfenazole, (4.4) diethofencarb, (4.5) ethaboxam, (4.6) fluopicolid, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine and (4.14) 3-chloro-5-(6-chloropyridin-3-yl)-6-methyl-4-(2,4,6-trifluorophenyppyridazine.

(5) Compounds having multisite activity such as, for example, (5.1) Bordeaux mixture, (5.2) captafol, (5.3) captan, (5.4) chlorothalonil, (5.5) copper preparations such as copper hydroxide, (5.6) copper naphthenate, (5.7) copper oxide, (5.8) copper oxychloride, (5.9) copper sulphate, (5.10) dichlofluanid, (5.11) dithianon, (5.12) dodine, (5.13) dodine free base, (5.14) ferbam, (5.15) fluorfolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) zinc metiram, (5.27) copperoxine, (5.28) propamidine, (5.29) propineb, (5.30) sulphur and sulphur preparations such as, for example, calcium polysulphide, (5.31) thiram, (5.32) tolylfluanid, (5.33) zineb, (5.34) ziram and (5.35) anilazine.

(6) Resistance inducers, for example (6.1) acibenzolar-S-methyl, (6.2) isotianil, (6.3) probenazole, (6.4) tiadinil and (6.5) laminarin (7) Amino acid and protein biosynthesis inhibitors, for example (7.1), (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline and (7.9) oxytetracycline and (7.10) streptomycin.

(8) ATP production inhibitors such as, for example, (8.1) fentin acetate, (8.2) fentin chloride, (8.3) fentin hydroxide and (8.4) silthiofam.

(9) Cell wall synthesis inhibitors, for example (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate and (9.10) polyoxin B.

(10) Lipid and membrane synthesis inhibitors, for example (10.1) biphenyl, (10.2) chlorneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene and (10.15) tolclofos-methyl.

(11) Melanin biosynthesis inhibitors, for example (11.1) carpropamid, (11.2) diclocymet, (11.3) fenoxanil, (11.4) fthalide, (11.5) pyroquilon, (11.6) tricyclazole and (11.7) 2,2,2-trifluoroethyl {3-methyl-1-[(4-methylbenzoyl)amino]butan-2-yl}carbamate.

(12) Nucleic acid synthesis inhibitors, for example (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazole, (12.9) metalaxyl, (12.10) metalaxyl-M (mefenoxam), (12.11) ofurace, (12.12) oxadixyl, (12.13) oxolinic acid and (12.14) octhilinone.

(13) Signal transduction inhibitors, for example (13.1) chlozolinate, (13.2) fenpiclonil, (13.3) fludioxonil, (13.4) iprodione, (13.5) procymidone, (13.6) quinoxyfen, (13.7) vinclozolin and (13.8) proquinazid.

(14) Decouplers, for example (14.1) binapacryl, (14.2) dinocap, (14.3) ferimzone, (14.4) fluazinam and (14.5) meptyldinocap.

(15) Further compounds, for example (15.1) benthiazole, (15.2) bethoxazine, (15.3) capsimycin, (15.4) carvone, (15.5) quinomethionate, (15.6) pyriofenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat methylsulphate, (15.17) diphenylamine, (15.18) EcoMate, (15.19) fenpyrazamine, (15.20) flumetover, (15.21) fluorimid, (15.22) flusulfamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.36) octhilinone, (15.37) oxamocarb, (15.38) oxyfenthiin, (15.39) pentachlorophenol and its salts, (15.40) phenothrin, (15.41) phosphoric acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrin, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulphonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulphonohydrazide, (15.74) 5-fluoro-2-[(4-fluorobenzyl)oxy]pyrimidine-4-amine, (15.75) 5-fluoro-2-[(4-methylbenzyl)oxy]pyrimidine-4-amine, (15.76) 5-methyl-6-octyl[1,2,4]triazolo[1,5-a]pyrimidine-7-amine, (15.77) ethyl (2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N-{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene]amino}oxy)methyl]pyridin-2-yl}carbamate, (15.91) phenazine-1-carboxylic acid, (15.92) quinolin-8-ol, (15.93) quinolin-8-ol sulphate (2:1), (15.94) tert-butyl {6-[({[(1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl]nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulphonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenypmethylene]amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenypoxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulphanyl)-1-{[3-(2-chlorophenyl)-2-(2,4-difluorophenypoxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulphanyl)-1-{[rel(2R,3S)-3-(2-chlorophenyl)-2-(2,4-difluorophenypoxiran-2-yl]methyl}-1H-1,2,4-triazole, (15.136) 5-(allylsulphanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4- isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazol-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazole-5-amine. All the mixing components mentioned in classes (1) to (15), as the case may be, may form salts with suitable bases or acids if they are capable of doing so on the basis of their functional groups.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, in particular *B. cereus* strain CNCM 1-1562 or *Bacillus firmus*, strain 1-1582 (Accession number CNCM 1-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421), or *Bacillus thuringiensis*, in particular *B. thuringiensis* subspecies israelensis (serotype H-14), strain AM65-52 (Accession No. ATCC 1276), or *B. thuringiensis* subsp. aizawai, in particular strain ABTS-1857 (SD-1372), or *B. thuringiensis* subsp. kurstaki strain HD-1, or *B. thuringiensis* subsp. tenebrionis strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (now: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (Accession Number CNCM 1-952).

Examples of viruses which are used or can be used as biological pesticides are:

*Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*,

*Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), pyrethrum/pyrethrins, *Quassia amara, Quercus, Quillaja*, Regalia, "Requiem™ Insecticide", rotenone, ryania/ryanodine, *Symphytum officinale, Tanacetum vulgare*, thymol, Triact 70, TriCon, *Tropaeulum majus, Urtica dioica, Veratrin, Viscum album, Brassicaceae* extract, especially oilseed rape powder or mustard powder.

Safeners as Mixing Components

The compounds of the formula (I) can be combined with safeners, for example benoxacor, cloquintocet(-mexyl), cyometrinil, cyprosulfamide, dichlormid, fenchlorazole(-ethyl), fenclorim, flurazole, fluxofenim, furilazole, isoxadifen(-ethyl), mefenpyr(-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material and vegetative and generative propagation material, for example cuttings, tubers, rhizomes, slips and seeds.

The inventive treatment of the plants and parts of plants with the compounds of the formula (I) is effected directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been grown by conventional breeding, by mutagenesis or by recombinant DNA techniques. They may be cultivars, varieties, biotypes or genotypes.

Transgenic plants, seed treatment and integration events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better storage life and/or processability of the harvested products. Further and particularly emphasized examples of such properties are increased resistance of the plants against animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain active herbicidal ingredients, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The treatment of the plants and plant parts with the compounds of the formula (I) is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for liquid seed treatment, a water-soluble powder for slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. the compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvement. However, the treatment of seed entails a series of problems which cannot always be solved in a satisfactory manner Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure of pesticides.

The present invention therefore in particular also relates to a method for the protection of seed and germinating plants, from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It also further comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and mixing components may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, rhizobia, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya bean, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been imbibed in water up to a certain stage (pigeon breast stage) for example, which leads to improved germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations. These formulations are prepared in a known manner, by mixing the compounds of the formula (I) with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations usable in accordance with the invention are all colorants which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical compounds. Preference is given to using alkyl naphthalenesulphonates, such as diisopropyl or diisobutyl naphthalenesulphonates.

Suitable dispersants and/or emulsifiers which may be present in the seed-dressing formulations usable in accordance with the invention are all nonionic, anionic and cationic dispersants customary for the formulation of active agrochemical compounds. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed-dressing formulations usable in accordance with the invention are all foam-inhibiting substances customary for formulation of active agrochemical compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutzund Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For treatment of seed with the seed-dressing formulations usable in accordance with the invention, or the use forms prepared therefrom, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the field of animal health, i.e. in the field of veterinary medicine, the compounds of the formula (I) are active against animal parasites, in particular ectoparasites or endoparasites. The term "endoparasites" includes especially helminths and protozoans, such as coccidia. Ectoparasites are typically and preferably arthropods, especially insects and acarids.

In the field of veterinary medicine, the compounds of the formula (I) having favourable toxicity to warm-blooded species are suitable for controlling parasites which occur in animal breeding and animal husbandry in livestock, breeding animals, zoo animals, laboratory animals, experimental animals and domestic animals They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal keeping is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods Include:

from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Aty lotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.;

from the order of the Heteropterida, for example *Cimex* spp., *Triatoma* spp., *Rhodnius* spp., *Panstrongylus* spp.; and also nuisance and hygiene pests from the order of the Blattarida.

Arthropods further include:

from the subclass of the Acari (Acarina) and the order of the Metastigmata, for example from the family of Argasidae like *Argas* spp., *Ornithodorus* spp., *Otobius* spp., from the family of Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order of Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic Protozoa Include:

Mastigophora (Flagellata), for example Trypanosomatidae, for example, *Trypanosoma b. brucei*, *T.b. gambiense*, *T.b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, for example Trichomonadidae, for example, *Giardia lamblia*, *G. canis;*

Sarcomastigophora (Rhizopoda) such as Entamoebidae, for example, *Entamoeba histolytica*, Hartmanellidae, for example, *Acanthamoeba* sp., *Harmanella* sp.;

Apicomplexa (Sporozoa) such as Eimeridae, for example, *Eimeria acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidales*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E ninakohlyakimovae*, *E. ovis*, *E. parva*, *E. pavonis*, *E. perforans*, *E. phasani*, *E. piriformis*, *E. praecox*, *E. residua*, *E. scabra*, *E. spec.*, *E. stiedai*, *E. suis*, *E. tenella*, *E. truncata*, *E. truttae*, *E. zuernii*, *Globidium* spec., *Isospora belli*, *I. canis*, *I. felis*, *I. ohioensis*, *I. rivolta*, *I.* spec., *I. suis*, *Cystisospora* spec., *Cryptosporidium* spec., in particular *C. parvum*; such as Toxoplasmadidae, for example *Toxoplasma gondii*, *Hammondia heydornii*, *Neospora caninum*, *Besnoitia besnoitii*; such as Sarcocystidae, for example *Sarcocystis bovicanis*, *S. bovihominis*, *S. ovicanis*, *S. ovifelis*, *S. neurona*, *S. spec.*, *S. suihominis*, such as Leucozoidae, for example *Leucozytozoon simondi*, such as Plasmodiidae, for example *Plasmodium berghei*, *P. falciparum*, *P. malariae*, *P. ovale*, *P. vivax*, *P.* spec., such as Piroplasmea, for example *Babesia argentina*, *B. bovis*, *B. canis*, *B.* spec., *Theileria parva*, *Theileria* spec., such as Adeleina, for example *Hepatozoon canis*, *H.* spec.

Pathogenic endoparasites which are helminths include Platyhelmintha (e.g. Monogenea, cestodes and trematodes), nematodes, Acanthocephala, and Pentastoma. These include:

Monogenea: for example: *Gyrodactylus* spp., *Dactylogyrus* spp., *Polystoma* spp.;

Cestodes: from the order of the Pseudophyllidea for example: *Diphyllobothrium* spp., *Spirometra* spp., *Schistocephalus* spp., *Ligula* spp., *Bothridium* spp., *Diplogonoporus* spp.;

from the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hyporaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp.,

*Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

Nematodes: Trichinellida, for example *Trichuris* spp., *Capillaria* spp., *Paracapillaria* spp., *Eucoleus* spp., *Trichomosoides* spp., *Trichinella* spp.; p From the order of the Tylenchida, for example: *Micronema* spp., *Strongyloides* spp.;

from the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

From the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of the Oligacanthorhynchida, for example: *Macracanthorhynchus* spp., *Prosthenorchis* spp.; from the order of the Polymorphida, for example *Filicollis* spp.; from the order of the Moniliformida, for example *Moniliformis* spp.;

From the order of the Echinorhynchida, for example, *Acanthocephalus* spp., *Echinorhynchus* spp., *Leptorhynchoides* spp.;

Pentastoma: from the order of the Porocephalida, for example, *Linguatula* spp.

In the veterinary field and in animal keeping, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic, in particular an arthropodicide such as an insecticide or an acaricide. A further aspect relates to the use of a compound of the formula (I) as an antiectoparasitic, in particular an arthropodicide such as an insecticide or an acaricide, for example in animal husbandry, in animal breeding, in animal houses or in the hygiene sector.

Vector Control

The compounds of the formula (I) can also be used in vector control. In the context of the present invention, a vector is an arthropod, especially an insect or arachnid, capable of transmitting pathogens, for example, viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) Mosquitoes

*Anopheles*: malaria, filariasis;

*Culex*: Japanese encephalitis, filariasis, other viral diseases, transmission of worms;

*Aedes*: yellow fever, dengue fever, filariasis, other viral diseases;

Simulidae: transmission of worms, in particular *Onchocerca volvulus*;

2) Lice: skin infections, epidemic typhus;

3) Fleas: plague, endemic typhus;

4) Flies: sleeping sickness (trypanosomiasis); cholera, other bacterial diseases;

5) Mites: acariosis, epidemic typhus, rickettsialpox, tularaemia, Saint Louis encephalitis, tick-borne encephalitis (TBE), Crimean-Congo haemorrhagic fever, borreliosis;

6) Ticks: borrelioses such as *Borrelia duttoni*, tick-borne encephalitis, Q fever (*Coxiella burnetii*), babesioses (*Babesia canis canis*).

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dims* (malaria) and *Culex*, lice, fleas, flies, mites and ticks, which can transmit pathogens to animals and/or humans Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forestry, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic sector, in the hygiene sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpresurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Elucidation of the Processes and Intermediates

The preparation and use examples which follow illustrate the invention without limiting it. The products were characterized by 1H NMR spectroscopy and/or LC/MS (liquid chromatography mass spectrometry).

The log P values were determined in accordance with OECD Guideline 117 (EC Directive 92/69/EEC) by HPLC (high-performance liquid chromatography) using reversed-phase (RP) columns (C18), by the following methods:

[a] The LC-MS determination in the acidic range was effected at pH 2.7 with 0.1% aqueous formic acid and acetonitrile (contains 0.1% formic acid) as eluents; linear gradient from 10% acetonitrile to 95% acetonitrile.

[b] LC-MS determination in the neutral range was effected at pH 7.8 with 0.001 molar aqueous ammonium hydrogencarbonate solution and acetonitrile as eluents; linear gradient from 10% acetonitrile to 95% acetonitrile.

Calibration was effected with unbranched alkan-2-ones (having 3 to 16 carbon atoms) with known log P values (log P values determined on the basis of the retention times by linear interpolation between two successive alkanones).

The NMR spectra were determined with a Bruker Avance 400 fitted with a flow probe head (volume 60 µl). In individual cases, the NMR spectra were measured with a Bruker Avance II 600.

The 1H NMR data of selected examples are stated in the form of 1H NMR peak lists. For each signal peak, first the δ value in ppm and then the signal intensity in round brackets are listed. The δ value signal intensity—number pairs for different signal peaks are listed with separation from one another by semicolons.

The peak list for one example therefore takes the form of: $\delta_1$ (intensity 1); $\delta_2$ (intensity 2); . . . ; $\delta_i$ (intensity i); . . . ; $\delta_n$ (intensity n)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of the 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject matter of the invention, and/or peaks of impurities.

In the reporting of compound signals in the delta range of solvents and/or water, our lists of 1H NMR peaks show the usual solvent peaks, for example peaks of DMSO in DMSO-D6 and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in Research Disclosure Database Number 564025.

Synthesis of Compounds of the Formula (I) by Process A

Preparation Example 1: 6-Isopropyl-2-(pyridin-3-yl)[1,3]thiazolo[4,5-d]pyrimidin-7(6H)-one (1)

Step 1: 4-Amino-N-isopropyl-2-(pyridin-3-yl)-1,3-thiazole-5-carboxamide (II-1)

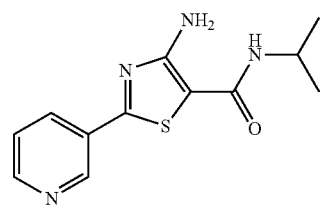 [SMILES: CC(C)NC(=O)c1sc(-c2cccnc2)nc1N]

Under argon, 3 ml of a 2M trimethylaluminium solution (6.02 mmol) in toluene were slowly added dropwise to 356 mg (6.02 mmol) of isopropylamine in 1,2-dichloroethane and the mixture was stirred at room temperature for 30 min 500 mg (2.00 mmol) of ethyl 4-amino-2-(pyridin-3-yl)-1,3-thiazole-5-carboxylate (III-1) were then added, and the reaction mixture was subsequently heated under reflux overnight. After cooling, the reaction mixture was carefully discharged into a 10% potassium sodium tartrate solution (about 100 ml). The mixture was extracted three times with dichloromethane, and the combined organic phases were dried over sodium sulphate, filtered and concentrated. The residue was stirred with a little acetonitrile to give a suspension. The insoluble portion was filtered off with suction and dried under reduced pressure. This gave 340 mg (99% pure, 63.9% of theory) of the title compound (II-1).

1H-NMR (400.0 MHz, $d_6$-DMSO): δ=9.046(2.3); 9.042 (2.4); 8.704(1.8); 8.700(2.0); 8.692(2.0); 8.688(1.9); 8.218 (1.0); 8.214(1.4); 8.208(1.0); 8.198(1.2); 8.194(1.5); 8.193 (1.5); 8.188(1.1); 7.639(1.3); 7.620(1.3); 7.581(1.4); 7.579 (1.4); 7.569(1.4); 7.567(1.4); 7.561(1.4); 7.559(1.3); 7.549 (1.3); 7.547(1.3); 6.982(4.0); 4.077(0.7); 4.061(1.0); 4.042 (1.0); 4.025(0.7); 3.904(0.9); 3.338(73.4); 2.526(0.6); 2.513 (11.6); 2.509(23.1); 2.504(30.0); 2.500(21.6); 2.495(10.5); 1.143(16.0); 1.126(15.8); 0.000(7.2); −0.008(0.3)

Step 2: 6-Isopropyl-2-(pyridin-3-yl)[1,3]thiazolo[4,5-d]pyrimidin-7(6H)-one (1)

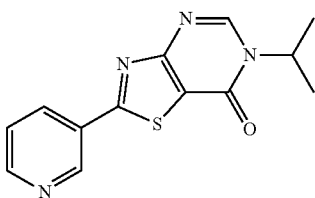 [SMILES: CC(C)n1cnc2nc(-c3cccnc3)sc2c1=O]

300 mg (1.14 mmol) of 4-amino-N-isopropyl-2-(pyridin-3-yl)-1,3-thiazole-5-carboxamide (II-1) were initially charged in N,N-dimethylacetamide. 98 mg (0.57 mmol) of p-toluenesulphonic acid and 339 mg (2.29 mmol) of triethyl orthoformate were added thereto and the reaction mixture was heated at 130° C. in a CEM Discover microwave at 200 watts for 1 h. The cooled reaction mixture was concentrated under reduced pressure, and the residue was triturated with acetonitrile and the solid was filtered off. The filtrate was then concentrated and purified chromatographically by MPLC on an RP(C-18) column. This gave 25 mg (96% pure, 7.6% of theory) of the title compound (1).

1H-NMR (400.0 MHz, $d_6$-DMSO): δ=9.307(2.2); 9.302 (2.2); 8.814(1.6); 8.811(1.7); 8.802(1.7); 8.799(1.7); 8.734 (6.2); 8.516(1.0); 8.512(1.3); 8.506(1.0); 8.496(1.1); 8.491 (1.4); 8.486(1.0); 8.144(3.9); 7.659(1.3); 7.647(1.3); 7.641 (1.3); 7.639(1.3); 7.628(1.2); 7.627(1.2); 5.054(0.4); 5.037 (1.1); 5.019(1.5); 5.002(1.1); 4.985(0.4); 3.337(1.4); 2.526 (0.8); 2.513(17.3); 2.508(34.7); 2.504(45.2); 2.499(32.4); 2.495(15.5); 1.483(16.0); 1.466(15.8); 1.142(0.4); 1.126 (0.4); 0.000(8.5)

Preparation Example 2: 6-Isobutyl-2-(pyridin-3-yl)[1,3]thiazolo[4,5-d]pyrimidin-7(6H)-one (3)

Step 1: 4-Amino-N-isobutyl-2-(pyridin-3-yl)-1,3-thiazole-5-carboxamide ((II-3))

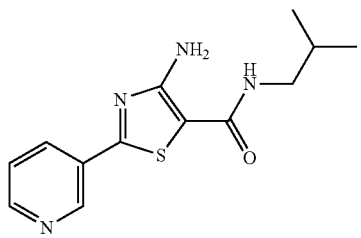 [SMILES: CC(C)CNC(=O)c1sc(-c2cccnc2)nc1N]

1.75 g (7.02 mmol) of ethyl 4-amino-2-(pyridin-3-yl)-1,3-thiazole-5-carboxylate (III-1) were initially charged in ethanol, and 1.97 g of potassium hydroxide (35.10 mmol), dissolved in ethanol, were added. The reaction mixture was stirred at 50° C. overnight and then concentrated to dryness. The residue was suspended in a little water and the product was precipitated with 10% strength aqueous citric acid solution. The insoluble fraction was filtered off with suction and dried well under reduced pressure. The resulting 4-amino-2-(pyridin-3-yl)-1,3-thiazole-5-carboxylic acid (1.32 g, 100% pure, 85.0% of theory) was directly reacted further.

1H-NMR (400.0 MHz, $d_6$-DMSO): δ=9.112(1.2); 9.108 (1.4); 9.099(0.7); 9.086(15.3); 9.085(15.4); 9.080(16.0); 9.018(0.3); 9.012(0.4); 8.730(1.2); 8.727(1.2); 8.719(1.4); 8.715(1.4); 8.701(13.6); 8.697(14.4); 8.689(14.5); 8.685 (14.2); 8.607(0.4); 8.603(0.4); 8.595(0.4); 8.297(0.7); 8.292 (0.9); 8.287(0.8); 8.277(0.9); 8.271(1.2); 8.262(8.1); 8.258 (10.9); 8.253(8.0); 8.242(8.7); 8.238(11.2); 8.233(8.1); 7.580(1.0); 7.566(1.5); 7.560(11.6); 7.558(11.0); 7.548 (11.5); 7.546(10.9); 7.540(10.5); 7.538(9.8); 7.528(10.0); 7.526(9.3); 7.506(0.4); 7.494(0.4); 7.486(0.4); 7.473(0.4); 7.133(1.1); 6.917(1.6); 6.028(1.3); 4.271(0.9); 4.253(2.8); 4.235(2.8); 4.218(0.9); 3.578(0.4); 3.545(0.5); 3.466(1.1); 3.448(1.5); 3.431(1.8); 3.324(25.6); 3.120(0.5); 3.092(0.4); 2.951(0.3); 2.675(2.3); 2.671(3.1); 2.667(2.3); 2.555(5.6); 2.541(2.3); 2.524(9.2); 2.517(30.9); 2.511(156.3); 2.506 (313.9); 2.502(413.1); 2.497(295.7); 2.493(141.3); 2.481 (18.0); 2.443(5.2); 2.338(1.1); 2.333(2.2); 2.329(3.0); 2.324 (2.2); 2.290(0.4); 1.909(0.8); 1.295(3.0); 1.277(6.4); 1.260 (3.0); 1.073(0.8); 1.055(1.5); 1.038(0.7); 0.146(1.3); 0.008 (11.0); 0.000(302.5); −0.009(11.0); −0.150(1.3)

100 mg (0.45 mmol) of this 4-amino-2-(pyridin-3-yl)-1,3-thiazole-5-carboxylic acid were then initially charged in toluene. 376 mg (3.16 mmol) of thionyl chloride were added and the reaction mixture was heated under reflux for 3 hours. After cooling, the reaction was concentrated under reduced pressure and dried under high vacuum. The acid chloride obtained in this manner was taken up in acetonitrile and added to a solution of 88 mg (0.68 mmol) of N,N-diisopropylethylamine and 36.36 mg (0.50 mmol) of isobutylamine in acetonitrile. The reaction mixture was then stirred at room temperature overnight. After evaporation of the solvent the residue was taken up in ethyl acetate and saturated sodium chloride solution. The organic phase was separated off, dried over sodium sulphate and concentrated. This gave 71 mg (84% pure, 47.7% of theory) of the title compound (II-3) which were converted directly further into (3) in Step 2.

LC-MS: mass found [m/z]=276.10

Step 2: 6-Isobutyl-2-(pyridin-3-yl)[1,3]thiazolo[4,5-d]pyrimidin-7(6H)-one (3)

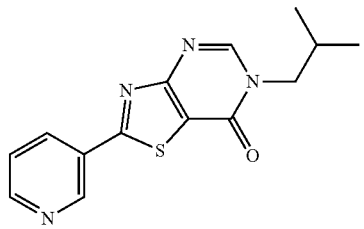 [SMILES: CC(C)Cn1cnc2nc(-c3cccnc3)sc2c1=O]

71 mg (0.22 mmol; 84% pure) of 4-amino-N-isobutyl-2-(pyridin-3-yl)-1,3-thiazole-5-carboxamide (II-3) were initially charged in 266 mg (3.05 mmol) of N,N-dimethylacetamide. 2 mg (0.013 mmol) of p-toluenesulphonic acid and 57 mg (0.39 mmol) of triethyl orthoformate were added and the reaction mixture was heated at 120° C. in a CEM Discover microwave at 200 watts for 10 min. The cooled reaction mixture was concentrated and purified chromatographically. This gave 24 mg (90% pure, 34.3% of theory) of the title compound (3).

1H-NMR (400.0 MHz, $d_6$-DMSO): δ=9.302(2.1); 9.297 (2.1); 9.049(0.4); 9.044(0.4); 8.815(1.8); 8.811(1.9); 8.803 (1.8); 8.799(1.8); 8.703(0.3); 8.699(0.4); 8.691(0.4); 8.687 (0.4); 8.634(6.2); 8.510(1.1); 8.506(1.4); 8.500(1.1); 8.490 (1.1); 8.486(1.4); 8.484(1.4); 8.480(1.1); 7.662(1.3); 7.660 (1.4); 7.650(1.3); 7.648(1.3); 7.642(1.3); 7.640(1.3); 7.630 (1.2); 7.628(1.3); 6.974(0.7); 3.895(4.7); 3.876(4.7); 3.323 (24.1); 3.022(0.4); 3.005(0.6); 2.990(0.4); 2.512(10.6); 2.508(21.2); 2.503(27.9); 2.499(20.3); 2.495(10.0); 2.162 (0.4); 2.145(0.8); 2.128(1.0); 2.111(0.9); 2.093(0.4); 0.916 (16.0); 0.899(15.5); 0.873(3.2); 0.856(3.1); 0.008(0.3); 0.000(8.4); −0.008(0.3)

Preparation Example 3: 2-(Pyridin-3-yl)-6-(2,2,2-trifluoroethyl)[1,3]thiazolo[4,5-d]pyrimidin-7(6H)-one (5)

Step 1: 4-Amino-2-(pyridin-3-yl)-N-(2,2,2-trifluoroethyl)-1,3-thiazole-5-carboxamide (II-5)

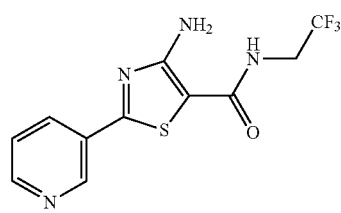 [SMILES: Nc1nc(-c2cccnc2)sc1C(=O)NCC(F)(F)F]

Under argon, 3 ml of a 2M trimethylaluminium solution (6.02 mmol) in toluene were slowly added dropwise to 596 mg (6.02 mmol) of 2,2,2-trifluoroethylamine in 1,2-dichloroethane, and the mixture was stirred at room temperature for 30 min 500 mg (2.0 mmol) of ethyl 4-amino-2-(pyridin-3-yl)-1,3-thiazole-5-carboxylate (III-1) were then added, and the reaction mixture was subsequently heated under reflux overnight. After cooling, the reaction mixture was carefully discharged into a 10% potassium sodium tartrate solution (about 100 ml). The mixture was extracted three times with methylene chloride, and the organic phase was removed, dried over sodium sulphate, filtered and concentrated. The residue was stirred with a little acetonitrile to give a suspension. The insoluble portion was filtered off with suction and dried under reduced pressure. This gave 299 mg (91% pure, 44.8% of theory) of the title compound (II-5).

1H-NMR (400.0 MHz, $d_6$-DMSO): δ=9.114(0.8); 9.110 (0.8); 9.074(9.3); 9.070(9.3); 8.728(7.9); 8.724(7.8); 8.716 (8.3); 8.712(7.5); 8.476(3.0); 8.461(6.3); 8.446(3.0); 8.318 (0.4); 8.298(0.4); 8.293(0.5); 8.288(0.4); 8.277(0.4); 8.272 (0.5); 8.268(0.5); 8.249(4.1); 8.245(5.6); 8.240(4.0); 8.229 (4.5); 8.225(5.8); 8.224(5.8); 8.220(4.1); 7.594(5.4); 7.593 (5.3); 7.582(5.6); 7.580(5.7); 7.574(5.3); 7.573(5.1); 7.562 (5.2); 7.560(5.2); 7.548(0.5); 7.164(16.0); 5.759(1.8); 4.272 (0.5); 4.254(1.5); 4.236(1.5); 4.218(0.5); 4.040(1.7); 4.016 (5.6); 4.000(5.7); 3.992(6.1); 3.976(5.5); 3.968(2.4); 3.952 (1.9); 3.905(2.0); 3.332(49.0); 2.678(0.5); 2.673(0.6); 2.669 (0.4); 2.509(72.6); 2.504(92.8); 2.500(67.2); 2.335(0.5); 2.331(0.6); 2.327(0.4); 1.296(1.6); 1.279(3.2); 1.261(1.5); 0.008(2.8); 0.000(58.8); −0.008(2.6)

Step 2: 2-(Pyridin-3-yl)-6-(2,2,2-trifluoroethyl)[1,3]thiazolo[4,5-d]pyrimidin-7(6H)-one (5)

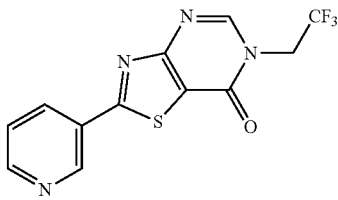 [SMILES: O=c1c2sc(-c3cccnc3)nc2ncn1CC(F)(F)F]

240 mg (0.79 mmol) of 4-amino-2-(pyridin-3-yl)-N-(2,2,2-trifluoroethyl)-1,3-thiazole-5-carboxamide (II-5) were initially charged in 3 ml of N,N-dimethylacetamide. 68 mg (0.40 mmol) of p-toluenesulphonic acid and 235 mg (1.59 mmol) of triethyl orthoformate were added thereto and the reaction mixture was heated at 130° C. in a CEM Discover microwave at 200 watts for 1 h. The cooled reaction mixture was concentrated under reduced pressure, and the residue was triturated with acetonitrile and the solid was filtered off. The solid was then purified by MPLC on an RP(C-18) column. This gave 69 mg (92% pure, 25.6% of theory) of the title compound (5).

1H-NMR (400.0 MHz, $d_6$-DMSO): δ=9.320(8.2); 9.315 (8.2); 9.302(0.4); 8.829(6.4); 8.825(6.8); 8.817(6.9); 8.813 (6.6); 8.698(16.0); 8.530(4.0); 8.526(5.1); 8.520(3.9); 8.510 (4.3); 8.506(5.3); 8.505(5.3); 8.500(4.0); 8.318(0.4); 7.672 (4.8); 7.671(4.8); 7.660(4.8); 7.659(4.7); 7.652(4.8); 7.651 (4.6); 7.640(4.5); 7.639(4.4); 5.143(0.3); 5.121(0.4); 5.089 (3.5); 5.067(11.4); 5.044(11.9); 5.021(4.0); 3.363(0.6); 3.336(289.1); 2.720(1.5); 2.678(0.6); 2.674(0.8); 2.669 (0.6); 2.527(2.1); 2.513(48.7); 2.509(96.7); 2.505(125.4); 2.500(89.6); 2.496(42.7); 2.336(0.6); 2.331(0.8); 2.327 (0.6); 2.077(0.4); 0.008(1.2); 0.000(30.0); −0.008(1.1)

Preparation Example 4: 6-(3-Methoxyphenyl)-2-(pyridin-3-yl)[1,3]thiazolo[4,5-d]pyrimidin-7(6H)-one (10)

Step 1: 4-Amino-N-(3-methoxyphenyl)-2-(pyridin-3-yl)-1,3-thiazole-5-carboxamide (II-10)

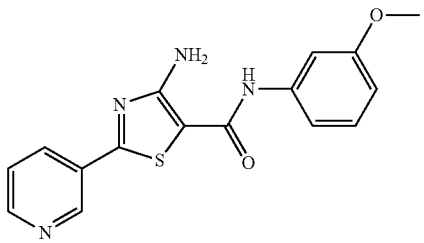 [SMILES: COc1cccc(NC(=O)c2sc(-c3cccnc3)nc2N)c1]

Under argon, 1.8 ml of a 2M trimethylaluminium solution (3.61 mmol) in toluene were slowly added dropwise to 445 mg (3.61 mmol) of 3-methoxy aniline in 1,2-dichloroethane and the mixture was stirred at room temperature for 1 h. 300 mg (1.2 mmol) of ethyl 4-amino-2-(pyridin-3-yl)-1,3-thiazole-5-carboxylate (III-1) were then added, and the reaction mixture was subsequently heated under reflux overnight. After cooling, the reaction mixture was carefully discharged into a 10% potassium sodium tartrate solution (about 120 ml). The mixture was extracted three times with methylene chloride, and the combined organic phases were dried over sodium sulphate, filtered and concentrated. The residue was stirred with a little acetonitrile to give a suspension. The insoluble portion was filtered off with suction and dried under reduced pressure. This gave 120 mg (96% pure, 29.3% of theory) of the title compound (II-10).

1H-NMR (400.0 MHz, $d_6$-DMSO): δ=9.618(2.9); 9.113 (0.4); 9.107(0.5); 9.099(2.3); 9.093(2.3); 8.736(1.5); 8.732 (1.7); 8.724(1.7); 8.720(1.7); 8.271(1.0); 8.266(1.5); 8.261 (0.9); 8.251(0.8); 8.246(1.4); 8.241(0.9); 7.607(1.3); 7.595 (1.3); 7.587(1.3); 7.575(1.4); 7.361(1.4); 7.355(2.5); 7.350 (1.7); 7.303(1.0); 7.282(1.7); 7.238(3.5); 7.232(3.1); 7.211 (2.7); 7.191(1.2); 6.658(1.2); 6.652(1.2); 6.638(1.1); 6.631 (1.1); 4.253(0.7); 4.235(0.7); 3.747(16.0); 3.330(15.3); 2.525(0.6); 2.507(25.7); 2.503(34.3); 2.499(26.3); 2.076 (0.7); 1.295(0.8); 1.278(1.5); 1.260(0.7); 0.008(1.5); 0.007 (1.5); 0.000(44.0); −0.008(1.9)

Step 2: 6-(3-Methoxyphenyl)-2-(pyridin-3-yl)[1,3]thiazolo[4,5-d]pyrimidin-7(6H)-one (10)

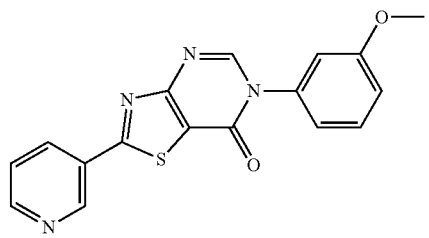 [SMILES: COc1cccc(-n2cnc3nc(-c4cccnc4)sc3c2=O)c1]

100 mg (0.29 mmol) of 4-amino-N-(3-methoxyphenyl)-2-(pyridin-3-yl)-1,3-thiazole-5-carboxamide (II-10) were initially charged in N,N-dimethylacetamide. 25 mg (0.15 mmol) of p-toluenesulphonic acid and 87 mg (0.59 mmol) of triethyl orthoformate were added thereto and the reaction mixture was heated at 130° C. in a CEM Discover microwave at 200 watts for 1 h. Water was added to the cooled reaction mixture which was then extracted repeatedly with dichloromethane. The combined organic phases were dried over sodium sulfate, filtered and concentrated. The residue was then purified by MPLC column chromatography. This gave 20 mg (100% pure, 20.2% of theory) of the title compound (10).

1H-NMR (400.0 MHz, $d_6$-DMSO): δ=9.345(0.5); 9.340 (0.5); 8.833(0.4); 8.829(0.4); 8.821(0.4); 8.817(0.4); 8.620 (1.4); 7.495(0.6); 7.475(0.4); 7.217(0.3); 7.211(0.6); 7.206 (0.4); 7.155(0.4); 7.134(0.5); 3.818(3.8); 3.328(15.7); 2.944 (16.0); 2.784(13.5); 2.507(16.3); 2.502(21.3); 2.498(16.0); 1.957(14.1); 0.008(1.0); 0.000(24.1); −0.008(1.1)

Preparation Example 5: 6-{2-Fluoro-4-methyl-5-[(2,2,2-trifluoroethyl)sulphinyl]phenyl}-2-(pyridin-3-yl)[1,3]thiazolo[4,5-d]pyrimidin-7(6H)-one (22)

Step 1: 4-Amino-N-{2-fluoro-4-methyl-5-[(2,2,2-trifluoroethyl)sulphanyl]phenyl}-2-(pyridin-3-yl)-1,3-thiazole-5-carboxamide (II-21)

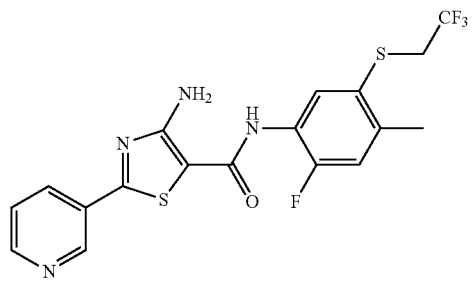

Under argon, 1.5 ml of a 2M trimethylaluminium solution (3.01 mmol) in toluene were slowly added dropwise to 720 mg (3.01 mmol) of 2-fluoro-4-methyl-5-[(2,2,2-trifluoroethyl)sulphanyl]aniline in 1,2-dichloroethane, and the mixture was stirred at room temperature for 30 min. 250 mg (1.00 mmol) of ethyl 4-amino-2-(pyridin-3-yl)-1,3-thiazole-5-carboxylate (III-1) were then added, and the reaction mixture was subsequently heated under reflux overnight. After cooling, the reaction mixture was carefully discharged into a 10% potassium sodium tartrate solution (about 200 ml). The mixture was extracted three times with methylene chloride, and the combined organic phases were dried over sodium sulphate, filtered and concentrated. The residue was stirred with a little acetonitrile to give a suspension. The insoluble portion was filtered off with suction and dried under reduced pressure. This gave 144 mg (92% pure, 29.9% of theory) of the title compound (II-21).

1H-NMR (601.6 MHz, $d_6$-DMSO): δ=9.566(4.6); 9.110 (0.4); 9.100(3.4); 9.096(3.4); 8.737(2.4); 8.734(2.6); 8.729 (2.8); 8.726(2.8); 8.270(1.3); 8.267(1.9); 8.264(1.3); 8.257 (1.3); 8.254(2.0); 8.251(1.3); 7.696(2.8); 7.683(2.8); 7.601 (1.7); 7.594(1.7); 7.588(1.7); 7.580(1.6); 7.268(2.5); 7.250 (2.5); 7.209(5.5); 4.250(0.6); 4.238(0.6); 3.891(1.1); 3.874 (3.4); 3.857(3.5); 3.840(1.2); 3.343(61.4); 2.616(0.4); 2.507 (51.6); 2.504(70.6); 2.501(53.2); 2.406(16.0); 1.290(0.6); 1.278(1.2); 1.266(0.6); 0.005(1.5); 0.000(41.7)

Step 2: 6-{2-Fluoro-4-methyl-5-[(2,2,2-trifluoro-ethyl)sulphanyl]phenyl}-2-(pyridin-3-yl)[1,3]thiazolo[4,5-d]pyrimidin-7(6H)-one (21)

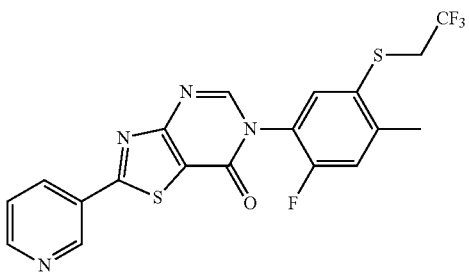

120 mg (0.27 mmol) of 4-amino-N-{2-fluoro-4-methyl-5-[(2,2,2-trifluoroethyl)sulphanyl]phenyl}-2-(pyridin-3-yl)-1,3-thiazole-5-carboxamide (II-21) were initially charged in N,N-dimethylacetamide. 23 mg (0.14 mmol) of p-toluenesulphonic acid and 80 mg (0.54 mmol) of triethyl orthoformate were added thereto and the reaction mixture was heated at 130° C. in a CEM Discover microwave at 200 watts for 1 h. The cooled reaction mixture was concentrated under reduced pressure, and the residue was triturated with acetonitrile and the product was filtered off as a solid. The filtrate was then concentrated and purified chromatographically by MPLC on an RP(C-18) column. This gave, in total, 43 mg (98% pure, 34.3% of theory) of the title compound (21).

1H-NMR (400.0 MHz, $d_6$-DMSO): δ=9.350(3.0); 9.346 (3.1); 9.344(3.0); 8.839(2.4); 8.836(2.6); 8.827(2.6); 8.824 (2.6); 8.679(8.7); 8.561(1.4); 8.557(1.8); 8.551(1.4); 8.541 (1.5); 8.537(1.9); 8.535(1.9); 8.531(1.5); 7.939(3.1); 7.921 (3.1); 7.684(1.8); 7.683(1.7); 7.672(1.7); 7.671(1.7); 7.664 (1.8); 7.663(1.7); 7.652(1.7); 7.651(1.7); 7.518(2.7); 7.491 (2.6); 4.062(1.2); 4.037(3.9); 4.011(4.0); 3.985(1.4); 3.330 (57.6); 2.945(1.0); 2.785(0.7); 2.672(0.4); 2.526(1.0); 2.512 (19.8); 2.508(40.6); 2.503(53.8); 2.499(39.4); 2.494(19.5); 2.471(16.0); 2.330(0.3); 2.076(10.9); 1.958(0.8); 0.008 (1.0); 0.000(30.1); −0.009(1.2)

Step 3—Main Product: 6-{2-Fluoro-4-methyl-5-[(2,2,2-trifluoroethyl)sulphinyl]phenyl}-2-(pyridin-3-yl)[1,3]thiazolo[4,5-d]pyrimidin-7(6H)-one (22)

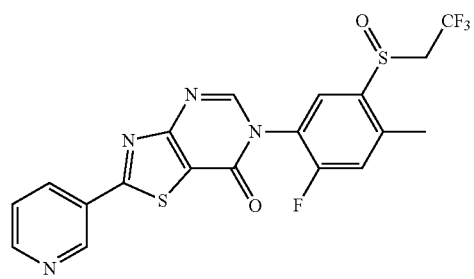

At 0° C., 19.18 mg (70% strength, 0.08 mmol) of meta-chloroperbenzoic acid were added to a solution of 32.0 mg (0.07 mmol) of 6-{2-fluoro-4-methyl-5-[(2,2,2-trifluoro-ethyl)sulphanyl]phenyl}-2-(pyridin-3-yl)[1,3]thiazolo[4,5-d]pyrimidin-7(6H)-one (21) in 3 ml of dichloromethane. The reaction mixture was stirred at room temperature for 2 hours, and saturated sodium carbonate solution was then added. After 20 minutes, the phases were separated, the aqueous phase was extracted two more times with dichloromethane and the combined organic phases were dried over sodium sulphate After evaporation of the solvent, the residue was then purified chromatographically by MPLC on an RP(C-18) column. This gave 10 mg (95% pure, 28.1% of theory) of the title compound (22).

1H-NMR (400.0 MHz, $d_6$-DMSO): δ=9.761(0.5); 9.353 (6.6); 9.347(6.9); 9.102(0.4); 8.836(5.2); 8.828(4.9); 8.824 (5.2); 8.738(0.5); 8.723(15.6); 8.557(4.0); 8.553(2.9); 8.543 (2.8); 8.537(4.3); 8.533(3.1); 8.315(2.5); 8.195(6.5); 8.176 (6.5); 8.039(0.4); 7.951(2.4); 7.685(3.8); 7.673(3.8); 7.665 (4.0); 7.653(3.8); 7.635(5.0); 7.608(5.1); 7.366(0.4); 7.238 (0.6); 5.755(1.0); 4.293(0.9); 4.271(1.2); 4.263(1.3); 4.233 (1.1); 4.182(0.4); 4.124(1.0); 4.100(1.2); 3.505(1.6); 3.322 (748.9); 2.944(1.9); 2.891(16.0); 2.784(1.6); 2.731(14.3); 2.716(0.5); 2.670(6.0); 2.666(4.8); 2.505(695.9); 2.501 (960.0); 2.497(767.5); 2.395(0.8); 2.373(2.4); 2.328(6.2); 2.324(5.1); 2.283(0.4); 1.957(1.9); 1.303(0.3); 1.284(0.6); 1.233(2.0); 0.854(0.4); 0.146(3.0); 0.008(21.8); 0.000 (638.0); −0.078(0.4); −0.150(3.2)

Step 3—Minor Product: 6-{2-Fluoro-4-methyl-5-[(2,2,2-trifluoroethyl)sulphinyl]phenyl}-2-(1-oxidopyridin-3-yl)[1,3]thiazolo[4,5-d]pyrimidin-7(6H)-one (23)

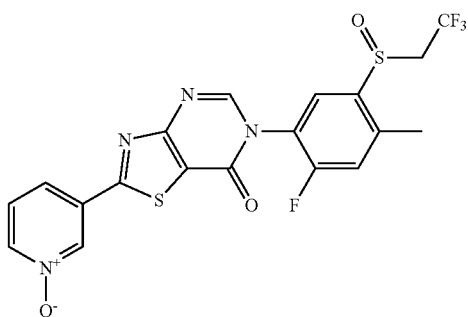 [SMILES: Cc1cc(F)c(-n2cnc3nc(-c4ccc[n+]([O-])c4)sc3c2=O)cc1S(=O)CC(F)(F)F]

In the course of the preparation of the compound (23) according to "Step 3—main product", compound (23) was simultaneously insulated as minor product. This gave 11 mg (94% pure, 30.5% of theory) of the title compound (23).

1H-NMR (400.0 MHz, $d_6$-DMSO): δ=8.928(9.2); 8.734 (16.0); 8.463(5.2); 8.446(5.3); 8.315(0.9); 8.196(7.0); 8.177 (7.1); 8.082(5.1); 8.061(5.7); 7.668(4.5); 7.649(5.9); 7.633 (8.7); 7.608(5.6); 7.573(0.4); 7.251(0.4); 4.265(1.6); 4.236 (1.3); 4.117(1.2); 4.106(1.2); 4.092(1.4); 3.322(182.5); 2.671(2.1); 2.502(339.3); 2.498(298.4); 2.402(0.7); 2.373 (1.6); 2.329(2.4); 0.146(1.6); 0.000(312.8); −0.083(0.4); −0.150(1.7)

Preparation Example 6: 2-(Pyridin-3-yl)-6-[3-(trifluoromethyl)benzyl][1,3]thiazolo[4,5-d]pyrimidin-7(6H)-one (28)

Step 1: 4-Amino-2-(pyridin-3-yl)-N-[3-(trifluoromethyl)benzyl]-1,3-thiazole-5-carboxamide (II-28)

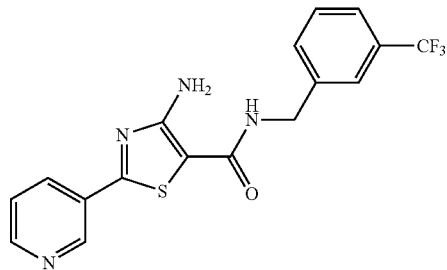 [SMILES: Nc1nc(-c2cccnc2)sc1C(=O)NCc1cccc(C(F)(F)F)c1]

Under argon, 2.4 ml of a 2M trimethylaluminium solution (4.81 mmol) in toluene were slowly added dropwise to 843 mg (4.81 mmol) of 3-(trifluoromethyl)benzylamine in 20 ml of 1,2-dichloroethane, and the mixture was stirred at room temperature for 30 min 400 mg (1.61 mmol) of ethyl 4-amino-2-(pyridin-3-yl)-1,3-thiazole-5-carboxylate (III-1) were then added, and the reaction mixture was subsequently heated under reflux overnight. After cooling, the reaction mixture was carefully discharged into a 10% potassium sodium tartrate solution (about 120 ml). The mixture was extracted three times with dichloromethane, and the combined organic phases were dried over sodium sulphate, filtered and concentrated. The residue was stirred with a little n-pentane to give a suspension. The insoluble portion was filtered off with suction and dried under reduced pressure. This gave 425 mg (100% pure, 70.0% of theory) of the title compound (II-28).

1H-NMR (400.0 MHz, $d_6$-DMSO): δ=9.063(9.1); 9.058 (9.1); 8.714(6.6); 8.710(7.3); 8.702(7.1); 8.698(7.3); 8.543 (2.9); 8.528(6.3); 8.514(3.0); 8.317(0.6); 8.237(3.6); 8.232 (5.3); 8.227(3.9); 8.217(4.0); 8.212(5.8); 8.207(4.1); 7.656 (9.5); 7.633(3.5); 7.615(8.3); 7.609(10.3); 7.591(9.1); 7.583 (6.9); 7.572(9.3); 7.563(5.7); 7.552(5.8); 7.161(0.4); 7.099 (0.5); 7.050(16.0); 6.941(0.4); 5.757(3.2); 4.483(12.6); 4.469(12.6); 3.903(1.3); 3.800(0.5); 3.327(183.9); 2.676 (1.2); 2.672(1.8); 2.667(1.3); 2.525(4.0); 2.511(99.6); 2.507 (202.4); 2.503(270.1); 2.498(201.5); 2.333(1.3); 2.329(1.8); 2.325(1.4); 1.989(0.6); 0.146(1.4); 0.008(9.9); 0.000 (288.4); −0.008(11.9); −0.150(1.4)

Step 2: 2-(Pyridin-3-yl)-6-[3-(trifluoromethyl)benzyl][1,3]thiazolo[4,5-d]pyrimidin-7(6H)-one (28)

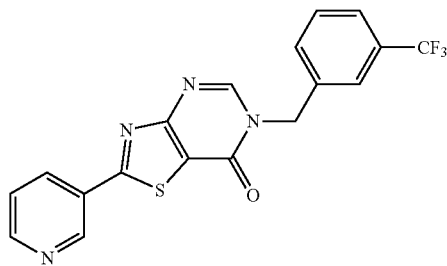 [SMILES: O=c1c2sc(-c3cccnc3)nc2ncn1Cc1cccc(C(F)(F)F)c1]

110 mg (0.29 mmol) of 4-amino-2-(pyridin-3-yl)-N-[3-(trifluoromethyl)benzyl]-1,3-thiazole-5-carboxamide (II-28) were initially charged in N,N-dimethylacetamide. 25 mg (0.14 mmol) of p-toluenesulphonic acid and 129 mg (0.87 mmol) of triethyl orthoformate were added thereto and the reaction mixture was heated at 130° C. in a CEM Discover microwave at 200 watts for 1 h. Saturated sodium bicarbonate solution was added to the cooled reaction mixture which was then extracted repeatedly with dichloromethane. The combined organic phases were dried over magnesium sulfate, filtered and concentrated. The residue was then purified by MPLC using the mobile phase cyclohexane/ethyl acetate. After evaporation of the solvent, the product was triturated with pentane/ethyl acetate and sonicated. The crystals obtained in this manner were filtered off with suction. This gave 38 mg (98.3% pure, 33.1% of theory) of the title compound (28).

1H-NMR (600.1 MHz, CD3CN): δ=9.2734(3.7); 9.2728 (3.7); 9.270(3.8); 8.751(2.8); 8.748(2.9); 8.743(2.9); 8.740 (2.8); 8.469(9.8); 8.403(1.8); 8.400(2.4); 8.399(2.3); 8.396 (1.7); 8.389(1.9); 8.387(2.4); 8.386(2.3); 8.383(1.7); 7.744 (3.9); 7.662(2.1); 7.650(3.1); 7.641(2.5); 7.576(2.2); 7.563 (3.2); 7.550(1.3); 7.534(2.3); 7.533(2.2); 7.526(2.3); 7.525 (2.2); 7.521(2.3); 7.520(2.1); 7.513(2.2); 7.512(2.0); 5.293 (16.0); 2.957(13.9); 2.827(11.1); 2.154(11.6); 1.972(12.0); 1.967(0.5); 1.959(0.6); 1.955(0.8); 1.951(5.6); 1.947(10.0); 1.943(14.5); 1.938(9.7); 1.934(4.8); 0.000(6.8)

Preparation Example 7: 2-(Pyridin-3-yl)-6-(pyridin-2-ylmethyl)[1,3]thiazolo[4,5-d]pyrimidin-7(6H)-one (34)

Step 1: 4-Amino-2-(pyridin-3-yl)-N-(pyridin-2-ylmethyl)-1,3-thiazole-5-carboxamide (II-34)

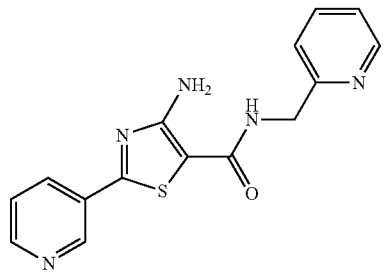 [SMILES: Nc1nc(-c2cccnc2)sc1C(=O)NCc1ccccn1]

1 g (4.0 mmol) of ethyl 4-amino-2-(pyridin-3-yl)-1,3-thiazole-5-carboxylate (III-1) were initially charged in ethanol, and 2.25 g of potassium hydroxide (40 mmol), dissolved in ethanol, were added. The reaction mixture was stirred at 50° C. for 4 h and then concentrated to dryness. The residue was suspended in a little water and the product was precipitated with 10% strength aqueous citric acid solution. The insoluble fraction was filtered off with suction and dried well under reduced pressure. The resulting 4-amino-2-(pyridin-3-yl)-1,3-thiazole-5-carboxylic acid (583 mg, 100% pure, 65.7% of theory) was directly reacted further.

LC-MS: mass found [m/z]=221.03

148 mg (0.67 mmol) of 4-amino-2-(pyridin-3-yl)-1,3-thiazole-5-carboxylic acid and 237 mg (0.74 mmol) of O-(1H-benzotriazol-1-yl)-N,N,N',N'-tetramethyluronium tetrafluoroborate (TBTU) were initially charged in DMF, and the mixture was stirred for 10 minutes. 73 mg (0.67 mmol) of 1-(pyridin-2-yl)methanamine and 130 mg (1 mmol) of N,N-diisopropylethylamine, dissolved in dimethylformamide, were then added. The reaction mixture was stirred at room temperature overnight and then concentrated under reduced pressure. Further purification of the residue was then carried out by column chromatography using MPLC. This gave 192 mg (43.0% pure, 39.5% of theory) of the title compound (II-34).

LC-MS: mass found [m/z]=311.08

Step 2: 2-(Pyridin-3-yl)-6-(pyridin-2-ylmethyl)[1,3]thiazolo[4,5-d]pyrimidin-7(6H)-one (34)

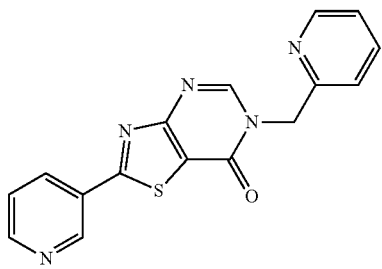 [SMILES: O=c1c2sc(-c3cccnc3)nc2ncn1Cc1ccccn1]

96 mg (0.31 mmol) of 4-amino-2-(pyridin-3-yl)-N-(pyridin-2-ylmethyl)-1,3-thiazole-5-carboxamide (II-34) were initially charged in 1.1 g of N,N-dimethylacetamide. 2.4 mg (0.015 mmol) of p-toluenesulphonic acid and 69 mg (0.46 mmol) of triethyl orthoformate were added and the reaction mixture was heated at 120° C. in a CEM Discover microwave at 200 watts for 10 min. Water was added to the cooled reaction mixture which was then extracted repeatedly with ethyl acetate. The combined organic phases were dried over sodium sulphate, filtered and concentrated. Further purification of the residue was then carried out by MPLC using the mobile phase dichloromethane/methanol (10:1) as a gradient. This gave 9.5 mg (100.0% pure, 9.6% of theory) of the title compound (34).

1H NMR (400.0 MHz, $d_6$-DMSO): δ=9.324 (8.2); 9.320 (8.0); 8.828 (5.9); 8.819 (5.7); 8.652 (16.0); 8.533 (4.1); 8.528 (5.4); 8.523 (3.9); 8.513 (4.3); 8.508 (5.6); 8.503 (3.8); 7.673 (4.7); 7.661 (4.8); 7.653 (4.6); 7.641 (4.2); 6.830 (1.0); 6.818 (1.8); 6.805 (0.9); 6.700 (2.0); 6.688 (3.9); 6.676 (2.0); 6.570 (1.0); 6.558 (2.0); 6.546 (1.0); 4.914 (5.2); 4.875 (10.9); 4.837 (5.5); 3.905 (7.6); 3.506 (0.4); 3.338 (626.8); 3.225 (1.1); 3.062 (0.9); 2.677 (2.1); 2.672 (2.7); 2.668 (2.1); 2.508 (339.6); 2.503 (425.1); 2.499 (319.3); 2.334 (1.9); 2.330 (2.5); 2.325 (1.9); 1.298 (0.4); 1.258 (0.5); 1.233 (0.7); 1.145 (0.7); 0.000 (37.7)

Preparation Example 8: 6-[(2-Methyl-1,3-thiazol-4-yl)methyl]-2-(pyridin-3-yl)[1,3]thiazolo[4,5-d]pyrimidin-7(6H)-one (38)

Step 1: 4-Amino-N-[(2-methyl-1,3-thiazol-4-yl)methyl]-2-(pyridin-3-yl)-1,3-thiazole-5-carboxamide (II-38)

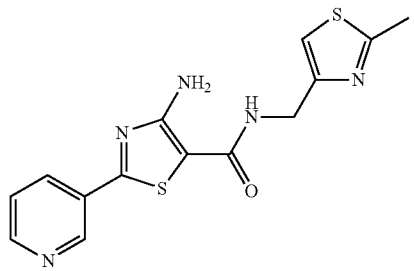 [SMILES: Cc1nc(CNC(=O)c2sc(-c3cccnc3)nc2N)cs1]

Under argon, 0.75 ml of a 2M trimethylaluminium solution (1.5 mmol) in toluene were slowly added dropwise to 193 mg (1.5 mmol) of 1-(2-methyl-1,3-thiazol-4-yl)methanamine in 12 ml of 1,2-dichloroethane, and the mixture was stirred at room temperature for 30 min 250 mg (1.0 mmol) of ethyl 4-amino-2-(pyridin-3-yl)-1,3-thiazole-5-carboxylate (III-1) were then added a little at a time, and the reaction mixture was subsequently heated under reflux overnight. After cooling, the reaction mixture was, with argon, carefully squeezed onto a 10% potassium sodium tartrate solution (about 120 ml). The mixture was extracted three times with dichloromethane, and the organic phase was removed, dried over sodium sulphate, filtered and concentrated. The residue was stirred with a little n-pentane/ethyl acetate to give a suspension. The insoluble fraction was filtered off with suction and then triturated with acetonitrile. The solid which had been filtered off was then dried under reduced pressure. This gave 71 mg (96.1% pure, 20.5% of theory) of the title compound.

1H-NMR (400.0 MHz, $d_6$-DMSO): δ=9.059 (2.1); 9.054 (2.0); 8.711 (1.5); 8.708 (1.6); 8.699 (1.6); 8.695 (1.6); 8.426 (0.7); 8.412 (1.4); 8.398 (0.7); 8.231 (0.8); 8.226 (1.2); 8.221 (0.9); 8.211 (0.9); 8.206 (1.3); 8.201 (0.9); 7.581 (1.2); 7.569 (1.2); 7.561 (1.1); 7.549 (1.1); 7.166 (3.7); 7.035 (3.4); 4.433 (2.9); 4.419 (2.9); 3.904 (1.0); 3.330 (28.0); 2.629 (16.0); 2.507 (25.7); 2.503 (33.6); 2.499 (25.3); 1.278 (0.5); 0.008 (1.1); 0.000 (26.2); −0.008 (1.2)

Step 2: 6-[(2-Methyl-1,3-thiazol-4-yl)methyl]-2-(pyridin-3-yl)[1,3]thiazolo[4,5-d]pyrimidin-7(6H)-one (38)

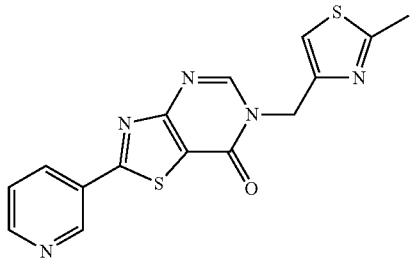 [SMILES: Cc1nc(Cn2cnc3nc(-c4cccnc4)sc3c2=O)cs1]

55 mg (0.17 mmol) of 4-amino-N-[(2-methyl-1,3-thiazol-4-yl)methyl]-2-(pyridin-3-yl)-1,3-thiazole-5-carboxamide (II-38) were initially charged in 0.5 ml of N,N-dimethylacetamide. 14 mg (0.08 mmol) of p-toluenesulphonic acid and 49 mg (0.33 mmol) of triethyl orthoformate were added thereto and the reaction mixture was heated at 130° C. in a CEM Discover microwave at 200 watts for 1 h. Water was added to the cooled reaction mixture which was then extracted repeatedly with dichloromethane. The combined organic phases were washed with saturated sodium chloride solution, dried over magnesium sulphate, filtered and concentrated. After evaporation of the solvent, the residue was triturated with acetonitrile/ethyl acetate and the crystals obtained in this manner were filtered off with suction. This gave 11 mg (80.0% pure, 15.5% of theory) of the title compound (38).

1H-NMR (400.0 MHz, $d_6$-DMSO): δ=9.305(2.2); 9.301 (2.3); 8.815(1.6); 8.812(1.9); 8.798(6.3); 8.511(1.3); 8.506 (1.0); 8.495(1.0); 8.490(1.4); 8.486(1.1); 7.661(1.3); 7.648 (1.3); 7.641(1.3); 7.628(1.2); 7.454(4.1); 7.277(0.5); 5.759 (0.4); 5.308(7.1); 4.489(0.4); 4.476(0.4); 3.332(61.6); 2.945

(0.9); 2.784(0.8); 2.672(0.9); 2.655(1.3); 2.637(2.1); 2.611 (16.0); 2.507(95.2); 2.503(124.7); 2.499(102.9); 2.446(0.4); 2.330(0.8); 2.288(0.7); 1.958(0.8); 1.313(0.5); 0.146(0.4); 0.000(71.2); −0.150(0.4)

Preparation Example 13: 6-(Cyclopropylmethyl)-2-(pyridin-3-yl)[1,3]thiazolo[4,5-d]pyrimidin-7(6H)-one (39)

Step 1: 4-Amino-N-(cyclopropylmethyl)-2-(pyridin-3-yl)-1,3-thiazole-5-carboxamide (II-39)

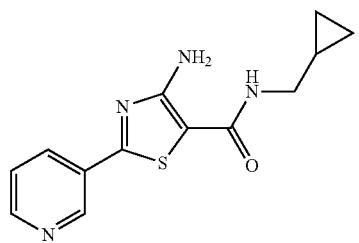 [SMILES: Nc1nc(-c2cccnc2)sc1C(=O)NCC1CC1]

Under argon, 1.5 ml of a 2M trimethylaluminium solution (3.01 mmol) in toluene were slowly added dropwise with ice cooling to 213 mg (3.00 mmol) of 1-cyclopropylmethanamine in 15 ml of 1,2-dichloroethane, and the mixture was stirred at room temperature for 60 min. 373 mg (1.50 mmol) of ethyl 4-amino-2-(pyridin-3-yl)-1,3-thiazole-5-carboxylate (III-1) were then added, and the reaction mixture was subsequently heated under reflux overnight. After cooling, the reaction mixture was carefully discharged into a 10% potassium sodium tartrate solution (about 100 ml). The mixture was extracted three times with methylene chloride, and the combined organic phases were dried over sodium sulphate, filtered and concentrated. The residue was stirred with a little acetonitrile to give a suspension. The insoluble portion was filtered off with suction and dried under reduced pressure. This gave 300 mg (100% pure, 73.0% of theory) of the title compound (II-39).

1H-NMR (400.0 MHz, d$_6$-DMSO): δ=9.056(9.2); 9.052 (9.7); 8.710(6.7); 8.707(7.1); 8.699(7.2); 8.695(7.1); 8.229 (3.8); 8.226(5.4); 8.220(3.9); 8.210(4.1); 8.205(5.7); 8.200 (4.0); 8.025(3.0); 8.012(5.9); 7.998(3.1); 7.579(4.9); 7.567 (5.0); 7.559(5.0); 7.547(4.6); 7.027(16.0); 3.454(4.0); 3.437 (9.3); 3.422(9.5); 3.404(4.3); 3.312(106.1); 2.671(1.1); 2.573(1.2); 2.556(2.1); 2.545(3.8); 2.527(7.5); 2.506 (132.9); 2.502(168.0); 2.498(133.8); 2.470(2.8); 2.452(1.3); 2.329(1.1); 0.000(11.5)

Step 2: 6-(Cyclopropylmethyl)-2-(pyridin-3-yl)[1,3]thiazolo[4,5-d]pyrimidin-7(6H)-one (39)

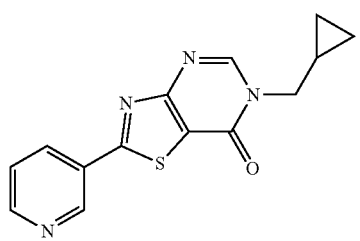 [SMILES: O=c1c2sc(-c3cccnc3)nc2ncn1CC1CC1]

100 mg (0.37 mmol) of 4-amino-N-(cyclopropylmethyl)-2-(pyridin-3-yl)-1,3-thiazole-5-carboxamide (II-39) were initially charged in 1 ml of N,N-dimethylacetamide. 31 mg (0.18 mmol) of p-toluenesulphonic acid and 162 mg (1.09 mmol) of triethyl orthoformate were added thereto and the reaction mixture was heated at 130° C. in a CEM Discover microwave at 200 watts for 1 h. The cooled reaction mixture was concentrated under reduced pressure and the residue was purified chromatographically by MPLC. This gave, in total, 2 mg (100% pure, 2.2% of theory) of the title compound (39).

1H-NMR (601.6 MHz, CDCl$_3$): δ=9.341(5.1); 9.338(5.0); 8.781(3.5); 8.775(3.6); 8.426(2.9); 8.423(3.9); 8.420(2.8); 8.413(3.1); 8.410(4.0); 8.407(2.8); 8.299(16.0); 7.484(3.2); 7.476(3.3); 7.471(3.3); 7.463(3.1); 7.432(0.6); 7.261(86.9); 7.084(0.5); 5.299(2.5); 3.958(15.5); 3.946(15.6); 3.278 (0.4); 3.269(0.5); 3.266(0.4); 3.257(0.4); 2.232(0.4); 2.220 (0.6); 2.207(0.4); 1.637(0.4); 1.558(13.5); 1.445(0.4); 1.368 (0.5); 1.360(0.9); 1.355(1.3); 1.352(0.9); 1.347(2.2); 1.342 (2.1); 1.339(1.8); 1.334(3.5); 1.329(2.0); 1.326(2.4); 1.321 (2.7); 1.313(2.0); 1.309(1.8); 1.301(1.4); 1.255(7.8); 0.892 (1.0); 0.881(1.8); 0.869(1.1); 0.856(0.4); 0.841(0.4); 0.715 (2.2); 0.707(6.7); 0.705(7.1); 0.697(3.5); 0.694(7.0); 0.692 (6.7); 0.684(2.5); 0.577(0.4); 0.575(0.4); 0.564(0.4); 0.562 (0.4); 0.491(2.4); 0.483(8.8); 0.473(8.4); 0.465(2.0); 0.276 (0.4); 0.267(0.5); 0.097(0.4); 0.005(2.9); 0.000(86.6); −0.006(3.2); −0.100(0.4)

Preparation Example 14: N,N-Dimethyl-3-[7-oxo-2-(pyridin-3-yl)[1,3]thiazolo[4,5-d]pyrimidin-6(7H)-yl]benzenesulphonamide (42)

Step 1: 4-Amino-N-[3-(dimethylsulphamoyl)phenyl]-2-(pyridin-3-yl)-1,3-thiazole-5-carboxamide (II-42)

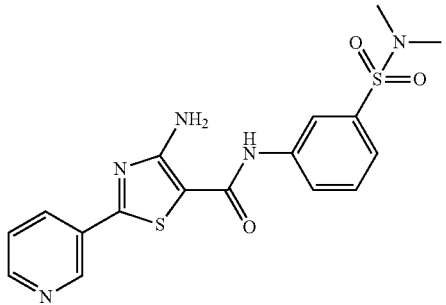 [SMILES: CN(C)S(=O)(=O)c1cccc(NC(=O)c2sc(-c3cccnc3)nc2N)c1]

Under argon, 9.0 ml of a 2M trimethylaluminium solution (18.1 mmol) in toluene were slowly added dropwise with ice cooling to 3.6 g (18.1 mmol) of 3-amino-N,N-dimethylbenzenesulphonamide in 200 ml of 1,2-dichloroethane, and the mixture was stirred at room temperature for 60 min 1.5 g (6.02 mmol) of ethyl 4-amino-2-(pyridin-3-yl)-1,3-thiazole-5-carboxylate (III-1) were then added, and the reaction mixture was subsequently heated under reflux overnight. After cooling, the reaction mixture was carefully discharged into a 10% potassium sodium tartrate solution (about 250 ml). The mixture was extracted three times with methylene chloride, and the combined organic phases were dried over sodium sulphate, filtered and concentrated. The residue was stirred with a little acetonitrile to give a suspension. The insoluble portion was washed with n-pentane, filtered off with suction and dried under reduced pressure. The solid was then purified by MPLC using the mobile phase cyclohexane/ethyl acetate. This gave 340 mg (100% pure, 14.0% of theory) of the title compound (II-42).

1H-NMR (400.0 MHz, d₆-DMSO): δ=9.997(1.7); 9.107 (1.2); 9.102(1.3); 8.745(0.8); 8.742(0.9); 8.734(0.9); 8.731 (0.9); 8.279(0.4); 8.275(0.7); 8.271(0.5); 8.259(0.5); 8.255 (0.8); 8.251(0.5); 8.169(1.5); 8.062(0.6); 8.040(0.7); 7.614 (1.2); 7.603(0.7); 7.594(1.8); 7.583(0.7); 7.574(0.8); 7.424 (0.9); 7.404(0.7); 7.322(1.9); 3.320(8.0); 2.638(16.0); 2.507 (14.9); 2.503(19.6); 2.499(15.3); 1.989(0.9); 1.176(0.5); 0.000(0.4)

Step 2: N,N-Dimethyl-3-[7-oxo-2-(pyridin-3-yl)[1,3]thiazolo[4,5-d]pyrimidin-6(7H)-yl]benzenesulphonamide (42)

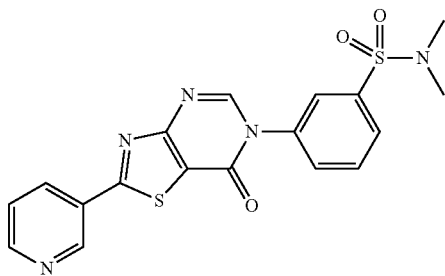 [SMILES: CN(C)S(=O)(=O)c1cccc(-n2cnc3nc(-c4cccnc4)sc3c2=O)c1]

320 mg (0.79 mmol) of 4-amino-N-[3-(dimethylsulphamoyl)phenyl]-2-(pyridin-3-yl)-1,3-thiazole-5-carboxamide (II-42) were initially charged in N,N-dimethylacetamide. 68 mg (0.40 mmol) of p-toluenesulphonic acid and 260 mg (1.75 mmol) of triethyl orthoformate were added thereto and the reaction mixture was heated at 130° C. in a CEM Discover microwave at 200 watts for 1 h. The cooled reaction mixture was concentrated under reduced pressure, and the residue was triturated with acetonitrile and the product was filtered off as a solid. The solid was then dried by pressing it onto a clay plate and purified by MPLC using the mobile phase n-hexane/ethyl acetate. This gave 320 mg (100% pure, 97.6% of theory) of the title compound (42).

1H-NMR (400.0 MHz, d₆-DMSO): δ=9.350(1.3); 9.345 (1.3); 8.835(0.9); 8.831(1.0); 8.823(1.0); 8.819(1.0); 8.714 (3.3); 8.560(0.5); 8.556(0.7); 8.551(0.5); 8.540(0.6); 8.535 (0.8); 8.531(0.5); 8.055(1.6); 7.967(0.6); 7.962(0.4); 7.948 (1.0); 7.944(0.7); 7.929(0.5); 7.925(0.4); 7.909(1.4); 7.894 (1.3); 7.875(1.1); 7.856(0.4); 7.680(0.7); 7.668(0.7); 7.660 (0.7); 7.648(0.7); 3.320(7.9); 2.681(16.0); 2.507(13.0); 2.502(16.4); 2.498(12.5); 0.000(16.1)

Preparation Example 15: 6-{2,4-Dimethyl-5-[(2,2,2-trifluoroethyl)sulphinyl]phenyl}-2-(pyridin-3-yl)[1,3]thiazolo[4,5-d]pyrimidin-7(6H)-one (50)

Step 1: 4-Amino-N-{2,4-dimethyl-5-[(2,2,2-trifluoroethyl)sulphanyl]phenyl}-2-(pyridin-3-yl)-1,3-thiazole-5-carboxamide (II-49)

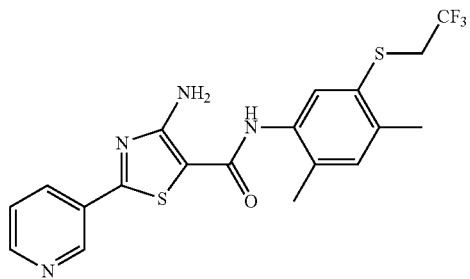 [SMILES: Cc1cc(C)c(SCC(F)(F)F)cc1NC(=O)c1sc(-c2cccnc2)nc1N]

Under argon, 1.5 ml of a 2M trimethylaluminium solution (3.01 mmol) in toluene were slowly added dropwise with ice cooling to 708 mg (3.01 mmol) of 2,4-dimethyl-5-[(2,2,2-trifluoroethyl)sulphanyl]aniline in 1,2-dichloroethane, and the mixture was stirred at room temperature for 30 min 250 mg (1.00 mmol) of ethyl 4-amino-2-(pyridin-3-yl)-1,3-thiazole-5-carboxylate (III-1) were then added, and the reaction mixture was subsequently heated under reflux overnight. After cooling, the reaction mixture was carefully discharged into a 10% potassium sodium tartrate solution (about 120 ml). The mixture was extracted three times with methylene chloride, and the combined organic phases were dried over sodium sulphate, filtered and concentrated. The residue was stirred with a little acetonitrile to give a suspension. The insoluble portion was filtered off with suction and dried under reduced pressure. This gave 158 mg (100% pure, 35.9% of theory) of the title compound (II-49).

1H-NMR (400.0 MHz, d₆-DMSO): δ=9.328(4.1); 9.086 (3.2); 9.081(3.1); 8.729(2.3); 8.726(2.4); 8.717(2.4); 8.714 (2.4); 8.259(1.3); 8.254(1.8); 8.249(1.3); 8.239(1.4); 8.234 (1.9); 8.229(1.3); 7.598(1.7); 7.586(1.7); 7.579(1.7); 7.566 (1.6); 7.468(5.9); 7.174(5.0); 7.133(5.2); 3.878(1.2); 3.852 (3.8); 3.826(4.0); 3.800(1.4); 3.330(19.9); 2.507(38.9); 2.503(48.8); 2.499(36.6); 2.365(14.9); 2.330(0.4); 2.325 (0.3); 2.163(16.0); 0.000(40.2)

Step 2: 6-{2,4-Dimethyl-5-[(2,2,2-trifluoroethyl)sulphanyl]phenyl}-2-(pyridin-3-yl)[1,3]thiazolo[4,5-d]pyrimidin-7(6H)-one (49)

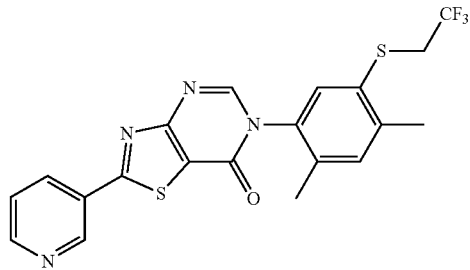

600 mg (1.37 mmol) of 4-amino-N-{2,4-dimethyl-5-[(2,2,2-trifluoroethyl)sulphanyl]phenyl}-2-(pyridin-3-yl)-1,3-thiazole-5-carboxamide (II-49) were initially charged in 15 ml (90.2 mmol) of triethyl orthoformate. 118 mg (0.68 mmol) of p-toluenesulphonic acid were added and the reaction mixture was heated at 170° C. in a CEM Discover microwave for 2 h. The cooled reaction mixture was concentrated under reduced pressure and purified chromatographically by MPLC using the mobile phase cyclohexane/ethyl acetate. This gave, in total, 200 mg (95.3% pure, 31.1% of theory) of the title compound (49).

1H-NMR (400.0 MHz, d₆-DMSO): δ=9.347(2.9); 9.342 (3.0); 8.838(2.3); 8.834(2.4); 8.826(2.4); 8.822(2.5); 8.558 (1.3); 8.554(1.9); 8.548(1.4); 536(10.2); 8.528(1.5); 8.317 (0.8); 7.924(0.4); 7.683(1.9); 7.675(6.4); 7.665(2.0); 7.651 (1.5); 7.360(4.7); 6.025(1.0); 4.055(0.6); 4.038(2.6); 4.020 (2.4); 4.014(3.6); 4.002(0.9); 3.988(3.6); 3.962(1.3); 3.855 (0.8); 3.837(0.8); 3.392(0.3); 3.374(0.5); 3.332(421.8); 2.676(1.7); 2.671(2.3); 2.667(1.7); 2.525(5.6); 2.511(131.6); 2.507(269.9); 2.502(357.0); 2.498(264.5); 2.494(133.5); 2.407(15.0); 2.365(0.4); 2.334(1.8); 2.329(2.4); 2.325(1.8); 2.078(16.0); 1.989(7.6); 1.890(0.3); 1.398(1.9); 1.235(0.6);

1.193(2.1); 1.175(4.1); 1.157(2.1); 1.100(0.8); 1.083(1.5); 1.065(0.8); 0.146(0.5); 0.008(3.7); 0.000(116.2); −0.008 (4.9); −0.150(0.5)

Step 3: 6-{2,4-Dimethyl-5-[(2,2,2-trifluoroethyl) sulphinyl]phenyl}-2-(pyridin-3-yl)[1,3]thiazolo[4,5-d]pyrimidin-7(6H)-one (50)

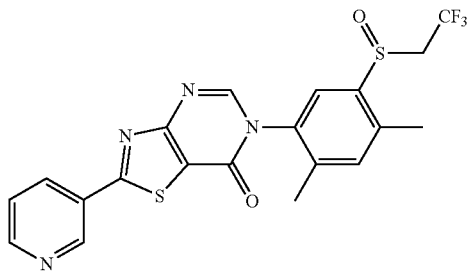 [SMILES: Cc1cc(C)c(S(=O)CC(F)(F)F)cc1-n1cnc2nc(-c3cccnc3)sc2c1=O]

At 0° C., 127 mg (77% strength, 0.57 mmol) of meta-chloroperbenzoic acid were added to a solution of 250.0 mg (0.56 mmol) of 6-{2,4-dimethyl-5-[(2,2,2-trifluoroethyl)sulphanyl]phenyl}-2-(pyridin-3-yl)[1,3]thiazolo[4,5-d]pyrimidin-7(6H)-one (49) in 10 ml of dichloromethane. The reaction mixture was stirred at room temperature for 1 hour, and aqueous sodium bisulphite solution was then added. The organic phase was separated off and then washed with saturated sodium carbonate solution and dried over sodium sulphate. After evaporation of the solvent, the residue was purified chromatographically by MPLC using the mobile phase cyclohexane/ethyl acetate. This gave 154 mg (99.0% pure, 58.88% of theory) of the title compound (50).

1H-NMR (400.0 MHz, $d_6$-DMSO): δ=9.351(4.6); 9.346 (4.6); 8.839(3.4); 8.835(3.7); 8.827(3.6); 8.823(3.7); 8.591 (14.3); 8.561(1.9); 8.556(2.7); 8.551(1.9); 8.541(2.0); 8.536 (2.8); 8.531(1.9); 8.317(1.3); 7.937(6.3); 7.928(4.2); 7.685 (2.6); 7.673(2.6); 7.667(2.5); 7.653(2.4); 7.496(3.0); 7.470 (4.4); 4.323(0.5); 4.295(0.6); 4.286(0.7); 4.259(0.7); 4.178 (0.6); 4.171(0.6); 4.151(1.8); 4.144(1.8); 4.124(1.8); 4.117 (1.8); 4.097(0.7); 4.090(0.6); 4.055(0.4); 4.037(1.0); 4.020 (1.0); 4.002(0.4); 3.977(0.7); 3.951(0.8); 3.940(0.7); 3.924 (0.3); 3.914(0.7); 3.372(0.9); 3.332(833.0); 2.676(2.9); 2.671(3.9); 2.667(2.9); 2.525(9.7); 2.507(449.3); 2.502 (587.2); 2.498(437.0); 2.451(12.1); 2.446(16.0); 2.408(0.8); 2.353(0.6); 2.334(3.2); 2.329(4.0); 2.325(3.0); 2.279(0.4); 2.258(0.5); 2.188(15.9); 2.182(12.0); 1.989(4.2); 1.193 (1.1); 1.175(2.3); 1.157(1.1); 0.146(0.8); 0.008(6.5); 0.000 (190.8); −0.008(8.2); −0.150(0.9)

Preparation Example 16: 2-({4-Fluoro-2-methyl-5-[7-oxo-2-(pyridin-3-yl)[1,3]thiazolo[4,5-d]pyrimidin-6(7H)-yl]phenyl}sulphinyl)-N,N-dimethylacetamide (55)

Step 1: 2-[(5-Amino-4-fluoro-2-methylphenyl)sulphanyl]-N,N-dimethylacetamide

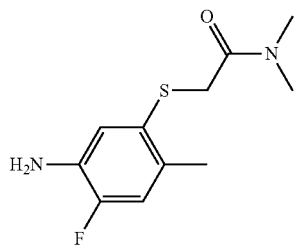 [SMILES: Cc1cc(F)c(N)cc1SCC(=O)N(C)C]

100 ml of dry acetone were added to 1.50 g (9.54 mmol) of 5-amino-4-fluoro-2-methylbenzenethiol, 1.28 g (10.50 mmol) of 2-chloro-N,N-dimethylacetamide and 6.22 g (19.08 mmol) of caesium carbonate, and the mixture was stirred under reflux overnight. The cooled reaction mixture was added to a mixture of ethyl acetate and sodium carbonate and the organic phase was separated off. The aqueous phase was subsequently extracted repeatedly with ethyl acetate, and the combined organic phases were dried over magnesium sulfate, filtered and concentrated. This gave 2.10 mg (90.0% pure, 81.75% of theory) of the title compound 2-[(5-amino-4-fluoro-2-methylphenypsulphanyl]-N,N-dimethylacetamide.

1H-NMR (601.6 MHz, CDCl$_3$): δ=7.264(2.5); 6.995(2.3); 6.980(2.3); 6.836(1.7); 6.816(1.7); 4.079(0.4); 3.605(10.1); 3.098(0.6); 3.034(0.4); 3.025(16.0); 2.991(0.6); 2.968(0.4); 2.951(14.4); 2.313(13.0); 2.170(1.4); 0.000(2.4)

Step 2: 4-Amino-N-(5-{[2-(dimethylamino)-2-oxo-ethyl]sulphanyl}-2-fluoro-4-methylphenyl)-2-(pyridin-3-yl)-1,3-thiazole-5-carboxamide (II-54)

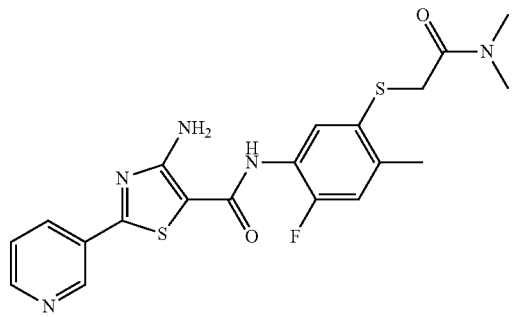 [SMILES: Cc1cc(F)c(NC(=O)c2sc(-c3cccnc3)nc2N)cc1SCC(=O)N(C)C]

Under argon, 3.94 ml of a 2M trimethylaluminium solution (7.88 mmol) in toluene were slowly added dropwise with ice cooling to 2.10 g (7.88 mmol) of 2-[(5-amino-4-fluoro-2-methylphenyl)sulphanyl]-N,N-dimethylacetamide (see Preparation Example 16, Step 1) in 150 ml of 1,2-dichloroethane, and the mixture was stirred at room temperature for 60 min 655 mg (2.63 mmol) of ethyl 4-amino-2-(pyridin-3-yl)-1,3-thiazole-5-carboxylate (III-1) were then added, and the reaction mixture was subsequently heated under reflux overnight. After cooling, the reaction mixture was carefully discharged into a 10% potassium sodium tartrate solution (about 200 ml). The mixture was extracted three times with methylene chloride, and the combined organic phases were dried over magnesium sulphate, filtered and concentrated. The residue was then purified chromatographically by MPLC using the mobile phase cyclohexane/ethyl acetate. This gave 370 mg (47.0% pure, 14.86% of theory) of the title compound (II-54) which was directly reacted further in Step 3 without further purification.

HPLC-MS (ESI positive, m/z): [M+H]=446.0

Step 3: 2-({4-Fluoro-2-methyl-5-[7-oxo-2-(pyridin-3-yl)[1,3]thiazolo[4,5-d]pyrimidin-6(7H)-yl]phenyl}sulphanyl)-N,N-dimethylacetamide (54)

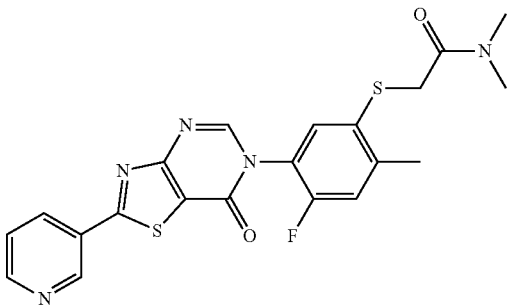 [SMILES: Cc1cc(F)c(-n2cnc3nc(-c4cccnc4)sc3c2=O)cc1SCC(=O)N(C)C]

370 mg (47% pure, 0.39 mmol) of 4-amino-N-(5-{[2-(dimethylamino)-2-oxoethyl]sulphanyl}-2-fluoro-4-methylphenyl)-2-(pyridin-3-yl)-1,3-thiazole-5-carboxamide (II-54) were initially charged in 1 ml of N,N-dimethylacetamide. 34 mg (0.20 mmol) of p-toluenesulphonic acid and 174 mg (1.17 mmol) of triethyl orthoformate were added thereto and the reaction mixture was heated at 130° C. in a CEM Discover microwave at 200 watts for 1 h. The cooled reaction mixture was concentrated under reduced pressure, and the residue was triturated with acetonitrile and the product was filtered off as a solid. The solid was then dried by pressing it onto a clay plate and purified by MPLC using the mobile phase acetonitrile/water. This gave 170 mg (100% pure, 95.61% of theory) of the title compound (54).

1H-NMR (400.0 MHz, $d_6$-DMSO): δ=9.347(2.8); 9.342 (2.6); 8.837(2.0); 8.825(2.0); 8.668(5.5); 8.552(1.6); 8.532 (1.6); 8.141(0.9); 7.718(2.4); 7.700(2.4); 7.682(1.5); 7.669 (1.5); 7.662(1.4); 7.649(1.3); 7.448(2.1); 7.422(2.1); 5.754 (0.6); 4.011(8.8); 3.320(45.4); 3.027(16.0); 2.891(0.5); 2.832(14.9); 2.731(0.5); 2.670(0.6); 2.502(95.0); 2.406 (12.3); 2.328(0.6); 0.000(4.0)

Step 4: 2-({4-Fluoro-2-methyl-5-[7-oxo-2-(pyridin-3-yl)[1,3]thiazolo[4,5-d]pyrimidin-6(7H)-yl]phenyl}sulphinyl)-N,N-dimethylacetamide (55)

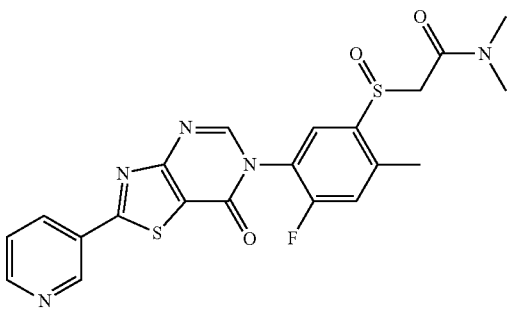 [SMILES: Cc1cc(F)c(-n2cnc3nc(-c4cccnc4)sc3c2=O)cc1S(=O)CC(=O)N(C)C]

At 0° C., 81 mg (77% strength, 0.36 mmol) of meta-chloroperbenzoic acid were added to a solution of 170 mg (0.36 mmol) of 2-({4-fluoro-2-methyl-5-[7-oxo-2-(pyridin-3-yl)[1,3]thiazolo[4,5-d]pyrimidin-6(7H)-yl]phenyl}sulphanyl)-N,N-dimethylacetamide (54) in 1 ml of dichloromethane. The reaction mixture was stirred at room temperature for 1 hour, and aqueous sodium carbonate solution was then added. The aqueous phase was separated off and extracted repeatedly with dichloromethane, and the combined organic phases were dried, filtered and concentrated. The residue was then purified chromatographically by MPLC using the mobile phase cyclohexane/ethyl acetate. This gave 119 mg (100% pure, 71.2% of theory) of the title compound (55).

1H-NMR (400.0 MHz, $d_6$-DMSO): δ=9.350(3.2); 9.345 (3.1); 8.838(2.2); 8.835(2.3); 8.826(2.3); 8.823(2.3); 8.722 (6.2); 8.556(1.8); 8.540(1.4); 8.535(1.9); 8.531(1.3); 8.139 (4.6); 8.119(2.9); 7.685(1.7); 7.672(1.7); 7.665(1.7); 7.653 (1.5); 7.568(2.4); 7.541(2.4); 4.185(1.3); 4.148(2.5); 4.086 (1.2); 4.047(0.6); 3.340(160.4); 2.955(16.0); 2.863(15.8); 2.672(0.6); 2.507(78.3); 2.503(97.2); 2.473(15.1); 2.330 (0.6); 0.000(3.2)

Preparation Example 17: 6-{2-Fluoro-4-methyl-5-[(2,2,2-trifluoroethyl)sulphinyl]phenyl}-5-methyl-2-(pyridin-3-yl)[1,3]thiazolo[4,5-d]pyrimidin-7(6H)-one (57)

Step 1: 6-{2-Fluoro-4-methyl-5-[(2,2,2-trifluoroethyl)sulphanyl]phenyl}-5-methyl-2-(pyridin-3-yl)[1,3]thiazolo[4,5-d]pyrimidin-7(6H)-one (56)

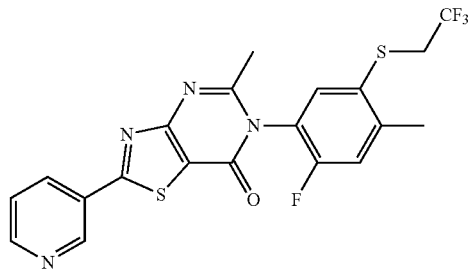 [SMILES: Cc1cc(F)c(-n2c(C)nc3nc(-c4cccnc4)sc3c2=O)cc1SCC(F)(F)F]

200 mg (0.45 mmol) of 4-amino-N-{2-fluoro-4-methyl-5-[(2,2,2-trifluoroethyl)sulphanyl]phenyl}-2-(pyridin-3-yl)-1,3-thiazole-5-carboxamide (II-21) were initially charged in 1 ml of N,N-dimethylacetamide. 39 mg (0.23 mmol) of p-toluenesulphonic acid and 220 mg (1.36 mmol) of triethyl orthoacetate were added and the reaction mixture was heated at 130° C. in a CEM Discover microwave at 200 watts for 30 min. The cooled reaction mixture was concentrated under high vacuum. The residue was then purified by MPLC using the mobile phase acetonitrile/water. This gave 30 mg (100% pure, 14.2% of theory) of the title compound (56).

1H-NMR (400.0 MHz, $d_6$-DMSO): δ=9.333(2.4); 9.328 (2.4); 8.834(1.8); 8.830(2.0); 8.822(1.9); 8.818(2.0); 8.535 (1.1); 8.531(1.4); 8.526(1.1); 8.515(1.2); 8.510(1.5); 8.506 (1.1); 7.939(2.4); 7.920(2.4); 7.680(1.4); 7.668(1.4); 7.661 (1.4); 7.648(1.3); 7.541(2.1); 7.515(2.1); 4.085(0.5); 4.071 (0.5); 4.060(0.6); 4.046(1.3); 4.037(0.6); 4.021(1.3); 4.012 (1.3); 3.995(0.7); 3.986(1.3); 3.972(0.5); 3.960(0.5); 3.946 (0.5); 3.329(49.4); 2.676(0.4); 2.672(0.5); 2.668(0.4); 2.525 (1.3); 2.512(29.6); 2.507(59.8); 2.503(79.0); 2.498(58.4); 2.494(29.1); 2.469(13.3); 2.443(0.6); 2.417(0.6); 2.339 (0.3); 2.334(0.5); 2.329(0.6); 2.325(0.5); 2.302(0.4); 2.281 (16.0); 2.076(1.0); 0.008(1.9); 0.000(57.6); −0.009(2.3)

Step 2: 6-{2-Fluoro-4-methyl-5-[(2,2,2-trifluoroethyl)sulphinyl]phenyl}-5-methyl-2-(pyridin-3-yl)[1,3]thiazolo[4,5-d]pyrimidin-7(6H)-one (57)

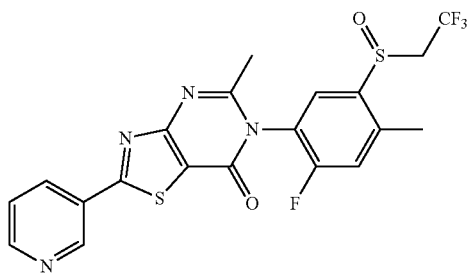 [SMILES: Cc1cc(F)c(-n2c(C)nc3nc(-c4cccnc4)sc3c2=O)cc1S(=O)CC(F)(F)F]

At 0° C., 12 mg (77% strength, 0.06 mmol) of meta-chloroperbenzoic acid were added to a solution of 25 mg (0.06 mmol) of 6-{2-fluoro-4-methyl-5-[(2,2,2-trifluoroethyl)sulphanyl]phenyl}-5-methyl-2-(pyridin-3-yl)[1,3]thiazolo[4,5-d]pyrimidin-7(6H)-one (56) in 1 ml of dichloromethane. The reaction mixture was stirred at room temperature for 1 hour, and aqueous sodium carbonate solution was then added. The aqueous phase was separated off and extracted repeatedly with dichloromethane, and the combined organic phases were dried, filtered and concentrated. This gave 14 mg (88.0% pure, 47.7% of theory) of the title compound (57).

1H-NMR (601.6 MHz, CDCl$_3$): δ=9.363(2.0); 8.807(1.5); 8.469(0.8); 8.466(1.1); 8.463(0.8); 8.452(1.9); 8.441(0.9); 8.438(1.1); 8.435(0.8); 8.065(1.7); 8.029(1.8); 8.017(1.8); 8.003(1.8); 7.991(1.8); 7.979(1.0); 7.966(1.1); 7.556(0.7); 7.554(0.7); 7.542(0.9); 7.541(0.9); 7.526(0.9); 7.519(1.3); 7.513(1.7); 7.507(1.3); 7.500(0.9); 7.415(1.0); 7.402(1.7); 7.389(0.8); 7.304(1.8); 7.302(1.9); 7.288(1.9); 7.286(1.8); 7.272(7.2); 5.302(6.3); 3.617(0.5); 3.609(0.4); 3.601(0.6); 3.593(1.0); 3.576(1.1); 3.563(1.1); 3.555(0.3); 3.547(3.0); 3.539(0.6); 3.530(3.1); 3.523(0.8); 3.514(1.2); 3.506(0.7); 2.590(0.5); 2.517(16.0); 2.501(0.6); 2.493(0.4); 2.484(0.3); 2.418(0.7); 2.408(12.8); 2.395(0.6); 2.386(12.7); 2.378 (1.1); 2.369(0.4); 2.356(0.5); 2.352(0.4); 2.344(0.4); 2.332 (0.4); 1.335(0.5); 1.329(0.3); 1.306(0.6); 1.295(0.9); 1.286 (1.3); 1.283(1.3); 1.271(1.3); 1.255(6.2); 1.232(0.7); 1.221 (0.5); 1.212(0.5); 0.891(0.8); 0.880(1.4); 0.868(1.0); 0.856 (0.5); 0.843(0.9); 0.841(0.9); 0.834(0.9); 0.005(0.5); 0.000 (14.7); −0.006(0.7)

Preparation Example 18: 3-{2-Fluoro-4-methyl-5-[(2,2,2-trifluoroethyl)sulphinyl]phenyl}-6-(pyridin-3-yl)[1,3]thiazolo[4,5-d][1,2,3]triazin-4(3H)-one (59)

Step 2: 3-{2-Fluoro-4-methyl-5-[(2,2,2-trifluoroethyl)sulphanyl]phenyl}-6-(pyridin-3-yl)[1,3]thiazolo[4,5-d][1,2,3]triazin-4(3H)-one (58)

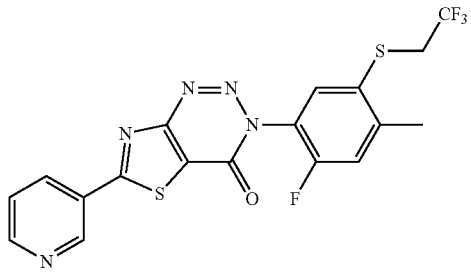 [SMILES: Cc1cc(F)c(-n2nnc3nc(-c4cccnc4)sc3c2=O)cc1SCC(F)(F)F]

160 mg (0.36 mmol) of 4-amino-N-{2-fluoro-4-methyl-5-[(2,2,2-trifluoroethyl)sulphanyl]phenyl}-2-(pyridin-3-yl)-1,3-thiazole-5-carboxamide (II-21) were initially charged in 4 ml of concentrated hydrochloric acid. 212 mg (3.07 mmol) of sodium nitrite, dissolved in 4 ml of water, were then added dropwise to this mixture, and the mixture was stirred at 70° C. for 4 h. The cooled mixture was then added to saturated sodium carbonate solution and extracted repeatedly with dichloromethane. The combined organic phases were dried over magnesium sulphate, filtered and concentrated. This gave 112 mg (90.0% pure, 61.5% of theory) of the title compound (58).

1H-NMR (400.0 MHz, DMSO): δ=9.430(10.3); 9.425 (10.4); 8.891(8.1); 8.887(8.8); 8.879(8.5); 8.875(8.7); 8.651 (4.7); 8.646(6.4); 8.641(4.7); 8.631(5.1); 8.625(6.5); 8.621 (4.7); 8.317(0.4); 8.260(1.0); 8.242(1.1); 7.992(9.9); 7.973 (9.9); 7.729(6.1); 7.717(6.0); 7.709(6.0); 7.697(6.2); 7.673 (0.9); 7.583(8.6); 7.556(8.5); 5.758(16.0); 4.361(0.7); 4.351 (0.4); 4.344(0.4); 4.324(0.4); 4.086(0.4); 4.059(0.4); 4.049 (0.4); 4.018(4.1); 3.993(12.7); 3.967(13.1); 3.941(4.5); 3.331(218.6); 2.677(1.1); 2.672(1.5); 2.668(1.1); 2.512 (92.5); 2.508(154.3); 2.503(197.3); 2.499(145.6); 2.495 (73.3); 2.374(0.4); 2.353(0.4); 2.334(1.0); 2.330(1.3); 2.326 (1.0); 1.343(0.4); 1.326(0.8); 1.308(0.4); 0.146(0.4); 0.008 (3.0); 0.000(84.9); −0.008(3.4); −0.150(0.4)

Step 2: 3-{2-Fluoro-4-methyl-5-[(2,2,2-trifluoroethyl)sulphinyl]phenyl}-6-(pyridin-3-yl)[1,3]thiazolo[4,5-d][1,2,3]triazin-4(3H)-one (59)

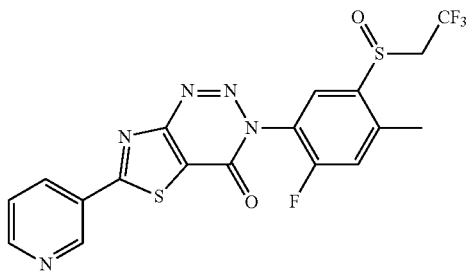 [SMILES: Cc1cc(F)c(-n2nnc3nc(-c4cccnc4)sc3c2=O)cc1S(=O)CC(F)(F)F]

At 0° C., 44 mg (77% strength, 0.19 mmol) of meta-chloroperbenzoic acid were added to a solution of 96 mg (90% pure, 0.19 mmol) of 3-{2-fluoro-4-methyl-5-[(2,2,2-trifluoroethyl)sulphanyl]phenyl}-6-(pyridin-3-yl)[1,3]thiazolo[4,5-d][1,2,3]triazin-4(3H)-one (58) in 1 ml of dichloromethane. The reaction mixture was stirred at room temperature for 40 minutes, and aqueous sodium carbonate solution was then added. The aqueous phase was separated off and extracted repeatedly with dichloromethane, and the combined organic phases were dried, filtered and concentrated. The residue was then purified by MPLC using the mobile phase acetonitrile/water. This gave 30 mg (100% pure, 33.5% of theory) of the title compound (59).

1H-NMR (400.0 MHz, DMSO): δ=9.432(5.9); 9.428 (6.0); 8.891(4.5); 8.887(4.8); 8.879(4.8); 8.875(4.8); 8.652 (2.6); 8.648(3.5); 8.642(2.6); 8.632(2.8); 8.626(3.7); 8.622 (2.7); 8.260(5.9); 8.241(6.0); 7.729(3.3); 7.717(3.3); 7.709 (3.5); 7.699(7.6); 7.673(4.8); 5.758(16.0); 4.415(0.5); 4.388 (1.7); 4.378(0.8); 4.360(2.0); 4.351(2.3); 4.333(0.8); 4.323 (2.3); 4.296(0.7); 4.112(0.6); 4.085(2.0); 4.075(0.7); 4.058 (2.3); 4.048(1.9); 4.031(0.9); 4.021(1.8); 3.994(0.6); 3.331 (101.6); 2.676(0.7); 2.672(1.0); 2.668(0.8); 2.507(117.2);

Preparation Example 19: 2-(Pyridin-3-yl)-6-{4-[(trifluoromethyl)sulphinyl]phenyl}[1,3]thiazolo[4,5-d]pyrimidin-7(6H)-one (63)

Step 1: 4-Amino-2-(pyridin-3-yl)-N-{4-[(trifluoromethyl)sulphanyl]phenyl}-1,3-thiazole-5-carboxamide (II-62)

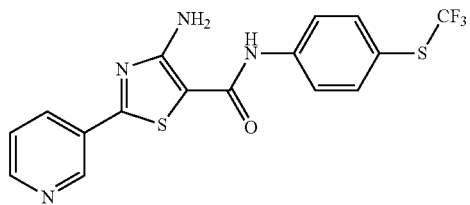 [SMILES: Nc1nc(-c2cccnc2)sc1C(=O)Nc1ccc(SC(F)(F)F)cc1]

Under argon, 3.0 ml of a 2M trimethylaluminium solution (6.0 mmol) in toluene were slowly added dropwise with ice cooling to 1.16 g (6.0 mmol) of 4-[(trifluoromethyl)sulphanyl]aniline in 50 ml of 1,2-dichloroethane, and the mixture was stirred at room temperature for 1 hour. 500 mg (2.0 mmol) of ethyl 4-amino-2-(pyridin-3-yl)-1,3-thiazole-5-carboxylate (III-1) were then added, and the reaction mixture was subsequently heated under reflux overnight. After cooling, the reaction mixture was carefully discharged into a 10% potassium sodium tartrate solution (about 120 ml). The mixture was extracted three times with methylene chloride, and the combined organic phases were dried over magnesium sulphate, filtered and concentrated. The residue was stirred with a little acetonitrile to give a suspension. The insoluble fraction was filtered off with suction and then purified by MPLC using the mobile phase acetonitrile/water. This gave 130 mg (99.0% pure, 16.2% of theory) of the title compound (II-62).

1H-NMR (400.0 MHz, $d_6$-DMSO): δ=9.958(9.7); 9.780 (0.6); 9.109(7.3); 9.104(7.2); 9.103(7.2); 9.096(0.8); 8.746 (5.4); 8.742(6.0); 8.734(6.2); 8.730(6.1); 8.283(3.0); 8.278 (4.1); 8.273(3.4); 8.263(3.6); 8.257(4.6); 8.253(3.5); 7.889 (1.4); 7.883(12.5); 7.878(4.6); 7.866(4.6); 7.861(16.0); 7.854(2.0); 7.730(0.9); 7.725(0.3); 7.713(0.3); 7.707(1.1); 7.679(12.9); 7.657(10.8); 7.615(3.8); 7.613(4.1); 7.601 (4.0); 7.595(3.9); 7.593(4.0); 7.583(3.6); 7.581(3.9); 7.384 (1.2); 7.379(0.5); 7.361(1.4); 7.337(10.7); 7.267(0.8); 3.329 (92.9); 2.677(0.8); 2.672(1.1); 2.668(0.8); 2.525(2.6); 2.512 (58.6); 2.508(119.3); 2.503(158.4); 2.499(116.9); 2.494 (58.1); 2.334(0.7); 2.330(1.0); 2.325(0.8); 2.321(0.4); 2.076 (1.4); 0.146 (0.6); 0.008(4.8); 0.000(137.9); −0.009(5.2); −0.150(0.6)

Step 2: 2-(Pyridin-3-yl)-6-{4-[(trifluoromethyl)sulphanyl]phenyl}[1,3]thiazolo[4,5-d]pyrimidin-7(6H)-one (62)

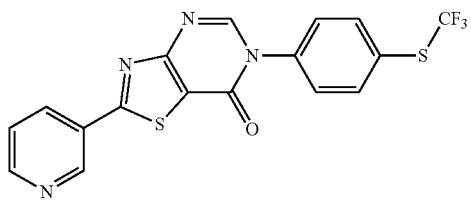 [SMILES: O=c1c2sc(-c3cccnc3)nc2ncn1-c1ccc(SC(F)(F)F)cc1]

65 mg (0.16 mmol) of 4-amino-2-(pyridin-3-yl)-N-{4-[(trifluoromethyl)sulphanyl]phenyl}-1,3-thiazole-5-carboxamide (II-62) were initially charged in 5 ml of absolute ethanol 14 mg (0.08 mmol) of p-toluenesulphonic acid and 72 mg (0.49 mmol) of triethyl orthoformate were added and the reaction mixture was heated at 80° C. in a CEM Discover microwave for 15 min. The reaction mixture was cooled, concentrated under reduced pressure and taken up in 3 ml of dichloromethane. The solution was washed with 2 ml of saturated sodium carbonate solution and the organic phase was separated off, filtered and dried. The residue was then purified chromatographically by MPLC. This gave, in total, 20 mg (86.0% pure, 26.1% of theory) of the title compound (62).

1H-NMR (400.0 MHz, $d_6$-DMSO): δ=9.954(1.2); 9.347 (5.1); 9.343(5.1); 9.341(5.2); 9.106(0.9); 9.100(0.9); 8.835 (3.9); 8.831(4.4); 8.823(4.0); 8.819(4.4); 8.744(0.7); 8.740 (0.8); 8.732(0.8); 8.728(0.8); 8.701(16.0); 8.636(1.4); 8.558 (2.1); 8.552(3.1); 8.548(2.5); 8.538(2.3); 8.532(3.3); 8.528 (2.5); 8.280(0.4); 8.275(0.5); 8.271(0.4); 8.260(0.4); 8.255 (0.6); 8.251(0.4); 7.969(7.3); 7.948(9.3); 7.881(1.5); 7.859 (2.0); 7.806(1.5); 7.799(11.4); 7.795(3.7); 7.783(3.0); 7.778 (9.2); 7.772(1.0); 7.688(0.6); 7.679(4.0); 7.667(4.3); 7.660 (3.6); 7.647(4.4); 7.625(0.4); 7.612(0.5); 7.600(0.5); 7.592 (0.5); 7.579(0.5); 7.333(1.3); 3.324(74.8); 2.676(0.7); 2.671 (0.9); 2.667(0.7); 2.524(2.5); 2.511(45.7); 2.507(92.5); 2.502(124.5); 2.498(94.2); 2.493(47.7); 2.333(0.5); 2.329 (0.8); 2.325(0.6); 1.298(0.5); 1.259(0.7); 1.233(1.0); 0.000 (1.1)

Step 3: 2-(Pyridin-3-yl)-6-{4-[(trifluoromethyl)sulphinyl]phenyl}[1,3]thiazolo[4,5-d]pyrimidin-7(6H)-one (63)

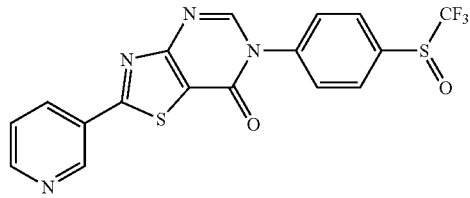 [SMILES: O=c1c2sc(-c3cccnc3)nc2ncn1-c1ccc(S(=O)C(F)(F)F)cc1]

At 0° C., 20 mg (77% strength, 0.09 mmol) of meta-chloroperbenzoic acid were added to a solution of 35.0 mg (0.09 mmol) of 2-(pyridin-3-yl)-6-{4-[(trifluoromethyl)sulphanyl]phenyl}[1,3]thiazolo[4,5-d]pyrimidin-7(6H)-one (62) in 1 ml of dichloromethane. The reaction mixture was stirred at room temperature for 90 minutes, and saturated sodium carbonate solution was then added. The aqueous phase was extracted three times with dichloromethane, and the combined organic phases were dried and filtered. After evaporation of the solvent, the residue was then purified chromatographically using the mobile phase dichloromethane/methanol (30:1). This gave 10 mg (95.0% pure, 26.1% of theory) of the title compound (63).

1H-NMR (400.0 MHz, $d_6$-DMSO): δ=9.344(0.4); 8.925 (9.0); 8.748(0.7); 8.714(16.0); 8.649(1.1); 8.542(0.3); 8.462 (5.6); 8.446(5.9); 8.317(1.5); 8.137(0.4); 8.117(0.7); 8.081 (5.4); 8.061(5.8); 7.970(10.5); 7.950(13.1); 7.793(14.1); 7.772(11.5); 7.689(0.8); 7.666(5.7); 7.647(6.7); 7.629(4.4); 5.757(7.6); 3.507(0.3); 3.487(0.3); 3.447(0.4); 3.439(0.4); 3.409(0.5); 3.326(536.7); 3.245(0.3); 2.840(0.4); 2.820 (0.4); 2.805(0.4); 2.765(0.4); 2.671(8.5); 2.622(1.1); 2.618 (1.1); 2.502(1215.9); 2.329(7.9); 2.184(0.3); 1.355(0.6);

1.299(1.8); 1.259(2.9); 1.235(7.6); 1.166(0.5); 1.149(1.1); 1.066(0.4); 0.854(1.6); 0.843(1.0); 0.834(1.1); 0.814(0.7); 0.784(0.5); 0.146(5.7); 0.083(0.5); 0.000(1101.9); −0.150 (5.9)

Preparation Example 20: 2-(Pyridin-3-yl)-6-{2-[(2,2,2-trifluoroethyl)sulphinyl]phenyl}[1,3]thiazolo[4,5-d]pyrimidin-7(6H)-one (69)

Step 1: 4-Amino-2-(pyridin-3-yl)-N-{2-[(2,2,2-trifluoroethyl)sulphanyl]phenyl}-1,3-thiazole-5-carboxamide (II-68)

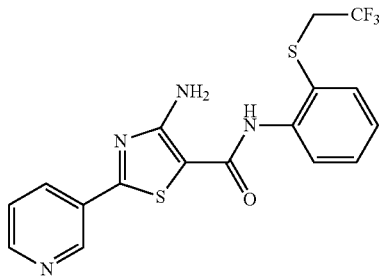 [SMILES: Nc1nc(-c2cccnc2)sc1C(=O)Nc1ccccc1SCC(F)(F)F]

Under argon, 3.6 ml of a 2M trimethylaluminium solution (7.22 mmol) in toluene were slowly added dropwise with ice cooling to 1.50 g (7.22 mmol) of 2-[(2,2,2-trifluoroethyl)sulphinyl]aniline in 50 ml of 1,2-dichloroethane, and the mixture was stirred at room temperature for 1 hour. 600 mg (2.41 mmol) of ethyl 4-amino-2-(pyridin-3-yl)-1,3-thiazole-5-carboxylate (III-1) were then added, and the reaction mixture was subsequently heated under reflux overnight. After cooling, the reaction mixture was carefully discharged into a 10% potassium sodium tartrate solution (about 120 ml). The mixture was extracted three times with methylene chloride, and the combined organic phases were dried over magnesium sulphate, filtered and concentrated. The residue was stirred with a little acetonitrile to give a suspension. The insoluble fraction was filtered off with suction and then purified by MPLC using the mobile phase acetonitrile/water. This gave 240 mg (96.0% pure, 23.3% of theory) of the title compound (II-68).

1H-NMR (400.0 MHz, d$_6$-DMSO): δ=9.458(10.4); 9.104 (6.7); 9.099(6.7); 8.738(5.3); 8.734(5.7); 8.726(5.8); 8.722 (5.6); 8.316(0.4); 8.279(3.0); 8.275(4.2); 8.269(3.1); 8.259 (3.3); 8.254(4.3); 8.249(3.1); 7.661(4.8); 7.644(5.2); 7.641 (5.2); 7.605(3.9); 7.603(3.9); 7.593(3.9); 7.591(3.9); 7.585 (3.9); 7.583(3.8); 7.573(3.7); 7.571(3.6); 7.536(4.8); 7.519 (5.5); 7.517(5.7); 7.365(2.4); 7.362(2.5); 7.346(5.0); 7.343 (5.0); 7.327(3.3); 7.324(3.1); 7.287(3.6); 7.283(3.6); 7.267 (4.9); 7.264(4.9); 7.249(2.2); 7.245(2.1); 7.176(12.1); 4.253 (0.6); 4.235(0.6); 3.944(2.8); 3.918(8.8); 3.892(9.1); 3.866 (3.1); 3.330(242.9); 2.676(0.9); 2.672(1.2); 2.667(0.9); 2.525(2.8); 2.507(127.7); 2.503(166.7); 2.498(124.1); 2.334 (0.9); 2.329(1.2); 2.325(0.9); 2.075(16.0); 1.295(0.6); 1.278 (1.3); 1.260(0.6); 1.233(0.7); 0.008(0.4); 0.000(10.3); −0.008(0.4)

Step 2: 2-(Pyridin-3-yl)-6-{2-[(2,2,2-trifluoroethyl)sulphanyl]phenyl}[1,3]thiazolo[4,5-d]pyrimidin-7(6H)-one (68)

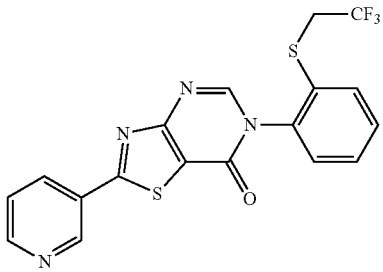 [SMILES: O=c1c2sc(-c3cccnc3)nc2ncn1-c1ccccc1SCC(F)(F)F]

5 ml (30.1 mmol) of triethyl orthoformate were added to 225 mg (0.53 mmol) of 4-amino-2-(pyridin-3-yl)-N-{2-[(2,2,2-trifluoroethyl)sulphanyl]phenyl}-1,3-thiazole-5-carboxamide (II-68) and 45 mg (0.26 mmol) of p-toluenesulphonic acid and the reaction mixture was heated at 170° C. in a CEM Discover microwave for 60 min. The cooled reaction mixture was concentrated under reduced pressure and purified chromatographically by MPLC using the mobile phase cyclohexane/ethyl acetate. This gave, in total, 95 mg (99.0% pure, 42.5% of theory) of the title compound (68).

1H-NMR (400.0 MHz, d$_6$-DMSO): δ=9.348(4.6); 9.344 (4.6); 8.841(3.7); 8.837(4.0); 8.829(4.0); 8.825(4.0); 8.558 (2.5); 8.551(16.0); 8.539(2.6); 8.533(3.3); 8.529(2.4); 7.918 (3.2); 7.915(3.1); 7.899(4.0); 7.688(2.9); 7.686(2.8); 7.676 (2.9); 7.674(2.9); 7.667(5.2); 7.663(4.0); 7.654(4.6); 7.648 (3.9); 7.645(5.9); 7.639(5.5); 7.635(3.0); 7.620(3.2); 7.616 (2.2); 7.598(3.4); 7.595(3.5); 7.579(3.1); 7.576(3.5); 7.561 (1.3); 7.557(1.2); 5.757(3.6); 4.056(0.6); 4.038(1.0); 4.031 (1.1); 4.020(1.3); 4.017(1.0); 4.006(1.3); 3.992(2.6); 3.980 (0.7); 3.967(3.0); 3.944(2.9); 3.930(0.6); 3.918(2.8); 3.905 (1.2); 3.892(1.0); 3.878(1.2); 3.852(0.4); 3.329(31.2); 2.677 (0.4); 2.672(0.5); 2.668(0.4); 2.526(1.3); 2.512(26.5); 2.508 (53.3); 2.503(70.5); 2.499(52.7); 2.495(27.0); 2.335(0.3); 2.330(0.5); 2.325(0.4); 1.990(3.7); 1.397(1.3); 1.299(0.8); 1.259(1.1); 1.250(0.4); 1.234(1.6); 1.193(1.2); 1.176(2.1); 1.158(1.1); 0.146(0.6); 0.008(4.9); 0.000(120.6); −0.008 (6.0); −0.150(0.6)

Step 3: 2-(Pyridin-3-yl)-6-{2-[(2,2,2-trifluoroethyl)sulphinyl]phenyl}[1,3]thiazolo[4,5-d]pyrimidin-7(6H)-one (69)

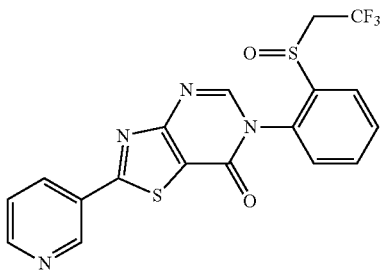 [SMILES: O=c1c2sc(-c3cccnc3)nc2ncn1-c1ccccc1S(=O)CC(F)(F)F]

At 0° C., 42 mg (77% strength, 0.19 mmol) of meta-chloroperbenzoic acid were added to a solution of 80.0 mg (0.18 mmol) of 2-(pyridin-3-yl)-6-{2-[(2,2,2-trifluoroethyl)sulphanyl]phenyl}[1,3]thiazolo[4,5-d]pyrimidin-7(6H)-one

(68) in 1 ml of dichloromethane. The reaction mixture was stirred at room temperature for 30 minutes, and saturated sodium carbonate solution was then added. The aqueous phase was extracted three times with dichloromethane, and the combined organic phases were dried and filtered. After evaporation of the solvent, the residue was then purified chromatographically by MPLC using the mobile phase cyclohexane/ethyl acetate. This gave 10 mg (90.0% pure, 11.3% of theory) of the title compound (69).

1H-NMR (601.6 MHz, CDCl₃): δ=9.372(12.3); 8.822 (9.3); 8.817(9.2); 8.465(7.5); 8.453(8.0); 8.307(16.0); 8.291 (8.4); 8.278(8.2); 8.192(1.6); 8.154(0.9); 7.937(0.8); 7.910 (4.3); 7.898(8.3); 7.885(5.1); 7.837(5.4); 7.825(9.3); 7.813 (6.0); 7.583(0.8); 7.525(6.1); 7.516(7.8); 7.513(7.9); 7.505 (6.3); 7.451(9.5); 7.439(8.9); 7.263(66.7); 7.086(0.4); 5.301 (4.1); 4.129(1.1); 4.112(3.4); 4.094(4.4); 4.072(3.5); 4.055 (1.2); 3.882(0.3); 3.859(0.5); 3.841(0.4); 3.642(0.4); 3.625 (0.5); 3.597(1.4); 3.580(3.6); 3.564(4.4); 3.558(4.0); 3.541 (3.2); 3.525(1.1); 3.490(0.5); 1.577(178.8); 1.426(0.4); 1.371(1.1); 1.333(2.4); 1.285(4.4); 1.256(10.6); 1.104(0.5); 0.881(1.6); 0.842(1.6); 0.070(0.6); 0.000(47.7)

Preparation Example 21: 6-{2-Fluoro-4-methyl-5-[(2,2,2-trifluoroethyl)sulphinyl]phenyl}-2-(5-fluoropyridin-3-yl)[1,3]thiazolo[4,5-d]pyrimidin-7(6H)-one (74)

Step 1: 4-Amino-N-{2-fluoro-4-methyl-5-[(2,2,2-trifluoroethyl)sulphanyl]phenyl}-2-(5-fluoropyridin-3-yl)-1,3-thiazole-5-carboxamide (II-73)

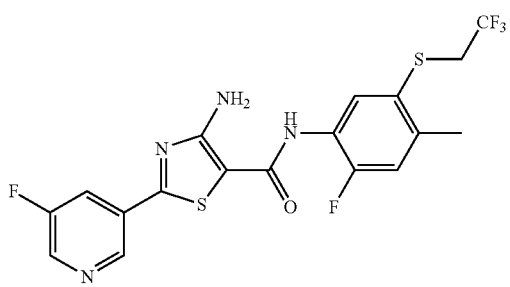 [SMILES: Cc1cc(F)c(NC(=O)c2sc(-c3cncc(F)c3)nc2N)cc1SCC(F)(F)F]

Under argon, 2.8 ml of a 2M trimethylaluminium solution (5.61 mmol) in toluene were slowly added dropwise with ice cooling to 1.34 g (5.61 mmol) of 2-fluoro-4-methyl-5-[(2,2,2-trifluoroethyl)sulphanyl]aniline in 50 ml of 1,2-dichloroethane, and the mixture was stirred at room temperature for 1 hour. 500 mg (1.87 mmol) of ethyl 4-amino-2-(5-fluoropyridin-3-yl)-1,3-thiazole-5-carboxylate (III-2) were then added, and the reaction mixture was subsequently heated under reflux overnight. After cooling, the reaction mixture was carefully discharged into a 10% potassium sodium tartrate solution (about 120 ml). The mixture was extracted three times with methylene chloride, and the combined organic phases were dried over magnesium sulphate, filtered and concentrated. The residue was stirred with a little acetonitrile to give a suspension. The insoluble fraction was filtered off with suction, washed with n-pentane and dried. This gave 330 mg (98.0% pure, 37.6% of theory) of the title compound (II-73).

1H-NMR (400.0 MHz, d₆-DMSO): δ=9.613(4.5); 8.971 (2.3); 8.968(4.0); 8.770(3.9); 8.763(4.1); 8.155(1.2); 8.150 (1.6); 8.144(1.2); 8.132(1.3); 8.127(1.7); 8.120(1.2); 7.705 (3.1); 7.686(3.1); 7.273(2.8); 7.245(2.8); 7.208(5.1); 4.259 (0.3); 4.241(0.3); 3.903(2.7); 3.875(4.0); 3.849(4.2); 3.823 (1.4); 3.329(26.3); 2.672(0.4); 2.668(0.3); 2.525(1.0); 2.512 (24.8); 2.507(49.6); 2.503(65.4); 2.499(49.2); 2.407(16.0); 2.334(0.3); 2.330(0.4); 2.325(0.3); 1.297(0.4); 1.279(0.7); 1.262(0.3); 0.008(1.0); 0.000(27.4); −0.008(1.2)

Step 2: 6-{2-Fluoro-4-methyl-5-[(2,2,2-trifluoroethyl)sulphanyl]phenyl}-2-(5-fluoropyridin-3-yl)[1,3]thiazolo[4,5-d]pyrimidin-7(6H)-one (73)

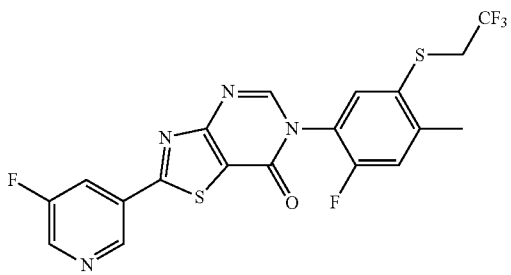 [SMILES: Cc1cc(F)c(-n2cnc3nc(-c4cncc(F)c4)sc3c2=O)cc1SCC(F)(F)F]

200 mg (98% pure, 0.43 mmol) of 4-amino-N-{2-fluoro-4-methyl-5-[(2,2,2-trifluoroethyl)sulphanyl]phenyl}-2-(5-fluoropyridin-3-yl)-1,3-thiazole-5-carboxamide (II-73) were initially charged in 1 ml of N,N-dimethylacetamide. 37 mg (0.21 mmol) of p-toluenesulphonic acid and 189 mg (1.28 mmol) of triethyl orthoformate were added thereto and the reaction mixture was heated at 130° C. in a CEM Discover microwave at 200 watts for 30 minutes. The cooled reaction mixture was concentrated under high vacuum and purified by MPLC using the mobile phase acetonitrile/water. This gave 50 mg (97.0% pure, 24.2% of theory) of the title compound (73).

1H-NMR (400.0 MHz, d₆-DMSO): δ=9.243(3.5); 8.875 (3.5); 8.868(3.6); 8.693(7.7); 8.535(1.2); 8.530(1.7); 8.524 (1.2); 8.512(1.2); 8.507(1.7); 8.501(1.1); 7.940(3.1); 7.922 (3.1); 7.521(2.7); 7.494(2.7); 4.061(1.2); 4.035(3.8); 4.009 (3.9); 3.984(1.4); 3.329(53.8); 2.676(0.3); 2.672(0.5); 2.668 (0.3); 2.507(49.1); 2.503(64.3); 2.499(49.1); 2.471(16.0); 2.414(0.5); 2.334(0.3); 2.330(0.4); 2.325(0.3); 2.076(14.3); 1.233(0.9); 0.000(0.4)

Step 3: 6-{2-Fluoro-4-methyl-5-[(2,2,2-trifluoroethyl)sulphinyl]phenyl}-2-(5-fluoropyridin-3-yl)[1,3]thiazolo[4,5-d]pyrimidin-7(6H)-one (74)

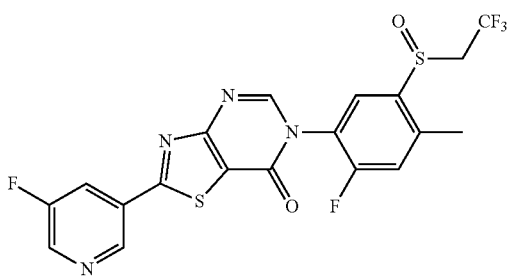 [SMILES: Cc1cc(F)c(-n2cnc3nc(-c4cncc(F)c4)sc3c2=O)cc1S(=O)CC(F)(F)F]

At 0° C., 42 mg (77% strength, 0.19 mmol) of meta-chloroperbenzoic acid were added to a solution of 96.0 mg (0.19 mmol) of 6-{2-fluoro-4-methyl-5-[(2,2,2-trifluoroethyl)sulphanyl]phenyl}-2-methyl-2-(5-fluoropyridin-3-yl)[1,3]thiazolo[4,5-d]pyrimidin-7(6H)-one (73) in 1 ml of dichloromethane. The reaction mixture was stirred at room temperature for 1 hour, and saturated sodium carbonate solution was then added. The aqueous phase was extracted three times with dichloromethane, and the combined organic phases were dried and filtered. After evaporation of the solvent, the residue was then purified chromatographically by MPLC using the mobile phase cyclohexane/ethyl acetate. This gave 65 mg (94.0% pure, 68.4% of theory) of the title compound (74).

1H-NMR (400.0 MHz, $d_6$-DMSO): δ=9.249(4.3); 9.246 (7.4); 9.242(4.4); 8.876(7.8); 8.870(8.1); 8.738(16.0); 8.538 (2.5); 8.533(3.1); 8.531(3.1); 8.527(2.4); 8.515(2.6); 8.510 (3.3); 8.503(2.4); 8.447(0.5); 8.317(0.7); 8.200(6.2); 8.182 (6.2); 7.639(4.3); 7.613(4.3); 5.758(2.5); 4.299(0.6); 4.266 (1.0); 4.241(0.8); 4.147(0.4); 4.126(0.7); 4.099(0.8); 4.038 (0.5); 4.020(0.4); 3.568(3.3); 3.329(336.9); 2.676(1.4); 2.671(2.0); 2.667(1.5); 2.525(5.0); 2.520(7.9); 2.511(110.1); 2.507(225.1); 2.502(308.8); 2.498(233.4); 2.494(111.7); 2.377(1.3); 2.334(1.5); 2.329(2.0); 2.325(1.5); 1.989(1.2); 1.234(0.4); 1.207(0.4); 1.193(0.6); 1.189(0.7); 1.175(0.8); 1.157(0.3); 0.000(0.9)

Preparation Example 22: 6-{2,4-Dimethyl-5-[(2,2,2-trifluoroethyl)sulphinyl]phenyl}-2-(pyrimidin-5-yl)[1,3]thiazolo[4,5-d]pyrimidin-7(6H)-one (77)

Step 1: 4-Amino-N-{2,4-dimethyl-5-[(2,2,2-trifluoroethyl)sulphanyl]phenyl}-2-(pyrimidin-5-yl)-1,3-thiazole-5-carboxamide (II-76)

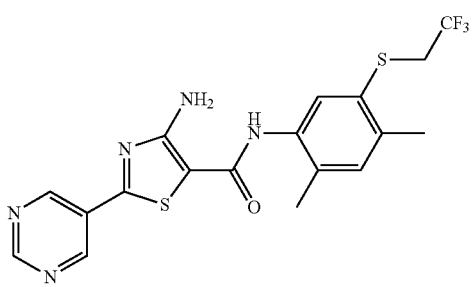 [SMILES: Cc1cc(C)c(SCC(F)(F)F)cc1NC(=O)c1sc(-c2cncnc2)nc1N]

Under argon, 2.1 ml of a 2M trimethylaluminium solution (4.20 mmol) in toluene were slowly added dropwise with ice cooling to 987 mg (4.20 mmol) of 2,4-dimethyl-5-[(2,2,2-trifluoroethyl)sulphanyl]aniline in 70 ml of 1,2-dichloroethane, and the mixture was stirred at room temperature for 1 hour. 350 mg (1.40 mmol) of ethyl 4-amino-2-(pyrimidin-5-yl)-1,3-thiazole-5-carboxylate (III-3) were then added, and the reaction mixture was subsequently heated under reflux overnight. After cooling, the reaction mixture was carefully discharged into a 10% potassium sodium tartrate solution (about 120 ml). The mixture was extracted three times with methylene chloride, and the combined organic phases were dried over magnesium sulphate, filtered and concentrated. The residue was stirred with a little acetonitrile to give a suspension. The insoluble fraction was filtered off with suction, washed with n-pentane and dried. This gave 215 mg (90.0% pure, 31.5% of theory) of the title compound (II-76).

1H-NMR (400.0 MHz, $d_6$-DMSO): δ=9.410(4.5); 9.327 (6.4); 9.285(1.2); 9.247(11.7); 7.465(5.7); 7.176(7.8); 7.170 (7.4); 6.814(0.5); 6.793(0.6); 5.754(0.7); 4.743(0.5); 4.264 (0.5); 4.246(0.5); 3.875(1.3); 3.849(4.0); 3.823(4.1); 3.798 (1.5); 3.691(0.5); 3.666(0.5); 3.320(121.1); 2.671(1.0); 2.502(151.6); 2.418(0.3); 2.367(15.3); 2.329(1.4); 2.205 (1.9); 2.162(16.0); 2.074(0.8); 2.000(1.8); 1.300(0.5); 1.282 (1.1); 1.265(0.6); 0.147(0.4); 0.000(72.2); −0.149(0.4)

Step 2: 6-{2,4-Dimethyl-5-[(2,2,2-trifluoroethyl)sulphanyl]phenyl}-2-(pyrimidin-5-yl)[1,3]thiazolo[4,5-d]pyrimidin-7(6H)-one (76)

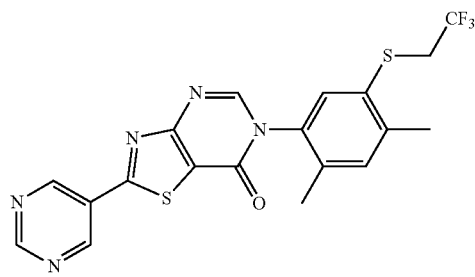 [SMILES: Cc1cc(C)c(-n2cnc3nc(-c4cncnc4)sc3c2=O)cc1SCC(F)(F)F]

5 ml (30.1 mmol) of triethyl orthoformate were added to 100 mg (0.23 mmol) of 4-amino-N-{2,4-dimethyl-5-[(2,2,2-trifluoroethyl)sulphanyl]phenyl}-2-(pyrimidin-5-yl)-1,3-thiazole-5-carboxamide (II-76) and 20 mg (0.11 mmol) of p-toluenesulphonic acid and the reaction mixture was heated at 150° C. in a CEM Discover microwave for 40 min. The cooled reaction mixture was concentrated under reduced pressure and then purified chromatographically by MPLC. This gave 36 mg (94.0% pure, 33.1% of theory) of the title compound (76).

1H-NMR (400.0 MHz, d6-DMSO): δ=9.538(16.0); 9.429 (7.5); 8.559(8.5); 7.680(4.9); 7.362(3.9); 5.754(1.8); 4.034 (1.0); 4.008(2.9); 3.982(3.1); 3.956(1.1); 3.318(38.5); 2.671 (0.4); 2.524(1.0); 2.511(23.9); 2.506(47.7); 2.502(62.3); 2.497(45.4); 2.493(22.1); 2.411(12.3); 2.368(0.6); 2.329 (0.4); 2.170(0.5); 2.080(13.3); 1.352(1.1); 1.336(0.4); 1.259 (0.4); 1.250(0.6); 1.229(1.2); 0.000(3.8)

Step 3: 6-{2,4-Dimethyl-5-[(2,2,2-trifluoroethyl)sulphinyl]phenyl}-2-(pyrimidin-5-yl)[1,3]thiazolo[4,5-d]pyrimidin-7(6H)-one (77)

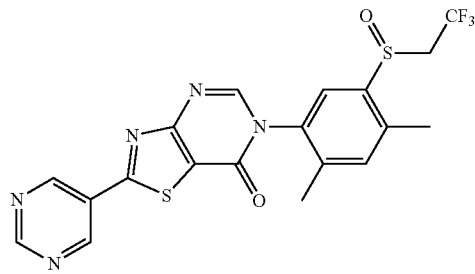 [SMILES: Cc1cc(C)c(S(=O)CC(F)(F)F)cc1-n1cnc2nc(-c3cncnc3)sc2c1=O]

At 0° C., 33 mg (77% strength, 0.15 mmol) of meta-chloroperbenzoic acid were added to a solution of 70.0 mg (0.15 mmol) of 6-{2,4-dimethyl-5-[(2,2,2-trifluoroethyl)sulphanyl]phenyl}-2-(pyrimidin-5-yl)[1,3]thiazolo[4,5-d]pyrimidin-7(6H)-one (76) in 3 ml of dichloromethane. The reaction mixture was stirred in the cold for another 1 hour and then at room temperature overnight. The reaction was washed successively with saturated sodium bisulphite solution, sodium bicarbonate solution and sodium chloride solution, dried and concentrated. The residue was then purified chromatographically by MPLC. This gave 20 mg (97.0% pure, 28.7% of theory) of the title compound (77).

1H-NMR (400.0 MHz, d$_6$-DMSO): δ=9.542(16.0); 9.429 (7.8); 8.612(8.8); 7.949(4.1); 7.939(2.8); 7.497(2.0); 7.471 (3.0); 5.754(0.9); 4.321(0.4); 4.293(0.5); 4.284(0.5); 4.257 (0.5); 4.175(0.4); 4.166(0.4); 4.148(1.1); 4.139(1.1); 4.121 (1.1); 4.112(1.2); 4.094(0.4); 4.085(0.4); 3.969(0.5); 3.942 (0.5); 3.932(0.4); 3.905(0.5); 3.317(54.5); 2.675(0.5); 2.671 (0.7); 2.666(0.5); 2.506(79.6); 2.502(106.3); 2.497(82.4); 2.452(8.0); 2.447(10.7); 2.338(0.5); 2.333(0.6); 2.328(0.7); 2.324(0.6); 2.258(0.4); 2.188(10.5); 2.182(8.0); 1.234(0.7); 0.008(0.5); 0.000(13.1)

Synthesis of Aminothiazoles of the Formula (III) by Process B

Preparation Example 9: Ethyl 4-amino-2-(pyridin-3-yl)-1,3-thiazole-5-carboxylate (III-1)

Step 1: Ethyl 4-hydroxy-2-(pyridin-3-yl)-1,3-thiazole-5-carboxylate (VI-1)

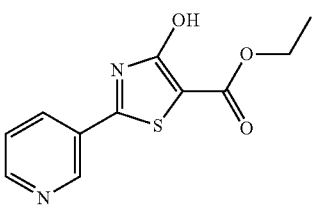 [SMILES: CCOC(=O)c1sc(-c2cccnc2)nc1O]

32.5 g (235.2 mmol) of pyridine-3-carbothioamide were initially charged in 200 ml of ethanol, and 58.5 g (244.6 mmol) of diethyl bromomalonate were added. The mixture was heated under reflux overnight and then cooled and filtered. The filter residue was washed thoroughly with ethanol and dried under reduced pressure. This gave 26.0 g (83.0% pure, 36.7% of theory) of the title compound (VI-1).

1H-NMR (399.9 MHz, d$_6$-DMSO): δ=9.150 (2.8); 9.145 (2.8); 8.771 (1.9); 8.768 (2.0); 8.759 (2.0); 8.756 (2.0); 8.399 (1.1); 8.395 (1.7); 8.390 (1.3); 8.379 (1.3); 8.375 (1.8); 7.670 (1.6); 7.657 (1.7); 7.649 (1.7); 7.637 (1.5); 7.249 (13.6); 7.121 (14.1); 6.993 (13.7); 4.695 (0.3); 4.673 (0.4); 4.609 (0.4); 4.597 (0.5); 4.584 (0.5); 4.578 (0.5); 4.559 (0.5); 4.507 (0.6); 4.498 (0.6); 4.488 (0.6); 4.475 (0.6); 4.459 (0.6); 4.441 (0.7); 4.435 (0.7); 4.404 (0.7); 4.397 (0.7); 4.387 (0.8); 4.369 (0.8); 4.351 (0.7); 4.335 (0.7); 4.294 (3.1); 4.276 (8.4); 4.259 (8.5); 4.241 (3.1); 4.111 (0.4); 4.089 (0.3); 4.071 (0.3); 2.533 (0.5); 2.504 (7.3); 2.500 (14.4); 2.495 (20.1); 2.490 (14.7); 2.486 (7.6); 1.306 (7.9); 1.288 (16.0); 1.270 (7.7); 1.064 (0.5); 0.000 (2.3)

Step 2: Ethyl 2-(pyridin-3-yl)-4-{[(trifluoromethyl)sulphonyl]oxy}-1,3-thiazole-5-carboxylate (V-1)

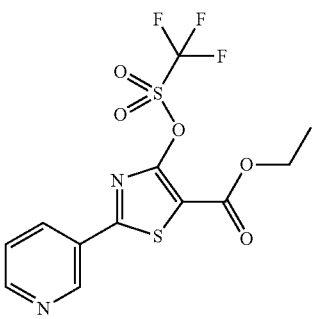 [SMILES: CCOC(=O)c1sc(-c2cccnc2)nc1OS(=O)(=O)C(F)(F)F]

Under argon, 500 mg (2 mmol) of dry ethyl 4-hydroxy-2-(pyridin-3-yl)-1,3-thiazole-5-carboxylate (VI-1) and 414 g (3 mmol) of potassium carbonate were initially charged in dichloromethane at room temperature. 620 mg (2.2 mmol) of trifluoromethanesulphonic anhydride were added dropwise over 10 minutes and the mixture was stirred at room temperature overnight. The mixture was then washed with saturated sodium bicarbonate solution, the organic phase was filtered through a little Celite, the filter cake was washed with dichloromethane and the filtrate was dried over sodium sulphate. Purification of the residue obtained after concentration was then carried out by MPLC using a gradient of the mobile phase cyclohexane/ethyl acetate. This gave 220 mg (100.0% pure, 28.7% of theory) of the title compound (V-1).

1H-NMR (399.9 MHz, d$_6$-DMSO): δ=3.115 (16.0); 2.498 (0.9); 2.493 (1.8); 2.489 (2.5); 2.484 (1.8); 2.479 (0.9); 1.341 (0.5)

Step 3: Ethyl 4-(benzylamino)-2-(pyridin-3-yl)-1,3-thiazole-5-carboxylate (IV-1)

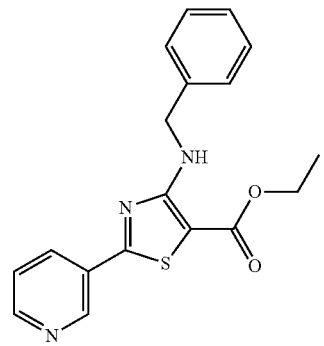 [SMILES: CCOC(=O)c1sc(-c2cccnc2)nc1NCc1ccccc1]

20.0 g (52.0 mmol) of ethyl 2-(pyridin-3-yl)-4-{[(trifluoromethyl)sulphonyl]oxy}-1,3-thiazole-5-carboxylate (V-1) and 11.2 g (104.1 mmol) of benzylamine in 100 ml of dioxane were stirred under reflux overnight. After cooling and concentration of the reaction mixture, methanol was added to the oily residue and the precipitated yellow solid was filtered off with suction and washed with pentane. Excess benzylamine in the crude product was subsequently removed by washing with 1 N hydrochloric acid. The crude product was then washed with water, stirred with pentane, filtered off with suction and dried under reduced pressure. This gave 13.5 g (100% pure, 76.4% of theory) of the title compound (IV-1).

1H-NMR (400.0 MHz, d$_6$-DMSO): δ=9.153(4.6); 9.148 (4.9); 8.745(3.2); 8.742(3.3); 8.733(3.3); 8.730(3.1); 8.374 (1.6); 8.370(2.5); 8.366(1.7); 8.354(1.9); 8.350(2.7); 7.618 (3.8); 7.605(3.4); 7.597(2.9); 7.585(2.4); 7.413(4.4); 7.394 (7.2); 7.347(4.0); 7.329(7.1); 7.309(3.6); 7.251(2.2); 7.233 (3.1); 7.215(1.1); 4.780(4.8); 4.767(4.8); 4.285(2.3); 4.267 (7.3); 4.249(7.4); 4.232(2.5); 4.039(0.4); 4.021(0.4); 3.913 (2.0); 3.775(0.7); 3.760(0.7); 3.744(0.7); 2.509(41.8); 2.505 (53.2); 2.501(40.7); 2.332(0.4); 1.990(1.1); 1.297(7.8); 1.280(16.0); 1.262(7.6); 1.176(0.6); 0.000(6.0)

Step 4: Ethyl 4-amino-2-(pyridin-3-yl)-1,3-thiazole-5-carboxylate (III-1)

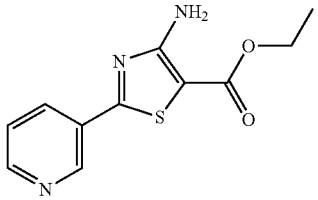 [SMILES: CCOC(=O)c1sc(-c2cccnc2)nc1N]

40 ml of concentrated sulphuric acid were initially charged and 8.5 g (25.0 mmol) of ethyl 4-(benzylamino)-2-(pyridin-3-yl)-1,3-thiazole-5-carboxylate (IV-1) were added slowly at 20° C. The reaction mixture was stirred at room temperature for 3 h and then added to 500 ml of ice-water, and the pH was adjusted carefully to pH 10 using 30% strength potassium hydroxide solution. The mixture was then extracted with ethyl acetate, and the organic phases were dried and concentrated. This gave 6.0 g (100% pure, 96.1% of theory) of the title compound (III-1).

1H-NMR (400.0 MHz, $d_6$-DMSO): δ=9.113(4.3); 9.109 (4.3); 9.107(4.3); 8.730(3.0); 8.727(3.4); 8.718(3.3); 8.715 (3.4); 8.296(1.7); 8.291(2.6); 8.286(1.9); 8.276(1.8); 8.271 (2.7); 8.266(2.0); 7.578(2.4); 7.566(2.5); 7.558(2.4); 7.546 (2.3); 7.139(3.5); 4.271(2.4); 4.253(7.5); 4.236(7.6); 4.218 (2.5); 3.333(25.6); 2.504(43.0); 2.500(34.6); 1.990(0.5); 1.296(7.8); 1.278(16.0); 1.261(7.7); 0.000(0.6)

Preparation Example 23: Ethyl 4-amino-2-(5-fluoropyridin-3-yl)-1,3-thiazole-5-carboxylate (III-2)

Step 1: Ethyl 2-(5-fluoropyridin-3-yl)-4-hydroxy-1,3-thiazole-5-carboxylate (VI-2)

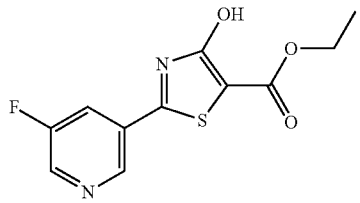 [SMILES: CCOC(=O)c1sc(-c2cncc(F)c2)nc1O]

38.6 g (247 mmol) of 5-fluoropyridine-3-carbothioamide were initially charged in 250 ml of ethanol, and 60 ml of pyridine and 177.3 g (741 mmol) of diethyl bromomalonate were then added. The mixture was heated under reflux overnight and then cooled and filtered. The filter residue was washed thoroughly with ethanol and dried under reduced pressure. This gave 37.0 g (94.9% pure, 53.0% of theory) of the title compound (VI-2).

1H-NMR (400.0 MHz, $d_6$-DMSO): δ=9.013(4.9); 8.765 (4.9); 8.758(5.0); 8.227(1.6); 8.221(2.1); 8.216(1.6); 8.204 (1.6); 8.198(2.1); 8.193(1.5); 4.275(2.3); 4.258(7.3); 4.240 (7.4); 4.222(2.4); 3.324(2.6); 2.508(32.1); 2.504(41.6); 2.500(31.7); 1.294(7.8); 1.276(16.0); 1.259(7.6); 0.000(3.7)

Step 2: Ethyl 2-(5-fluoropyridin-3-yl)-4-{[(trifluoromethyl)sulphonyl]oxy}-1,3-thiazole-5-carboxylate (V-2)

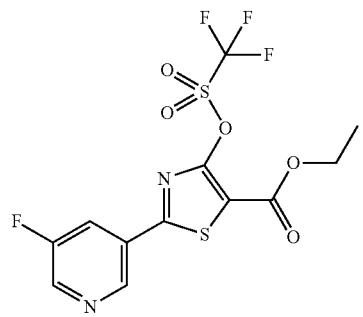 [SMILES: CCOC(=O)c1sc(-c2cncc(F)c2)nc1OS(=O)(=O)C(F)(F)F]

Under argon, 37.0 g (138 mmol) of ethyl 2-(5-fluoropyridin-3-yl)-4-hydroxy-1,3-thiazole-5-carboxylate (VI-2) were initially charged in 300 ml of dichloromethane, 45 ml of pyridine were added and the reaction was cooled to 0° C. Thereafter, 54.5 g (193 mmol) of trifluoromethanesulphonic anhydride were slowly added dropwise, and the mixture was stirred at room temperature overnight. The reaction solution was filtered, the filter residue was washed with dichloromethane and the filtrate was concentrated. The residue obtained was warmed with 400 ml of methyl tert-butyl ether (MTBE) at 55° C. for 30 min and decanted while still warm. This procedure was repeated with a further 300 ml of MTBE. The combined MTBE fractions were concentrated and the residue obtained was dried under reduced pressure. This gave 55.8 g (98.6% pure, 99.6% of theory) of the title compound (V-2).

1H-NMR (400.0 MHz, $d_6$-DMSO): δ=9.083(2.7); 9.079 (4.5); 9.076(2.7); 8.849(4.5); 8.842(4.5); 8.364(1.5); 8.359 (1.9); 8.357(1.9); 8.353(1.5); 8.341(1.6); 8.336(2.0); 8.334 (1.8); 8.329(1.4); 4.427(2.2); 4.409(7.2); 4.392(7.3); 4.374 (2.3); 3.569(13.3); 3.344(8.3); 2.672(0.3); 2.526(0.8); 2.512 (19.0); 2.508(38.3); 2.503(50.2); 2.499(37.2); 2.494(18.6); 2.330(0.3); 1.355(7.6); 1.337(16.0); 1.319(7.4); 0.000(3.2)

Step 3: Ethyl 4-(benzylamino)-2-(5-fluoropyridin-3-yl)-1,3-thiazole-5-carboxylate (IV-2)

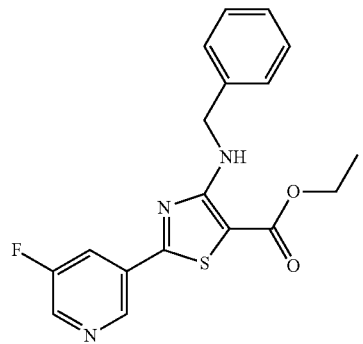 [SMILES: CCOC(=O)c1sc(-c2cncc(F)c2)nc1NCc1ccccc1]

55.8 g (139 mmol) of ethyl 2-(5-fluoropyridin-3-yl)-4-{[(trifluoromethyl)sulphonyl]oxy}-1,3-thiazole-5-carboxylate (V-1) and 29.7 g (277 mmol) of benzylamine in 300 ml of dioxane were stirred under reflux overnight. After cooling and concentration of the reaction mixture, methanol was added to the oily residue and the precipitated yellow solid was filtered off with suction and washed with pentane. Excess benzylamine in the crude product was subsequently removed by washing with 1 N hydrochloric acid. The crude product was then washed with water, stirred with pentane, filtered off with suction and dried under reduced pressure. This gave 42.6 g (100% pure, 85.9% of theory) of the title compound (IV-2).

1H-NMR (400.0 MHz, $d_6$-DMSO): δ=9.015(2.9); 9.011 (4.9); 8.746(4.6); 8.740(4.7); 8.249(1.5); 8.244(1.9); 8.242 (1.9); 8.238(1.5); 8.225(1.6); 8.220(2.0); 8.214(1.5); 7.628 (1.1); 7.612(2.3); 7.596(1.2); 7.444(0.4); 7.411(4.0); 7.393 (6.2); 7.344(3.6); 7.340(1.3); 7.326(6.6); 7.307(3.3); 7.249 (2.0); 7.231(2.8); 7.213(1.0); 4.782(5.7); 4.766(5.7); 4.289 (2.2); 4.271(7.1); 4.253(7.3); 4.236(2.3); 4.029(0.5); 3.568 (0.4); 3.318(32.2); 2.676(0.4); 2.671(0.6); 2.667(0.4); 2.524 (1.1); 2.511(33.4); 2.507(65.6); 2.502(85.2); 2.498(63.3); 2.494(31.8); 2.333(0.4); 2.329(0.6); 2.324(0.4); 1.298(7.6); 1.280(16.0); 1.262(7.5); 0.146(0.4); 0.008(3.4); 0.000 (85.6); −0.008(3.8); −0.019(0.4); −0.150(0.4)

Step 4: Ethyl 4-amino-2-(5-fluoropyridin-3-yl)-1,3-thiazole-5-carboxylate (III-2)

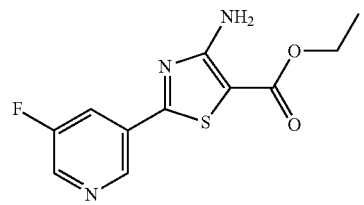 [SMILES: CCOC(=O)c1sc(-c2cncc(F)c2)nc1N]

3 ml of concentrated sulphuric acid were initially charged and 500 mg (1.39 mmol) of ethyl 4-(benzylamino)-2-(5-fluoropyridin-3-yl)-1,3-thiazole-5-carboxylate (IV-2) were added slowly at 20° C. The reaction mixture was stirred at room temperature overnight and then added to 10 ml of ice-water, and the pH was adjusted carefully to pH 10 using 30% strength potassium hydroxide solution. The mixture was then extracted with ethyl acetate, and the organic phases were dried over magnesium sulphate and concentrated. The residue was triturated with n-pentane, filtered and dried. This gave 200 mg (100% pure, 53.5% of theory) of the title compound (III-2).

1H-NMR (400.0 MHz, d6-DMSO): δ=8.994(6.0); 8.757 (5.4); 8.750(5.8); 8.193(2.8); 8.170(2.8); 7.143(4.8); 4.278 (2.6); 4.260(7.7); 4.242(7.8); 4.225(2.7); 3.319(18.0); 2.673 (0.3); 2.504(52.6); 2.331(0.3); 1.298(8.1); 1.280(16.0); 1.263(7.9); 0.000(11.1)

Further compounds of the formula (I) are compiled in the table which follows.

TABLE 1

Compounds of the formula (I)

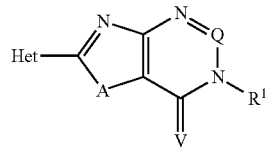

| Compound No. | Het | A | Q | V | R¹ |
|---|---|---|---|---|---|
| 1 | 3-pyridyl | S | CH | O | isopropyl |
| 2 | 3-pyridyl | S | CH | O | cyclopropyl |
| 3 | 3-pyridyl | S | CH | O | isobutyl |

TABLE 1-continued
Compounds of the formula (I)
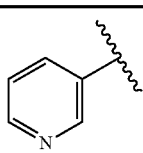
| Compound No. | Het | A | Q | V | R¹ |
|---|---|---|---|---|---|
| 4 | 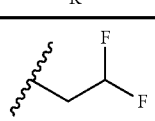 | S | CH | O | 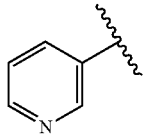 |
| 5 | 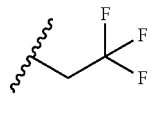 [SMILES: *CC(F)(F)F] | S | CH | O | 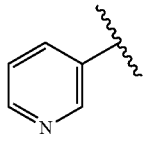 |
| 6 | 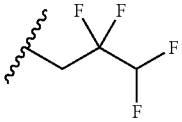 [SMILES: *CC(F)(F)C(F)F] | S | CH | O | 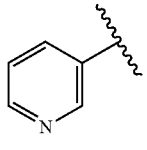 |
| 7 | 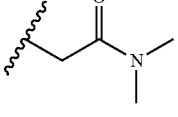 | S | CH | O | 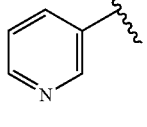 |
| 8 | 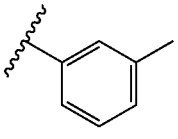 [SMILES: *c1cccc(C)c1] | S | CH | O | 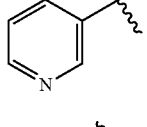 |
| 9 | 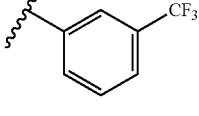 | S | CH | O | 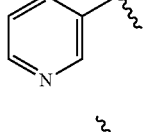 |
| 10 | 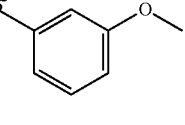 | S | CH | O | 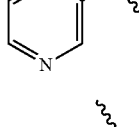 |
| 11 | 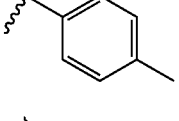 | S | CH | O | 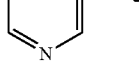 |
| 12 | 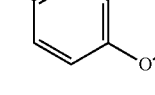 | S | CH | O |  |

TABLE 1-continued

Compounds of the formula (I)

| Compound No. | Het | A | Q | V | R¹ |
|---|---|---|---|---|---|
| 13 | 3-pyridyl | S | CH | O | 3-(methylthio)phenyl |
| 14 | 3-pyridyl | S | CH | O | 3-(methylsulfinyl)phenyl |
| 15 | 3-pyridyl | S | CH | O | 3-(methylthio)-4-methylphenyl |
| 16 | 3-pyridyl | S | CH | O | 3-(methylsulfinyl)-4-methylphenyl |
| 17 | 3-pyridyl | S | CH | O | 3-(trifluoromethylthio)-4-fluorophenyl |
| 18 | 3-pyridyl | S | CH | O | 3-(trifluoromethylsulfinyl)-4-fluorophenyl |
| 19 | 3-pyridyl | S | CH | O | 3-(ethylthio)phenyl |
| 20 | 3-pyridyl | S | CH | O | 3-(ethylsulfinyl)phenyl |

TABLE 1-continued

Compounds of the formula (I)

| Compound No. | Het | A | Q | V | R¹ |
|---|---|---|---|---|---|
| 21 | 3-pyridyl | S | CH | O | 4-F-2-methyl-5-(SCH₂CF₃)phenyl |
| 22 | 3-pyridyl | S | CH | O | 4-F-2-methyl-5-(S(O)CH₂CF₃)phenyl |
| 23 | pyridine N-oxide (3-yl) | S | CH | O | 4-F-2-methyl-5-(S(O)CH₂CF₃)phenyl |
| 24 | 3-pyridyl | S | CH | O | 3-(S-iPr)phenyl |
| 25 | 3-pyridyl | S | CH | O | 3-(S(O)-iPr)phenyl |
| 26 | 3-pyridyl | S | CH | O | 3-(S-iBu)phenyl |
| 27 | 3-pyridyl | S | CH | O | 3-(S(O)-iBu)phenyl |
| 28 | 3-pyridyl | S | CH | O | 3-(CF₃)benzyl |

TABLE 1-continued

Compounds of the formula (I)

| Compound No. | Het | A | Q | V | R¹ |
|---|---|---|---|---|---|
| 32 | 3-pyridyl | S | CH | O | 3-methoxybenzyl |
| 34 | 3-pyridyl | S | CH | O | (pyridin-2-yl)methyl |
| 35 | 3-pyridyl | S | CH | O | (pyridin-3-yl)methyl |
| 36 | 3-pyridyl | S | CH | O | (pyridin-4-yl)methyl |
| 37 | 3-pyridyl | S | CH | O | (1-methyl-1H-pyrazol-3-yl)methyl |
| 38 | 3-pyridyl | S | CH | O | (2-methylthiazol-4-yl)methyl |
| 39 | 3-pyridyl | S | CH | O | cyclopropylmethyl |
| 40 | 3-pyridyl | S | CH | O | 2-fluorobenzyl |
| 41 | 3-pyridyl | S | CH | O | 3-(2,2,2-trifluoroethoxy)benzyl |

TABLE 1-continued

Compounds of the formula (I)

| Compound No. | Het | A | Q | V | R¹ |
|---|---|---|---|---|---|
| 42 | 3-pyridyl | S | CH | O | 3-(N,N-dimethylsulfamoyl)phenyl |
| 43 | 3-pyridyl | S | CH | O | 4-chlorophenyl |
| 44 | 3-pyridyl | S | CH | O | 4-fluoro-3-(cyclopropylmethylthio)phenyl |
| 45 | 3-pyridyl | S | CH | O | 4-fluoro-3-(cyclopropylmethylsulfinyl)phenyl |
| 46 | 3-pyridyl | S | CH | O | 4-fluoro-3-(2,2,2-trifluoroethylthio)phenyl |
| 47 | 3-pyridyl | S | CH | O | 4-methyl-3-(2,2,2-trifluoroethylthio)phenyl |
| 48 | 3-pyridyl | S | CH | O | 4-methyl-3-(2,2,2-trifluoroethylsulfinyl)phenyl |
| 49 | 3-pyridyl | S | CH | O | 2,5-dimethyl-4-(2,2,2-trifluoroethylthio)phenyl |

TABLE 1-continued

Compounds of the formula (I)

| Compound No. | Het | A | Q | V | R¹ |
|---|---|---|---|---|---|
| 50 | 3-pyridyl | S | CH | O | 2,4-dimethyl-5-(2,2,2-trifluoroethylsulfinyl)phenyl |
| 51 | 3-pyridyl | S | CH | O | 2,4-dichloro-5-(2,2,2-trifluoroethylthio)phenyl |
| 52 | 3-pyridyl | S | CH | O | 3-((N,N-dimethylcarbamoylmethyl)thio)phenyl |
| 53 | 3-pyridyl | S | CH | O | 3-((N,N-dimethylcarbamoylmethyl)sulfinyl)phenyl |
| 54 | 3-pyridyl | S | CH | O | 4-fluoro-2-methyl-5-((N,N-dimethylcarbamoylmethyl)thio)phenyl |
| 55 | 3-pyridyl | S | CH | O | 4-fluoro-2-methyl-5-((N,N-dimethylcarbamoylmethyl)sulfinyl)phenyl |
| 56 | 3-pyridyl | S | C—CH3 | O | 4-fluoro-2-methyl-5-(2,2,2-trifluoroethylthio)phenyl |
| 57 | 3-pyridyl | S | C—CH3 | O | 4-fluoro-2-methyl-5-(2,2,2-trifluoroethylsulfinyl)phenyl |

TABLE 1-continued

Compounds of the formula (I)

| Compound No. | Het | A | Q | V | R¹ |
|---|---|---|---|---|---|
| 58 | 3-pyridyl | S | N | O | 4-fluoro-2-methyl-5-(2,2,2-trifluoroethylthio)phenyl |
| 59 | 3-pyridyl | S | N | O | 4-fluoro-2-methyl-5-(2,2,2-trifluoroethylsulfinyl)phenyl |
| 60 | 3-pyridyl | S | CH | O | 4-(ethylthio)phenyl |
| 61 | 3-pyridyl | S | CH | O | 4-(ethylsulfinyl)phenyl |
| 62 | 3-pyridyl | S | CH | O | 4-(trifluoromethylthio)phenyl |
| 63 | 3-pyridyl | S | CH | O | 4-(trifluoromethylsulfinyl)phenyl |
| 64 | 3-pyridyl | S | CH | O | 2-methyl-4-(trifluoromethylthio)phenyl |
| 65 | 3-pyridyl | S | CH | O | 2-(N,N-dimethylcarbamoyl)benzothiophen-5-yl |

TABLE 1-continued

Compounds of the formula (I)

| Compound No. | Het | A | Q | V | R¹ |
|---|---|---|---|---|---|
| 66 | 3-pyridyl | S | CH | O | 2-(ethylthio)phenyl |
| 67 | 3-pyridyl | S | CH | O | 2-(ethylsulfinyl)phenyl |
| 68 | 3-pyridyl | S | CH | O | 2-(2,2,2-trifluoroethylthio)phenyl |
| 69 | 3-pyridyl | S | CH | O | 2-(2,2,2-trifluoroethylsulfinyl)phenyl |
| 70 | 5-fluoro-3-pyridyl | S | CH | O | 3-(methylthio)-4-methylphenyl |
| 71 | 5-fluoro-3-pyridyl | S | CH | O | 2,5-dimethyl-4-(2,2,2-trifluoroethylthio)phenyl |
| 72 | 5-fluoro-3-pyridyl | S | CH | O | 2,5-dimethyl-4-(2,2,2-trifluoroethylsulfinyl)phenyl |
| 73 | 5-fluoro-3-pyridyl | S | CH | O | 4-fluoro-2-methyl-5-(2,2,2-trifluoroethylthio)phenyl |

TABLE 1-continued
Compounds of the formula (I)
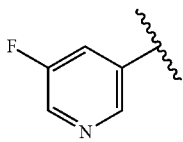
| Compound No. | Het | A | Q | V | R¹ |
|---|---|---|---|---|---|
| 74 | 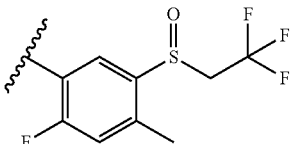 [SMILES: *c1cc(S(=O)CC(F)(F)F)c(C)cc1C] | S | CH | O | 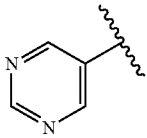 [SMILES: *c1cncnc1] |
| 75 | 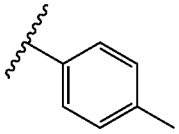 [SMILES: *c1ccc(C)cc1] | S | CH | O | 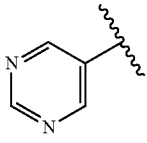 [SMILES: *c1cncnc1] |
| 76 | 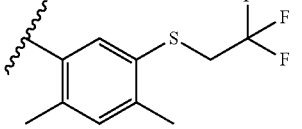 | S | CH | O | 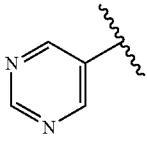 [SMILES: *c1cncnc1] |
| 77 | 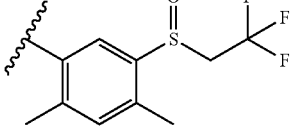 | S | CH | O | 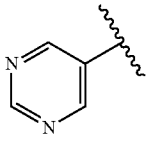 [SMILES: *c1cncnc1] |
| 78 | 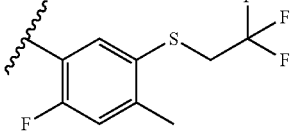 | S | CH | O | 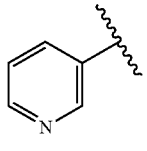 [SMILES: *c1cccnc1] |
| 79 | 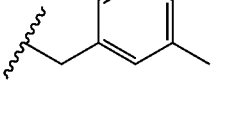 | S | CH | O | 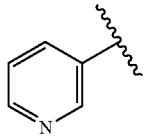 |
| 80 | 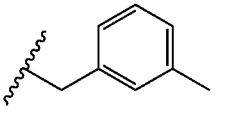 | S | C—CH3 | O | 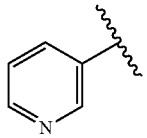 |
| 81 | 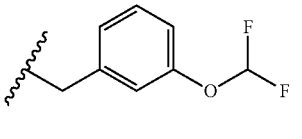 [SMILES: *Cc1cccc(OC(F)F)c1] | S | CH | O |  |

TABLE 1-continued

Compounds of the formula (I)

| Compound No. | Het | A | Q | V | R¹ |
|---|---|---|---|---|---|
| 82 | 3-pyridyl | S | CH | O | 4-methoxybenzyl |
| 83 | 3-pyridyl | S | CH | O | 2-fluoro-4-methylbenzyl |
| 84 | 3-pyridyl | S | CH | O | pyrimidin-2-ylmethyl |
| 85 | 3-pyridyl | S | CH | O | pyrazin-2-ylmethyl |
| 86 | 3-pyridyl | S | CH | O | 1-(1-methyl-1H-1,2,4-triazol-5-yl)ethyl |

TABLE 2

Analytical data for the compounds reported

| Ex. No. | logP[a] | logP[b] | 1H-NMR [σ (ppm)] or LC-MS [m/z] |
|---|---|---|---|
| 1 | 1.35 | 1.43 | 1H-NMR(400.0 MHz, d₆-DMSO): δ = 9.307(2.2); 9.302(2.2); 8.814(1.6); 8.811(1.7); 8.802(1.7); 8.799(1.7); 8.734(6.2); 8.516(1.0); 8.512(1.3); 8.506(1.0); 8.496(1.1); 8.491(1.4); 8.486(1.0); 8.144(3.9); 7.659(1.3); 7.647(1.3); 7.641(1.3); 7.639(1.3); 7.628(1.2); 7.627(1.2); 5.054(0.4); 5.037(1.1); 5.019(1.5); 5.002(1.1); 4.985(0.4); 3.337(1.4); 2.526(0.8); 2.513(17.3); 2.508(34.7); 2.504(45.2); 2.499(32.4); 2.495(15.5); 1.483(16.0); 1.466(15.8); 1.142(0.4); 1.126(0.4); 0.000(8.5) |
| 2 | | 1.05 | LC-MS: mass found [m/z] = 270.06 |
| 3 | 1.70 | | 1H-NMR(400.0 MHz, d₆-DMSO): δ = 9.302(2.1); 9.297(2.1); 9.049(0.4); 9.044(0.4); 8.815(1.8); 8.811(1.9); 8.803(1.8); 8.799(1.8); 8.703(0.3); 8.699(0.4); 8.691(0.4); 8.687(0.4); 8.634(6.2); 8.510(1.1); 8.506(1.4); 8.500(1.1); 8.490(1.1); 8.486(1.4); 8.484(1.4); 8.480(1.1); 7.662(1.3); 7.660(1.4); 7.650(1.3); 7.648(1.3); 7.642(1.3); 7.640(1.3); 7.630(1.2); 7.628(1.3); 6.974(0.7); 3.895(4.7); 3.876(4.7); 3.323(24.1); 3.022(0.4); 3.005(0.6); 2.990(0.4); 2.512(10.6); 2.508(21.2); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 2.503(27.9); 2.499(20.3); 2.495(10.0); 2.162(0.4); 2.145(0.8); 2.128(1.0); 2.111(0.9); 2.093(0.4); 0.916(16.0); 0.899(15.5); 0.873(3.2); 0.856(3.1); 0.008(0.3); 0.000(8.4); −0.008(0.3) |
| 4 | 1.19 | | 1H-NMR(400.0 MHz, $d_6$-DMSO): δ = 9.317(7.3); 9.313(7.0); 9.064(1.2); 9.060(1.2); 8.824(5.6); 8.820(6.0); 8.812(5.9); 8.808(5.8); 8.719(0.9); 8.716(1.0); 8.707(1.0); 8.704(0.9); 8.642(16.0); 8.527(3.3); 8.522(4.3); 8.517(3.2); 8.507(3.5); 8.502(4.6); 8.497(3.3); 8.317(0.5); 8.238(0.7); 8.233(1.1); 8.229(0.7); 8.218(1.3); 8.214(1.0); 8.208(0.8); 8.149(2.5); 7.666(4.2); 7.654(4.2); 7.646(4.1); 7.636(3.8); 7.634(3.9); 7.586(0.7); 7.574(0.7); 7.566(0.6); 7.554(0.6); 7.101(2.0); 6.573(1.0); 6.564(2.0); 6.555(0.9); 6.436(2.0); 6.427(4.2); 6.418(1.9); 6.298(1.0); 6.289(2.1); 6.280(1.0); 6.077(0.6); 5.937(0.3); 4.626(3.1); 4.617(3.4); 4.589(6.9); 4.580(6.7); 4.551(3.5); 4.542(3.3); 3.622(0.4); 3.611(0.3); 3.597(0.6); 3.583(0.7); 3.573(0.6); 3.559(0.3); 3.545(0.4); 3.334(26.6); 2.677(0.6); 2.673(0.8); 2.669(0.6); 2.526(1.7); 2.513(45.8); 2.508(92.2); 2.504(120.6); 2.500(86.8); 2.495(41.6); 2.335(0.6); 2.331(0.8); 2.326(0.6); 2.288(0.5); 0.008(0.6); 0.000(15.7); −0.009 (0.6) |
| 5 | 1.54 | | 1H-NMR(400.0 MHz, $d_6$-DMSO): δ = 9.320(8.2); 9.315(8.2); 9.302(0.4); 8.829(6.4); 8.825(6.8); 8.817(6.9); 8.813(6.6); 8.698(16.0); 8.530(4.0); 8.526(5.1); 8.520(3.9); 8.510(4.3); 8.506(5.3); 8.505(5.3); 8.500(4.0); 8.318(0.4); 7.672(4.8); 7.671(4.8); 7.660(4.8); 7.659(4.7); 7.652(4.8); 7.651(4.6); 7.640(4.5); 7.639(4.4); 5.143(0.3); 5.121(0.4); 5.089(3.5); 5.067(11.4); 5.044(11.9); 5.021(4.0); 3.363(0.6); 3.336(289.1); 2.720(1.5); 2.678(0.6); 2.674(0.8); 2.669(0.6); 2.527(2.1); 2.513(48.7); 2.509(96.7); 2.505(125.4); 2.500(89.6); 2.496(42.7); 2.336(0.6); 2.331(0.8); 2.327(0.6); 2.077(0.4); 0.008(1.2); 0.000(30.0); −0.008(1.1) |
| 6 | 1.57 | | 1H-NMR(400.0 MHz, $d_6$-DMSO): δ = 9.313(4.1); 9.308 (4.1); 8.818 (2.9); 8.809 (2.9); 8.806 (3.0); 8.789 (13.6); 8.521 (2.0); 8.517 (2.8); 8.511 (2.1); 8.501 (2.3); 8.496 (3.3); 8.491 (4.6); 8.477 (3.1); 7.841 (1.8); 7.837 (1.8); 7.822 (3.6); 7.818 (3.7); 7.803 (2.1); 7.798 (2.1); 7.666 (2.5); 7.654 (2.5); 7.646 (2.4); 7.634 (2.3); 7.478 (4.2); 7.458 (3.8); 7.333 (2.2); 7.321 (2.3); 7.316 (2.3); 7.304 (2.0); 5.399 (16.0); 3.904 (5.6); 3.508 (0.3); 3.477 (0.4); 3.455 (0.5); 3.354 (684.8); 3.268 (0.4); 3.175 (0.6); 3.162 (0.6); 2.678 (0.9); 2.673 (1.3); 2.669 (1.0); 2.526 (3.9); 2.513 (80.9); 2.509 (159.9); 2.504 (207.8); 2.500 (153.1); 2.496 (77.4); 2.335 (0.9); 2.331 (1.2); 2.327 (0.9); 1.234 (0.5); 0.008 (0.5); 0.000 (16.1); −0.008 (0.6) |
| 7 | 0.65 | | 1H-NMR(400.0 MHz, $d_6$-DMSO): δ = 9.317(2.0); 9.312(2.1); 8.821(1.7); 8.817(1.8); 8.809(1.8); 8.805(1.7); 8.525(1.0); 8.521(1.4); 8.516(1.1); 8.501(7.3); 7.667(1.3); 7.655(1.3); 7.647(1.3); 7.635(1.2); 5.010(7.5); 3.320(48.4); 3.297(0.4); 3.104(16.0); 2.884(14.6); 2.670(0.4); 2.540(0.3); 2.506(47.9); 2.502(61.3); 2.497(44.5); 2.328(0.4); 0.008(0.8); 0.000(16.9); −0.008(0.8) |
| 8 | 1.94 | 1.94 | 1H-NMR(400.0 MHz, $d_6$-DMSO): δ = 9.342(3.0); 9.337(2.9); 8.832(2.2); 8.828(2.5); 8.820(2.4); 8.816(2.5); 8.612(9.7); 8.553(1.3); 8.548(1.7); 8.543(1.4); 8.533(1.4); 8.527(1.8); 8.523(1.4); 7.678(1.8); 7.666(1.7); 7.658(1.7); 7.646(1.6); 7.497(1.3); 7.477(2.7); 7.459(2.4); 7.398(3.1); 7.381(4.4); 7.362(3.0); 5.758(0.5); 3.327(46.7); 2.676(0.4); 2.671(0.6); 2.667(0.4); 2.525(1.4); 2.520(2.2); 2.511(31.8); 2.507(65.7); 2.502(87.7); 2.498(64.6); 2.493(31.9); 2.402(16.0); 2.333(0.4); 2.329(0.6); 2.325(0.4); 2.309(0.5); 1.299(0.5); 1.259(0.7); 1.233(0.9); 1.183(0.3); 0.146(0.5); 0.008(3.7); 0.000(106.2); −0.009(3.7); −0.150(0.5) |
| 9 | 2.26 | 2.23 | 1H-NMR(400.0 MHz, $d_6$-DMSO): δ = 9.352(4.9); 9.346(4.8); 8.836(3.7); 8.833(4.1); 8.824(4.0); 8.821(4.1); 8.707(16.0); 8.563(2.1); 8.558(2.8); 8.553(2.2); 8.543(2.3); 8.537(3.1); 8.533(2.2); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 8.089(5.0); 7.953(3.6); 7.933(6.0); 7.868(3.1); 7.848(3.3); 7.829(1.4); 7.681(2.8); 7.669(2.8); 7.661(2.7); 7.650(2.5); 7.649(2.7); 4.038(0.5); 4.020(0.5); 3.328(60.0); 2.944(5.2); 2.784(4.1); 2.676(0.4); 2.672(0.5); 2.667(0.4); 2.525(1.3); 2.512(28.1); 2.507(57.8); 2.503(77.3); 2.498(57.0); 2.494(28.2); 2.334(0.4); 2.329(0.5); 2.325(0.4); 1.989(2.2); 1.957(4.3); 1.193(0.9); 1.175(1.3); 1.157(0.6); 0.008(2.3); 0.000(68.3); −0.009(2.6) |
| 10 | 1.73 | 1.76 | 1H-NMR(400.0 MHz, $d_6$-DMSO): δ = 9.345(0.5); 9.340(0.5); 8.833(0.4); 8.829(0.4); 8.821(0.4); 8.817(0.4); 8.620(1.4); 7.495(0.6); 7.475(0.4); 7.217(0.3); 7.211(0.6); 7.206(0.4); 7.155(0.4); 7.134(0.5); 3.818(3.8); 3.328(15.7); 2.944(16.0); 2.784(13.5); 2.507(16.3); 2.502(21.3); 2.498(16.0); 1.957(14.1); 0.008(1.0); 0.000(24.1); −0.008(1.1) |
| 11 | 1.92 | 1.96 | 1H-NMR(400.0 MHz, $d_6$-DMSO): δ = 9.341(3.2); 9.336(3.1); 8.831(2.4); 8.827(2.6); 8.819(2.5); 8.815(2.6); 8.598(10.7); 8.552(1.4); 8.547(1.9); 8.542(1.4); 8.532(1.5); 8.526(2.0); 8.522(1.4); 8.317(0.4); 7.677(1.9); 7.665(1.8); 7.657(1.8); 7.645(1.8); 7.462(4.1); 7.442(8.2); 7.399(6.4); 7.378(3.3); 5.758(0.4); 3.325(150.9); 2.675(1.1); 2.671(1.5); 2.666(1.2); 2.524(3.5); 2.510(82.2); 2.506(170.6); 2.502(229.7); 2.497(169.6); 2.493(83.7); 2.408(16.0); 2.333(1.1); 2.328(1.5); 2.324(1.1); 1.298(0.7); 1.258(1.0); 1.234(1.3); 0.000(2.4) |
| 12 | 1.73 | 1.76 | 1H-NMR(400.0 MHz, $d_6$-DMSO): δ = 8.591(0.4); 3.841(1.0); 3.328(7.1); 2.945(16.0); 2.784(13.9); 2.506(6.9); 2.502(8.5); 2.498(6.5); 1.958(14.6); 0.000(5.1) |
| 13 | 2.09 | 2.08 | 1H-NMR(400.0 MHz, $d_6$-DMSO): δ = 9.344(5.3); 9.340(5.4); 8.829(4.0); 8.820(4.1); 8.631(16.0); 8.554(2.6); 8.550(3.8); 8.545(2.8); 8.534(2.9); 8.529(4.0); 8.525(2.8); 8.150(2.0); 7.678(3.4); 7.666(3.5); 7.658(3.5); 7.646(3.3); 7.534(2.8); 7.515(7.2); 7.495(13.4); 7.459(0.3); 7.440(5.4); 7.420(3.2); 7.350(4.5); 7.329(3.5); 3.324(14.3); 2.859(0.4); 2.768(0.4); 2.671(0.9); 2.554(1.1); 2.529(47.8); 2.506(102.3); 2.502(131.0); 2.498(102.0); 2.476(2.9); 2.329(0.9); 1.295(0.3); 1.278(0.6); 1.187(0.4); 0.000(38.9) |
| 14 | 1.04 | 1.09 | 1H-NMR(400.0 MHz, $d_6$-DMSO): δ = 9.351(2.4); 9.346(2.2); 8.835(1.7); 8.832(1.8); 8.823(1.8); 8.820(1.8); 8.721(1.4); 8.707(6.9); 8.561(1.1); 8.556(1.4); 8.551(1.0); 8.541(1.2); 8.536(1.5); 8.531(1.0); 8.213(0.5); 8.208(0.3); 8.152(0.6); 7.939(1.5); 7.935(2.7); 7.907(0.4); 7.888(0.5); 7.879(0.7); 7.875(1.2); 7.871(0.8); 7.860(1.2); 7.856(2.2); 7.852(1.3); 7.828(1.2); 7.808(2.5); 7.789(1.8); 7.786(1.7); 7.782(2.4); 7.777(1.5); 7.767(0.6); 7.762(0.8); 7.758(0.4); 7.682(1.4); 7.670(1.3); 7.662(1.4); 7.650(1.3); 5.756(0.7); 3.323(10.5); 3.314(5.1); 2.847(0.7); 2.837(16.0); 2.671(0.4); 2.511(20.1); 2.507(40.7); 2.502(54.5); 2.498(41.2); 2.494(21.4); 2.329(0.3); 0.146(0.4); 0.008(3.0); 0.000(74.0); −0.008(4.1); −0.150(0.3) |
| 15 | 2.42 | 2.35 | 1H-NMR(601.6 MHz, $d_6$-DMSO): δ = 9.357(2.9); 9.354(2.9); 9.353(2.8); 8.842(2.5); 8.839(2.6); 8.834(2.6); 8.831(2.6); 8.636(10.4); 8.564(1.4); 8.561(1.9); 8.560(1.7); 8.557(1.4); 8.551(1.5); 8.548(1.8); 8.547(1.9); 8.544(1.5); 7.686(1.7); 7.685(1.7); 7.678(1.7); 7.677(1.7); 7.672(1.7); 7.671(1.7); 7.665(1.7); 7.663(1.7); 7.403(3.7); 7.400(3.9); 7.393(2.6); 7.380(2.9); 7.266(2.3); 7.263(2.2); 7.253(1.9); 7.249(1.9); 3.342(244.4); 2.955(1.3); 2.794(1.0); 2.627(0.7); 2.625(1.0); 2.622(0.7); 2.534(1.7); 2.531(2.2); 2.528(2.4); 2.519(52.0); 2.516(108.9); 2.513(148.0); 2.510(110.3); 2.507(54.0); 2.500(25.7); 2.400(0.7); 2.397(1.0); 2.394(0.7); 2.327(16.0); 2.297(0.4); 1.968(1.1) |
| 16 | 1.25 | 1.26 | 1H-NMR(400.0 MHz, $d_6$-DMSO): δ = 9.348(2.8); 9.343(2.8); 8.831(2.2); 8.819(2.3); 8.675(6.0); 8.554(1.7); 8.534(1.8); 7.960(3.2); 7.956(3.2); 7.679(1.7); 7.667(2.9); 7.660(2.0); 7.647(3.3); 7.541(2.8); 7.521(2.1); 3.326(55.5); 2.944(0.5); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 2.773(16.0); 2.690(0.5); 2.671(0.5); 2.502(76.7); 2.436(13.1); 2.328(0.5); 2.301(0.4); 1.957(0.4); 1.234(0.6); 0.000(0.5) |
| 17 | 2.70 | 2.66 | 1H-NMR(400.0 MHz, $d_6$-DMSO): δ = 9.353(5.0); 9.347(5.0); 8.837(3.7); 8.833(4.2); 8.825(4.0); 8.821(4.2); 8.659(16.0); 8.563(2.1); 8.558(2.9); 8.554(2.2); 8.543(2.2); 8.538(3.1); 8.534(2.3); 8.443(0.5); 8.317(0.6); 8.187(2.6); 8.181(2.8); 8.172(2.7); 8.165(2.8); 7.993(1.6); 7.986(1.6); 7.982(1.9); 7.975(1.8); 7.971(2.1); 7.964(2.1); 7.960(2.1); 7.953(1.9); 7.773(3.5); 7.751(6.1); 7.729(2.9); 7.682(2.9); 7.669(2.8); 7.662(2.8); 7.649(2.8); 5.758(0.5); 3.326(262.3); 2.675(2.1); 2.671(3.0); 2.666(2.3); 2.524(7.8); 2.519(11.5); 2.511(161.4); 2.506(336.0); 2.502(452.0); 2.497(336.0); 2.493(167.4); 2.333(2.1); 2.329(3.0); 2.324(2.2); 1.298(0.6); 1.259(0.8); 1.234(1.2); 1.203(0.4); 1.185(0.8); 1.167(0.4); 1.148(0.3); 0.146(2.7); 0.025(0.6); 0.008(19.5); 0.000(584.9); −0.009(21.7); −0.150(2.7) |
| 18 | 2.01 | 1.95 | 1H-NMR(400.0 MHz, $d_6$-DMSO): δ = 9.347(0.3); 8.927(7.1); 8.670(16.0); 8.659(1.1); 8.461(3.7); 8.459(3.6); 8.445(3.9); 8.443(3.8); 8.317(0.5); 8.182(3.0); 8.175(3.3); 8.166(3.2); 8.160(3.1); 8.083(3.7); 8.063(4.1); 7.987(1.8); 7.980(1.9); 7.976(2.1); 7.969(2.0); 7.965(2.4); 7.958(2.4); 7.954(2.4); 7.947(1.9); 7.773(3.7); 7.751(6.6); 7.730(3.1); 7.665(3.7); 7.648(4.1); 7.645(4.1); 7.628(3.2); 5.758(0.4); 3.325(270.0); 2.675(2.0); 2.671(2.7); 2.667(2.1); 2.574(0.4); 2.506(313.6); 2.502(411.0); 2.498(314.6); 2.333(1.9); 2.329(2.7); 2.324(2.0); 1.297(0.3); 1.259(0.4); 1.235(1.5); 1.196(0.4); 1.178(0.7); 1.160(0.4); 0.146(1.4); 0.008(11.9); 0.000(302.6); −0.150(1.5) |
| 19 | 2.39 | 2.43 | 1H-NMR(400.0 MHz, $d_6$-DMSO): δ = 9.343(3.7); 9.338(3.7); 8.832(2.7); 8.828(3.0); 8.820(2.9); 8.816(3.1); 8.633(11.2); 8.554(1.5); 8.549(2.2); 8.544(1.7); 8.534(1.7); 8.528(2.3); 8.524(1.7); 8.316(0.7); 7.677(2.1); 7.665(2.1); 7.657(2.1); 7.645(2.0); 7.545(2.7); 7.540(5.9); 7.519(4.3); 7.500(3.6); 7.468(3.5); 7.448(1.7); 7.373(2.6); 7.357(1.6); 7.353(2.0); 3.324(30.1); 3.083(2.3); 3.065(7.5); 3.046(7.6); 3.028(2.5); 2.945(1.3); 2.785(1.1); 2.671(0.4); 2.525(1.0); 2.507(46.5); 2.502(62.8); 2.498(47.8); 2.329(0.4); 1.957(1.1); 1.302(7.8); 1.284(16.0); 1.266(7.5); 0.008(2.3); 0.000(63.4); −0.008(3.2) |
| 20 | 1.24 | 1.26 | 1H-NMR(400.0 MHz, $d_6$-DMSO): δ = 9.356(4.7); 9.351(4.7); 8.841(3.4); 8.838(3.6); 8.829(3.6); 8.826(3.6); 8.735(0.5); 8.712(12.7); 8.566(2.0); 8.562(2.8); 8.557(2.0); 8.546(2.2); 8.541(2.9); 8.537(2.0); 8.164(2.1); 7.889(5.6); 7.823(5.6); 7.821(5.6); 7.814(4.9); 7.809(7.5); 7.797(1.3); 7.787(3.5); 7.782(2.9); 7.778(2.2); 7.772(2.6); 7.764(1.0); 7.759(0.9); 7.687(2.6); 7.675(2.6); 7.667(2.6); 7.655(2.5); 3.407(0.5); 3.388(0.7); 3.332(3.2); 3.172(0.5); 3.154(1.8); 3.136(2.2); 3.120(2.5); 3.102(2.2); 3.084(0.7); 2.901(0.6); 2.883(2.2); 2.864(2.5); 2.849(2.1); 2.830(1.8); 2.812(0.5); 2.679(0.4); 2.674(0.3); 2.514(50.7); 2.510(65.6); 2.506(49.5); 2.341(0.3); 2.337(0.4); 1.169(0.6); 1.106(7.5); 1.088(16.0); 1.070(7.3); 1.058(0.8) |
| 21 | 2.95 | 2.91 | 1H-NMR(400.0 MHz, $d_6$-DMSO): δ = 9.350(3.0); 9.346(3.1); 9.344(3.0); 8.839(2.4); 8.836(2.6); 8.827(2.6); 8.824(2.6); 8.679(8.7); 8.561(1.4); 8.557(1.8); 8.551(1.4); 8.541(1.5); 8.537(1.9); 8.535(1.9); 8.531(1.5); 7.939(3.1); 7.921(3.1); 7.684(1.8); 7.683(1.7); 7.672(1.7); 7.671(1.7); 7.664(1.8); 7.663(1.7); 7.652(1.7); 7.651(1.7); 7.518(2.7); 7.491(2.6); 4.062(1.2); 4.037(3.9); 4.011(4.0); 3.985(1.4); 3.330(57.6); 2.945(1.0); 2.785(0.7); 2.672(0.4); 2.526(1.0); 2.512(19.8); 2.508(40.6); 2.503(53.8); 2.499(39.4); 2.494(19.5); 2.471(16.0); 2.330(0.3); 2.076(10.9); 1.958(0.8); 0.008(1.0); 0.000(30.1); −0.009(1.2) |

TABLE 2-continued

Analytical data for the compounds reported

| Ex. No. | logP[a] | logP[b] | 1H-NMR [σ (ppm)] or LC-MS [m/z] |
|---|---|---|---|
| 22 | 2.01 | 1.98 | 1H-NMR(400.0 MHz, $d_6$-DMSO): δ = 9.761(0.5); 9.353(6.6); 9.347(6.9); 9.102(0.4); 8.836(5.2); 8.828(4.9); 8.824(5.2); 8.738(0.5); 8.723(15.6); 8.557(4.0); 8.553(2.9); 8.543(2.8); 8.537(4.3); 8.533(3.1); 8.315(2.5); 8.195(6.5); 8.176(6.5); 8.039(0.4); 7.951(2.4); 7.685(3.8); 7.673(3.8); 7.665(4.0); 7.653(3.8); 7.635(5.0); 7.608(5.1); 7.366(0.4); 7.238(0.6); 5.755(1.0); 4.293(0.9); 4.271(1.2); 4.263(1.3); 4.233(1.1); 4.182(0.4); 4.124(1.0); 4.100(1.2); 3.505(1.6); 3.322(748.9); 2.944(1.9); 2.891(16.0); 2.784(1.6); 2.731(14.3); 2.716(0.5); 2.670(6.0); 2.666(4.8); 2.505(695.9); 2.501(960.0); 2.497(767.5); 2.395(0.8); 2.373(2.4); 2.328(6.2); 2.324(5.1); 2.283(0.4); 1.957(1.9); 1.303(0.3); 1.284(0.6); 1.233(2.0); 0.854(0.4); 0.146(3.0); 0.008(21.8); 0.000(638.0); −0.078(0.4); −0.150(3.2) |
| 23 | 1.49 | 1.45 | 1H-NMR(400.0 MHz, $d_6$-DMSO): δ = 8.928(9.2); 8.734(16.0); 8.463(5.2); 8.446(5.3); 8.315(0.9); 8.196(7.0); 8.177(7.1); 8.082(5.1); 8.061(5.7); 7.668(4.5); 7.649(5.9); 7.633(8.7); 7.608(5.6); 7.573(0.4); 7.251(0.4); 4.265(1.6); 4.236(1.3); 4.117(1.2); 4.106(1.2); 4.092(1.4); 3.322(182.5); 2.671(2.1); 2.502(339.3); 2.498(298.4); 2.402(0.7); 2.373(1.6); 2.329(2.4); 0.146(1.6); 0.000(312.8); −0.083(0.4); −0.150(1.7) |
| 24 | 2.76 | 2.70 | 1H-NMR(400.0 MHz, $d_6$-DMSO): δ = 9.345(0.4); 9.340(0.4); 8.640(1.0); 7.597(0.5); 7.539(0.3); 7.520(0.4); 7.512(0.4); 3.327(6.0); 2.945(16.0); 2.785(13.5); 2.507(6.8); 2.503(9.0); 2.498(6.9); 1.989(0.6); 1.958(14.1); 1.305(2.7); 1.289(2.7); 0.000(8.3); −0.008(0.4) |
| 25 | 1.39 | 1.43 | 1H-NMR(400.0 MHz, $d_6$-DMSO): δ = 9.351(4.6); 9.347(4.5); 8.835(3.5); 8.832(3.8); 8.823(3.7); 8.820(3.8); 8.727(0.5); 8.701(15.5); 8.562(2.1); 8.558(2.7); 8.556(2.6); 8.552(2.1); 8.542(2.3); 8.538(2.7); 8.536(2.9); 8.532(2.1); 8.317(0.3); 7.858(3.3); 7.853(5.8); 7.828(0.7); 7.821(0.4); 7.810(2.1); 7.791(7.7); 7.788(7.6); 7.785(6.6); 7.783(5.9); 7.777(5.1); 7.772(3.1); 7.765(1.1); 7.759(1.4); 7.754(1.0); 7.682(2.6); 7.680(2.6); 7.670(2.5); 7.668(2.6); 7.662(2.5); 7.660(2.5); 7.650(2.4); 7.648(2.5); 5.757(16.0); 3.325(116.5); 3.085(0.8); 3.068(2.2); 3.051(3.1); 3.034(2.3); 3.016(0.9); 2.680(0.4); 2.676(0.9); 2.671(1.3); 2.667(0.9); 2.524(3.1); 2.511(71.5); 2.507(145.1); 2.502(193.0); 2.498(144.3); 2.493(72.7); 2.425(0.5); 2.333(1.0); 2.329(1.3); 2.324(1.0); 1.259(0.6); 1.241(15.6); 1.224(15.5); 1.205(1.6); 1.186(1.2); 1.172(0.6); 1.169(0.5); 0.996(15.2); 0.979(15.1); 0.965(0.8); 0.853(0.3); 0.000(1.5) |
| 26 | 3.18 | 3.08 | 1H-NMR(400.0 MHz, $d_6$-DMSO): δ = 9.345(1.9); 9.340(2.0); 8.833(1.4); 8.829(1.6); 8.821(1.5); 8.817(1.6); 8.625(6.3); 8.556(0.8); 8.551(1.2); 8.546(0.9); 8.536(0.9); 8.530(1.2); 8.526(0.9); 7.679(1.1); 7.667(1.1); 7.660(1.1); 7.646(1.0); 7.550(1.4); 7.546(2.6); 7.542(1.7); 7.525(0.7); 7.505(2.0); 7.486(2.0); 7.477(1.3); 7.473(2.2); 7.469(1.4); 7.457(0.6); 7.453(0.8); 7.364(1.0); 7.360(1.5); 7.355(1.0); 7.345(0.9); 7.340(1.1); 7.337(0.8); 3.329(56.9); 2.941(4.9); 2.924(5.0); 2.676(0.4); 2.671(0.5); 2.667(0.4); 2.524(1.7); 2.511(32.1); 2.507(63.8); 2.502(83.8); 2.498(62.6); 2.333(0.4); 2.329(0.5); 2.324(0.4); 1.895(0.4); 1.878(0.9); 1.862(1.1); 1.845(0.9); 1.828(0.5); 1.234(0.5); 1.020(16.0); 1.003(15.4); 0.000(8.1) |
| 27 | 1.73 | 1.68 | 1H-NMR(400.0 MHz, $d_6$-DMSO): δ = 9.351(5.0); 9.346(5.1); 8.835(3.7); 8.831(4.0); 8.823(4.0); 8.819(3.9); 8.724(0.3); 8.706(14.0); 8.561(2.1); 8.557(2.9); 8.552(2.2); 8.541(2.3); 8.536(3.1); 8.532(2.2); 7.924(6.3); 7.860(2.3); 7.857(1.6); 7.846(3.0); 7.842(5.0); 7.838(3.2); 7.824(2.8); 7.805(5.5); 7.786(4.3); 7.784(4.2); 7.779(5.4); 7.774(3.3); 7.764(1.3); 7.760(1.8); 7.755(1.0); 7.681(2.8); 7.669(2.8); 7.661(2.8); 7.649(2.6); 5.757(4.4); 3.332(67.3); 2.853(0.6); 2.820(4.9); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 2.814(4.8); 2.800(8.5); 2.782(0.7); 2.766(0.3); 2.672(0.7); 2.507(77.9); 2.503(99.5); 2.498(76.3); 2.330(0.7); 2.325(0.5); 2.160(0.9); 2.143(1.5); 2.126(1.8); 2.108(1.5); 2.091(0.9); 2.075(0.3); 1.233(1.0); 1.192(0.4); 1.130(15.9); 1.113(15.7); 1.094(0.8); 1.034(15.8); 1.017(16.0); 1.004(1.2); 0.995(0.9); 0.977(0.3); 0.000(0.8) |
| 28 | 2.47 | 2.43 | 1H-NMR(600.1 MHz, CD3CN): = 9.2734(3.7); 9.2728(3.7); 9.270(3.8); 8.751(2.8); 8.748(2.9); 8.743(2.9); 8.740(2.8); 8.469(9.8); 8.403(1.8); 8.400(2.4); 8.399(2.3); 8.396(1.7); 8.389(1.9); 8.387(2.4); 8.386(2.3); 8.383(1.7); 7.744(3.9); 7.662(2.1); 7.650(3.1); 7.641(2.5); 7.576(2.2); 7.563(3.2); 7.550(1.3); 7.534(2.3); 7.533(2.2); 7.526(2.3); 7.525(2.2); 7.521(2.3); 7.520(2.1); 7.513(2.2); 7.512(2.0); 5.293(16.0); 2.957(13.9); 2.827(11.1); 2.154(11.6); 1.972(12.0); 1.967(0.5); 1.959(0.6); 1.955(0.8); 1.951(5.6); 1.947(10.0); 1.943(14.5); 1.938(9.7); 1.934(4.8); 0.000(6.8) |
| 32 | 1.91 | 1.92 | 1H-NMR(400.0 MHz, d$_6$-DMSO): δ = 9.303(2.1); 9.297(2.1); 8.859(5.1); 8.814(1.4); 8.810(1.7); 8.802(1.5); 8.798(1.6); 8.513(0.8); 8.508(1.2); 8.503(0.9); 8.493(0.9); 8.487(1.3); 8.483(0.9); 7.658(1.2); 7.646(1.2); 7.638(1.1); 7.626(1.1); 7.300(1.2); 7.280(2.2); 7.260(1.4); 6.987(2.0); 6.943(1.5); 6.924(1.3); 6.899(1.2); 6.894(1.1); 6.879(1.0); 6.873(1.0); 5.241(6.2); 3.744(16.0); 3.332(39.1); 2.945(0.5); 2.785(0.5); 2.673(0.4); 2.668(0.4); 2.508(50.3); 2.504(67.2); 2.499(52.6); 2.330(0.4); 1.958(0.5); 1.233(0.5); 0.008(1.6); 0.000(42.7) |
| 34 | 1.09 | | 1H-NMR(400.0 MHz, d$_6$-DMSO): δ = 9.324 (8.2); 9.320 (8.0); 8.828 (5.9); 8.819 (5.7); 8.652 (16.0); 8.533 (4.1); 8.528 (5.4); 8.523 (3.9); 8.513 (4.3); 8.508 (5.6); 8.503 (3.8); 7.673 (4.7); 7.661 (4.8); 7.653 (4.6); 7.641 (4.2); 6.830 (1.0); 6.818 (1.8); 6.805 (0.9); 6.700 (2.0); 6.688 (3.9); 6.676 (2.0); 6.570 (1.0); 6.558 (2.0); 6.546 (1.0); 4.914 (5.2); 4.875 (10.9); 4.837 (5.5); 3.905 (7.6); 3.506 (0.4); 3.338 (626.8); 3.225 (1.1); 3.062 (0.9); 2.677 (2.1); 2.672 (2.7); 2.668 (2.1); 2.508 (339.6); 2.503 (425.1); 2.499 (319.3); 2.334 (1.9); 2.330 (2.5); 2.325 (1.9); 1.298 (0.4); 1.258 (0.5); 1.233 (0.7); 1.145 (0.7); 0.000 (37.7) |
| 35 | | 0.72 | LC-MS: mass found [m/z] = 321.07 |
| 36 | 0.55 | | 1H-NMR(400.0 MHz, d$_6$-DMSO): δ = 9.319 (4.3); 9.314 (4.3); 8.846 (14.5); 8.822 (3.1); 8.813 (3.3); 8.554 (4.4); 8.542 (4.4); 8.527 (2.8); 8.522 (3.4); 8.517 (2.5); 8.507 (2.8); 8.501 (3.4); 8.497 (2.4); 8.489 (0.5); 8.364 (0.4); 8.357 (0.4); 7.669 (2.7); 7.657 (2.8); 7.649 (2.9); 7.637 (2.6); 7.331 (6.3); 7.317 (6.1); 5.316 (16.0); 3.905 (6.2); 3.508 (0.4); 3.469 (0.4); 3.349 (770.9); 2.678 (1.1); 2.673 (1.5); 2.669 (1.1); 2.526 (4.9); 2.513 (93.8); 2.508 (184.1); 2.504 (238.5); 2.500 (175.4); 2.495 (88.2); 2.335 (1.1); 2.331 (1.4); 2.326 (1.1); 1.234 (0.6); 0.008 (0.7); 0.000 (21.0); −0.008 (0.8) |
| 37 | 0.97 | 1.08 | 1H-NMR(400.0 MHz, d$_6$-DMSO): δ = 9.295(1.6); 9.290(1.6); 8.809(6.3); 8.797(1.4); 8.793(1.4); 8.746(0.3); 8.743(0.3); 8.503(0.8); 8.498(1.1); 8.493(0.9); 8.483(0.9); 8.478(1.2); 8.473(0.9); 8.350(0.3); 7.772(3.5); 7.652(1.1); 7.640(1.1); 7.632(1.1); 7.622(1.3); 7.603(0.3); 7.595(0.4); 7.583(0.3); 7.563(0.6); 7.554(0.3); 7.506(3.6); 7.480(0.5); 7.460(0.5); 7.363(0.8); 7.325(0.5); 7.118(0.4); 7.008(0.3); 5.757(1.6); 5.097(6.4); 4.268(0.7); 4.254(0.7); 4.205(0.4); 4.191(0.4); 3.950(0.3); 3.788(4.5); 3.782(16.0); 3.750(0.6); 3.703(0.3); 3.394(0.4); 3.328(25.5); 3.264(0.5); 2.676(0.4); 2.672(0.5); 2.667(0.4); 2.542(0.4); 2.525(1.2); 2.512(29.4); 2.507(60.8); 2.503(81.9); 2.498(62.0); 2.494(32.1); 2.334(0.4); 2.330(0.6); 2.325(0.4); 2.287(1.3); 1.318(0.3); 1.298(1.0); 1.278(0.4); 1.259(1.3); 1.233(1.3); 1.212(0.4); 1.196(0.3); 0.008(2.4); 0.000(75.0); −0.008(3.4); −0.150 (0.3) |
| 38 | 1.36 | 1.42 | 1H-NMR(400.0 MHz, d$_6$-DMSO): δ = 9.305(2.2); 9.301(2.3); 8.815(1.6); 8.812(1.9); 8.798(6.3); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 8.511(1.3); 8.506(1.0); 8.495(1.0); 8.490(1.4); 8.486(1.1); 7.661(1.3); 7.648(1.3); 7.641(1.3); 7.628(1.2); 7.454(4.1); 7.277(0.5); 5.759(0.4); 5.308(7.1); 4.489(0.4); 4.476(0.4); 3.332(61.6); 2.945(0.9); 2.784(0.8); 2.672(0.9); 2.655(1.3); 2.637(2.1); 2.611(16.0); 2.507(95.2); 2.503(124.7); 2.499(102.9); 2.446(0.4); 2.330(0.8); 2.288(0.7); 1.958(0.8); 1.313(0.5); 0.146(0.4); 0.000(71.2); −0.150 (0.4) |
| 39 | 1.53 | 1.52 | 1H-NMR(601.6 MHz, CDCl$_3$): δ = 9.341(5.1); 9.338(5.0); 8.781(3.5); 8.775(3.6); 8.426(2.9); 8.423(3.9); 8.420(2.8); 8.413(3.1); 8.410(4.0); 8.407(2.8); 8.299(16.0); 7.484(3.2); 7.476(3.3); 7.471(3.3); 7.463(3.1); 7.432(0.6); 7.261(86.9); 7.084(0.5); 5.299(2.5); 3.958(15.5); 3.946(15.6); 3.278(0.4); 3.269(0.5); 3.266(0.4); 3.257(0.4); 2.232(0.4); 2.220(0.6); 2.207(0.4); 1.637(0.4); 1.558(13.5); 1.445(0.4); 1.368(0.5); 1.360(0.9); 1.355(1.3); 1.352(0.9); 1.347(2.2); 1.342(2.1); 1.339(1.8); 1.334(3.5); 1.329(2.0); 1.326(2.4); 1.321(2.7); 1.313(2.0); 1.309(1.8); 1.301(1.4); 1.255(7.8); 0.892(1.0); 0.881(1.8); 0.869(1.1); 0.856(0.4); 0.841(0.4); 0.715(2.2); 0.707(6.7); 0.705(7.1); 0.697(3.5); 0.694(7.0); 0.692(6.7); 0.684(2.5); 0.577(0.4); 0.575(0.4); 0.564(0.4); 0.562(0.4); 0.491(2.4); 0.483(8.8); 0.473(8.4); 0.465(2.0); 0.276(0.4); 0.267(0.5); 0.097(0.4); 0.005(2.9); 0.000(86.6); −0.006(3.2); −0.100(0.4) |
| 40 | 1.70 | 1.69 | 1H-NMR(400.0 MHz, d6-DMSO): δ = 9.347(5.5); 9.343(5.8); 8.838(4.1); 8.835(4.6); 8.826(4.5); 8.823(4.6); 8.709(16.0); 8.692(0.3); 8.558(3.0); 8.554(4.0); 8.553(3.9); 8.549(3.2); 8.538(3.3); 8.534(4.1); 8.533(4.3); 8.528(3.4); 8.319(0.3); 8.236(1.6); 7.749(2.1); 7.745(2.5); 7.730(4.4); 7.726(5.0); 7.711(2.6); 7.706(2.9); 7.683(4.8); 7.678(1.9); 7.670(4.7); 7.664(6.0); 7.650(5.7); 7.644(3.1); 7.639(2.1); 7.630(1.9); 7.626(1.7); 7.556(3.1); 7.554(3.4); 7.532(4.4); 7.528(3.8); 7.510(2.4); 7.507(2.4); 7.481(0.3); 7.470(3.3); 7.468(3.3); 7.451(5.2); 7.449(5.3); 7.432(2.5); 7.429(2.5); 5.758(1.7); 4.354(0.3); 4.336(0.4); 4.252(0.6); 4.234(0.6); 3.364(1.0); 2.678(0.5); 2.673(0.7); 2.669(0.5); 2.526(1.6); 2.522(2.4); 2.513(34.4); 2.508(71.9); 2.504(96.4); 2.499(71.1); 2.495(35.5); 2.335(0.6); 2.331(0.8); 2.326(0.6); 2.287(0.4); 2.077(2.4); 1.342(0.5); 1.335(0.6); 1.318(1.0); 1.300(0.8); 1.296(1.0); 1.278(1.5); 1.260(0.9); 1.232(0.7); 0.146(0.9); 0.008(7.0); 0.000(192.4); −0.009(8.3); −0.150(0.9) |
| 41 | 2.33 | 2.34 | 1H-NMR(400.0 MHz, d6-DMSO): δ = 9.344(5.7); 9.339(6.0); 8.833(4.1); 8.829(4.6); 8.821(4.4); 8.817(4.6); 8.627(16.0); 8.554(2.3); 8.549(3.4); 8.544(2.5); 8.534(2.5); 8.529(3.6); 8.524(2.5); 7.678(3.2); 7.666(3.2); 7.658(3.2); 7.646(3.0); 7.576(3.2); 7.556(6.7); 7.535(4.2); 7.372(3.8); 7.366(6.9); 7.361(4.9); 7.283(4.3); 7.278(4.5); 7.275(4.6); 7.266(4.6); 7.261(3.9); 7.254(3.7); 7.248(3.1); 5.754(0.8); 4.878(2.5); 4.856(8.1); 4.834(8.5); 4.812(2.9); 4.738(0.4); 3.319(61.3); 2.676(0.6); 2.671(0.8); 2.667(0.7); 2.506(96.9); 2.502(128.4); 2.498(98.2); 2.333(0.6); 2.329(0.8); 2.324(0.6); 1.234(1.8); 1.187(0.5); 0.008(0.6); 0.000(16.4) |
| 42 | 1.63 | 1.72 | 1H-NMR(400.0 MHz, d6-DMSO): δ = 9.350(1.3); 9.345(1.3); 8.835(0.9); 8.831(1.0); 8.823(1.0); 8.819(1.0); 8.714(3.3); 8.560(0.5); 8.556(0.7); 8.551(0.5); 8.540(0.6); 8.535(0.8); 8.531(0.5); 8.055(1.6); 7.967(0.6); 7.962(0.4); 7.948(1.0); 7.944(0.7); 7.929(0.5); 7.925(0.4); 7.909(1.4); 7.894(1.3); 7.875(1.1); 7.856(0.4); 7.680(0.7); 7.668(0.7); 7.660(0.7); 7.648(0.7); 3.320(7.9); 2.681(16.0); 2.507(13.0); 2.502(16.4); 2.498(12.5); 0.000(16.1) |
| 43 | 2.05 | 2.06 | 1H-NMR(400.0 MHz, d6-DMSO): δ = 9.343(2.6); 8.829(1.8); 8.820(1.9); 8.635(3.7); 8.549(1.5); 8.530(1.6); 7.666(6.6); 7.647(6.5); 7.625(2.2); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 7.459(0.4); 7.412(0.5); 7.390(0.6); 7.364(0.7); 7.333(0.9); 7.267(0.4); 7.245(0.3); 7.181(1.3); 7.115(0.4); 3.318(83.2); 2.671(2.4); 2.501(395.6); 2.327(3.0); 2.286(1.2); 2.180(0.5); 1.988(0.4); 1.386(2.2); 1.335(12.4); 1.298(9.2); 1.249(16.0); 1.235(16.0); 1.188(3.6); 1.105(1.7); 0.852(4.1); 0.834(3.9); 0.146(0.4); 0.000(59.8); −0.151(0.4) |
| 44 | 2.91 | 3.00 | 1H-NMR(400.0 MHz, d6-DMSO): δ = 9.345(7.4); 9.340(7.7); 8.836(5.3); 8.834(5.7); 8.825(5.5); 8.822(5.6); 8.700(16.0); 8.550(4.4); 8.534(3.2); 8.530(4.5); 7.753(4.1); 7.747(4.7); 7.736(4.3); 7.730(4.5); 7.681(4.1); 7.669(4.1); 7.661(4.1); 7.649(3.9); 7.601(1.9); 7.595(2.1); 7.589(2.3); 7.579(3.1); 7.573(3.1); 7.568(3.1); 7.562(2.6); 7.490(4.6); 7.467(6.6); 7.444(3.2); 3.312(33.5); 2.988(15.3); 2.970(15.6); 2.672(0.7); 2.502(104.5); 2.329(0.6); 2.074(2.1); 1.234(0.4); 1.085(0.6); 1.078(1.0); 1.066(1.9); 1.059(1.8); 1.047(2.9); 1.035(1.9); 1.029(2.1); 1.016(1.1); 1.010(0.7); 0.998(0.3); 0.567(2.3); 0.556(7.5); 0.552(8.2); 0.536(7.6); 0.532(7.5); 0.522(2.6); 0.282(2.7); 0.269(9.5); 0.256(9.5); 0.245(2.2); 0.000(8.6) |
| 45 | 1.63 | 1.66 | 1H-NMR(400.0 MHz, d6-DMSO): δ = 9.354(9.8); 9.353(9.9); 9.349(9.7); 8.841(7.9); 8.837(8.0); 8.829(8.1); 8.825(7.7); 8.759(8.5); 8.753(16.0); 8.564(4.8); 8.560(6.0); 8.554(4.1); 8.544(5.1); 8.540(6.0); 8.538(5.7); 8.534(3.9); 8.369(1.6); 8.363(1.7); 8.352(1.6); 8.346(1.6); 8.318(1.2); 8.185(0.9); 8.179(0.9); 8.173(1.1); 8.167(1.1); 8.163(1.1); 8.157(1.1); 8.152(1.1); 8.146(0.9); 8.087(4.6); 8.082(5.1); 8.070(4.8); 8.065(4.8); 7.965(2.7); 7.960(2.7); 7.954(3.4); 7.948(3.1); 7.943(3.4); 7.938(3.3); 7.932(3.3); 7.927(2.7); 7.872(1.0); 7.869(1.3); 7.862(1.7); 7.851(0.7); 7.840(2.5); 7.817(1.4); 7.785(5.2); 7.762(7.2); 7.740(4.3); 7.687(6.0); 7.675(5.9); 7.667(5.8); 7.655(5.5); 7.589(0.4); 7.571(0.6); 5.758(8.2); 5.599(0.5); 4.153(0.4); 4.142(0.5); 4.129(0.4); 3.852(0.4); 3.601(0.5); 3.589(0.5); 3.577(0.4); 3.519(1.8); 3.506(0.8); 3.378(4.0); 3.360(4.6); 3.329(329.8); 3.279(0.4); 3.273(0.5); 2.977(0.4); 2.927(7.4); 2.909(7.4); 2.891(3.0); 2.844(0.4); 2.820(8.6); 2.748(0.5); 2.732(1.9); 2.676(2.3); 2.672(3.1); 2.667(2.4); 2.650(0.3); 2.621(0.4); 2.595(2.0); 2.584(0.8); 2.525(12.9); 2.511(184.2); 2.507(356.1); 2.503(459.1); 2.498(337.4); 2.494(171.5); 2.334(2.2); 2.329(2.9); 2.325(2.2); 2.087(6.4); 1.492(0.4); 1.474(0.5); 1.454(0.4); 1.291(0.4); 1.274(0.6); 1.259(0.9); 1.234(2.5); 1.187(0.4); 0.996(0.9); 0.984(1.8); 0.977(1.8); 0.965(2.6); 0.953(1.9); 0.946(2.0); 0.934(1.4); 0.921(0.9); 0.915(1.0); 0.902(1.1); 0.889(0.8); 0.883(0.9); 0.870(0.8); 0.862(1.0); 0.852(0.9); 0.844(1.8); 0.825(1.8); 0.806(0.7); 0.608(0.5); 0.585(2.5); 0.574(8.6); 0.565(4.7); 0.554(8.4); 0.545(2.8); 0.531(0.7); 0.522(1.0); 0.504(2.6); 0.484(2.4); 0.342(1.8); 0.336(1.9); 0.322(4.0); 0.311(3.7); 0.296(0.9); 0.284(0.9); 0.270(3.7); 0.258(4.0); 0.245(2.0); 0.238(1.7); 0.227(0.8); 0.146(5.9); 0.137(2.5); 0.053(0.3); 0.008(34.5); 0.000(766.5); −0.008(43.1); −0.064(0.6); −0.079(0.4); −0.099(0.3); −0.150(3.6) |
| 46 | 2.60 | 2.56 | 1H-NMR(400.0 MHz, d6-DMSO): δ = 9.351(5.7); 9.347(5.7); 8.841(4.5); 8.837(5.0); 8.829(4.8); 8.825(4.9); 8.710(16.0); 8.563(2.6); 8.558(3.5); 8.553(2.7); 8.543(2.9); 8.537(3.6); 8.533(2.7); 8.317(1.0); 7.948(3.6); 7.942(4.0); 7.931(3.7); 7.925(3.8); 7.791(1.9); 7.785(2.0); 7.780(2.2); 7.774(2.1); 7.770(2.3); 7.763(2.4); 7.758(2.4); 7.752(2.0); 7.685(3.4); 7.672(3.3); 7.666(3.3); 7.654(3.1); 7.652(3.1); 7.571(3.9); 7.548(5.4); 7.525(3.2); 4.139(2.5); 4.114(7.7); 4.088(8.1); 4.062(2.7); 3.330(493.3); 3.288(0.4); 2.676(2.0); 2.671(2.7); 2.667(2.0); 2.525(7.4); 2.511(147.5); 2.507(299.9); 2.502(398.3); 2.498(297.0); 2.494(151.2); 2.457(1.0); 2.437(0.6); 2.334(2.0); 2.329(2.7); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 2.325(2.0); 2.075(3.9); 0.146(0.9); 0.008(6.8); 0.000(200.5); −0.008(8.5); −0.150(0.9) |
| 47 | 2.73 | 2.75 | 1H-NMR(400.0 MHz, d6-DMSO): δ = 10.481(0.3); 9.349(3.0); 9.344(3.0); 8.834(2.4); 8.830(2.6); 8.822(2.5); 8.818(2.6); 8.612(10.2); 8.559(1.4); 8.554(1.8); 8.549(1.4); 8.539(1.5); 8.534(2.0); 8.529(1.5); 8.435(0.6); 7.787(0.4); 7.769(3.7); 7.764(3.7); 7.679(1.8); 7.667(1.8); 7.659(1.8); 7.647(1.7); 7.472(2.0); 7.451(3.9); 7.415(2.9); 7.410(2.8); 7.395(1.5); 7.390(1.5); 5.757(0.9); 4.118(1.2); 4.092(3.8); 4.066(4.0); 4.040(1.4); 3.880(0.4); 3.865(0.4); 3.854(0.4); 3.848(0.4); 3.328(110.4); 2.676(0.7); 2.671(0.9); 2.667(0.7); 2.525(2.5); 2.511(52.6); 2.507(105.2); 2.502(138.7); 2.498(103.1); 2.493(51.6); 2.427(16.0); 2.358(1.6); 2.334(0.7); 2.329(1.0); 2.324(0.8); 1.233(0.5); 1.201(0.4); 1.184(0.9); 1.166(0.4); 0.146(0.9); 0.008(7.4); 0.000(188.5); −0.009(7.9); −0.150(0.9) |
| 48 | 1.86 | 1.85 | 1H-NMR(400.0 MHz, d6-DMSO): δ = 9.350(3.3); 9.345(3.3); 8.834(2.3); 8.830(2.5); 8.822(2.4); 8.818(2.4); 8.689(8.7); 8.559(1.4); 8.555(1.9); 8.550(1.4); 8.539(1.5); 8.534(2.0); 8.530(1.4); 8.145(1.0); 8.046(4.0); 8.041(4.2); 7.895(0.7); 7.891(0.6); 7.878(0.4); 7.758(1.9); 7.753(1.8); 7.738(2.4); 7.733(2.4); 7.679(1.9); 7.668(2.0); 7.660(1.8); 7.648(1.7); 7.594(3.3); 7.573(2.6); 7.531(0.4); 4.272(0.9); 4.263(0.5); 4.253(0.7); 4.245(1.1); 4.235(1.8); 4.217(0.6); 4.208(1.3); 4.181(0.4); 4.123(0.4); 4.096(1.2); 4.087(0.4); 4.069(1.4); 4.059(1.0); 4.042(0.5); 4.032(0.9); 3.320(6.0); 2.996(0.5); 2.671(0.5); 2.667(0.4); 2.506(55.7); 2.502(71.4); 2.498(55.1); 2.477(16.0); 2.329(0.5); 1.296(0.5); 1.278(1.1); 1.260(0.5); 0.000(2.1) |
| 49 | 3.04 | 2.98 | 1H-NMR(400.0 MHz, $d_6$-DMSO): δ = 9.347(2.9); 9.342(3.0); 8.838(2.3); 8.834(2.4); 8.826(2.4); 8.822(2.5); 8.558(1.3); 8.554(1.9); 8.548(1.4); ,536(10.2); 8.528(1.5); 8.317(0.8); 7.924(0.4); 7.683(1.9); 7.675(6.4); 7.665(2.0); 7.651(1.5); 7.360(4.7); 6.025(1.0); 4.055(0.6); 4.038(2.6); 4.020(2.4); 4.014(3.6); 4.002(0.9); 3.988(3.6); 3.962(1.3); 3.855(0.8); 3.837(0.8); 3.392(0.3); 3.374(0.5); 3.332(421.8); 2.676(1.7); 2.671(2.3); 2.667(1.7); 2.525(5.6); 2.511(131.6); 2.507(269.9); 2.502(357.0); 2.498(264.5); 2.494(133.5); 2.407(15.0); 2.365(0.4); 2.334(1.8); 2.329(2.4); 2.325(1.8); 2.078(16.0); 1.989(7.6); 1.890(0.3); 1.398(1.9); 1.235(0.6); 1.193(2.1); 1.175(4.1); 1.157(2.1); 1.100(0.8); 1.083(1.5); 1.065(0.8); 0.146(0.5); 0.008(3.7); 0.000(116.2); −0.008(4.9); −0.150(0.5) |
| 50 | 2.06 | 2.01 | 1H-NMR(400.0 MHz, $d_6$-DMSO): δ = 9.351(4.6); 9.346(4.6); 8.839(3.4); 8.835(3.7); 8.827(3.6); 8.823(3.7); 8.591(14.3); 8.561(1.9); 8.556(2.7); 8.551(1.9); 8.541(2.0); 8.536(2.8); 8.531(1.9); 8.317(1.3); 7.937(6.3); 7.928(4.2); 7.685(2.6); 7.673(2.6); 7.667(2.5); 7.653(2.4); 7.496(3.0); 7.470(4.4); 4.323(0.5); 4.295(0.6); 4.286(0.7); 4.259(0.7); 4.178(0.6); 4.171(0.6); 4.151(1.8); 4.144(1.8); 4.124(1.8); 4.117(1.8); 4.097(0.7); 4.090(0.6); 4.055(0.4); 4.037(1.0); 4.020(1.0); 4.002(0.4); 3.977(0.7); 3.951(0.8); 3.940(0.7); 3.924(0.3); 3.914(0.7); 3.372(0.9); 3.332(833.0); 2.676(2.9); 2.671(3.9); 2.667(2.9); 2.525(9.7); 2.507(449.3); 2.502(587.2); 2.498(437.0); 2.451(12.1); 2.446(16.0); 2.408(0.8); 2.353(0.6); 2.334(3.2); 2.329(4.0); 2.325(3.0); 2.279(0.4); 2.258(0.5); 2.188(15.9); 2.182(12.0); 1.989(4.2); 1.193(1.1); 1.175(2.3); 1.157(1.1); 0.146(0.8); 0.008(6.5); 0.000(190.8); −0.008(8.2); −0.150(0.9) |
| 51 | 3.25 | 3.17 | 1H-NMR(400.0 MHz, d6-DMSO): δ = 9.354(5.1); 9.348(5.2); 8.844(3.9); 8.840(4.4); 8.832(4.1); 8.828(4.4); 8.658(16.0); 8.565(2.1); 8.561(3.0); 8.556(2.3); 8.546(2.3); 8.540(3.2); 8.536(2.3); 8.138(10.9); 8.091(13.9); 8.003(0.3); 7.812(0.5); 7.687(2.9); 7.675(2.9); 7.667(2.9); 7.655(2.8); 5.757(3.1); 4.262(0.4); 4.248(0.9); 4.238(1.2); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 4.223(2.7); 4.213(2.8); 4.198(2.9); 4.188(2.8); 4.173(1.3); 4.163(1.0); 4.149(0.4); 3.340(73.8); 2.676(0.9); 2.671(1.2); 2.667(0.9); 2.524(3.2); 2.511(67.2); 2.507(136.2); 2.502(181.2); 2.498(135.3); 2.493(68.1); 2.333(0.8); 2.329(1.2); 2.324(0.9); 2.287(0.6); 1.234(0.3); 0.000(7.9) |
| 52 | 1.57 | 1.55 | 1H-NMR(400.0 MHz, d6-DMSO): δ = 9.342(2.1); 9.337(2.1); 8.831(1.5); 8.828(1.6); 8.819(1.6); 8.816(1.6); 8.620(5.9); 8.552(0.9); 8.547(1.3); 8.542(0.9); 8.532(1.0); 8.527(1.3); 8.522(0.9); 7.677(1.2); 7.664(1.2); 7.657(1.3); 7.645(1.2); 7.601(2.8); 7.543(0.5); 7.539(0.5); 7.525(4.0); 7.509(2.3); 7.489(0.8); 7.397(1.0); 7.392(1.6); 7.386(1.0); 7.380(0.9); 7.375(1.3); 7.370(0.8); 5.754(9.1); 4.101(8.1); 3.986(0.9); 3.977(0.6); 3.962(0.4); 3.320(15.8); 3.053(16.0); 3.044(2.3); 2.849(15.1); 2.507(32.7); 2.502(41.4); 2.498(30.9); 1.187(0.4); 0.000(3.5) |
| 53 | 0.91 | 1.08 | 1H-NMR(400.0 MHz, d6-DMSO): δ = 9.349(2.0); 8.833(1.5); 8.823(1.5); 8.697(5.9); 8.556(1.4); 8.552(1.1); 8.541(1.1); 8.536(1.5); 8.140(1.0); 7.968(3.1); 7.904(0.8); 7.900(0.8); 7.893(1.7); 7.886(1.2); 7.882(1.3); 7.878(1.2); 7.820(0.4); 7.799(3.8); 7.788(3.6); 7.682(1.3); 7.669(1.3); 7.662(1.4); 7.649(1.2); 5.754(3.5); 4.219(0.7); 4.182(3.7); 4.166(3.5); 4.129(0.8); 4.100(0.4); 4.090(0.3); 3.318(8.9); 3.053(0.6); 2.934(16.0); 2.915(1.8); 2.858(14.1); 2.844(2.3); 2.671(0.7); 2.505(83.9); 2.502(106.8); 2.498(84.9); 2.328(0.7); 2.074(0.6); 0.000(3.2) |
| 54 | 1.90 | 1.91 | 1H-NMR(400.0 MHz, $d_6$-DMSO): δ = 9.347(2.8); 9.342(2.6); 8.837(2.0); 8.825(2.0); 8.668(5.5); 8.552(1.6); 8.532(1.6); 8.141(0.9); 7.718(2.4); 7.700(2.4); 7.682(1.5); 7.669(1.5); 7.662(1.4); 7.649(1.3); 7.448(2.1); 7.422(2.1); 5.754(0.6); 4.011(8.8); 3.320(45.4); 3.027(16.0); 2.891(0.5); 2.832(14.9); 2.731(0.5); 2.670(0.6); 2.502(95.0); 2.406(12.3); 2.328(0.6); 0.000(4.0) |
| 55 | 1.38 | 1.38 | 1H-NMR(400.0 MHz, $d_6$-DMSO): δ = 9.350(3.2); 9.345(3.1); 8.838(2.2); 8.835(2.3); 8.826(2.3); 8.823(2.3); 8.722(6.2); 8.556(1.8); 8.540(1.4); 8.535(1.9); 8.531(1.3); 8.139(4.6); 8.119(2.9); 7.685(1.7); 7.672(1.7); 7.665(1.7); 7.653(1.5); 7.568(2.4); 7.541(2.4); 4.185(1.3); 4.148(2.5); 4.086(1.2); 4.047(0.6); 3.340(160.4); 2.955(16.0); 2.863(15.8); 2.672(0.6); 2.507(78.3); 2.503(97.2); 2.473(15.1); 2.330(0.6); 0.000(3.2) |
| 56 | 3.25 | 3.00 | 1H-NMR(400.0 MHz, $d_6$-DMSO): δ = 9.333(2.4); 9.328(2.4); 8.834(1.8); 8.830(2.0); 8.822(1.9); 8.818(2.0); 8.535(1.1); 8.531(1.4); 8.526(1.1); 8.515(1.2); 8.510(1.5); 8.506(1.1); 7.939(2.4); 7.920(2.4); 7.680(1.4); 7.668(1.4); 7.661(1.4); 7.648(1.3); 7.541(2.1); 7.515(2.1); 4.085(0.5); 4.071(0.5); 4.060(0.6); 4.046(1.3); 4.037(0.6); 4.021(1.3); 4.012(1.3); 3.995(0.7); 3.986(1.3); 3.972(0.5); 3.960(0.5); 3.946(0.5); 3.329(49.4); 2.676(0.4); 2.672(0.5); 2.668(0.4); 2.525(1.3); 2.512(29.6); 2.507(59.8); 2.503(79.0); 2.498(58.4); 2.494(29.1); 2.469(13.3); 2.443(0.6); 2.417(0.6); 2.339(0.3); 2.334(0.5); 2.329(0.6); 2.325(0.5); 2.302(0.4); 2.281(16.0); 2.076(1.0); 0.008(1.9); 0.000(57.6); −0.009(2.3) |
| 57 | 2.25 | 2.05 | 1H-NMR(601.6 MHz, CDCl$_3$): δ = 9.363(2.0); 8.807(1.5); 8.469(0.8); 8.466(1.1); 8.463(0.8); 8.452(1.9); 8.441(0.9); 8.438(1.1); 8.435(0.8); 8.065(1.7); 8.029(1.8); 8.017(1.8); 8.003(1.8); 7.991(1.8); 7.979(1.0); 7.966(1.1); 7.556(0.7); 7.554(0.7); 7.542(0.9); 7.541(0.9); 7.526(0.9); 7.519(1.3); 7.513(1.7); 7.507(1.3); 7.500(0.9); 7.415(1.0); 7.402(1.7); 7.389(0.8); 7.304(1.8); 7.302(1.9); 7.288(1.9); 7.286(1.8); 7.272(7.2); 5.302(6.3); 3.617(0.5); 3.609(0.4); 3.601(0.6); 3.593(1.0); 3.576(1.1); 3.563(1.1); 3.555(0.3); 3.547(3.0); 3.539(0.6); 3.530(3.1); 3.523(0.8); 3.514(1.2); 3.506(0.7); 2.590(0.5); 2.517(16.0); 2.501(0.6); 2.493(0.4); 2.484(0.3); 2.418(0.7); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 2.408(12.8); 2.395(0.6); 2.386(12.7); 2.378(1.1); 2.369(0.4); 2.356(0.5); 2.352(0.4); 2.344(0.4); 2.332(0.4); 1.335(0.5); 1.329(0.3); 1.306(0.6); 1.295(0.9); 1.286(1.3); 1.283(1.3); 1.271(1.3); 1.255(6.2); 1.232(0.7); 1.221(0.5); 1.212(0.5); 0.891(0.8); 0.880(1.4); 0.868(1.0); 0.856(0.5); 0.843(0.9); 0.841(0.9); 0.834(0.9); 0.005(0.5); 0.000(14.7); −0.006(0.7) |
| 58 | 3.45 | 3.32 | 1H-NMR(400.0 MHz, DMSO): δ = 9.430(10.3); 9.425(10.4); 8.891(8.1); 8.887(8.8); 8.879(8.5); 8.875(8.7); 8.651(4.7); 8.646(6.4); 8.641(4.7); 8.631(5.1); 8.625(6.5); 8.621(4.7); 8.317(0.4); 8.260(1.0); 8.242(1.1); 7.992(9.9); 7.973(9.9); 7.729(6.1); 7.717(6.0); 7.709(6.0); 7.697(6.2); 7.673(0.9); 7.583(8.6); 7.556(8.5); 5.758(16.0); 4.361(0.7); 4.351(0.4); 4.344(0.4); 4.324(0.4); 4.086(0.4); 4.059(0.4); 4.049(0.4); 4.018(4.1); 3.993(12.7); 3.967(13.1); 3.941(4.5); 3.331(218.6); 2.677(1.1); 2.672(1.5); 2.668(1.1); 2.512(92.5); 2.508(154.3); 2.503(197.3); 2.499(145.6); 2.495(73.3); 2.374(0.4); 2.353(0.4); 2.334(1.0); 2.330(1.3); 2.326(1.0); 1.343(0.4); 1.326(0.8); 1.308(0.4); 0.146(0.4); 0.008(3.0); 0.000(84.9); −0.008(3.4); −0.150 (0.4) |
| 59 | 2.40 | 2.35 | 1H-NMR(400.0 MHz, DMSO): δ = 9.432(5.9); 9.428(6.0); 8.891(4.5); 8.887(4.8); 8.879(4.8); 8.875(4.8); 8.652(2.6); 8.648(3.5); 8.642(2.6); 8.632(2.8); 8.626(3.7); 8.622(2.7); 8.260(5.9); 8.241(6.0); 7.729(3.3); 7.717(3.3); 7.709(3.5); 7.699(7.6); 7.673(4.8); 5.758(16.0); 4.415(0.5); 4.388(1.7); 4.378(0.8); 4.360(2.0); 4.351(2.3); 4.333(0.8); 4.323(2.3); 4.296(0.7); 4.112(0.6); 4.085(2.0); 4.075(0.7); 4.058(2.3); 4.048(1.9); 4.031(0.9); 4.021(1.8); 3.994(0.6); 3.331(101.6); 2.676(0.7); 2.672(1.0); 2.668(0.8); 2.507(117.2); 2.503(134.4); 2.498(99.6); 2.334(0.6); 2.330(0.9); 2.325(0.7); 1.233(0.7); 0.008(1.1); 0.000(27.5) |
| 60 | 2.41 | 2.45 | 1H-NMR(400.0 MHz, d6-DMSO): δ = 9.339(7.0); 8.827(5.1); 8.818(4.9); 8.618(9.6); 8.546(4.0); 8.527(4.0); 8.312(0.4); 7.676(3.3); 7.661(3.9); 7.646(2.9); 7.529(5.3); 7.509(15.6); 7.494(14.9); 7.475(4.6); 3.643(0.5); 3.637(0.5); 3.606(0.5); 3.586(0.6); 3.331(671.5); 3.145(0.9); 3.109(3.6); 3.091(8.5); 3.073(8.4); 3.055(3.4); 3.009(0.5); 2.987(0.4); 2.974(0.3); 2.959(0.3); 2.937(0.3); 2.919(0.4); 2.897(0.4); 2.885(0.3); 2.803(0.4); 2.671(3.3); 2.502(411.9); 2.395(1.4); 2.330(3.0); 2.243(0.3); 2.073(0.6); 1.318(8.9); 1.300(16.0); 1.282(8.2); 1.235(0.6); 0.146(0.7); 0.000(103.8); −0.073 (0.5); −0.141(0.3); −0.150(0.7) |
| 61 | 1.10 | 1.22 | 1H-NMR(400.0 MHz, d6-DMSO): δ = 9.349(4.7); 9.344(4.8); 8.835(3.5); 8.831(3.6); 8.823(3.7); 8.819(3.5); 8.683(11.9); 8.558(2.0); 8.554(2.8); 8.548(1.9); 8.538(2.2); 8.533(2.8); 8.528(1.9); 8.313(0.4); 7.870(4.9); 7.849(12.5); 7.822(12.3); 7.801(4.7); 7.681(2.6); 7.669(2.6); 7.661(2.6); 7.649(2.4); 5.753(3.4); 3.317(42.6); 3.178(0.5); 3.159(1.7); 3.141(2.1); 3.125(2.5); 3.107(2.2); 3.089(0.7); 2.898(0.6); 2.879(2.1); 2.861(2.5); 2.845(2.1); 2.827(1.8); 2.809(0.5); 2.671(0.9); 2.506(103.2); 2.502(129.1); 2.498(96.5); 2.333(0.6); 2.329(0.8); 1.235(0.7); 1.113(7.6); 1.094(16.0); 1.076(7.2); 0.146(1.0); 0.033(0.4); 0.000(200.8); −0.150 (1.0) |
| 62 | 2.71 | 2.69 | 1H-NMR(400.0 MHz, $d_6$-DMSO): δ = 9.954(1.2); 9.347(5.1); 9.343(5.1); 9.341(5.2); 9.106(0.9); 9.100(0.9); 8.835(3.9); 8.831(4.4); 8.823(4.0); 8.819(4.4); 8.744(0.7); 8.740(0.8); 8.732(0.8); 8.728(0.8); 8.701(16.0); 8.636(1.4); 8.558(2.1); 8.552(3.1); 8.548(2.5); 8.538(2.3); 8.532(3.3); 8.528(2.5); 8.280(0.4); 8.275(0.5); 8.271(0.4); 8.260(0.4); 8.255(0.6); 8.251(0.4); 7.969(7.3); 7.948(9.3); 7.881(1.5); 7.859(2.0); 7.806(1.5); 7.799(11.4); 7.795(3.7); 7.783(3.0); 7.778(9.2); 7.772(1.0); 7.688(0.6); 7.679(4.0); 7.667(4.3); 7.660(3.6); 7.647(4.4); 7.625(0.4); 7.612(0.5); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 7.600(0.5); 7.592(0.5); 7.579(0.5); 7.333(1.3); 3.324(74.8); 2.676(0.7); 2.671(0.9); 2.667(0.7); 2.524(2.5); 2.511(45.7); 2.507(92.5); 2.502(124.5); 2.498(94.2); 2.493(47.7); 2.333(0.5); 2.329(0.8); 2.325(0.6); 1.298(0.5); 1.259(0.7); 1.233(1.0); 0.000(1.1) |
| 63 | 2.03 | 1.99 | 1H-NMR(400.0 MHz, $d_6$-DMSO): δ = 9.344(0.4); 8.925(9.0); 8.748(0.7); 8.714(16.0); 8.649(1.1); 8.542(0.3); 8.462(5.6); 8.446(5.9); 8.317(1.5); 8.137(0.4); 8.117(0.7); 8.081(5.4); 8.061(5.8); 7.970(10.5); 7.950(13.1); 7.793(14.1); 7.772(11.5); 7.689(0.8); 7.666(5.7); 7.647(6.7); 7.629(4.4); 5.757(7.6); 3.507(0.3); 3.487(0.3); 3.447(0.4); 3.439(0.4); 3.409(0.5); 3.326(536.7); 3.245(0.3); 2.840(0.4); 2.820(0.4); 2.805(0.4); 2.765(0.4); 2.671(8.5); 2.622(1.1); 2.618(1.1); 2.502(1215.9); 2.329(7.9); 2.184(0.3); 1.355(0.6); 1.299(1.8); 1.259(2.9); 1.235(7.6); 1.166(0.5); 1.149(1.1); 1.066(0.4); 0.854(1.6); 0.843(1.0); 0.834(1.1); 0.814(0.7); 0.784(0.5); 0.146(5.7); 0.083(0.5); 0.000(1101.9); −0.150(5.9) |
| 64 | 2.91 | 2.89 | 1H-NMR(400.0 MHz, d6-DMSO): δ = 9.343(2.9); 9.338(3.0); 8.837(2.1); 8.833(2.4); 8.825(2.3); 8.821(2.4); 8.623(8.0); 8.552(1.2); 8.548(1.7); 8.543(1.3); 8.532(1.3); 8.527(1.8); 8.523(1.3); 7.871(3.3); 7.793(1.4); 7.772(1.9); 7.769(1.9); 7.691(4.1); 7.683(1.9); 7.670(4.3); 7.663(1.8); 7.650(1.6); 5.751(1.5); 3.310(93.8); 2.675(0.6); 2.670(0.8); 2.666(0.6); 2.523(2.1); 2.506(94.0); 2.501(124.8); 2.497(95.6); 2.328(0.8); 2.323(0.6); 2.200(16.0); 1.235(0.4); 0.008(0.4); 0.000(12.5) |
| 65 | 1.70 | 1.70 | 1H-NMR(400.0 MHz, d6-DMSO): δ = 10.654(0.5); 10.355(0.5); 9.356(2.4); 9.351(2.4); 9.213(0.4); 8.839(2.0); 8.835(2.0); 8.827(1.9); 8.823(1.7); 8.775(0.4); 8.718(7.1); 8.560(1.4); 8.557(1.3); 8.546(1.4); 8.542(1.6); 8.466(0.9); 8.383(0.5); 8.362(0.6); 8.337(1.0); 8.314(5.1); 8.241(2.4); 8.220(2.6); 8.143(2.9); 8.138(2.9); 8.110(0.4); 7.994(0.4); 7.973(0.4); 7.940(0.9); 7.910(5.0); 7.848(0.7); 7.837(0.5); 7.794(1.6); 7.715(0.6); 7.685(1.4); 7.673(1.7); 7.667(1.6); 7.651(2.4); 7.645(2.1); 7.629(2.0); 7.624(2.0); 7.593(0.5); 7.530(0.4); 7.520(0.6); 7.516(0.6); 7.494(0.6); 5.924(0.4); 5.754(1.3); 5.584(0.4); 4.637(0.4); 4.306(0.4); 4.273(0.5); 4.186(0.4); 4.151(0.4); 4.130(0.4); 4.096(0.4); 4.055(0.4); 4.039(0.5); 4.021(0.5); 3.986(0.5); 3.967(0.6); 3.941(0.4); 3.921(0.5); 3.905(0.6); 3.884(0.6); 3.868(0.7); 3.851(0.5); 3.838(0.5); 3.823(0.5); 3.765(0.5); 3.692(0.6); 3.637(0.6); 3.608(0.6); 3.585(0.7); 3.573(0.7); 3.544(0.7); 3.530(0.7); 3.509(0.9); 3.470(1.0); 3.452(1.0); 3.438(1.0); 3.398(1.3); 3.392(1.4); 3.378(1.8); 3.317(1231.0); 3.277(1.8); 3.265(2.1); 3.259(1.7); 3.254(1.7); 3.217(1.2); 3.189(1.1); 3.174(1.2); 3.147(1.3); 3.123(1.4); 3.095(2.1); 3.071(2.2); 3.041(1.8); 3.002(2.0); 2.979(1.8); 2.937(1.6); 2.916(0.8); 2.902(0.7); 2.889(0.8); 2.861(0.9); 2.830(0.9); 2.812(1.0); 2.775(1.2); 2.710(1.6); 2.694(2.0); 2.675(12.0); 2.670(16.0); 2.666(12.5); 2.561(4.8); 2.557(5.4); 2.523(51.5); 2.510(893.1); 2.506(1772.8); 2.501(2326.4); 2.497(1726.9); 2.332(9.4); 2.328(13.4); 2.324(9.8); 1.352(0.6); 1.336(0.7); 1.300(0.5); 1.235(6.1); 1.213(1.1); 1.194(1.3); 1.176(1.0); 1.158(0.7); 0.854(1.1); 0.837(0.7); 0.214(0.4); 0.196(0.4); 0.146(13.9); 0.121(0.7); 0.112(0.7); 0.104(0.8); 0.091(0.7); 0.082(1.1); 0.074(1.0); 0.061(1.2); 0.056(1.0); 0.008(120.2); 0.000(2914.5); −0.008 (142.9); −0.052(1.8); −0.058(0.9); −0.063(0.7); −0.068 (0.7); −0.150(13.4) |
| 66 | 2.20 | 2.21 | 1H-NMR(400.0 MHz, d6-DMSO): δ = 9.340(4.1); 9.334(4.3); 8.836(2.9); 8.833(3.2); 8.825(3.0); 8.821(3.2); 8.548(1.6); 8.544(2.5); 8.539(1.8); 8.525(12.5); 7.682(2.3); 7.670(2.3); 7.661(2.7); 7.656(2.6); 7.650(2.8); 7.638(3.8); 7.635(3.5); 7.599(2.2); 7.585(4.8); 7.566(4.6); 7.459(2.0); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 7.456(2.1); 7.437(3.1); 7.421(1.2); 7.418(1.3); 4.039(0.5); 4.021(0.5); 3.321(22.4); 2.983(1.3); 2.979(1.6); 2.964(4.1); 2.961(4.4); 2.946(4.3); 2.943(4.4); 2.928(1.6); 2.671(0.3); 2.507(39.0); 2.503(51.4); 2.499(39.7); 2.330(0.3); 1.989(1.9); 1.187(7.9); 1.175(1.7); 1.168(16.0); 1.158(1.1); 1.150(7.6); 0.000(1.1) |
| 67 | 1.28 | 1.29 | 1H-NMR(400.0 MHz, d6-DMSO): δ = 9.347(8.0); 9.342(8.3); 8.839(6.5); 8.832(13.6); 8.734(8.2); 8.553(4.6); 8.533(4.8); 8.315(0.3); 8.010(3.0); 7.991(3.8); 7.974(2.1); 7.955(2.9); 7.883(2.4); 7.864(5.3); 7.845(3.6); 7.834(1.8); 7.818(4.0); 7.816(4.1); 7.797(4.2); 7.781(1.6); 7.712(7.0); 7.688(6.1); 7.675(4.2); 7.667(4.2); 7.655(3.9); 4.356(0.5); 4.343(0.9); 4.331(0.5); 3.456(0.9); 3.443(0.9); 3.439(1.0); 3.426(0.9); 3.409(0.3); 3.319(49.2); 2.979(0.5); 2.961(1.6); 2.943(2.1); 2.927(2.4); 2.920(1.6); 2.908(2.3); 2.902(1.7); 2.886(2.0); 2.867(1.6); 2.849(0.5); 2.700(0.6); 2.690(0.8); 2.682(2.1); 2.672(3.4); 2.664(2.7); 2.654(2.7); 2.648(2.0); 2.638(2.3); 2.630(1.6); 2.620(1.8); 2.611(0.7); 2.602(0.7); 2.541(1.1); 2.502(179.7); 2.329(1.0); 1.077(7.4); 1.059(16.0); 1.040(8.1); 1.026(5.7); 1.007(11.5); 0.989(5.3); 0.146(1.0); 0.027(0.5); 0.000(183.4); −0.150(1.0) |
| 68 | 2.34 | 2.29 | 1H-NMR(400.0 MHz, $d_6$-DMSO): δ = 9.348(4.6); 9.344(4.6); 8.841(3.7); 8.837(4.0); 8.829(4.0); 8.825(4.0); 8.558(2.5); 8.551(16.0); 8.539(2.6); 8.533(3.3); 8.529(2.4); 7.918(3.2); 7.915(3.1); 7.899(4.0); 7.688(2.9); 7.686(2.8); 7.676(2.9); 7.674(2.9); 7.667(5.2); 7.663(4.0); 7.654(4.6); 7.648(3.9); 7.645(5.9); 7.639(5.5); 7.635(3.0); 7.620(3.2); 7.616(2.2); 7.598(3.4); 7.595(3.5); 7.579(3.1); 7.576(3.5); 7.561(1.3); 7.557(1.2); 5.757(3.6); 4.056(0.6); 4.038(1.0); 4.031(1.1); 4.020(1.3); 4.017(1.0); 4.006(1.3); 3.992(2.6); 3.980(0.7); 3.967(3.0); 3.944(2.9); 3.930(0.6); 3.918(2.8); 3.905(1.2); 3.892(1.0); 3.878(1.2); 3.852(0.4); 3.329(31.2); 2.677(0.4); 2.672(0.5); 2.668(0.4); 2.526(1.3); 2.512(26.5); 2.508(53.3); 2.503(70.5); 2.499(52.7); 2.495(27.0); 2.335(0.3); 2.330(0.5); 2.325(0.4); 1.990(3.7); 1.397(1.3); 1.299(0.8); 1.259(1.1); 1.250(0.4); 1.234(1.6); 1.193(1.2); 1.176(2.1); 1.158(1.1); 0.146(0.6); 0.008(4.9); 0.000(120.6); −0.008(6.0); −0.150(0.6) |
| 69 | 1.74 | 1.75 | 1H-NMR(601.6 MHz, CDCl$_3$): δ = 9.372(12.3); 8.822(9.3); 8.817(9.2); 8.465(7.5); 8.453(8.0); 8.307(16.0); 8.291(8.4); 8.278(8.2); 8.192(1.6); 8.154(0.9); 7.937(0.8); 7.910(4.3); 7.898(8.3); 7.885(5.1); 7.837(5.4); 7.825(9.3); 7.813(6.0); 7.583(0.8); 7.525(6.1); 7.516(7.8); 7.513(7.9); 7.505(6.3); 7.451(9.5); 7.439(8.9); 7.263(66.7); 7.086(0.4); 5.301(4.1); 4.129(1.1); 4.112(3.4); 4.094(4.4); 4.072(3.5); 4.055(1.2); 3.882(0.3); 3.859(0.5); 3.841(0.4); 3.642(0.4); 3.625(0.5); 3.597(1.4); 3.580(3.6); 3.564(4.4); 3.558(4.0); 3.541(3.2); 3.525(1.1); 3.490(0.5); 1.577(178.8); 1.426(0.4); 1.371(1.1); 1.333(2.4); 1.285(4.4); 1.256(10.6); 1.104(0.5); 0.881(1.6); 0.842(1.6); 0.070(0.6); 0.000(47.7) |
| 70 | 2.82 | 2.75 | 1H-NMR(400.0 MHz, d6-DMSO): δ = 9.238(3.7); 8.867(3.7); 8.861(4.0); 8.636(9.5); 8.528(1.2); 8.522(1.6); 8.517(1.2); 8.505(1.3); 8.500(1.7); 8.494(1.2); 8.175(0.4); 7.395(3.9); 7.389(5.0); 7.366(3.3); 7.259(2.5); 7.254(2.4); 7.239(2.0); 7.234(1.9); 7.199(0.4); 5.758(0.4); 3.437(0.3); 3.329(65.1); 2.676(0.7); 2.671(1.0); 2.667(0.8); 2.662(0.5); 2.541(0.4); 2.525(2.4); 2.511(55.7); 2.507(114.5); 2.502(153.6); 2.498(117.2); 2.494(63.2); 2.489(35.6); 2.474(2.6); 2.424(0.4); 2.333(1.1); 2.329(1.5); 2.316(16.0); 2.287(0.4); 2.216(1.0); 1.434(0.6); 1.296(0.4); 1.234(1.3); 1.073(0.9); 1.055(1.8); 1.038(0.9); 0.700(0.7); 0.000(0.3) |
| 71 | 3.64 | 3.34 | 1H-NMR(400.0 MHz, d6-DMSO): δ = 9.238(2.3); 9.234(3.8); 8.869(3.7); 8.862(3.9); 8.547(9.3); 8.524(1.2); 8.519(1.5); 8.517(1.5); 8.512(1.2); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 8.500(1.3); 8.496(1.6); 8.489(1.1); 7.676(5.9); 7.360(4.8); 5.754(0.4); 4.038(0.8); 4.033(1.2); 4.021(0.8); 4.007(3.6); 3.981(3.7); 3.955(1.3); 3.319(43.7); 2.671(0.4); 2.525(1.1); 2.511(20.9); 2.507(41.2); 2.502(53.7); 2.498(39.5); 2.494(19.6); 2.410(14.9); 2.329(0.4); 2.080(16.0); 1.989(2.6); 1.398(0.9); 1.193(0.7); 1.176(1.4); 1.158(0.7); 0.008(0.8); 0.000(20.9); −0.008(0.8) |
| 72 | 2.35 | 2.29 | 1H-NMR(400.0 MHz, d6-DMSO): δ = 9.241(5.8); 8.872(5.8); 8.866(6.0); 8.604(14.2); 8.532(1.9); 8.526(2.5); 8.521(1.8); 8.509(2.0); 8.504(2.6); 8.498(1.8); 7.944(6.4); 7.934(4.4); 7.496(3.1); 7.470(4.6); 5.757(13.7); 4.324(0.6); 4.297(0.7); 4.287(0.7); 4.260(0.7); 4.178(0.6); 4.168(0.5); 4.160(0.5); 4.150(1.7); 4.142(1.6); 4.133(0.5); 4.124(1.8); 4.115(1.8); 4.105(0.5); 4.097(0.6); 4.087(0.7); 3.970(0.7); 3.943(0.8); 3.933(0.6); 3.906(0.6); 3.328(81.6); 2.676(0.5); 2.672(0.7); 2.667(0.5); 2.507(83.1); 2.503(109.0); 2.498(81.5); 2.451(12.1); 2.446(15.8); 2.408(0.6); 2.333(0.6); 2.329(0.8); 2.325(0.6); 2.189(16.0); 2.183(11.7); 2.076(11.2); 0.000(1.0) |
| 73 | 3.36 | 3.25 | 1H-NMR(400.0 MHz, $d_6$-DMSO): δ = 9.243(3.5); 8.875(3.5); 8.868(3.6); 8.693(7.7); 8.535(1.2); 8.530(1.7); 8.524(1.2); 8.512(1.2); 8.507(1.7); 8.501(1.1); 7.940(3.1); 7.922(3.1); 7.521(2.7); 7.494(2.7); 4.061(1.2); 4.035(3.8); 4.009(3.9); 3.984(1.4); 3.329(53.8); 2.676(0.3); 2.672(0.5); 2.668(0.3); 2.507(49.1); 2.503(64.3); 2.499(49.1); 2.471(16.0); 2.414(0.5); 2.334(0.3); 2.330(0.4); 2.325(0.3); 2.076(14.3); 1.233(0.9); 0.000(0.4) |
| 74 | 2.34 | 2.26 | 1H-NMR(400.0 MHz, $d_6$-DMSO): δ = 9.249(4.3); 9.246(7.4); 9.242(4.4); 8.876(7.8); 8.870(8.1); 8.738(16.0); 8.538(2.5); 8.533(3.1); 8.531(3.1); 8.527(2.4); 8.515(2.6); 8.510(3.3); 8.503(2.4); 8.447(0.5); 8.317(0.7); 8.200(6.2); 8.182(6.2); 7.639(4.3); 7.613(4.3); 5.758(2.5); 4.299(0.6); 4.266(1.0); 4.241(0.8); 4.147(0.4); 4.126(0.7); 4.099(0.8); 4.038(0.5); 4.020(0.4); 3.568(3.3); 3.329(336.9); 2.676(1.4); 2.671(2.0); 2.667(1.5); 2.525(5.0); 2.520(7.9); 2.511(110.1); 2.507(225.1); 2.502(308.8); 2.498(233.4); 2.494(111.7); 2.377(1.3); 2.334(1.5); 2.329(2.0); 2.325(1.5); 1.989(1.2); 1.234(0.4); 1.207(0.4); 1.193(0.6); 1.189(0.7); 1.175(0.8); 1.157(0.3); 0.000(0.9) |
| 75 | 1.80 | 1.72 | 1H-NMR(400.0 MHz, d6-DMSO): δ = 9.532(12.8); 9.421(6.3); 9.396(0.9); 9.367(0.5); 8.619(6.6); 8.449(0.5); 7.792(0.7); 7.772(0.8); 7.525(0.5); 7.493(1.2); 7.466(4.3); 7.446(7.2); 7.401(6.7); 7.381(4.2); 7.252(0.3); 7.239(0.4); 7.183(0.6); 7.163(0.6); 7.116(0.3); 5.754(1.6); 4.095(0.3); 4.077(0.8); 4.060(0.8); 4.041(0.3); 3.865(0.3); 3.846(0.3); 3.318(48.1); 2.671(0.9); 2.566(0.8); 2.502(128.3); 2.424(4.2); 2.409(16.0); 2.328(1.3); 2.306(0.5); 2.284(2.0); 1.344(0.4); 1.326(0.4); 1.302(0.5); 1.285(0.6); 1.265(0.5); 1.248(0.5); 1.242(0.5); 1.225(0.6); 1.205(1.4); 1.187(2.1); 1.178(1.2); 1.169(1.3); 1.098(0.4); 0.146(0.6); 0.000(109.4); −0.150(0.6) |
| 76 | 2.88 | 2.77 | 1H-NMR(400.0 MHz, d6-DMSO): δ = 9.538(16.0); 9.429(7.5); 8.559(8.5); 7.680(4.9); 7.362(3.9); 5.754(1.8); 4.034(1.0); 4.008(2.9); 3.982(3.1); 3.956(1.1); 3.318(38.5); 2.671(0.4); 2.524(1.0); 2.511(23.9); 2.506(47.7); 2.502(62.3); 2.497(45.4); 2.493(22.1); 2.411(12.3); 2.368(0.6); 2.329(0.4); 2.170(0.5); 2.080(13.3); 1.352(1.1); 1.336(0.4); 1.259(0.4); 1.250(0.6); 1.229(1.2); 0.000(3.8) |
| 77 | 1.84 | 1.82 | 1H-NMR(400.0 MHz, $d_6$-DMSO): δ = 9.542(16.0); 9.429(7.8); 8.612(8.8); 7.949(4.1); 7.939(2.8); 7.497(2.0); 7.471(3.0); 5.754(0.9); 4.321(0.4); 4.293(0.5); 4.284(0.5); 4.257(0.5); 4.175(0.4); 4.166(0.4); 4.148(1.1); 4.139(1.1); 4.121(1.1); 4.112(1.2); 4.094(0.4); 4.085(0.4); 3.969(0.5); 3.942(0.5); 3.932(0.4); 3.905(0.5); 3.317(54.5); 2.675(0.5); 2.671(0.7); 2.666(0.5); 2.506(79.6); 2.502(106.3); 2.497(82.4); 2.452(8.0); 2.447(10.7); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 2.338(0.5); 2.333(0.6); 2.328(0.7); 2.324(0.6); 2.258(0.4); 2.188(10.5); 2.182(8.0); 1.234(0.7); 0.008(0.5); 0.000(13.1) |
| 78 | 2.73 | 2.65 | 1H-NMR(400.0 MHz, d6-DMSO): δ = 9.543(16.0); 9.448(1.1); 9.430(7.6); 9.399(0.4); 9.365(0.8); 8.700(6.9); 8.313(0.4); 7.943(2.5); 7.925(2.5); 7.520(2.1); 7.493(2.0); 6.896(0.8); 6.706(0.5); 5.753(0.7); 4.364(0.5); 4.346(0.6); 4.058(1.0); 4.032(3.1); 4.006(3.2); 3.981(1.2); 3.974(0.6); 3.317(53.6); 2.675(0.6); 2.671(0.8); 2.666(0.6); 2.538(0.6); 2.524(2.2); 2.519(3.5); 2.511(44.1); 2.506(91.2); 2.502(121.8); 2.497(89.5); 2.493(43.8); 2.473(12.9); 2.415(0.6); 2.333(0.6); 2.329(0.8); 2.324(0.6); 1.352(7.8); 1.336(2.3); 1.322(1.5); 1.315(0.6); 1.304(0.9); 1.298(1.5); 1.259(2.2); 1.250(3.5); 1.229(7.3); 1.180(0.4); 0.868(0.3); 0.851(0.8); 0.834(0.3); 0.008(0.4); 0.000(12.0); −0.008(0.4) |
| 79 | 2.20 | 2.17 | 1H-NMR(400.0 MHz, d6-DMSO): δ = 9.302(2.4); 9.298(2.4); 9.296(2.3); 8.849(7.4); 8.813(1.9); 8.809(2.1); 8.801(2.1); 8.797(2.1); 8.511(1.1); 8.507(1.5); 8.506(1.4); 8.501(1.2); 8.491(1.2); 8.487(1.5); 8.485(1.6); 8.481(1.2); 7.658(1.4); 7.657(1.5); 7.646(1.4); 7.645(1.4); 7.638(1.4); 7.637(1.4); 7.626(1.4); 7.625(1.4); 7.271(1.0); 7.252(2.8); 7.233(2.2); 7.209(2.7); 7.184(2.0); 7.164(1.2); 7.134(1.7); 7.115(1.5); 7.030(0.5); 5.232(8.1); 4.363(0.3); 4.348(0.3); 3.329(63.9); 2.672(0.5); 2.668(0.3); 2.543(1.8); 2.526(0.9); 2.512(24.0); 2.508(49.4); 2.503(66.3); 2.499(49.7); 2.494(25.0); 2.334(0.3); 2.330(0.5); 2.325(0.3); 2.288(16.0); 0.000(0.4) |
| 80 | 2.39 | 2.42 | 1H-NMR(400.0 MHz, d6-DMSO): δ = 9.307(2.7); 8.818(2.1); 8.808(2.0); 8.506(1.8); 8.486(1.8); 7.669(1.5); 7.657(1.7); 7.649(1.6); 7.637(1.4); 7.270(1.2); 7.251(2.7); 7.232(1.7); 7.124(2.2); 7.106(1.7); 7.048(3.5); 7.014(2.1); 6.995(1.8); 5.390(6.4); 3.329(45.5); 2.672(0.8); 2.564(16.0); 2.503(112.3); 2.330(0.9); 2.281(14.1); 1.398(0.4); 0.000(18.3) |
| 81 | 2.17 | 2.13 | 1H-NMR(400.0 MHz, d6-DMSO): δ = 9.895(0.4); 9.305(5.1); 9.300(5.1); 9.276(0.3); 9.215(0.6); 8.956(0.7); 8.940(0.8); 8.871(12.3); 8.815(4.1); 8.811(4.4); 8.803(4.3); 8.799(4.1); 8.514(2.4); 8.509(3.3); 8.504(2.5); 8.494(2.6); 8.489(3.4); 8.484(2.4); 8.362(0.4); 8.150(0.5); 7.659(3.0); 7.647(3.1); 7.640(3.1); 7.627(2.8); 7.481(0.6); 7.461(0.9); 7.446(2.4); 7.438(1.3); 7.425(6.7); 7.406(3.8); 7.385(0.5); 7.363(0.3); 7.294(0.5); 7.266(4.8); 7.247(10.3); 7.238(9.9); 7.215(0.9); 7.202(0.7); 7.143(3.5); 7.138(3.6); 7.120(3.6); 7.099(0.9); 7.069(1.1); 7.053(3.7); 7.030(0.4); 5.286(16.0); 4.789(0.4); 4.770(0.4); 4.583(0.6); 4.570(0.6); 4.327(0.8); 4.311(0.7); 4.198(0.5); 4.181(0.5); 3.329(67.5); 2.945(1.8); 2.785(1.5); 2.672(1.0); 2.508(109.0); 2.504(135.0); 2.499(106.7); 2.330(1.0); 2.288(2.1); 2.076(1.3); 1.959(1.5); 1.630(0.5); 1.612(1.0); 1.594(0.5); 1.248(0.7); 1.231(1.3); 1.213(0.6); 0.146(0.6); 0.000(110.1); −0.150(0.6) |
| 82 | 1.91 | 1.90 | 1H-NMR(400.0 MHz, d6-DMSO): δ = 9.296(1.8); 9.291(1.7); 8.862(4.8); 8.809(1.3); 8.805(1.4); 8.797(1.4); 8.794(1.3); 8.505(0.9); 8.500(1.2); 8.495(0.8); 8.485(0.9); 8.480(1.2); 8.475(0.8); 7.653(1.1); 7.641(1.1); 7.633(1.1); 7.621(1.0); 7.391(3.4); 7.369(3.6); 6.940(0.8); 6.933(4.0); 6.911(3.6); 5.193(6.3); 3.750(0.9); 3.728(16.0); 3.331(54.2); 2.508(36.4); 2.503(46.4); 2.499(35.6); 2.330(0.3); 2.287(0.7); 1.397(0.6); 1.183(0.3) |
| 83 | 2.27 | 2.27 | 1H-NMR(400.0 MHz, d6-DMSO): δ = 9.310(3.1); 9.306(3.1); 8.817(2.4); 8.808(2.4); 8.781(5.0); 8.525(1.9); 8.505(2.0); 8.673(1.6); 7.660(1.8); 7.653(1.8); 7.641(1.5); 7.481(1.4); 7.461(1.6); 7.243(1.3); 7.223(2.6); 7.203(1.5); 7.119(1.6); 7.099(1.6); 7.083(2.2); 7.054(2.1); 7.009(2.5); 6.990(2.1); 5.271(8.3); 4.109(1.6); 2.672(0.7); |

TABLE 2-continued

Analytical data for the compounds reported

| Ex. No. | logP[a] | logP[b] | 1H-NMR [σ (ppm)] or LC-MS [m/z] |
|---|---|---|---|
| | | | 2.503(100.4); 2.329(1.0); 2.295(16.0); 0.146(0.3); 0.000(64.6); −0.150(0.4) |
| 84 | 0.90 | | 1H-NMR(600.1 MHz, d6-DMSO): δ = 9.317(4.7); 9.314(4.5); 9.313(4.4); 8.941(0.8); 8.927(0.7); 8.821(3.7); 8.819(3.9); 8.813(3.9); 8.810(3.9); 8.794(13.9); 8.788(14.8); 8.785(15.5); 8.521(2.1); 8.518(2.7); 8.517(2.7); 8.514(2.1); 8.508(2.2); 8.505(2.7); 8.504(2.9); 8.501(2.1); 7.664(2.6); 7.663(2.6); 7.656(2.6); 7.655(2.6); 7.651(2.6); 7.649(2.6); 7.643(2.5); 7.641(2.5); 7.468(2.9); 7.460(5.5); 7.452(2.8); 5.513(16.0); 4.987(0.4); 4.973(0.4); 4.966(0.4); 4.952(0.4); 3.325(57.1); 3.256(0.3); 3.085(2.2); 3.075(0.4); 2.788(2.2); 2.524(0.7); 2.521(0.9); 2.518(1.0); 2.509(17.5); 2.506(35.7); 2.503(48.2); 2.500(35.3); 2.498(16.9); 2.076(1.3); 1.352(0.6); 1.232(1.0); 1.225(0.7); 0.000(0.8) |
| 85 | 0.90 | 1.00 | 1H-NMR(400.0 MHz, d6-DMSO): δ = 9.306(5.5); 8.832(9.0); 8.817(14.8); 8.696(0.4); 8.685(0.4); 8.587(7.8); 8.571(7.3); 8.513(3.8); 8.493(3.8); 8.317(0.3); 7.663(3.2); 7.650(3.5); 7.643(3.5); 7.631(2.9); 5.758(1.0); 5.481(16.0); 3.327(92.7); 2.808(0.3); 2.785(0.3); 2.672(2.6); 2.502(293.6); 2.329(2.1); 2.288(0.5); 1.990(0.5); 1.397(1.9); 1.175(0.4); 1.150(0.4); 0.146(1.2); 0.000(186.4); −0.084(0.5); −0.150(1.1) |
| 86 | 1.01 | 1.07 | 1H-NMR(400.0 MHz, d6-DMSO): δ = 9.307(1.7); 9.303(1.7); 8.817(1.4); 8.814(1.5); 8.805(1.4); 8.802(1.5); 8.701(5.3); 8.519(0.8); 8.514(1.0); 8.509(0.8); 8.498(0.9); 8.493(1.1); 8.489(0.8); 7.941(4.3); 7.661(1.0); 7.660(1.0); 7.647(1.0); 7.641(1.0); 7.640(1.0); 7.629(0.9); 7.627(0.9); 6.445(0.4); 6.427(1.4); 6.409(1.4); 6.392(0.4); 5.758(1.5); 3.895(16.0); 3.329(46.3); 2.672(0.4); 2.542(1.1); 2.525(1.0); 2.512(22.5); 2.507(45.6); 2.503(60.2); 2.498(44.0); 2.494(21.6); 2.330(0.4); 1.890(4.9); 1.872(4.9); 0.000(1.4) |

BIOLOGICAL EXAMPLES

*Boophilus microplus*—Injection Test
Solvent: dimethyl sulphoxide
To produce a suitable preparation of active compound, 10 mg of active compound are mixed with 0.5 ml of solvent and the concentrate is diluted with solvent to the desired concentration.

1 μl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compound from the preparation examples showed an efficacy of 100% at an application rate of 20 μg/animal: 57

*Meloidogyne Incognita* Test
Solvent: 125.0 parts by weight of acetone
To produce a suitable preparation of active compound, 1 part by weight of active compound is mixed with the stated amount of solvent and the concentrate is diluted with water to the desired concentration.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compound from the preparation examples showed an efficacy of 90% at an application rate of 20 ppm: 63

*Myzus persicae*—Spray Test
Solvent: 78 parts by weight of acetone
1.5 parts by weight of dimethylformamide
Emulsifier: alkylaryl polyglycol ether
To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active compound preparation of the desired concentration.

After 6 days, the efficacy in % is determined 100% means that all the aphids have been killed; 0% means that none of the aphids have been killed.

In this test, for example, the following compounds from the preparation examples showed an efficacy of 100% at an application rate of 500 g/ha: 1, 2, 3, 4, 5, 7, 9, 15, 20, 23, 34, 35, 39, 40, 43, 45, 48, 49, 50, 51, 54, 57, 60, 61, 64, 66, 70, 77, 83, 84

In this test, for example, the following compounds from the preparation examples showed an efficacy of 90% at an application rate of 500 g/ha: 6, 8, 12, 13, 14, 16, 17, 18, 21, 22, 24, 25, 26, 27, 36, 37, 41, 46, 47, 52, 53, 55, 56, 58, 59, 62, 63, 67, 71, 72, 73, 74, 76, 78, 80, 81, 86

In this test, for example, the following compounds from the preparation examples showed an efficacy of 90% at an application rate of 100 g/ha: 19, 79

*Phaedon cochleariae*—Spray Test
Solvent: 78.0 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined 100% means that all the beetle larvae have been killed; 0% means that no beetle larvae have been killed.

In this test, for example, the following compounds from the preparation examples showed an efficacy of 100% at an application rate of 500 g/ha: 11, 37, 62

*Spodoptera frugiperda*—Spray Test
Solvent: 78.0 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active compound preparation of the desired concentration and, after drying, populated with caterpillars of the armyworm (*Spodoptera frugiperda*).

After 7 days, the efficacy in % is determined 100% means that all the caterpillars have been killed; 0% means that no caterpillars have been killed.

In this test, for example, the following compounds from the preparation examples showed an efficacy of 100% at an application rate of 500 g/ha: 11, 37

*Tetranychus urticae*—Spray Test, OP-Resistant
Solvent: 78.0 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested with all stages of the greenhouse red spider mite (*Tetranychus urticae*) are sprayed with an active compound preparation of the desired concentration.

After 6 days, the efficacy in % is determined. 100% means that all the spider mites have been killed; 0% means that none of the spider mites have been killed.

In this test, for example, the following compounds from the preparation examples showed an efficacy of 90% at an application rate of 500 g/ha: 11, 57

*Myzus persicae*—Spray Test
Solvent: 7 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the preparation solution.

Bell pepper plants (*Capsicum annuum*) severely infested with the green peach aphid (*Myzus persicae*) are treated by spraying with the active compound preparation in the desired concentration.

After 6 days, the kill in % is determined 100% means that all the aphids have been killed; 0% means that no aphids have been killed.

In this test, for example, the following compound from the preparation examples showed an efficacy of 100% at an application rate of 4 ppm: 44

In this test, for example, the following compound from the preparation examples showed an efficacy of 96% at an application rate of 4 ppm: 10

The invention claimed is:
1. A compound of formula (I)

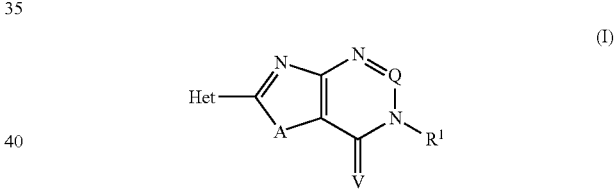

wherein
Het represents a radical from the group consisting of

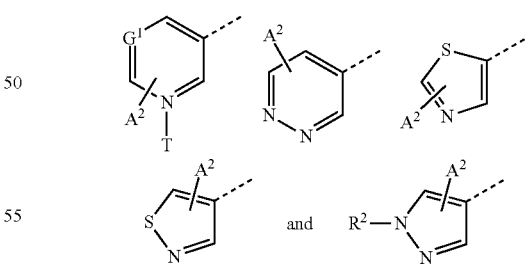

where the dotted line represents the bond to the carbon atom in the N=C-A group attached to Het and
$G^1$ represents N or C-$A^1$,
$A^1$ represents hydrogen, halogen, cyano, nitro, alkyl, haloalkyl, alkoxy, haloalkoxy or in each case optionally substituted cycloalkyl or cycloalkenyl,
$A^2$ represents hydrogen, halogen, cyano, nitro, alkyl, haloalkyl, alkoxy, haloalkoxy or in each case optionally substituted cycloalkyl or cycloalkenyl, T represents oxygen or an electron pair,
R² represents hydrogen, alkyl, haloalkyl or optionally substituted cycloalkyl,
R¹ represents a radical from the group consisting of hydrogen, alkyl, haloalkyl, cyanoalkyl, alkenyl, haloalkenyl, alkynyl, haloalkynyl, alkoxy, haloalkoxy, optionally halogen-substituted alkoxyalkyl, optionally halogen-substituted bis(alkoxy)alkyl, optionally halogen-substituted alkylsulphanylalkyl, optionally halogen-substituted alkylcarbonylalkyl, optionally halogen-substituted alkylsulphinylalkyl, optionally halogen-substituted alkylsulphonylalkyl, dialkylaminosulphanylalkyl, dialkylaminosulphinylalkyl, dialkylaminosulphonylalkyl, optionally halogen-substituted alkoxycarbonyl, optionally halogen-substituted alkoxycarbonylalkyl, optionally halogen-substituted alkynyloxy, optionally halogen-substituted alkynyloxycarbonyl, dialkylaminocarbonyl, N-alkyl-N-cycloalkylaminocarbonyl, dialkylaminocarbonylalkyl, N-alkyl-N-cycloalkylaminocarbonylalkyl, heterocyclylcarbonylalkyl, alkylsulphanyl, haloalkylsulphanyl, alkylsulphinyl, haloalkylsulphinyl, alkylsulphonyl, haloalkylsulphonyl, optionally halogen-, cyano-, nitro-, alkyl-, cycloalkyl-, haloalkyl-, alkoxy-, haloalkoxy-, alkoxycarbonyl-, haloalkoxycarbonyl- or hetaryl- (which for its part may optionally be alkyl- or halogen-substituted) substituted cycloalkyl, optionally halogen-, cyano-, nitro-, alkyl-, haloalkyl-, cycloalkyl-, alkoxy-, haloalkoxy-, alkoxycarbonyl-, haloalkoxycarbonyl- or hetaryl- (which for its part may optionally be alkyl- or halogen-substituted) substituted cycloalkylcarbonyl, optionally halogen-, cyano-, nitro-, alkyl-, haloalkyl-, cycloalkyl-, alkoxy-, haloalkoxy-, alkoxycarbonyl-, haloalkoxycarbonyl- or hetaryl- (which for its part may optionally be alkyl- or halogen-substituted) substituted cycloalkylalkyl, optionally substituted heterocyclyl, optionally halogen-, cyano- (also in the alkyl part), nitro-, hydroxy-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted heterocyclylalkyl, optionally halogen-, cyano-, nitro-, hydroxy-, amino-, alkyl-, haloalkyl-, cycloalkyl- (which is optionally substituted) alkoxy- or haloalkoxy-substituted aryl, optionally halogen-, cyano-(also in the alkyl part), nitro-, hydroxy-, amino-, alkyl-, cycloalkyl- (which is optionally substituted), haloalkyl-, alkoxy- or haloalkoxy-substituted arylalkyl, optionally halogen-, cyano-, nitro-, hydroxy-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylaminocarbonyl-, dialkylaminocarbonyl-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetaryl, optionally halogen-, cyano- (also in the alkyl part), nitro-, hydroxy-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetarylalkyl, or
R¹ represents a radical from the group consisting of

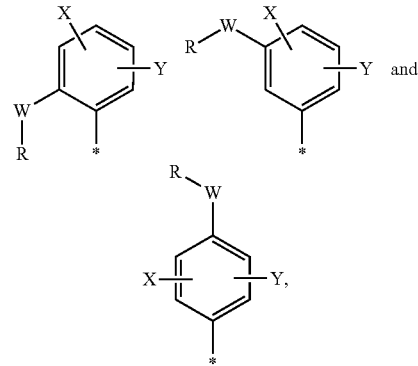

in which the bond to the nitrogen atom in the C(=V)—N-Q group in formula (I) is marked by the asterisk (*),
R represents NR⁷R⁸, or represents an in each case optionally substituted radical from the group consisting of alkyl, alkenyl, alkynyl, alkoxyalkyl, alkyl-S(O)$_m$-alkyl, R⁷—CO-alkyl, NR⁷R⁸—CO-alkyl, cycloalkyl, cycloalkenyl, cycloalkylalkyl, cycloalkenylalkyl, heterocyclyl, heterocyclylalkyl, phenyl, phenylalkyl, hetaryl and hetarylalkyl,
W represents a radical from the group consisting of O, S, SO and SO₂,
X represents a radical from the group consisting of hydrogen, halogen, cyano, nitro, alkyl, haloalkyl, alkoxy, haloalkoxy and cycloalkyl,
Y represents a radical from the group consisting of hydrogen, halogen, alkyl, cycloalkyl, haloalkyl, alkoxy, haloalkoxy, cyano and NR⁵R⁶,
A represents oxygen or sulphur,
Q represents nitrogen or C—R³ in which
R³ represents a radical from the group consisting of hydrogen, alkyl, cycloalkyl, haloalkyl, OH, alkoxy, haloalkoxy, SH, alkylsulphanyl, alkylsulphinyl, alkylsulphonyl, NH₂, alkylamino and dialkylamino,
V represents a radical from the group consisting of oxygen, sulphur and NR⁴,
R⁴ represents a radical from the group consisting of hydrogen, cyano, alkyl, haloalkyl and cycloalkyl,
R⁵ represents a radical from the group consisting of hydrogen, alkyl, cycloalkyl and haloalkyl,
R⁶ represents a radical from the group consisting of hydrogen, alkyl, cycloalkyl and haloalkyl,
or
R⁵ and R⁶ together with the nitrogen to which they are bonded represent an optionally substituted saturated or unsaturated 3- to 6-membered ring which optionally contains one or more further heteroatoms,
R⁷ represents hydrogen, hydroxy or an in each case optionally substituted radical from the group consisting of alkyl, alkoxy, alkoxyalkyl, alkyl-S(O)$_m$-alkyl, alkylcarbonyl, alkoxycarbonyl, cycloalkyl, cycloalkenyl, cycloalkylalkyl, cycloalkenylalkyl, heterocyclyl, heterocyclylalkyl, phenyl, phenylalkyl, hetaryl and hetarylalkyl, R[8] represents hydrogen, a metal ion, an optionally substituted ammonium ion or an in each case optionally substituted radical from the group consisting of alkyl, alkoxy, alkoxyalkyl, alkyl-S(O)$_m$— alkyl and m represents a number from the group consisting of 0, 1 and 2.

2. A compound of formula (I) according to claim 1, wherein

Het represents a radical from the group consisting of

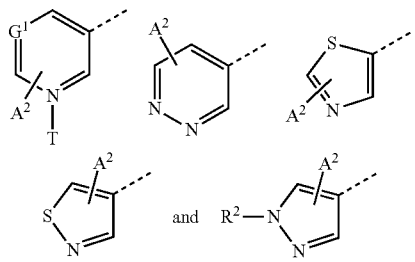

where the dotted line represents the bond to the carbon atom in the N=C-A group attached to Het and $G^1$ represents N or C-$A^1$, $A^1$ represents a radical from the group consisting of hydrogen, halogen, $C_1$-$C_6$-alkyl and $C_1$-$C_4$-haloalkyl, $A^2$ represents a radical from the group consisting of hydrogen, halogen, $C_1$-$C_6$-alkyl and $C_1$-$C_4$-haloalkyl, T represents oxygen or an electron pair, $R^2$ represents a radical from the group consisting of hydrogen, $C_1$-$C_6$-alkyl, $C_1$-$C_6$-haloalkyl and $C_3$-$C_6$-cycloalkyl which is optionally mono- to trisubstituted by halogen, cyano, nitro, $C_1$-$C_3$-alkyl, $C_1$-$C_3$-alkoxy and monosubstituted by $C_3$-$C_6$-cycloalkyl, $R^1$ represents a radical from the group consisting of hydrogen, $C_1$-$C_6$-alkyl, $C_2$-$C_6$-haloalkyl, cyano-$C_1$-$C_6$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_6$-alkoxy, $C_1$-$C_6$-haloalkoxy, optionally halogen-substituted $C_1$-$C_6$-alkoxy-$C_1$-$C_6$-alkyl, optionally halogen-substituted bis(C$_1$-$C_6$-alkoxy)-$C_1$-$C_6$-alkyl, optionally halogen-substituted $C_1$-$C_6$-alkylsulphanyl-$C_1$-$C_6$-alkyl, optionally halogen-substituted $C_1$-$C_4$-alkylcarbonyl-$C_1$-$C_4$-alkyl, optionally halogen-substituted $C_1$-$C_6$-alkylsulphinyl-$C_1$-$C_6$-alkyl, optionally halogen-substituted $C_1$-$C_6$-alkylsulphonyl-$C_1$-$C_6$-alkyl, di-($C_1$-$C_6$-alkyl)-aminosulphanyl-$C_1$-$C_6$-alkyl, di-($C_1$-$C_6$)-alkylaminosulphinyl-$C_1$-$C_6$-alkyl, di-($C_1$-$C_6$-alkyl)-aminosulphonyl-$C_1$-$C_6$-alkyl, optionally halogen-substituted $C_1$-$C_6$-alkoxycarbonyl, optionally halogen-substituted $C_1$-$C_6$-alkoxycarbonyl-$C_1$-$C_6$-alkyl, optionally halogen-substituted $C_2$-$C_4$-alkynyloxy, optionally halogen-substituted $C_2$-$C_4$-alkynyloxycarbonyl, di-($C_1$-$C_6$-alkyl)-aminocarbonyl, N—$C_1$-$C_6$-alkyl-N—$C_3$-$C_6$-cycloalkylaminocarbonyl, di-($C_1$-$C_6$-alkyl)-aminocarbonyl-$C_1$-$C_6$-alkyl, N—$C_1$-$C_6$-alkyl-N—$C_3$-$C_6$-cycloalkylaminocarbonyl-$C_1$-$C_6$-alkyl, heterocyclylcarbonyl-$C_1$-$C_6$-alkyl, $C_1$-$C_6$-alkylsulphanyl, $C_1$-$C_6$-haloalkylsulphanyl, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl- (which for its part is optionally $C_1$-$C_6$-alkyl- or halogen-substituted) substituted $C_3$-$C_6$-cycloalkyl, optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl- (which for its part is optionally $C_1$-$C_6$-alkyl- or halogen-substituted) substituted $C_3$-$C_6$-cycloalkylcarbonyl, optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl- (which for its part is optionally $C_1$-$C_6$-alkyl- or halogen-substituted) substituted $C_3$-$C_6$-cycloalkyl-$C_1$-$C_6$-alkyl, optionally halogen-, cyano- (also in the $C_1$-$C_6$-alkyl part of heterocyclyl-$C_1$-$C_6$-alkyl), nitro-, hydroxy-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di-($C_1$-$C_6$-alkyl)-amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted heterocyclyl-$C_1$-$C_6$-alkyl, optionally halogen-, cyano-, nitro-, hydroxy-, amino-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy- or $C_1$-$C_6$-haloalkoxy-substituted aryl, optionally halogen-, cyano- (also in the $C_1$-$C_6$-alkyl part of aryl-$C_1$-$C_6$-alkyl), nitro-, hydroxy-, amino-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy- or $C_1$-$C_6$-haloalkoxy-substituted aryl-$C_1$-$C_6$-alkyl, optionally halogen-, cyano-, nitro-, hydroxy-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di-($C_1$-$C_6$-alkyl)-amino-, $C_1$-$C_6$-alkylcarbonylamino-, $C_1$-$C_6$-alkylaminocarbonyl-, di-($C_1$-$C_6$-alkyl)-aminocarbonyl-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted hetaryl, optionally halogen-, cyano- (also in the $C_1$-$C_6$-alkyl part of hetaryl-$C_1$-$C_6$-alkyl), nitro-, hydroxy-, $C_1$-$C_6$-alkyl-, $C_1$-$C_6$-haloalkyl-, $C_3$-$C_6$-cycloalkyl-(which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di-($C_1$-$C_6$-alkyl)-amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted hetaryl-$C_1$-$C_6$-alkyl, or $R^1$ represents a radical from the group consisting of

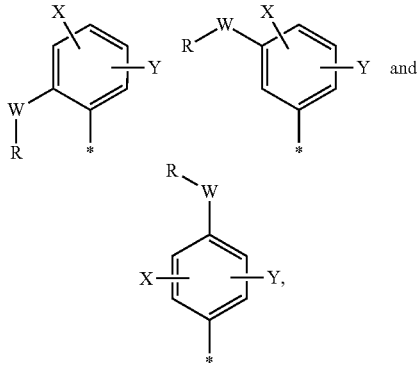

in which the bond to the nitrogen atom in the C(=V)—N—Q group in formula (I) is marked by the asterisk (*), R represents $NR^7R^8$ or represents in each case optionally halogen-, oxygen- (leads to C=O) or cyano-substituted $C_1$-$C_6$-alkyl, $C_3$-$C_6$-alkenyl, $C_3$-$C_6$-alkynyl, $C_1$-$C_6$-alkoxy-$C_1$-$C_4$-alkyl, $C_1$-$C_6$-alkyl-S(O)$_m$—$C_1$-$C_4$-alkyl, represents $R^7$—CO—$C_1$-$C_4$-alkyl, represents $NR^7R^8$—CO—$C_1$-$C_4$-alkyl, represents $C_3$-$C_6$-cycloalkyl which is optionally mono- or disubstituted by oxygen (leads to C=O), $C_1$-$C_4$-alkyl, $C_3$-$C_8$-cycloalkyl, $C_1$-$C_4$-alkoxy and $C_1$-$C_4$-haloalkyl, represents $C_3$-$C_8$-cycloalkenyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents $C_3$-$C_6$-cycloalkyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents $C_3$-$C_6$-cycloalkenyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents heterocyclyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents heterocyclyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl or represents phenyl, phenyl-$C_1$-$C_4$-alkyl, hetaryl or hetaryl-$C_1$-$C_4$-alkyl, each of which is optionally mono- to trisubstituted by halogen, cyano, $C_1$-$C_4$-alkyl, $C_3$-$C_6$-cycloalkyl, $C_1$-$C_4$-haloalkyl, $C_1$-$C_4$-alkoxy or $C_1$-$C_4$-haloalkoxy, W represents a radical from the group consisting of O, S, SO and $SO_2$, X represents a radical from the group consisting of hydrogen, halogen, cyano, nitro, $C_1$-$C_6$-alkyl, $C_1$-$C_6$-haloalkyl, $C_3$-$C_6$-cycloalkyl, $C_1$-$C_6$-alkoxy and $C_1$-$C_6$-haloalkoxy, Y represents a radical from the group consisting of hydrogen, halogen, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, cyano and $NR^5R^6$, A represents sulphur, Q represents nitrogen or C—$R^3$, $R^3$ represents a radical from the group consisting of hydrogen, $C_1$-$C_6$-alkyl, $C_1$-$C_6$-haloalkyl, $C_3$-$C_6$-cycloalkyl, OH, $C_1$-$C_6$-alkoxy, $C_1$-$C_6$-haloalkoxy, SH, $C_1$-$C_6$-alkylsulphanyl, $C_1$-$C_6$-alkylsulphinyl, $C_1$-$C_6$-alkylsulphonyl, $NH_2$, $C_1$-$C_6$-alkylamino and di-($C_1$-$C_6$-alkyl)-amino, V represents a radical from the group consisting of oxygen, sulphur and $NR^4$, $R^4$ represents a radical from the group consisting of hydrogen, cyano, $C_1$-$C_6$-alkyl, $C_2$-$C_6$-haloalkyl and $C_3$-$C_6$-cycloalkyl, $R^5$ represents a radical from the group consisting of hydrogen, $C_1$-$C_6$-alkyl, $C_3$-$C_6$-cycloalkyl and $C_2$-$C_6$-haloalkyl, $R^6$ represents a radical from the group consisting of hydrogen, $C_1$-$C_6$-alkyl, $C_3$-$C_6$-cycloalkyl and $C_2$-$C_6$-haloalkyl, $R^5$ and $R^6$ can also together with the nitrogen atom to which they are bonded represent a saturated to triunsaturated 3- to 6-membered ring which is optionally substituted by halogen, cyano, $C_1$-$C_4$-alkyl, $C_1$-$C_4$-haloalkyl, $C_1$-$C_4$-alkoxy, $C_1$-$C_4$-haloalkoxy, $R^7$ represents a radical from the group consisting of hydrogen, hydroxy, and $C_1$-$C_6$-alkyl, $C_1$-$C_6$-alkoxy, $C_1$-$C_6$-alkoxy-$C_1$-$C_4$-alkyl, $C_1$-$C_6$-alkyl-S(O)$_m$—$C_1$-$C_4$-alkyl, $C_1$-$C_6$-alkylcarbonyl, $C_1$-$C_6$-alkoxycarbonyl, $C_3$-$C_6$-cycloalkyl, $C_3$-$C_6$-cycloalkenyl, $C_3$-$C_6$-cycloalkyl-$C_1$-$C_3$-alkyl, $C_3$-$C_6$-cycloalkenyl-$C_1$-$C_3$-alkyl, heterocyclyl, heterocyclyl-$C_1$-$C_3$-alkyl, each of which is optionally mono- or polysubstituted by halogen or mono- or disubstituted by cyano, and represents phenyl, phenyl-$C_1$-$C_3$-alkyl, hetaryl and hetaryl-$C_1$-$C_3$-alkyl, each of which is optionally mono- to tetrasubstituted by $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, halogen or cyano, $R^8$ represents hydrogen, an alkali or alkaline earth metal ion, or represents an ammonium ion which is optionally mono- to tetrasubstituted by $C_1$-$C_4$-alkyl, or represents a radical from the group consisting of $C_1$-$C_4$-alkyl, $C_1$-$C_4$-alkoxy, $C_1$-$C_4$-alkoxy-$C_1$-$C_4$-alkyl and $C_1$-$C_4$-alkyl-S(O)$_m$—$C_1$-$C_4$-alkyl, each of which is optionally mono- or polysubstituted by halogen or mono- or disubstituted by cyano, m represents a number from the group consisting of 0, 1 and 2, and where alkali metal ion is selected from the group consisting of lithium, sodium, potassium, rubidium, caesium, alkaline earth metal ion is selected from the group consisting of beryllium, magnesium, calcium, strontium, barium, halogen is selected from the group consisting of fluorine, chlorine, bromine and iodine, aryl (including as part of a larger unit, for example arylalkyl) is selected from the group consisting of phenyl, naphthyl, anthryl, phenanthrenyl, hetaryl (synonymous with heteroaryl, including as part of a larger unit, for example hetarylalkyl) is selected from the group consisting of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzoisofuryl, benzothienyl, benzoisothienyl, indolyl, isoindolyl, indazolyl, benzothiazolyl, benzoisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, and heterocyclyl represents a saturated 4-, 5- or 6-membered ring which contains 1 or 2 nitrogen atoms and/or one oxygen atom and/or one sulphur atom.

3. A compound of formula (I) according to claim 1, wherein

Het represents a radical from the group consisting of

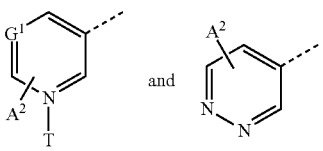

where the dotted line represents the bond to the carbon atom in the N=C-A group attached to Het, $G^1$ represents N or C-$A^1$, $A^1$ represents a radical from the group consisting of hydrogen, halogen, $C_1$-$C_4$-alkyl and $C_1$-$C_4$-haloalkyl, $A^2$ represents a radical from the group consisting of hydrogen, halogen, $C_1$-$C_4$-alkyl and $C_1$-$C_4$-haloalkyl, T represents oxygen or an electron pair, $R^1$ represents a radical from the group consisting of hydrogen, $C_1$-$C_4$-alkyl, $C_2$-$C_4$-haloalkyl, cyano-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, optionally halogen-substituted $C_1$-$C_2$-alkoxy-$C_1$-$C_4$-alkyl, optionally halogen-substituted bis($C_1$-$C_2$-alkoxy)-$C_1$-$C_4$-alkyl, optionally halogen-substituted $C_1$-$C_4$-alkylsulphanyl-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, di-($C_1$-$C_4$-alkyl)-aminosulphanyl-$C_1$-$C_4$-alkyl, di-($C_1$-$C_4$-alkyl)-aminosulphinyl-$C_1$-$C_4$-alkyl, di-($C_1$-$C_4$-alkyl)-aminosulphonyl-$C_1$-$C_4$-alkyl, optionally halogen-substituted $C_1$-$C_4$-alkoxycarbonyl, optionally halogen-substituted $C_1$-$C_4$-alkoxycarbonyl-$C_1$-$C_4$-alkyl, optionally halogen-substituted $C_2$-$C_4$-alkynyloxy, optionally halogen-substituted $C_2$-$C_4$-alkynyloxycarbonyl, di-($C_1$-$C_4$-alkyl)-aminocarbonyl, N—$C_1$-$C_4$-alkyl-N—$C_3$-$C_6$-cycloalkylaminocarbonyl, di-($C_1$-$C_4$-alkyl)-aminocarbonyl-$C_1$-$C_4$-alkyl, N—$C_1$-$C_4$-alkyl-N—$C_3$-$C_6$-cycloalkylaminocarbonyl-$C_1$-$C_4$-alkyl, heterocyclylcarbonyl-$C_1$-$C_4$-alkyl, $C_1$-$C_4$-alkylsulphanyl, $C_1$-$C_4$-haloalkylsulphanyl, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, optionally halogen-, cyano-, nitro-, $C_1$-$C_4$-alkyl-, $C_1$-$C_4$-haloalkyl-, $C_3$-$C_6$-cycloalkyl- $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl- (which for its part is optionally substituted by $C_1$-$C_4$-alkyl or halogen) substituted $C_3$-$C_6$-cycloalkyl, optionally halogen-, cyano-, nitro-, $C_1$-$C_4$-alkyl-, $C_1$-$C_4$-haloalkyl-, $C_3$-$C_6$-cycloalkyl-$C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl- (which for its part is optionally substituted by $C_1$-$C_4$-alkyl or halogen) substituted $C_3$-$C_6$-cycloalkylcarbonyl, optionally halogen-, cyano-, nitro-, $C_1$-$C_4$-alkyl-, $C_1$-$C_4$-haloalkyl-, $C_3$-$C_6$-cycloalkyl-$C_1$-$C_4$-alkoxy-, $C_1$-$C_4$-haloalkoxy-, $C_1$-$C_4$-alkoxycarbonyl-, $C_1$-$C_4$-haloalkoxycarbonyl-, pyridyl-, pyrimidyl-, pyrazanyl-, pyridazinyl-, thiazolyl-, isothiazolyl-, thiadiazolyl-, oxazolyl-, isoxazolyl-, oxadiazolyl-, pyrazolyl-, triazinyl- or triazolyl- (where the hetaryls mentioned for their part are optionally substituted by $C_1$-$C_4$-alkyl or halogen) substituted $C_3$-$C_6$-cycloalkyl-$C_1$-$C_4$-alkyl, optionally halogen-, cyano- (also in the $C_1$-$C_4$-alkyl part of heterocyclyl-$C_1$-$C_4$-alkyl), nitro-, hydroxy-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino, —$C_1$-$C_4$-alkylamino-, di-($C_1$-$C_4$-alkyl)-amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted heterocyclyl-$C_1$-$C_4$-alkyl, optionally halogen-, cyano-, nitro-, hydroxy-, amino-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy- or $C_1$-$C_4$-haloalkoxy-substituted aryl, optionally halogen-, cyano- (also in the $C_1$-$C_4$-alkyl part of aryl-$C_1$-$C_4$-alkyl), nitro-, hydroxy-, amino-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy- or $C_1$-$C_4$-haloalkoxy-substituted aryl-$C_1$-$C_4$-alkyl, optionally halogen-, cyano-, nitro-, hydroxy-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di-($C_1$-$C_4$-alkyl)-amino-, $C_1$-$C_4$-alkylcarbonylamino-, $C_1$-$C_4$-alkylaminocarbonyl-, di-($C_1$-$C_4$-alkyl)-aminocarbonyl-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted hetaryl, optionally halogen-, cyano- (also in the $C_1$-$C_4$-alkyl part of hetaryl-$C_1$-$C_4$-alkyl), nitro-, hydroxy-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di-($C_1$-$C_4$-alkyl)-amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted hetaryl-$C_1$-$C_4$-alkyl, or $R^1$ represents a radical from the group consisting of

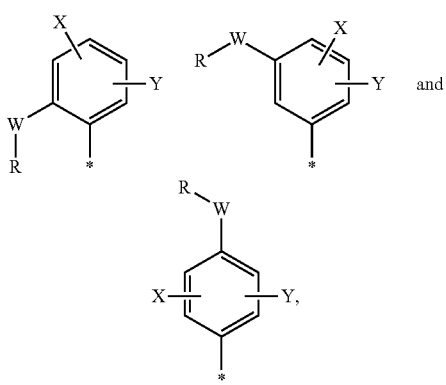

in which the bond to the nitrogen atom in the C(=V)—N-Q group in formula (I) is marked by the asterisk (*), R represents $NR^7R^8$ or represents $C_1$-$C_6$-alkyl, $C_3$-$C_6$-alkenyl, $C_3$-$C_6$-alkynyl, $C_1$-$C_4$-alkoxy-$C_1$-$C_3$-alkyl, $C_1$-$C_4$-alkyl-S(O)$_m$—$C_1$-$C_3$-alkyl, each of which is optionally mono- to heptasubstituted by halogen, mono- or disubstituted by oxygen (leads to C=O) or mono- or disubstituted by cyano, represents $R^7$—CO—$C_1$-$C_2$-alkyl, represents $NR^7R^8$—CO—$C_1$-$C_2$-alkyl, represents $C_3$-$C_8$-cycloalkyl which is optionally mono- or disubstituted by oxygen (leads to C=O), $C_1$-$C_4$-alkyl, $C_3$-$C_6$-cycloalkyl, $C_1$-$C_4$-alkoxy or $C_1$-$C_4$-haloalkyl, represents $C_3$-$C_8$-cycloalkenyl which is optionally mono- or disubstituted by oxygen (leads to C=O), $C_1$-$C_4$-alkyl, $C_3$-$C_6$-cycloalkyl, $C_1$-$C_4$-alkoxy or $C_1$-$C_4$-haloalkyl, represents $C_3$-$C_6$-cycloalkyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy or $C_1$-$C_4$-haloalkyl, represents $C_3$-$C_6$-cycloalkenyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy or $C_1$-$C_4$-haloalkyl, represents heterocyclyl which is optionally mono- or disubstituted by oxygen (leads to C=O), $C_1$-$C_4$-alkyl, $C_3$-$C_6$-cycloalkyl, $C_1$-$C_4$-alkoxy or $C_1$-$C_4$-haloalkyl, represents heterocyclyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy or $C_1$-$C_4$-haloalkyl or represents phenyl, phenyl-$C_1$-$C_4$-alkyl, hetaryl or hetaryl-$C_1$-$C_4$-alkyl, each of which is optionally mono- to trisubstituted by halogen, cyano, $C_1$-$C_4$-alkyl, $C_1$-$C_4$-haloalkyl, $C_3$-$C_6$-cycloalkyl, $C_1$-$C_4$-alkoxy or $C_1$-$C_4$-haloalkoxy, W represents a radical from the group consisting of S, SO and $SO_2$, X represents a radical from the group consisting of hydrogen, fluorine, chlorine, bromine, iodine, cyano, nitro, $C_1$-$C_4$-alkyl, $C_1$-$C_4$-haloalkyl, $C_3$-$C_6$-cycloalkyl, $C_1$-$C_4$-alkoxy and $C_1$-$C_4$-haloalkoxy, Y represents a radical from the group consisting of hydrogen, fluorine, chlorine, bromine, iodine, cyano, $C_1$-$C_4$-alkyl, $C_1$-$C_4$-haloalkyl, $C_3$-$C_6$-cycloalkyl, $C_1$-$C_4$-alkoxy and $C_1$-$C_4$-haloalkoxy, A represents sulphur, Q represents nitrogen or C—$R^3$, $R^3$ represents a radical from the group consisting of hydrogen, $C_1$-$C_4$-alkyl, $C_1$-$C_4$-haloalkyl, $C_3$-$C_6$-cycloalkyl, OH, $C_1$-$C_4$-alkoxy, $C_1$-$C_4$-haloalkoxy, SH, $C_1$-$C_4$-alkylsulphanyl, $C_1$-$C_4$-alkylsulphinyl, $C_1$-$C_4$-alkylsulphonyl, $NH_2$, $C_1$-$C_4$-alkylamino and di-($C_1$-$C_4$-alkyl)-amino, V represents oxygen, $R^7$ represents a radical from the group consisting of hydrogen, hydroxy, or $C_1$-$C_4$-alkyl, $C_1$-$C_4$-alkoxy, $C_1$-$C_4$-alkoxy-$C_1$-$C_4$-alkyl, $C_1$-$C_4$-alkyl-S(O)$_m$—$C_1$-$C_3$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_3$-alkyl, heterocyclyl and heterocyclyl-$C_1$-$C_3$-alkyl, each of which is optionally mono- or polysubstituted by halogen or mono- or disubstituted by cyano, or represents phenyl, benzyl, pyridyl, pyrimidyl, thiazolyl, oxazolyl, pyrazolyl, thienyl, furanyl, pyridinylmethyl or thiazolylmethyl, each of which is optionally mono- to trisubstituted by $C_1$-$C_4$-alkyl, $C_1$-$C_3$-haloalkyl, $C_1$-$C_3$-alkoxy, $C_1$-$C_3$-haloalkoxy, cyclopropyl, fluorine, chlorine, bromine or cyano, $R^8$ represents hydrogen, represents an alkali or alkaline earth metal ion, or represents an ammonium ion which is optionally mono- to tetrasubstituted by $C_1$-$C_4$-alkyl, or represents a radical from the group consisting of $C_1$-$C_4$-alkyl, $C_1$-$C_4$-alkoxy, $C_1$-$C_4$-alkoxy-$C_1$-$C_2$-alkyl and $C_1$-$C_4$-alkyl-S(O)$_m$—$C_1$-$C_2$-alkyl, each of which is optionally mono- or polysubstituted by halogen or mono- or disubstituted by cyano, m represents a number from the group consisting of 0, 1 and 2, and where alkali metal ion is selected from the group consisting of lithium, sodium, potassium, rubidium, caesium, alkaline earth metal ion is selected from the group consisting of beryllium, magnesium, calcium, strontium, barium, halogen is selected from the group consisting of fluorine, chlorine, bromine and iodine, aryl (including as part of a larger unit, for example arylalkyl) is selected from the group consisting of phenyl, naphthyl, anthryl and phenanthrenyl, hetaryl (synonymous with heteroaryl, also as part of a larger unit such as, for example, hetarylalkyl) is selected from the group consisting of pyrazolyl, imidazolyl, 1,2,3-triazolyl, 1,2,4-triazolyl, oxazolyl, isoxazolyl, thiazolyl, isothiazolyl, pyridyl, pyrimidinyl, pyridazinyl, pyrazinyl, 1,2,3-triazinyl, 1,2,4-triazinyl, 1,3,5-triazinyl, benzothienyl, and heterocyclyl is selected from the group consisting of azetidinyl, azolidinyl, azinanyl, oxetanyl, oxolanyl, oxanyl, dioxanyl, thiethanyl, thiolanyl, thianyl, tetrahydrofuryl, piperazinyl, morpholinyl.

4. A compound of formula (I) according to claim 1, wherein

Het is a radical from the group of

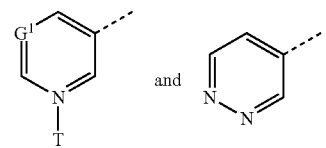

where the dotted line represents the bond to the carbon atom in the N=C-A group attached to Het, $G^1$ represents N or C-$A^1$, $A^1$ represents a radical from the group consisting of hydrogen, fluorine and chlorine, T represents oxygen or an electron pair, R¹ represents a radical from the group consisting of methyl, ethyl, isopropyl, n-propyl, n-butyl, isobutyl, sec-butyl, tert-butyl, 2,2,2-trifluoroethyl, 2,2-difluoroethyl, 2,2-difluoro-n-propyl, methylsulphanylmethyl, methylsulphanylethyl, methyl sulphanyl-n-propyl, trifluoromethylsulphonylmethyl, ethylsulphonylmethyl, 2,2,2-trifluoroethylsulphonylmethyl, 2,2-difluoroethylsulphonylmethyl, isopropylsulphanylmethyl, methylsulphinylmethyl, trifluoromethylsulphinylmethyl, ethylsulphinylmethyl, 2,2,2-trifluoroethylsulphinylmethyl, 2,2-difluoroethylsulphinylmethyl, isopropylsulphinylmethyl, methylsulphonylmethyl, trifluoromethylsulphonylmethyl, ethylsulphonylmethyl, 2,2,2-trifluoroethylsulphonylmethyl, 2,2-difluoroethylsulphonylmethyl, isopropylsulphonylmethyl, methoxycarbonyl, ethoxycarbonyl, methoxycarbonylmethyl, ethoxycarbonylmethyl, methoxycarbonylethyl, ethoxycarbonylethyl, dimethylaminocarbonyl, diethylaminocarbonyl, N-ethyl-N-methylaminocarbonyl, N-isopropyl-N-methylaminocarbonyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, methylsulphanyl, trifluoromethylsulphanyl, ethylsulphanyl, 2,2,2-trifluoroethyl sulphanyl, 2,2-difluoroethyl sulphanyl, isopropylsulphanyl, methylsulphinyl, trifluoromethylsulphinyl, ethylsulphinyl, 2,2,2-trifluoroethylsulphinyl, 2,2-difluoroethylsulphinyl, isopropylsulphinyl, methylsulphonyl, trifluoromethylsulphonyl, ethylsulphonyl, 2,2,2-trifluoroethylsulphonyl, 2,2-difluoroethylsulphonyl, isopropylsulphonyl, cyclopropyl, 1-cyanocyclopropyl, 1-chlorocyclopropyl, 1-fluorocyclopropyl, 2-cyanocyclopropyl, 2-chlorocyclopropyl, 2-fluorocyclopropyl, 2,2,3,3-tetrafluorocyclopropyl, 2-cyclopropylcyclopropyl, cyclobutyl, cyclopentyl, cyclohexyl, 4-trifluoromethylcyclohexyl, cyclopropylmethyl, cyclopropylethyl, cyclobutylmethyl, N-cyclopropyl-N-methylaminocarbonyl, morpholin-4-ylcarbonylmethyl, piperazin-1-ylcarbonylmethyl, 4-methylpiperazin-1-ylcarbonylmethyl, of heterocyclylmethyl and heterocyclylethyl, each of which is optionally mono-, di- or trisubstituted by identical or different substitutents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy and difluoromethoxy, of in each case cyclopropyl-substituted heterocyclylmethyl and heterocyclylethyl, where the cyclopropyl radical is optionally mono- or disubstituted by methyl, fluorine, chlorine, cyano or monosubstituted by cyclopropyl, of hetaryl which is optionally mono- or disubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy, dimethylaminocarbonyl, of hetaryl substituted by cyclopropyl, where the cyclopropyl radical is optionally mono- or disubstituted by methyl, fluorine, chlorine, cyano or monosubstituted by cyclopropyl, of aryl which is optionally mono-, di- or trisubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy and trifluoroethoxy, of aryl substituted by cyclopropyl, where the cyclopropyl radical is optionally mono- or disubstituted by methyl, fluorine, chlorine, cyano or monosubstituted by cyclopropyl, of arylmethyl and arylethyl, each of which is optionally mono-, di- or trisubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy, of arylmethyl and arylethyl in each case substituted by cyclopropyl, where the cyclopropyl radical is optionally mono- or disubstituted by methyl, fluorine, chlorine, cyano or monosubstituted by cyclopropyl, of hetarylmethyl and hetarylethyl, each of which is optionally mono- or disubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy, of hetarylmethyl and hetarylethyl in each case substituted by cyclopropyl, where the cyclopropyl radical is optionally mono- or disubstituted by methyl, fluorine, chlorine, cyano or monosubstituted by cyclopropyl, or R¹ represents a radical from the group consisting of

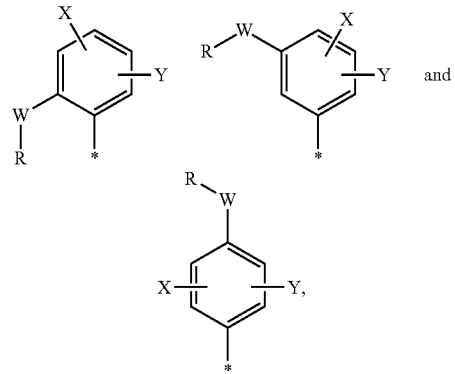

in which the bond to the nitrogen atom in the C(=V)—N-Q group in formula (I) is marked by the asterisk (*), R represents $NR^7R^8$ or represents a radical from the group consisting of $C_1$-$C_4$-alkyl, $C_3$-$C_4$-alkenyl, $C_3$-$C_4$-alkynyl, $C_1$-$C_2$-alkoxy-$C_1$-$C_2$-alkyl and $C_1$-$C_2$-alkyl-$S(O)_m$—$C_1$-$C_2$-alkyl, each of which is optionally mono-, di-, tri-, tetra- or pentasubstituted by fluorine, chlorine or mono- or disubstituted by cyano, represents $R^7$—CO—$C_1$-$C_2$-alkyl, represents $NR^7R^8$—CO—$C_1$-$C_2$-alkyl, represents $C_3$-$C_6$-cycloalkyl which is optionally mono- or disubstituted by $C_1$-$C_2$-alkyl, $C_1$-$C_2$-alkoxy or $C_1$-$C_2$-haloalkyl or by an oxygen atom (leads to C=O), represents $C_3$-$C_6$-cycloalkenyl which is optionally mono- or disubstituted by $C_1$-$C_2$-alkyl, $C_1$-$C_2$-alkoxy or $C_1$-$C_2$-haloalkyl or by an oxygen atom (leads to C=O), represents $C_3$-$C_6$-cycloalkyl-$C_1$-$C_2$-alkyl which is optionally mono- or disubstituted by $C_1$-$C_2$-alkyl, $C_1$-$C_2$-alkoxy or $C_1$-$C_2$-haloalkyl, represents $C_3$-$C_6$-cycloalkenyl-$C_1$-$C_2$-alkyl which is optionally mono- or disubstituted by $C_1$-$C_2$-alkyl, $C_1$-$C_2$-alkoxy or $C_1$-$C_2$-haloalkyl, represents heterocyclyl which is optionally mono- or disubstituted by $C_1$-$C_2$-alkyl, $C_1$-$C_2$-alkoxy or $C_1$-$C_2$-haloalkyl, represents heterocyclyl-$C_1$-$C_2$-alkyl which is optionally mono- or disubstituted by $C_1$-$C_2$-alkyl, $C_1$-$C_2$-alkoxy or $C_1$-$C_2$-haloalkyl or represents phenyl, benzyl, pyridyl, pyrimidyl, thiazolyl, oxazolyl, pyrazolyl, thienyl, furanyl, pyridinylmethyl or thiazolylmethyl, each of which is optionally mono- or disubstituted by fluorine, chlorine, bromine, cyano, methyl, ethyl, difluoromethyl, trifluoromethyl, methoxy, ethoxy, difluoromethoxy or trifluoromethoxy, W represents a radical from the group consisting of S, SO and $SO_2$, X represents a radical from the group consisting of hydrogen, fluorine, chlorine, bromine, cyano, methyl, ethyl, trifluoromethyl, methoxy, ethoxy, difluoromethoxy and trifluoromethoxy, Y represents a radical from the group consisting of hydrogen, fluorine, chlorine, bromine, cyano, methyl, ethyl, trifluoromethyl, methoxy, ethoxy, difluoromethoxy and trifluoromethoxy, A represents sulphur, Q represents nitrogen or C—$R^3$, $R^3$ represents hydrogen, V represents oxygen, $R^7$ represents a radical from the group consisting of hydrogen, hydroxy, or represents $C_1$-$C_4$-alkyl, $C_1$-$C_4$-alkoxy, $C_1$-$C_4$-alkoxy-$C_1$-$C_4$-alkyl, $C_1$-$C_4$-alkyl-$S(O)_m$—$C_1$-$C_2$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_3$-alkyl, heterocyclyl or heterocyclyl-$C_1$-$C_3$-alkyl, each of which is optionally mono-, di-, tri-, tetra- or pentasubstituted by fluorine, chlorine or mono- or disubstituted by cyano, or represents phenyl, benzyl, pyridyl, pyrimidyl, thiazolyl, oxazolyl, pyrazolyl, thienyl, furanyl, pyridinylmethyl or thiazolylmethyl, each of which is optionally mono- to trisubstituted by $C_1$-$C_4$-alkyl, $C_1$-$C_3$-haloalkyl, $C_1$-$C_3$-alkoxy, $C_1$-$C_3$-haloalkoxy, cyclopropyl, fluorine, chlorine, bromine or cyano, $R^8$ represents hydrogen, an alkali or alkaline-earth metal ion, an ammonium ion which is optionally mono- to tetrasubstituted by $C_1$-$C_4$-alkyl, or represents a radical from the group consisting of $C_1$-$C_4$-alkyl, $C_1$-$C_4$-alkoxy, $C_1$-$C_4$-alkoxy-$C_1$-$C_2$-alkyl and $C_1$-$C_4$-alkyl-$S(O)_m$—$C_1$-$C_2$-alkyl, each of which is optionally mono-, di-, tri-, tetra- or pentasubstituted by fluorine, chlorine or is mono- or disubstituted by cyano, m represents a number from the group consisting of 0, 1 and 2, and where alkali metal ion represents an ion from the group consisting of lithium, sodium, potassium, rubidium, caesium, alkaline earth metal ion represents an ion from the group consisting of beryllium, magnesium, calcium, strontium, barium, halogen represents fluorine, chlorine, bromine and iodine, heterocyclyl represents a radical from the group consisting of oxetanyl, thiethanyl, tetrahydrofuryl and morpholinyl, aryl represents phenyl and hetaryl (synonymous with heteroaryl, including as part of a larger unit such as, for example, hetarylalkyl) represents a radical from the group consisting of pyridyl, pyrimidyl, pyrazinyl, pyridazinyl, thiazolyl, pyrazolyl and benzothienyl.

5. A compound of formula (I) according to claim 1, wherein

Het represents a radical from the group consisting of

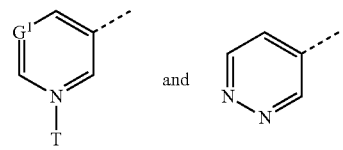

where the dotted line represents the bond to the carbon atom in the N=C-A group attached to Het, $G^1$ represents N or C-$A^1$, $A^1$ represents a radical from the group consisting of hydrogen, fluorine and chlorine, T represents oxygen or an electron pair, $R^1$ represents a radical from the group consisting of methyl, ethyl, isopropyl, n-propyl, n-butyl, isobutyl, sec-butyl, tert-butyl, 2,2,2-trifluoroethyl, 2,2-difluoroethyl, 2,2-difluoro-n-propyl, methylsulphanylmethyl, methylsulphanylethyl, methyl sulphanyl-n-propyl, trifluoromethylsulphonylmethyl, ethylsulphonylmethyl, 2,2,2-trifluoroethylsulphonylmethyl, 2,2-difluoroethylsulphonylmethyl, isopropylsulphanylmethyl, methylsulphinylmethyl, trifluoromethylsulphinylmethyl, ethylsulphinylmethyl, 2,2,2-trifluoroethylsulphinylmethyl, 2,2-difluoroethylsulphinylmethyl, isopropylsulphinylmethyl, methylsulphonylmethyl, trifluoromethylsulphonylmethyl, ethylsulphonylmethyl, 2,2,2-trifluoroethylsulphonylmethyl, 2,2-difluoroethylsulphonylmethyl, isopropylsulphonylmethyl, methoxycarbonyl, ethoxycarbonyl, methoxycarbonylmethyl, ethoxycarbonylmethyl, methoxycarbonylethyl, ethoxycarbonylethyl, dimethylaminocarbonyl, diethylaminocarbonyl, N-ethyl-N-methylaminocarbonyl, N-isopropyl-N-methylaminocarbonyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, methylsulphanyl, trifluoromethylsulphanyl, ethylsulphanyl, 2,2,2-trifluoroethyl sulphanyl, 2,2-difluoroethyl sulphanyl, isopropylsulphanyl, methylsulphinyl, trifluoromethylsulphinyl, ethylsulphinyl, 2,2,2-trifluoroethylsulphinyl, 2,2-difluoroethylsulphinyl, isopropylsulphinyl, methylsulphonyl, trifluoromethylsulphonyl, ethylsulphonyl, 2,2,2-trifluoroethylsulphonyl, 2,2-difluoroethylsulphonyl, isopropylsulphonyl, cyclopropyl, 1-cyanocyclopropyl, 1-chlorocyclopropyl, 1-fluorocyclopropyl, 2-cyanocyclopropyl, 2-chlorocyclopropyl, 2-fluorocyclopropyl, 2,2,3,3-tetrafluorocyclopropyl, 2-cyclopropylcyclopropyl, cyclobutyl, cyclopentyl, cyclohexyl, 4-trifluoromethylcyclohexyl, cyclopropylmethyl, cyclopropylethyl, cyclobutylmethyl, N-cyclopropyl-N-methylaminocarbonyl, morpholin-4-ylcarbonylmethyl, piperazin-1-ylcarbonylmethyl, 4-methylpiperazin-1-ylcarbonylmethyl, of heterocyclylmethyl and heterocyclylethyl, each of which is optionally mono-, di- or trisubstituted by identical or different substitutents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy and difluoromethoxy, of in each case cyclopropyl-substituted heterocyclylmethyl and heterocyclylethyl, where the cyclopropyl radical is optionally mono- or disubstituted by methyl, fluorine, chlorine, cyano or monosubstituted by cyclopropyl, of hetaryl which is optionally mono- or disubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy, dimethylaminocarbonyl, of hetaryl substituted by cyclopropyl, where the cyclopropyl radical is optionally mono- or disubstituted by methyl, fluorine, chlorine, cyano or monosubstituted by cyclopropyl, of aryl which is optionally mono-, di- or trisubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy and trifluoroethoxy, of aryl substituted by cyclopropyl, where the cyclopropyl radical is optionally mono- or disubstituted by methyl, fluorine, chlorine, cyano or monosubstituted by cyclopropyl, of arylmethyl and arylethyl, each of which is optionally mono-, di- or trisubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy, of arylmethyl and arylethyl in each case substituted by cyclopropyl, where the cyclopropyl radical is optionally mono- or disubstituted by methyl, fluorine, chlorine, cyano or monosubstituted by cyclopropyl, of hetarylmethyl and hetarylethyl, each of which is optionally mono- or disubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy, of hetarylmethyl and hetarylethyl in each case substituted by cyclopropyl, where the cyclopropyl radical is optionally mono- or disubstituted by methyl, fluorine, chlorine, cyano or monosubstituted by cyclopropyl, or $R^1$ represents the radical of the formula

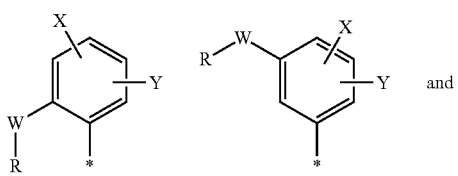

and

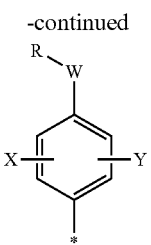

in which the bond to the nitrogen atom in the C(=V)—N-Q group in formula (I) is marked by the asterisk (*), R represents methyl, ethyl, propyl, isopropyl, n-butyl, isobutyl, sec-butyl, tert-butyl, allyl, 2-butenyl, propargyl, 2-butynyl, each of which is optionally mono-, di- or trisubstituted by fluorine or monosubstituted by cyano, or represents $C_3$-$C_6$-cycloalkyl which is optionally monosubstituted by methyl, ethyl, methoxy, ethoxy or trifluoromethyl, or represents $C_3$-$C_6$-cycloalkylmethyl which is optionally monosubstituted by methyl, ethyl, methoxy or trifluoromethyl, or represents phenyl, benzyl, pyridyl, pyrimidyl, thiazolyl and pyridinylmethyl, each of which is optionally mono- or disubstituted by fluorine, chlorine, bromine, cyano, methyl, ethyl, isopropyl, tert-butyl, trifluoromethyl, difluoromethyl, methoxy, ethoxy, difluoromethoxy or trifluoromethoxy, W represents a radical from the group consisting of S, SO and $SO_2$, X represents a radical from the group consisting of hydrogen, fluorine, chlorine, bromine, cyano, methyl, ethyl, trifluoromethyl, methoxy, ethoxy, difluoromethoxy and trifluoromethoxy, Y represents a radical from the group consisting of hydrogen, fluorine, chlorine, bromine, cyano, methyl, ethyl, trifluoromethyl, methoxy, ethoxy, difluoromethoxy and trifluoromethoxy, A represents sulphur, Q represents nitrogen or C—$R^3$, $R^3$ represents hydrogen or methyl, V represents oxygen and where alkali metal ion represents an ion from the group consisting of lithium, sodium, potassium, rubidium, caesium, alkaline earth metal ion represents an ion from the group consisting of beryllium, magnesium, calcium, strontium, barium, halogen represents fluorine, chlorine, bromine and iodine, heterocyclyl represents a radical from the group consisting of oxetanyl, thiethanyl, tetrahydrofuryl and morpholinyl, aryl represents phenyl and hetaryl (synonymous with heteroaryl, including as part of a larger unit such as, for example, hetarylalkyl) represents a radical from the group consisting of pyridyl, pyrimidyl, pyrazinyl, pyridazinyl, thiazolyl, pyrazolyl and benzothienyl.

6. A compound of formula (I) according to claim 1
wherein
Het represents

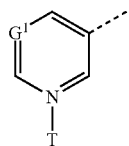

where the dotted line represents the bond to the carbon atom in the N=C-A group attached to Het,
$G^1$ represents $C-A^1$,
$A^1$ represents hydrogen,
T represents oxygen or an electron pair,
$R^1$ represents
  methyl, ethyl, isopropyl, n-propyl, n-butyl, isobutyl, sec-butyl, tert-butyl, 2,2,2-trifluoroethyl, 2,2-difluoroethyl, 2,2-difluoro-n-propyl, dimethylaminocarbonyl, diethylaminocarbonyl, N-ethyl-N-methylaminocarbonyl, N-isopropyl-N-methylaminocarbonyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, cyclopropyl, cyclobutyl, cyclopentyl, cyclohexyl, represents hetarylmethyl or hetarylethyl, each of which is optionally mono- or disubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy,
$R^1$ also represents

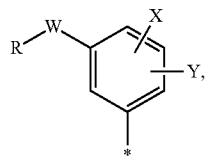

in which the bond to the nitrogen atom in the C(=V)—N-Q group in formula (I) is marked by the asterisk (*),
R represents $C_1-C_4$-alkyl which is optionally mono- to trisubstituted by fluorine or chlorine,
W represents a radical from the group S and SO,
X represents a radical from the group consisting of hydrogen, fluorine, chlorine, bromine, methyl, ethyl, difluoromethyl and trifluoromethyl,
Y represents a radical from the group consisting of hydrogen, fluorine, chlorine, bromine, iodine, methyl and ethyl,
A represents sulphur,
Q represents nitrogen or $C-R^3$,
$R^3$ represents hydrogen,
V represents oxygen and where
  halogen represents fluorine, chlorine, bromine and iodine and
hetaryl represents a radical from the group consisting of pyridyl, pyrimidinyl, thiazolyl, pyrazolyl and benzothienyl.

7. A compound of formula (I) according to claim 1
wherein
Het represents

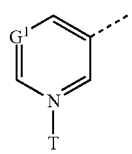

where the dotted line represents the bond to the carbon atom in the N=C-A group attached to Het,
$G^1$ represents $C-A^1$ or N,
$A^1$ represents hydrogen or fluorine,
T represents oxygen or an electron pair,
$R^1$ represents methyl, ethyl, isopropyl, n-propyl, n-butyl, isobutyl, sec-butyl, tert-butyl, 2,2,2-trifluoroethyl, 2,2-difluoroethyl, 2,2-difluoro-n-propyl, dimethylaminocarbonyl, diethylaminocarbonyl, N-ethyl-N-methylaminocarbonyl, N-isopropyl-N-methylaminocarbonyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, cyclopropyl, cyclobutyl, cyclopentyl, cyclohexyl, cyclopropylmethyl, optionally dimethylaminocarbonyl-substituted benzothienyl, optionally halogen-, methyl- or trifluoroethoxy-substituted phenyl, optionally methyl-, methoxy-, difluoromethoxy- or halogen-substituted phenylmethyl, represents hetarylmethyl or hetarylethyl, each of which is optionally mono- or disubstituted by identical or different substituents from the group consisting of fluorine, chlorine, bromine, cyano, nitro, hydroxy, amino, methyl, ethyl, isopropyl, tert-butyl, trifluoromethyl, difluoromethyl, methoxy, trifluoromethoxy, difluoromethoxy,
$R^1$ also represents

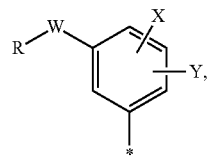

in which the bond to the nitrogen atom in the C(=V)—N-Q group in formula (I) is marked by the asterisk (*),
R represents $C_1-C_4$-alkyl which is optionally mono- to trisubstituted by fluorine or chlorine,
W represents a radical from the group consisting of S, SO and $SO_2$,
X represents a radical from the group consisting of hydrogen, fluorine, chlorine, bromine, methyl, ethyl, difluoromethyl and trifluoromethyl,
Y represents a radical from the group consisting of hydrogen, fluorine, chlorine, bromine, iodine, methyl and ethyl, A represents sulphur,
Q represents nitrogen or C—R³,
R³ represents hydrogen or methyl,
V represents oxygen and where
 halogen represents fluorine, chlorine, bromine and iodine and
 hetaryl represents a radical from the group consisting of pyridyl, pyrimidinyl, thiazolyl, pyrazolyl and benzothienyl.

8. A compound of formula (I) according to claim 1 wherein Het represents the radical of the formula

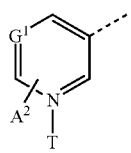.

9. A compound of formula (I) according to claim 1 wherein T represents an electron pair.

10. A compound of formula (I) according to claim 1 wherein Het represents pyridin-3-yl.

11. A compound of formula (I) according to claim 1 wherein Het represents 5-fluoropyridin-3-yl.

12. A compound of formula (I) according to claim 1 wherein R¹ represents the radical

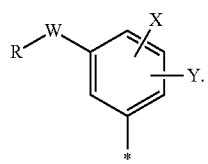

13. A composition, comprising at least one compound of formula (I) according to claim 1 and one or more customary extenders and/or surfactants.

14. A method for controlling an animal pest comprising applying one or more compounds of the formula (I) according to claim 1 to the pest and/or a habitat thereof.

15. The compound according to claim 1, wherein Het represents

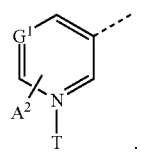.

16. The compound according to claim 10, wherein
A is S;
Q is CH;
V is O; and
R¹ is

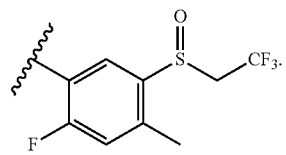 [SMILES: *c1cc(S(=O)CC(F)(F)F)c(C)cc1F]

* * * * *